United States Patent
Berger et al.

(10) Patent No.: US 7,858,629 B2
(45) Date of Patent: *Dec. 28, 2010

(54) SUBSTITUTED IMIDAZOLE 4-CARBOXAMIDES AS CHOLECYSTOKININ-1 RECEPTOR MODULATORS

(75) Inventors: Richard Berger, Princeton, NJ (US); Scott Edmondson, Clark, NJ (US); Alexa Hansen, Danville, CA (US); Cheng Zhu, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 23 days.

This patent is subject to a terminal disclaimer.

(21) Appl. No.: 12/226,048

(22) PCT Filed: Apr. 10, 2007

(86) PCT No.: PCT/US2007/008901

§ 371 (c)(1),
(2), (4) Date: Oct. 6, 2008

(87) PCT Pub. No.: WO2007/120688

PCT Pub. Date: Oct. 25, 2007

(65) Prior Publication Data

US 2009/0239862 A1   Sep. 24, 2009

Related U.S. Application Data

(60) Provisional application No. 60/791,962, filed on Apr. 14, 2006.

(51) Int. Cl.
*A61K 31/496* (2006.01)
*A61K 31/4709* (2006.01)
*A61K 31/454* (2006.01)
*C07D 405/14* (2006.01)
*C07D 413/14* (2006.01)

(52) U.S. Cl. .......................... 514/253.06; 514/254.05; 514/254.07; 514/314; 514/326; 544/121; 544/129; 544/363; 544/370; 546/175; 546/205

(58) Field of Classification Search .................. None
See application file for complete search history.

(56) References Cited

U.S. PATENT DOCUMENTS

| 6,960,601 B2 | 11/2005 | Smith et al. |
| 2004/0063691 A1 | 4/2004 | Smith et al. |
| 2005/0054679 A1 | 3/2005 | Kruse et al. |
| 2005/0124660 A1 | 6/2005 | Antel et al. |
| 2005/0197377 A1 | 9/2005 | Breitenbucher et al. |
| 2005/0256167 A1 | 11/2005 | Smith et al. |

FOREIGN PATENT DOCUMENTS

| EP | 0646648 | 4/1995 |
| WO | WO 01/85723 | 11/2001 |
| WO | WO 02/055495 | 7/2002 |
| WO | WO 03/007887 | 1/2003 |
| WO | WO 03/040107 | 5/2003 |
| WO | WO 03/063781 | 8/2003 |
| WO | WO 2004/007463 | 1/2004 |
| WO | WO 2004/094407 | 11/2004 |
| WO | WO 2005/009974 | 2/2005 |
| WO | WO 2005/040130 | 5/2005 |
| WO | WO 2005/063716 | 7/2005 |
| WO | WO 2005/095354 | 10/2005 |
| WO | WO 2007/120655 | 10/2007 |
| WO | WO 2007/120718 | 10/2007 |

OTHER PUBLICATIONS

Zhu et al. Bioorganic & Medicinal Chemistry Letters, vol. 18, p. 4393-4396 (2008).*
Little et al., Obesity Rev., vol. 6 (2005), pp. 297-306, "Role of cholecystokinin in appetite control and body weight regulation".
Moran et al., Am. J. Physiol. Gastrointest. Liver Physiol., vol. 286 (2004), pp. G183-G188, "Gastrointestinal satiety signals".
Lange et al., J. Med. Chem., vol. 48 (2005), pp. 1823-1838, "Bioisosteric replacements of the pyrazole moiety of rimonabant . . . ".
Asproni et al., J. Med. Chem., vol. 48 (2005), pp. 2638-2645, "Synthesis, structure—activity relationships at the GABAA receptor in rat brain, . . .".
Khanna et al., J. Med. Chem., vol. 40 (1997), pp. 1634-1647, "1,2-Diarylimidazoles as potent, cyclooxygenase-2 selective, and orally active antiinflarnmatory agents".
Khanna et al., J. Med. Chem., vol. 43 (2000), pp. 3168-3185, "Selective cyclooxygenase-2 inhibitors: heteroaryl modified 1,2-diarylimidazoles are potent, orally active antiinflammatory agents".
Asproni et al., J. Med. Chem., vol. 45 (2002), pp. 4655-4668, "Synthesis and pharmacological evaluation of 1-[(1,2-Diphenyl-1H-4-imidazolyl)methyl]-4-phenylpiperazines . . .".
Szewczyk et al., Curr. Topics in Med. Chem., vol. 3 (2003), pp. 837-854, "CCK1R agonists: a promising target for the pharmacological treatment of obesity".
Varga et al., Br. J. Pharmacol., vol. 141 (2004), pp. 1275-1284, "Involvement of endogenous CCK and CCK1 receptors in colonic motor function".

* cited by examiner

*Primary Examiner*—Emily Bernhardt
(74) *Attorney, Agent, or Firm*—Baerbel R. Brown; John C. Todaro

(57) ABSTRACT

Certain novel substituted imidazole 4-carboxamides are ligands of the human cholecystokinin receptor and, in particular, are selective ligands of the human cholecystokinin-1 receptor (CCK-1R). They are therefore useful for the treatment, control, or prevention of diseases and disorders responsive to the modulation of CCK-1R, such as obesity, and diabetes.

17 Claims, No Drawings

SUBSTITUTED IMIDAZOLE 4-CARBOXAMIDES AS CHOLECYSTOKININ-1 RECEPTOR MODULATORS

CROSS-REFERENCE TO RELATED APPLICATIONS

This application is a U.S. National Phase application under 35 U.S.C. §371 of PCT Application No. PCT/US2007/008901, filed 10 Apr. 2007, which claims priority from and the benefit of U.S. Provisional Application No. 60/791962, filed Apr. 14, 2006.

BACKGROUND OF THE INVENTION

Obesity is a major health concern in Western societies. It is estimated that about 97 million adults in the United States are overweight or obese. Obesity is now recognized as a chronic disease that requires treatment to reduce its associated health risks. The medical problems associated with obesity, which can be serious and life-threatening, include hypertension; type 2 diabetes mellitus; elevated plasma insulin concentrations; insulin resistance; hyperinsulinemia; glucose intolerance; dyslipidemias; hyperlipidemia; endometrial, breast, prostate and colon cancer; osteoarthritis; respiratory complications, such as obstructive sleep apnea; cholescystitis; cholelithiasis; gout; gallstones; gall bladder disease; respiratory problems; psychological disorders (such as depression, eating disorders, distorted body image and low self esteem); arteriosclerosis; heart disease; abnormal heart rhythms; angina pectoris; and heart arrythmias (Kopelman, P. G., Nature 404, 635-643 (2000)). Obesity is further associated with premature death and with a significant increase in mortality and morbidity from stroke, myocardial infarction, congestive heart failure, coronary heart disease, and sudden death. Recent studies have found that obesity and its associated health risks also affect children and adolescents. According to the Centers for Disease Control, 15 percent of children and adolescents are defined as overweight and obese, a doubling since the early 1970s. Important outcomes for the treatment of obesity include weight loss, and weight management to improve cardiovascular and metabolic health and to reduce obesity-related morbidity and mortality. It has been shown that 5-10% loss of body weight can substantially improve metabolic values, such as blood glucose, blood pressure, and lipid concentrations, and may reduce morbidity and mortality.

Cholecystokinin (CCK) is a brain-gut peptide that acts as a gastrointestinal hormone, neurotransmitter and neuromodulator in the central and the peripheral nervous systems. It has been shown that CCK is released from mucosal 1-cells of the duodenum and jejunum in response to a meal, particularly in response to fat or protein in the meal. Once released, CCK initiates a number of responses coordinated to promote digestion and regulate food intake, including mediating bile emptying from the gall bladder, regulating the release of digestive enzymes from the pancreas, controlling gastric emptying by regulation of the pyloric sphincter, as well as neuronal signaling to the central nervous system via vagal afferent neurons. Neuronal CCK is believed to mediate a number of events within the CNS, including modulating dopaminergic neurotransmission and anxiogenic effects, as well as affecting cognition and nociception. See, e.g., J. N. Crawley and R. L. Corwin, 1994, Peptides, 15:731-755; N. S. Baber, C. T. Dourish, and D. R. Hill, Pain (1989), 39(3), 307-29; and P. De Tullio, J. Delarge and B. Pirotte, Expert Opinion on Investigational Drugs (2000), 9(1), 129-146. Cholecystokinin has been shown to mediate its diverse hormonal and neuromodulatory functions through two receptor subtypes: the CCK-A (CCK1) and CCK-B (CCK2) subtypes (see, e.g., G. N. Woodruff and J. Hughes, Annu. Rev. Pharmacol. Toxicol. (1991), 31: 469-501). Both CCK-1 and CCK-2 receptor subtypes belong to the seven transmembrane G-protein-coupled superfamily of receptors. A number of studies suggest that CCK mediates its satiety effect through the CCK-1 receptor, which relays the postprandial satiety signal via the vagal afferents to the CNS. See, e.g., G. P. Smith et al., Science 213 (1981) pp. 1036-1037; and J. N. Crawley et al., J. Pharmacol. Exp. Ther., 257 (1991) pp. 1076-1080. The nucleotide sequences of the peripheral CCK-1 receptor and central CCK-1 receptor are identical in humans. See, e.g., S. A. Wank et al., (1994), NY Acad. Sci. 713, pp. 49-66.

It has been reported that cholecystokinin (CCK) inhibits gastric emptying and increases satiety in a variety of species, including humans, resulting in a reduction of food intake (Moran, T. H. Physiology & Behavior 2004, 82, 175-180). Selective CCK1R antagonists have been shown to reverse the anorexigenic effect of CCK thus increasing food intake and meal size in several species, including humans (Beglinger, C. et. al. Am. J. Physiol. Regul. Integr. Comp. Physiol. 2001, 280, R1149-R1154). Conversely, administration of CCK1R agonists to a variety of species, including humans, results in a reduction of food intake (Geary, N. Physiology & Behavior 2004, 81, 719-733). Consequently, selective small molecule CCK1R agonists are useful for the treatment or prevention of obesity and related metabolic disorders such as diabetes and dyslipidemia (Woods, S. C. Am. J. Gastrointest. Liver Physiol. 2004, 286, G7-13; Moran, T. H., Kinzig, K. P. Am. J. Gastrointest. Liver Physiol. 2004, 286, G183-G188). In humans, bulimia nervosa has been linked with reduced secretion of postprandial CCK (Deylin, M. J. et. al. J. Pharmacol. Exp. Ther. 1987, 241, 100-116), lower CCK concentrations in cerebrospinal fluid (Lydiard, R. B. et. al. Am. J. Psychiatry 1993, 150, 1099-1101), and lower CCK levels in T lymphocytes which could reflect central CCK secretion levels (Brambilla, F. et. al. Psychiatry Research 1995, 37, 51-56). Accordingly, CCK1R agonists are also useful in treating, preventing, or diagnosing bulimia nervosa and related eating disorders.

CCK agonists stimulate gallbladder contraction, stimulate pancreatic enzyme secretions, stimulate intestinal blood flow, and affect intestinal motor activity (See Rehfeld, J. F. Best Practice & Res. Clin. Endocrin. & Metab. 2004, 18, 569-586). Consequently, CCK1R agonists are useful for the treatment, prevention, or diagnosis of disorders related to the gall bladder including, but not limited to, cholecystitis (inflammation of the gallbladder) and cholelithiasis (gallstones). Furthermore, CCK agonists are useful for the treatment, prevention, or diagnosis of disorders related to the pancreas. Finally, CCK1R agonists are useful for the treatment, prevention, or diagnosis of disorders related to the gastrointestinal tract and gastrointestinal motility.

CCK receptors are abundant in the central nervous system, and agonists can be used for the treatment, prevention, or diagnosis of emotional or sexual behavior disorders and memory disorders (Itoh, S.; et. al. Drug Develop. Res. 1990, 21, 257-276). Furthermore, CCK agonists can be used for the treatment, prevention, or diagnosis of tardive dyskinesia (Nishikawa, T. et. al. Prog. Neuropsycho-pharmnacol. Biol. Psych. 1988, 12, 903-812; Bignon, E. et. al. J. Pharm. Exp. Ther. 1999, 289, 752-761), Parkinson's disease (Bednar, I. et. al. Biogenic Amine, 1996, 12, 275-284), schizophrenia, and psychosis (Crawley, J. N. Trends in Pharmacol. Sci., 1991, 12, 232-236).

Imidazole compounds useful for the treatment of obesity and obesity related disorders have been disclosed in WO 01/085723, WO 03/040107, WO 03/063781, WO 03/007887, WO 2004/094407, WO 2005/009974, WO 2005/040130, WO 2005/063716, WO 2005/095354, US 2005/0054679, US 2005/0124660, US 2005/0197377, U.S. Pat. No. 6,960,601, and J. Med. Chem. 2005, 48, 1823-1838. Other imidazoles are disclosed in J. Med. Chem. 2005, 48, 2638-2645; J. Med. Chem., 2002, 45, 4655-4668; J. Med. Chem. 2000, 43, 3168-3185; and J. Med. Chem. 1997, 40, 1634-1647.

Because of the unresolved deficiencies of the various pharmacological agents discussed above, there is a continuing need for a weight loss treatment with enhanced efficacy and fewer undesirable side effects. The instant invention addresses this problem by providing CCK receptor agonists, and in particular selective agonists of the cholecystokinin-1 receptor (CCK-1R), useful in the treatment and prevention of obesity and obesity-related disorders, including diabetes.

It is therefore an object of the present invention to provide substituted imidazole 4-carboxamides which are selective agonists of the cholecystokinin-1 (CCK-1R) receptor. It is another object of the present invention to provide substituted imidazole 4-carboxamides which are cholecystokinin-1 receptor agonists and thereby useful to treat obesity, diabetes, and obesity related disorders. It is another object of the present invention to provide pharmaceutical compositions comprising the cholecystokinin-1 receptor agonists of the present invention with a pharmaceutically acceptable carrier. It is another object of the present invention to provide methods for the treatment or prevention of disorders, diseases, or conditions responsive to the activation of the cholecystokinin-1 receptor in a mammal in need thereof by administering the compounds and pharmaceutical compositions of the present invention. It is another object of the present invention to provide methods for the treatment or prevention of obesity, diabetes mellitus, and obesity related disorders by administering the compounds and pharmaceutical compositions of the present invention to a mammal in need thereof. These and other objects will become readily apparent from the detailed description that follows.

SUMMARY OF THE INVENTION

The present invention relates to novel substituted imidazole 4-carboxamides of formula I:

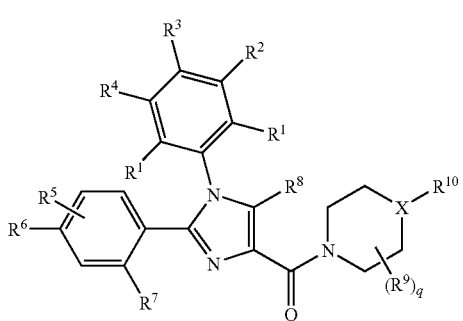

The compounds of formula I are effective as cholecystokinin receptor ligands and are particularly effective as selective ligands of the cholecystokinin-1 receptor. They are therefore useful for the treatment and/or prevention of disorders responsive to the modulation of the cholecystokinin-1 receptor, such as obesity, diabetes, and obesity-related disorders.

The present invention also relates to pharmaceutical compositions comprising the compounds of the present invention and a pharmaceutically acceptable carrier.

The present invention also relates to methods for the treatment or prevention of disorders, diseases, or conditions responsive to the modulation of the cholecystokinin-1 receptor in a mammal in need thereof by administering the compounds and pharmaceutical compositions of the present invention.

The present invention further relates to the use of the compounds of the present invention in the preparation of a medicament useful for the treatment or prevention of disorders, diseases, or conditions responsive to the modulation of the cholecystokinin-1 receptor in a mammal in need thereof by administering the compounds and pharmaceutical compositions of the present invention.

DETAILED DESCRIPTION OF THE INVENTION

The present invention relates to substituted imidazole 4-carboxamides useful as cholecystokinin receptor modulators, in particular, as selective cholecystokinin-1 receptor agonists. Compounds of the present invention are described by formula I:

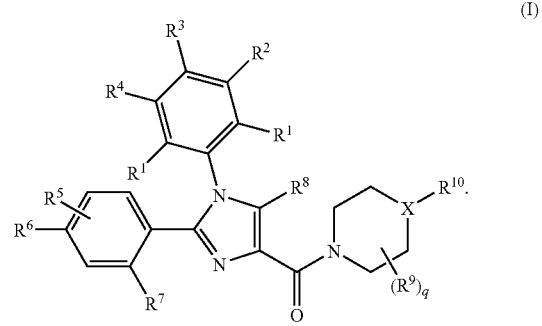

or a pharmaceutically acceptable salt thereof; wherein
X is N or $CR^{16}$;
$R^1$, $R^2$, $R^3$ and $R^4$ are each independently selected from the group consisting of:
(1) hydrogen,
(2) halogen,
(3) —OH,
(4) —$C_{1-6}$alkyl,
(5) —$C_{1-6}$alkoxy,
(6) —$SC_{1-6}$-alkyl,
(7) —$S(O)C_{1-6}$-alkyl,
(8) —$S(O)_2C_{1-6}$-alkyl,
(9) —$NHC_{1-6}$-alkyl, and
(10) —$N(C_{1-6}$-alkyl$)_2$, wherein alkyl and alkoxy are unsubstituted or substituted with one to five substituents selected from halogen, OH, $C_{1-6}$alkyl, and $C_{1-6}$alkoxy, or $R^2$ and $R^3$ or $R^3$ and $R^4$ together with the atoms to which they are attached form a 4-8 membered ring containing 0-2 heteroatoms independently selected from oxygen, sulfur, and N—$R^{15}$, and wherein the 4-8 membered ring is unsubstituted or substituted with a substituent selected from OH, halogen, $C_{1-6}$alkyl, and $C_{1-6}$alkoxy;

$R^5$, $R^6$ and $R^7$ are each independently selected from the group consisting of:
- (1) hydrogen,
- (2) halogen,
- (3) —OH,
- (4) —$C_{1-6}$alkyl, and
- (5) —$C_{1-6}$alkoxy, wherein alkyl and alkoxy are unsubstituted or substituted with one to five substituents independently selected from halogen, —OH, $C_{1-6}$alkyl, and $C_{1-6}$alkoxy, or $R^5$ and $R^6$ or $R^6$ and $R^7$ together with the atoms to which they are attached form a 4-8 membered ring containing 0-2 heteroatoms independently selected from oxygen, sulfur, and N—$R^{15}$, and wherein the 4-8 membered ring is unsubstituted or substituted with a substituent selected from OH, halogen, $C_{1-6}$alkyl, and $C_{1-6}$alkoxy;

$R^8$ is independently selected from the group consisting of:
- (1) hydrogen,
- (2) halogen,
- (3) —$C_{1-6}$alkyl,
- (4) —$C_{1-6}$alkoxy, and
- (5) —$C_{3-6}$cycloalkyl;

$R^9$ and $R^{16}$ are each independently selected from the group consisting of:
- (1) hydrogen,
- (2) —$(CH_2)_n CF_3$,
- (3) —$(CH_2)_n OH$,
- (4) —$(CH_2)_n CN$,
- (5) —$C_{1-6}$alkyl,
- (6) —$C_{1-6}$alkoxy,
- (7) —$(CH_2)_n C_{3-8}$cycloalkyl,
- (8) —$(CH_2)_n NR^{11}R^{12}$,
- (9) -a 5-10 membered aromatic monocyclic or bicyclic heterocyclic ring,
- (10) phenyl,
- (11) —$C_{2-6}$alkene-$CO_2R^{12}$,
- (12) —$(CH_2)_n C(O)R^{12}$,
- (13) —$(CH_2)_n CO_2R^{12}$,
- (14) —$(CH_2)_n OC(O)R^{12}$,
- (15) —$(CH_2)_n O(CH_2)_n CO_2R^{12}$,
- (16) —$(CH_2)_n O(CH_2)_n C(O)NR^{11}R^{12}$,
- (17) —$(CH_2)_n C(O)NR^{11}R^{12}$,
- (18) —$(CH_2)_n C(O)NR^{11}(CH_2)_n CO_2R^{12}$,
- (19) —$(CH_2)_n NR^{11}C(O)R^{12}$,
- (20) —$(CH_2)_n NR^{11}C(O)NR^{11}R^{12}$,
- (21) —$(CH_2)_n NR^{11}(CH_2)_n CO_2R^{12}$,
- (22) —$(CH_2)_n NR^{11}CO_2R^{12}$, and
- (23) —$(CH_2)_n NR^{11}SO_2R^{12}$, wherein alkyl, alkene, alkoxy, cycloalkyl, the heterocyclic ring, phenyl and —$(CH_2)$, are unsubstituted or substituted with one to eight substituents selected from oxo, halogen, —$C_{1-6}$alkyl, —$C_{1-6}$alkoxy, phenyl, —$(CH_2)_n OH$, —$(CH_2)_n CN$, —$(CH_2)_n CF_3$, —$(CH_2)_n SO_3H$, —$(CH_2)_n CO_2H$, —$(CH_2)_n CO_2C_{1-6}$alkyl, and —$(CH_2)_n CO_2C_{2-6}$alkene, and alkyl and alkoxy are unsubstituted or substituted with one to five substituents selected from halogen, —OH, —$SO_3H$, —$CO_2H$, and —$CO_2C_{1-6}$alkyl, provided that at least one of $R^9$ and $R^{16}$ is selected from the group consisting of: —$C_{2-6}$alkene-$CO_2R^{12}$, —$(CH_2)_n C(O)R^{12}$, —$(CH_2)_n CO_2R^{12}$, —$(CH_2)_n OC(O)R^{12}$, —$(CH_2)_n O(CH_2)_n CO_2R^{12}$, —$(CH_2)_n O(CH_2)_n C(O)NR^{11}R^{12}$, —$(CH_2)_n C(O)NR^{11}R^{12}$, —$(CH_2)_n C(O)NR^{11}(CH_2)_n CO_2R^{12}$, —$(CH_2)_n NR^{11}C(O)R^{12}$, —$(CH_2)_n NR^{11}C(O)NR^{11}R^{12}$, —$(CH_2)_n NR^{11}(CH_2)_n CO_2R^{12}$, —$(CH_2)_n NR^{11}CO_2R^{12}$, and —$(CH_2)_n NR^{11}SO_2R^{12}$; each $R^{10}$ is independently selected from the group consisting of:
- (1) aryl, and
- (2) heteroaryl, wherein each aryl and heteroaryl ring is unsubstituted or substituted with one to four $R^{14}$ substituents;

each $R^{11}$, $R^{12}$ and $R^{13}$ is independently selected from the group consisting of:
- (1) hydrogen,
- (2) —$C_{1-8}$alkyl,
- (3) —$(CH_2)_n OH$,
- (4) —$(CH_2)_n C_{3-8}$cycloalkyl,
- (5) —$(CH_2)_n C_{2-8}$heterocycloalkyl,
- (6) —$(CH_2)_n$aryl, and
- (7) —$(CH_2)_n$heteroaryl, wherein alkyl, cycloalkyl, heterocycloalkyl, and —$(CH_2)_n$ are unsubstituted or substituted with one to eight substituents selected from oxo, halogen, —$C_{1-6}$alkyl, —$C_{1-6}$alkoxy, —$(CH_2)_n OH$, —$(CH_2)_n CN$, —$(CH_2)_n CF_3$, —$(CH_2)_n SO_3H$, —$(CH_2)_n CO_2H$, —$(CH_2)_n CO_2C_{1-6}$alkyl, and —$(CH_2)_n CO_2C_{2-6}$alkene, and alkyl and alkoxy are unsubstituted or substituted with one to five substituents selected from halogen, —OH, —$SO_3H$, —$CO_2H$, and —$CO_2C_{1-6}$alkyl, and wherein aryl and heteroaryl are unsubstituted or substituted with one to eight substituents independently selected from halogen, —$C_{1-6}$alkyl, —$C_{1-6}$alkoxy, —$(CH_2)_n OH$, —$(CH_2)_n CN$, —$(CH_2)_n CF_3$, —$(CH_2)_n SO_3H$, —$(CH_2)_n CO_2H$, —$(CH_2)_n CO_2C_{1-6}$alkyl, and —$(CH_2)_n CO_2C_{2-6}$alkene, and alkyl and alkoxy are unsubstituted or substituted with one to five substituents selected from halogen, —OH, —$SO_3H$, —$CO_2H$, and —$CO_2C_{1-6}$alkyl, or $R^{11}$ and $R^{12}$ together with the nitrogen to which they are attached form a 4-8 membered heterocyclic ring containing 0-2 additional heteroatoms selected from oxygen, sulfur, and $NR^{15}$, and wherein the 4-8 membered heterocyclic ring is unsubstituted or substituted with one to five substituents independently selected from oxo, halogen, —$C_{1-6}$alkyl, —$C_{1-6}$alkoxy, —$(CH_2)_n OH$, —$(CH_2)_n CN$, —$(CH_2)_n CF_3$, —$(CH_2)_n SO_3H$, —$(CH_2)_n CO_2H$, —$(CH_2)_n CO_2C_{1-6}$alkyl, and —$(CH_2)_n CO_2C_{2-6}$alkene, and alkyl and alkoxy are unsubstituted or substituted with one to five substituents selected from halogen, —OH, —$SO_3H$, —$CO_2H$, and —$CO_2C_{1-6}$alkyl;

each $R^{14}$ is independently selected from the group consisting of:
- (1) hydrogen,
- (2) —$(CH_2)_n$halogen,
- (3) —$(CH_2)_n CN$,
- (4) —$(CH_2)_n NO_2$,
- (5) —$(CH_2)_n OR^{13}$,
- (6) —$C_{2-6}$alkene-$CO_2R^{12}$,
- (7) —$(CH_2)_n COR^{13}$,
- (8) —$(CH_2)_n CO_2R^{13}$,
- (9) —$(CH_2)_n C(O)NR^{11}R^{12}$,
- (10) —$(CH_2)_n CONR^{11}COR^{13}$,
- (11) —$(CH_2)_n C(O)NR^{11}(CH_2)_n CO_2R^{13}$,
- (12) —$(CH_2)_n C(O)NR^{11}CH(CO_2R^{13})_2$,
- (13) —$(CH_2)_n NR^{11}R^{12}$,
- (14) —$(CH_2)_n NR^{13}C(O)NR^{11}R^{12}$,
- (15) —$(CH_2)_n NR^{13}C(O)R^{13}$,
- (16) —$(CH_2)_n OC(O)NR^{11}R^{12}$,
- (17) —$(CH_2)_n NR^{13}CO_2R^{13}$,
- (18) —$(CH_2)_n NR^{13}SO_2R^{13}$,
- (19) —$(CH_2)_n SO_2NR^{11}R^{13}$,
- (20) —$(CH_2)_n SO_2R^{13}$,
- (21) —$(CH_2)_n SO_3H$,
- (22) —$(CH_2)_n PO_2R^{13}$,
- (23) —$(CH_2)_n PO_3H$,
- (24) —$C_{1-6}$alkyl,

(25) —(CH$_2$)$_n$aryl,
(26) —(CH$_2$)$_n$heteroaryl,
(27) —(CH$_2$)$_n$C$_{2-8}$heterocycloalkyl, and
(28) —(CH$_2$)$_n$C$_{3-8}$cycloalkyl, wherein alkyl, cycloalkyl, heterocycloalkyl, and —(CH$_2$)$_n$ are unsubstituted or substituted with one to five substituents selected from oxo, halogen, —C$_{1-6}$alkyl, —C$_{1-6}$alkoxy, —(CH$_2$)$_n$OH, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene, and alkyl and alkoxy are unsubstituted or substituted with one to five substituents independently selected from halogen, —OH, —SO$_3$H, —CO$_2$H, and —CO$_2$C$_{1-6}$alkyl, and wherein alkene, aryl and heteroaryl are unsubstituted or substituted with one to five substituents independently selected from halogen, —C$_{1-6}$alkyl, —C$_{1-6}$alkoxy, —(CH$_2$)$_n$OH, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene, and alkyl and alkoxy are unsubstituted or substituted with one to five substituents independently selected from halogen, —OH, —SO$_3$H, —CO$_2$H, and —CO$_2$C$_{1-6}$alkyl;

each R$^{15}$ is independently selected from the group consisting of:
(1) hydrogen,
(2) —C$_{1-6}$alkyl,
(3) —C$_{3-8}$cycloalkyl,
(4) —SO$_2$R$^{12}$,
(5) —COR$^{13}$, and
(6) —CO$_2$R$^{12}$, wherein alkyl and cycloalkyl are unsubstituted or substituted with one to six substituents selected from halogen, —OH, and —(CH$_2$)$_n$CO$_2$H;
each n is independently 0, 1, 2, 3, 4, 5, 6, 7 or 8; and
each q is independently 1, 2, 3 or 4.

In a further embodiment of the compounds of the present invention, there are provided compounds of formula II:

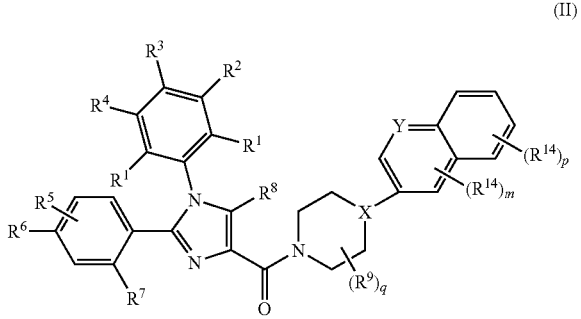

(II)

or a pharmaceutically acceptable salt thereof; wherein
X is N or CR$^{16}$;
Y is N or CR$^{14}$;
R$^1$, R$^2$, R$^3$ and R$^4$ are each independently selected from the group consisting of:
(1) hydrogen,
(2) halogen,
(3) —OH,
(4) —C$_{1-6}$alkyl,
(5) —C$_{1-6}$alkoxy,
(6) —SC$_{1-6}$-alkyl,
(7) —S(O)C$_{1-6}$-alkyl,
(8) —S(O)$_2$C$_{1-6}$-alkyl,
(9) —NHC$_{1-6}$-alkyl, and
(10) —N(C$_{1-6}$-alkyl)$_2$, wherein alkyl and alkoxy are unsubstituted or substituted with one to five substituents selected from halogen, OH, C$_{1-6}$alkyl, and C$_{1-6}$alkoxy, or R$^2$ and R$^3$ or R$^3$ and R$^4$ together with the atoms to which they are attached form a 4-8 membered ring containing 0-2 heteroatoms independently selected from oxygen, sulfur, and N—R$^{15}$, and wherein the 4-8 membered ring is unsubstituted or substituted with a substituent selected from OH, halogen, C$_{1-6}$alkyl, and C$_{1-6}$alkoxy;

R$^5$, R$^6$ and R$^7$ are each independently selected from the group consisting of:
(1) hydrogen,
(2) halogen,
(3) —OH,
(4) —C$_{1-6}$alkyl, and
(5) —C$_{1-6}$alkoxy, wherein alkyl and alkoxy are unsubstituted or substituted with one to five substituents independently selected from halogen, —OH, C$_{1-6}$alkyl, and C$_{1-6}$alkoxy;

R$^8$ is independently selected from the group consisting of:
(1) hydrogen,
(2) halogen,
(3) —C$_{1-6}$alkyl,
(4) —C$_{1-6}$alkoxy, and
(5) —C$_{3-6}$cycloalkyl;

R$^9$ and R$^{16}$ are each independently selected from the group consisting of:
(1) hydrogen,
(2) —(CH$_2$)$_n$CF$_3$,
(3) —(CH$_2$)$_n$OH,
(4) —(CH$_2$)$_n$CN,
(5) —C$_{1-6}$alkyl,
(6) —C$_{1-6}$alkoxy,
(7) —(CH$_2$)$_n$C$_{3-8}$cycloalkyl,
(8) —(CH$_2$)$_n$NR$^{11}$R$^{12}$,
(9) —a 5-10 membered aromatic monocyclic or bicyclic heterocyclic ring,
(10) phenyl,
(11) —C$_{2-6}$alkene-CO$_2$R$^{12}$,
(12) —(CH$_2$)$_n$C(O)R$^{12}$,
(13) —(CH$_2$)$_n$CO$_2$R$^{12}$,
(14) —(CH$_2$)$_n$OC(O)R$^{12}$,
(15) —(CH$_2$)$_n$O(CH$_2$)$_n$CO$_2$R$^{12}$,
(16) —(CH$_2$)$_n$O(CH$_2$)$_n$C(O)NR$^{11}$R$^{12}$,
(17) —(CH$_2$)$_n$C(O)NR$^{11}$R$^{12}$,
(18) —(CH$_2$)$_n$C(O)NR$^{11}$(CH$_2$)$_n$CO$_2$R$^{11}$,
(19) —(CH$_2$)$_n$NR$^{11}$C(O)R$^{12}$,
(20) —(CH$_2$)$_n$NR$^{11}$C(O)NR$^{11}$R$^{12}$,
(21) —(CH$_2$)$_n$NR$^{11}$(CH$_2$)$_n$CO$_2$R$^{12}$,
(22) —(CH$_2$)$_n$NR$^{11}$CO$_2$R$^{12}$, and
(23) —(CH$_2$)$_n$NR$^{11}$SO$_2$R$^{12}$, wherein alkyl, alkene, alkoxy, cycloalkyl, the heterocyclic ring, phenyl and —(CH$_2$)$_n$ are unsubstituted or substituted with one to eight substituents selected from oxo, halogen, —C$_{1-6}$alkyl, —C$_{1-6}$alkoxy, phenyl, —(CH$_2$)$_n$OH, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene, and alkyl and alkoxy are unsubstituted or substituted with one to five substituents selected from halogen, —OH, —SO$_3$H, —CO$_2$H, and —CO$_2$C$_{1-6}$alkyl, provided that at least one of R$^9$ and R$^{16}$ is selected from the group consisting of: —C$_{2-6}$alkene-CO$_2$R$^{12}$, —(CH$_2$)$_n$C(O)R$^{12}$, —(CH$_2$)$_n$CO$_2$R$^{12}$, —(CH$_2$)$_n$OC(O)R$^{12}$, —(CH$_2$)$_n$O(CH$_2$)$_n$CO$_2$R$^{12}$, —(CH$_2$)$_n$O(CH$_2$)$_n$C(O)NR$^{11}$R$^{12}$, —(CH$_2$)$_n$C(O)NR$^{11}$R$^{12}$, —(CH$_2$)$_n$C(O)NR$^{11}$(CH$_2$)$_n$CO$_2$R$^{12}$, —(CH$_2$)$_n$NR$^{11}$C(O)

$R^{12}$, —$(CH_2)_nNR^{11}C(O)NR^{11}R^{12}$, —$(CH_2)_nNR^{11}(CH_2)_n$ $CO_2R^{12}$, —$(CH_2)_nNR^{11}CO_2R^{12}$, and —$(CH_2)_n$ $NR^{11}SO_2R^{12}$;

each $R^{11}$, $R^{12}$ and $R^{13}$ is independently selected from the group consisting of:
(1) hydrogen,
(2) —$C_{1-8}$alkyl,
(3) —$(CH_2)_nOH$,
(4) —$(CH_2)_nC_{3-8}$cycloalkyl,
(5) —$(CH_2)_nC_{2-8}$heterocycloalkyl,
(6) —$(CH_2)_n$aryl, and
(7) —$(CH_2)_n$heteroaryl, wherein alkyl, cycloalkyl, heterocycloalkyl, and —$(CH_2)_n$ are unsubstituted or substituted with one to eight substituents selected from oxo, halogen, —$C_{1-6}$alkyl, —$C_{1-6}$alkoxy, —$(CH_2)_nOH$, —$(CH_2)_nCN$, —$(CH_2)_nCF_3$, —$(CH_2)_nSO_3H$, —$(CH_2)_nCO_2H$, —$(CH_2)_nCO_2C_{1-6}$alkyl, and —$(CH_2)_n$ $CO_2C_{2-6}$alkene, and alkyl and alkoxy are unsubstituted or substituted with one to five substituents selected from halogen, —OH, —$SO_3H$, —$CO_2H$, and —$CO_2C_{1-6}$alkyl, and wherein aryl and heteroaryl are unsubstituted or substituted with one to eight substituents independently selected from halogen, —$C_{1-6}$alkyl, —$C_{1-6}$alkoxy, —$(CH_2)_nOH$, —$(CH_2)_n$ $CN$, —$(CH_2)_nCF_3$, —$(CH_2)_nSO_3H$, —$(CH_2)_nCO_2H$, —$(CH_2)_nCO_2C_{1-6}$alkyl, and —$(CH_2)_nCO_2C_{2-6}$alkene, and alkyl and alkoxy are unsubstituted or substituted with one to five substituents selected from halogen, —OH, —$SO_3H$, —$CO_2H$, and —$CO_2C_{1-6}$alkyl, or $R^{11}$ and $R^{12}$ together with the nitrogen to which they are attached form a 4-8 membered heterocyclic ring containing 0-2 additional heteroatoms selected from oxygen, sulfur, and $NR^{15}$, and wherein the 4-8 membered heterocyclic ring is unsubstituted or substituted with one to five substituents independently selected from oxo, halogen, —$C_{1-6}$alkyl, —$C_{1-6}$alkoxy, —$(CH_2)_nOH$, —$(CH_2)_n$ $CN$, 7$(CH_2)_nCF_3$, —$(CH_2)_nSO_3H$, —$(CH_2)_nCO_2H$, —$(CH_2)_n$ $CO_2C_{1-6}$alkyl, and —$(CH_2)_nCO_2C_{2-6}$alkene, and alkyl and alkoxy are unsubstituted or substituted with one to five substituents selected from halogen, —OH, —$SO_3H$, —$CO_2H$, and —$CO_2C_{1-6}$alkyl;

each $R^{14}$ is independently selected from the group consisting of:
(1) hydrogen,
(2) —$(CH_2)_n$halogen,
(3) —$(CH_2)_nCN$,
(4) —$(CH_2)_nNO_2$,
(5) —$(CH_2)_nOR^{13}$,
(6) —$C_{2-6}$alkene-$CO_2R^{12}$,
(7) —$(CH_2)_nCOR^{13}$,
(8) —$(CH_2)_nCO_2R^{13}$,
(9) —$(CH_2)_nC(O)NR^{11}R^{12}$,
(10) —$(CH_2)_nCONR^{11}COR^{13}$,
(11) —$(CH_2)_nC(O)NR^{11}(CH_2)_nCO_2R^{13}$,
(12) —$(CH_2)_nC(O)NR^{11}CH(CO_2R^{13})_2$,
(13) —$(CH_2)_nNR^{11}R^{12}$,
(14) —$(CH_2)_nNR^{13}C(O)NR^{11}R^{12}$,
(15) —$(CH_2)_nNR^{13}C(O)R^{13}$,
(16) —$(CH_2)_nOC(O)NR^{11}R^{12}$,
(17) —$(CH_2)_nNR^{13}CO_2R^{13}$,
(18) —$(CH_2)_nNR^{13}SO_2R^{13}$,
(19) —$(CH_2)_nSO_2NR^{11}R^{12}$,
(20) —$(CH_2)_nSO_2R^{13}$,
(21) —$(CH_2)_nSO_3H$,
(22) —$(CH_2)_nPO_2R^{13}$,
(23) —$(CH_2)_nPO_3H$,
(24) —$C_{1-6}$alkyl,
(25) —$(CH_2)_n$aryl,
(26) —$(CH_2)_n$heteroaryl,
(27) —$(CH_2)_nC_{2-8}$heterocycloalkyl, and
(28) —$(CH_2)_nC_{3-8}$cycloalkyl, wherein alkyl, cycloalkyl, heterocycloalkyl, and —$(CH_2)_n$ are unsubstituted or substituted with one to five substituents selected from oxo, halogen, —$C_{1-6}$alkyl, —$C_{1-6}$alkoxy, —$(CH_2)_nOH$, —$(CH_2)_nCN$, —$(CH_2)_nCF_3$, —$(CH_2)_nSO_3H$, —$(CH_2)_nCO_2H$, —$(CH_2)_nCO_2C_{1-6}$alkyl, and —$(CH_2)_n$ $CO_2C_{2-6}$alkene, and alkyl and alkoxy are unsubstituted or substituted with one to five substituents independently selected from halogen, —OH, —$SO_3H$, —$CO_2H$, and —$CO_2C_{1-6}$alkyl, and wherein alkene, aryl and heteroaryl are unsubstituted or substituted with one to five substituents independently selected from halogen, —$C_{1-6}$alkyl, —$C_{1-6}$alkoxy, —$(CH_2)_nOH$, —$(CH_2)_nCN$, —$(CH_2)_nCF_3$, —$(CH_2)_nSO_3H$, —$(CH_2)_nCO_2H$, —$(CH_2)_nCO_2C_{1-6}$alkyl, and —$(CH_2)_n$ $CO_2C_{7-6}$alkene, and alkyl and alkoxy are unsubstituted or substituted with one to five substituents independently selected from halogen, —OH, —$SO_3H$, —$CO_2H$, and —$CO_2C_{1-6}$alkyl;

each $R^{15}$ is independently selected from the group consisting of:
(1) hydrogen,
(2) —$C_{1-6}$alkyl,
(3) —$C_{3-8}$cycloalkyl,
(4) —$SO_2R^{12}$,
(5) —$COR^{13}$, and
(6) —$CO_2R^{12}$, wherein alkyl and cycloalkyl are unsubstituted or substituted with one to six substituents selected from halogen, —OH, and —$(CH_2)_nCO_2H$;

each m is independently 0, 1, 2, 3 or 4;
each n is independently 0, 1, 2, 3, 4, 5, 6, 7 or 8;
each p is independently 0, 1, 2, or 3; and
each q is independently 1, 2, 3 or 4.

In a further embodiment of the compounds of the present invention, there are provided compounds of formula III:

(III)

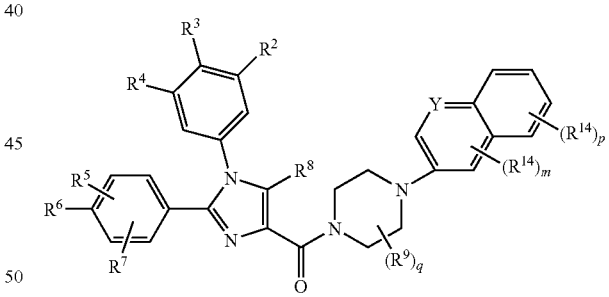

or a pharmaceutically acceptable salt thereof; wherein
Y is N or $CR^{14}$;
$R^2$, $R^3$ and $R^4$ are each independently selected from the group consisting of:
(1) hydrogen,
(2) halogen,
(3) —OH,
(4) —$C_{1-6}$alkyl,
(5) —$C_{1-6}$alkoxy,
(6) —$SC_{1-6}$-alkyl,
(7) —$S(O)C_{1-6}$-alkyl,
(8) —$S(O)_2C_{1-6}$-alkyl,
(9) —$NHC_{1-6}$-alkyl, and
(10) —$N(C_{1-6}$-alkyl$)_2$, wherein alkyl and alkoxy are unsubstituted or substituted with one to five substituents selected from halogen, OH, $C_{1-6}$alkyl, and $C_{1-6}$alkoxy, and wherein $R^2$ and $R^3$ or $R^3$ and $R^4$ together with the atoms to which they are attached may form a 4-8 membered ring containing 0-2 heteroatoms independently selected from oxygen, sulfur, and N—$R^{15}$, and wherein the 4-8 membered ring is unsubstituted or substituted with a substituent selected from OH, halogen, $C_{1-6}$alkyl, and $C_{1-6}$alkoxy;

$R^5$, $R^6$ and $R^7$ are each independently selected from the group consisting of:
(1) hydrogen,
(2) halogen,
(3) —OH,
(4) —$C_{1-6}$alkyl, and
(5) —$C_{1-6}$alkoxy, wherein alkyl and alkoxy are unsubstituted or substituted with one to five substituents independently selected from halogen, —OH, $C_{1-6}$alkyl, and $C_{1-6}$alkoxy;

$R^8$ is independently selected from the group consisting of:
(1) hydrogen,
(2) halogen,
(3) —$C_{1-6}$alkyl,
(4) —$C_{1-6}$alkoxy, and
(5) —$C_{3-6}$cycloalkyl;

$R^9$ is independently selected from the group consisting of:
(1) —$C_{2-6}$alkene-$CO_2R^{12}$,
(2) —$(CH_2)_nC(O)R^{12}$,
(3) —$(CH_2)_nCO_2R^{12}$,
(4) —$(CH_2)_nOC(O)R^{12}$,
(5) —$(CH_2)_nO(CH_2)_nCO_2R^{12}$,
(6) —$(CH_2)_nO(CH_2)_nC(O)NR^{11}R^{12}$,
(7) —$(CH_2)_nC(O)NR^{11}R^{12}$,
(8) —$(CH_2)_nC(O)NR^{11}(CH_2)_nCO_2R^{12}$,
(9) —$(CH_2)_nNR^{11}C(O)R^{12}$,
(10) —$(CH_2)_nNR^{11}C(O)NR^{11}R^{12}$,
(11) —$(CH_2)_nNR^{11}(CH_2)_nCO_2R^{12}$,
(12) —$(CH_2)_nNR^{11}CO_2R^{12}$, and
(13) —$(CH_2)_nNR^{11}SO_2R^{12}$, wherein alkene and —$(CH_2)_n$ are unsubstituted or substituted with one to eight substituents selected from oxo, halogen, —$C_{1-6}$alkyl, —$C_{1-6}$alkoxy, phenyl, —$(CH_2)_nOH$, —$(CH_2)_nCN$, —$(CH_2)_nCF_3$, —$(CH_2)_nSO_3H$, —$(CH_2)_nCO_2H$, —$(CH_2)_nCO_2C_{1-6}$alkyl, and —$(CH_2)_nCO_2C_{2-6}$alkene, and alkyl and alkoxy are unsubstituted or substituted with one to five substituents selected from halogen, —OH, —$SO_3H$, —$CO_2H$, and —$CO_2C_{1-6}$alkyl;

each $R^{11}$, $R^{12}$ and $R^{13}$ is independently selected from the group consisting of:
(1) hydrogen,
(2) —$C_{1-8}$alkyl,
(3) —$(CH_2)_nOH$,
(4) —$(CH_2)_nC_{3-8}$cycloalkyl,
(5) —$(CH_2)_nC_{2-8}$ heterocycloalkyl,
(6) —$(CH_2)_n$aryl, and
(7) —$(CH_2)_n$heteroaryl, wherein alkyl, cycloalkyl, heterocycloalkyl, and —$(CH_2)$, are unsubstituted or substituted with one to eight substituents selected from oxo, halogen, —$C_{1-6}$alkyl, —$C_{1-6}$alkoxy, —$(CH_2)_nOH$, —$(CH_2)_nCN$, —$(CH_2)_nCF_3$, —$(CH_2)_nSO_3H$, —$(CH_2)_nCO_2H$, —$(CH_2)_nCO_2C_{1-6}$alkyl, and —$(CH_2)_nCO_2C_{2-6}$alkene, and alkyl and alkoxy are unsubstituted or substituted with one to five substituents selected from halogen, —OH, —$SO_3H$, —$CO_2H$, and —$CO_2C_{1-6}$alkyl, and wherein aryl and heteroaryl are unsubstituted or substituted with one to eight substituents independently selected from halogen, —$C_{1-6}$alkyl, —$C_{1-6}$alkoxy, —$(CH_2)_nOH$, —$(CH_2)_n$CN, —$(CH_2)_nCF_3$, —$(CH_2)_nSO_3H$, —$(CH_2)_nCO_2H$, —$(CH_2)_nCO_2C_{1-6}$alkyl, and —$(CH_2)_nCO_2C_{2-6}$alkene, and alkyl and alkoxy are unsubstituted or substituted with one to five substituents selected from halogen, —OH, —$SO_3H$, —$CO_2H$, and —$CO_2C_{1-6}$alkyl, or $R^{11}$ and $R^{12}$ together with the nitrogen to which they are attached form a 4-8 membered heterocyclic ring containing 0-2 additional heteroatoms selected from oxygen, sulfur, and $NR^{15}$, and wherein the 4-8 membered heterocyclic ring is unsubstituted or substituted with one to five substituents independently selected from oxo, halogen, —$C_{1-6}$alkyl, —$C_{1-6}$alkoxy, —$(CH_2)_nOH$, —$(CH_2)_n$CN, —$(CH_2)_nCF_3$, —$(CH_2)_nSO_3H$, —$(CH_2)_nCO_2H$, —$(CH_2)_nCO_2C_{1-6}$alkyl, and —$(CH_2)_nCO_2C_{2-6}$alkene, and alkyl and alkoxy are unsubstituted or substituted with one to five substituents selected from halogen, —OH, —$SO_3H$, —$CO_2H$, and —$CO_2C_{1-6}$alkyl;

each $R^{14}$ is independently selected from the group consisting of:
(1) hydrogen,
(2) —$(CH_2)_n$halogen,
(3) —$(CH_2)_nCN$,
(4) —$(CH_2)_nNO_2$,
(5) —$(CH_2)_nOR^{13}$,
(6) —$C_{2-6}$alkene-$CO_2R^{12}$,
(7) —$(CH_2)_nCOR^{13}$,
(8) —$(CH_2)_nCO_2R^{13}$,
(9) —$(CH_2)_nC(O)NR^{11}R^{12}$,
(10) —$(CH_2)_nCONR^{11}COR^{13}$,
(11) —$(CH_2)_nC(O)NR^{11}(CH_2)_nCO_2R^{13}$,
(12) —$(CH_2)_nC(O)NR^{11}CH(CO_2R^{13})_2$,
(13) —$(CH_2)_nNR^{11}R^{12}$,
(14) —$(CH_2)_nNR^{13}C(O)NR^{11}R^{12}$,
(15) —$(CH_2)_nNR^{13}C(O)R^{13}$,
(16) —$(CH_2)_nOC(O)NR^{11}R^{12}$,
(17) —$(CH_2)_nNR^{13}CO_2R^{13}$,
(18) —$(CH_2)_nNR^{13}SO_2R^{13}$,
(19) —$(CH_2)_nSO_2NR^{11}R^{12}$,
(20) —$(CH_2)_nSO_2R^{13}$,
(21) —$(CH_2)_nSO_3H$,
(22) —$(CH_2)_nPO_2R^{13}$,
(23) —$(CH_2)_nPO_3H$,
(24) —$C_{1-6}$alkyl,
(25) —$(CH_2)_n$aryl,
(26) —$(CH_2)_n$heteroaryl,
(27) —$(CH_2)_nC_{2-8}$heterocycloalkyl, and
(28) —$(CH_2)_nC_{3-8}$cycloalkyl, wherein alkyl, cycloalkyl, heterocycloalkyl, and —$(CH_2)$, are unsubstituted or substituted with one to five substituents selected from oxo, halogen, —$C_{1-6}$alkyl, —$C_{1-6}$alkoxy, —$(CH_2)_nOH$, —$(CH_2)_nCN$, —$(CH_2)_nCF_3$, —$(CH_2)_nSO_3H$, —$(CH_2)_nCO_2H$, —$(CH_2)_nCO_2C_{1-6}$alkyl, and —$(CH_2)_nCO_2C_{2-6}$alkene, and alkyl and alkoxy are unsubstituted or substituted with one to five substituents independently selected from halogen, —OH, —$SO_3H$, —$CO_2H$, and —$CO_2C_{1-6}$alkyl, and wherein alkene, aryl and heteroaryl are unsubstituted or substituted with one to five substituents independently selected from halogen, —$C_{1-6}$alkyl, —$C_{1-6}$alkoxy, —$(CH_2)_nOH$, —$(CH_2)_nCN$, —$(CH_2)_nCF_3$, —$(CH_2)_nSO_3H$, —$(CH_2)_nCO_2H$, —$(CH_2)_nCO_2C_{1-6}$alkyl, and —$(CH_2)_nCO_2C_{2-6}$alkene, and alkyl and alkoxy are unsubstituted or substituted with one to five substituents independently selected from halogen, —OH, —$SO_3H$, —$CO_2H$, and —$CO_2C_{1-6}$alkyl;

each $R^{15}$ is independently selected from the group consisting of:
(1) hydrogen,
(2) —$C_{1-6}$alkyl, unsubstituted or substituted with one to six halogens,
(3) —$C_{3-8}$cycloalkyl, unsubstituted or substituted with one to six halogens,
(4) —$SO_2R^{12}$,
(5) —$COR^{12}$, and
(6) —$CO_2R^{12}$;

each m is independently 0, 1, 2, 3 or 4;
each n is independently 0, 1, 2, 3, 4, 5, 6, 7 or 8;
each p is independently 0, 1, 2, or 3; and
each q is independently 1, 2, 3 or 4.

In a further embodiment of the compounds of the present invention, there are provided compounds of formula IV:

(IV)

or a pharmaceutically acceptable salt thereof; wherein
Y is N or $CR^{14}$;
$R^2$, $R^3$ and $R^4$ are each independently selected from the group consisting of:
(1) hydrogen,
(2) halogen,
(3) —OH,
(4) —$C_{1-6}$alkyl,
(5) —$C_{1-6}$alkoxy,
(6) —$SC_{1-6}$-alkyl,
(7) —$S(O)C_{1-6}$-alkyl,
(8) —$S(O)_2C_{1-6}$alkyl,
(9) —$NHC_{1-6}$-alkyl, and
(10) —$N(C_{1-6}$-alkyl$)_2$, wherein alkyl and alkoxy are unsubstituted or substituted with one to five substituents selected from halogen, OH, $C_{1-6}$alkyl, and $C_{1-6}$alkoxy, or $R^2$ and $R^3$ or $R^3$ and $R^4$ together with the atoms to which they are attached may form a 4-8 membered ring containing 0-2 heteroatoms independently selected from oxygen, sulfur, and N—$R^{15}$, and wherein the 4-8 membered ring is unsubstituted or substituted with a substituent selected from OH, halogen, $C_{1-6}$alkyl, and $C_{1-6}$alkoxy;
$R^5$, $R^6$ and $R^7$ are each independently selected from the group consisting of:
(1) hydrogen,
(2) halogen,
(3) —OH,
(4) —$C_{1-6}$alkyl, and
(5) —$C_{1-6}$alkoxy, wherein alkyl and alkoxy are unsubstituted or substituted with one to five substituents independently selected from halogen, —OH, $C_{1-6}$alkyl, and $C_{1-6}$alkoxy;
$R^8$ is independently selected from the group consisting of:
(1) hydrogen,
(2) halogen,
(3) —$C_{1-6}$alkyl,
(4) —$C_{1-6}$alkoxy, and
(5) —$C_{3-6}$cycloalkyl;

$R^9$ and $R^{16}$ are each independently selected from the group consisting of:
(1) hydrogen,
(2) —$(CH_2)_nCF_3$,
(3) —$(CH_2)_nOH$,
(4) —$(CH_2)_nCN$,
(5) —$C_{1-6}$alkyl,
(6) —$C_{1-6}$alkoxy,
(7) —$(CH_2)_nC_{3-8}$cycloalkyl,
(8) —$(CH_2)_nNR^{11}R^{12}$,
(9) -a 5-10 membered aromatic monocyclic or bicyclic heterocyclic ring,
(10) phenyl,
(11) —$C_{2-6}$alkene-$CO_2R^{12}$,
(12) —$(CH_2)_nC(O)R^{12}$,
(13) —$(CH_2)_nCO_2R^{12}$,
(14) —$(CH_2)_nOC(O)R^{12}$,
(15) —$(CH_2)_nO(CH_2)_nCO_2R^{12}$,
(16) —$(CH_2)_nO(CH_2)_nC(O)NR^{11}R^{12}$,
(17) —$(CH_2)_nC(O)NR^{11}R^{12}$,
(18) —$(CH_2)_nC(O)NR^{11}(CH_2)_nCO_2R^{12}$,
(19) —$(CH_2)_nNR^{11}C(O)R^{12}$,
(20) —$(CH_2)_nNR^{11}C(O)NR^{11}R^{12}$,
(21) —$(CH_2)_nNR^{11}(CH_2)_nCO_2R^{12}$,
(22) —$(CH_2)_nNR^{11}CO_2R^{12}$, and
(23) —$(CH_2)_nNR^{11}SO_2R^{12}$, wherein alkyl, alkene, alkoxy, cycloalkyl, the heterocyclic ring, phenyl and —$(CH_2)_n$ are unsubstituted or substituted with one to eight substituents selected from oxo, halogen, —$C_{1-6}$alkyl, —$C_{1-6}$alkoxy, phenyl, —$(CH_2)_nOH$, —$(CH_2)_nCN$, —$(CH_2)_nCF_3$, —$(CH_2)_nSO_3H$, —$(CH_2)_nCO_2H$, —$(CH_2)_nCO_2C_{1-6}$alkyl, and —$(CH_2)_nCO_2C_{2-6}$alkene, and alkyl and alkoxy are unsubstituted or substituted with one to five substituents selected from halogen, —OH, —$SO_3H$, —$CO_2H$, and —$CO_2C_{1-6}$alkyl, provided that at least one of $R^9$ and $R^{16}$ is selected from the group consisting of: —$C_{2-6}$alkene-$CO_2R^{12}$, —$(CH_2)_nC(O)R^{12}$, —$(CH_2)_nCO_2R^{12}$, —$(CH_2)_nOC(O)R^{12}$, —$(CH_2)_nO(CH_2)_nCO_2R^{12}$, —$(CH_2)_nO(CH_2)_nC(O)NR^{11}R^{12}$, —$(CH_2)_nC(O)NR^{11}R^{12}$, —$(CH_2)_nC(O)NR^{11}(CH_2)_nCO_2R^{12}$, —$(CH_2)_nNR^{11}C(O)R^{12}$, —$(CH_2)_nNR^{11}C(O)NR^{11}R^{12}$, —$(CH_2)_nNR^{11}(CH_2)_nCO_2R^{12}$, —$(CH_2)_nNR^{11}CO_2R^{12}$, and —$(CH_2)_nNR^{11}SO_2R^{12}$;

each $R^{11}$, $R^{12}$ and $R^{13}$ is independently selected from the group consisting of:
(1) hydrogen,
(2) —$C_{1-8}$alkyl,
(3) —$(CH_2)_nOH$,
(4) —$(CH_2)_nC_{3-8}$cycloalkyl,
(5) —$(CH_2)_nC_{2-8}$heterocycloalkyl,
(6) —$(CH_2)_n$aryl, and
(7) —$(CH_2)_n$heteroaryl, wherein alkyl, cycloalkyl, heterocycloalkyl, and —$(CH_2)_n$ are unsubstituted or substituted with one to eight substituents selected from oxo, halogen, —$C_{1-6}$alkyl, —$C_{1-6}$alkoxy, —$(CH_2)_nOH$, —$(CH_2)_nCN$, —$(CH_2)_nCF_3$, —$(CH_2)_nSO_3H$, —$(CH_2)_nCO_2H$, —$(CH_2)_nCO_2C_{1-6}$alkyl, and —$(CH_2)_nCO_2C_{2-6}$alkene, and alkyl and alkoxy are unsubstituted or substituted with one to five substituents selected from halogen, —OH, —$SO_3H$, —$CO_2H$, and —$CO_2C_{1-6}$alkyl, and wherein aryl and heteroaryl are unsubstituted or substituted with one to eight substituents independently selected from halogen, —$C_{1-6}$alkyl, —$C_{1-6}$alkoxy, —$(CH_2)_n$OH, —$(CH_2)_n$CN, —$(CH_2)_n$CF$_3$, —$(CH_2)_n$SO$_3$H, —$(CH_2)_n$CO$_2$H, —$(CH_2)_n$CO$_2$C$_{1-6}$alkyl, and —$(CH_2)_n$CO$_2$C$_{2-6}$alkene, and alkyl and alkoxy are unsubstituted or substituted with one to five substituents selected from halogen, —OH, —SO$_3$H, —CO$_2$H, and —CO$_2$C$_{1-6}$alkyl, or $R^{11}$ and $R^{12}$ together with the nitrogen to which they are attached form a 4-8 membered heterocyclic ring containing 0-2 additional heteroatoms selected from oxygen, sulfur, and $NR^{15}$, and wherein the 4-8 membered heterocyclic ring is unsubstituted or substituted with one to five substituents independently selected from oxo, halogen, —$C_{1-6}$alkyl, —$C_{1-6}$alkoxy, —$(CH_2)_n$OH, —$(CH_2)_n$CN, —$(CH_2)_n$CF$_3$, —$(CH_2)_n$SO$_3$H, —$(CH_2)_n$CO$_2$H, —$(CH_2)_n$CO$_2$C$_{1-6}$alkyl, and —$(CH_2)_n$CO$_2$C$_{2-6}$alkene, and alkyl and alkoxy are unsubstituted or substituted with one to five substituents selected from halogen, —OH, —SO$_3$H, —CO$_2$H, and —CO$_2$C$_{1-6}$alkyl;

each $R^{14}$ is independently selected from the group consisting of:
(1) hydrogen,
(2) —$(CH_2)_n$halogen,
(3) —$(CH_2)_n$CN,
(4) —$(CH_2)_n$NO$_2$,
(5) —$(CH_2)_n$OR$^{13}$,
(6) —$C_{2-6}$alkene-CO$_2$R$^{12}$,
(7) —$(CH_2)_n$COR$^{13}$,
(8) —$(CH_2)_n$CO$_2$R$^{13}$,
(9) —$(CH_2)_n$C(O)NR$^{11}$R$^{12}$,
(10) —$(CH_2)_n$CONR$^{11}$R$^{13}$,
(11) —$(CH_2)_n$C(O)NR$^{11}$(CH$_2$)$_n$CO$_2$R$^{13}$,
(12) —$(CH_2)_n$C(O)NR$^{11}$CH(CO$_2$R$^{13}$)$_2$,
(13) —$(CH_2)_n$NR$^{11}$R$^{12}$,
(14) —$(CH_2)_n$NR$^{13}$C(O)NR$^{11}$R$^{12}$,
(15) —$(CH_2)$ NR$^{13}$C(O)R$^{13}$,
(16) —$(CH_2)_n$OC(O)NR$^{11}$R$^{12}$,
(17) —$(CH_2)_n$NR$^{13}$CO$_2$R$^{13}$,
(18) —$(CH_2)_n$NR$^{13}$SO$_2$R$^{13}$,
(19) —$(CH_2)_n$SO$_2$NR$^{11}$R$^{12}$,
(20) —$(CH_2)_n$SO$_2$R$^{13}$,
(21) —$(CH_2)_n$SO$_3$H,
(22) —$(CH_2)_n$PO$_2$R$^{13}$,
(23) —$(CH_2)_n$PO$_3$H,
(24) —$C_{1-6}$alkyl,
(25) —$(CH_2)_n$aryl,
(26) —$(CH_2)_n$heteroaryl,
(27) —$(CH_2)_n$C$_{2-8}$heterocycloalkyl, and
(28) —$(CH_2)_n$C$_{3-8}$cycloalkyl, wherein alkyl, cycloalkyl, heterocycloalkyl, and —$(CH_2)_n$ are unsubstituted or substituted with one to five substituents selected from oxo, halogen, —$C_{1-6}$alkyl, —$C_{1-6}$alkoxy, —$(CH_2)_n$OH, —$(CH_2)_n$CN, —$(CH_2)_n$CF$_3$, —$(CH_2)_n$SO$_3$H, —$(CH_2)_n$CO$_2$H, —$(CH_2)_n$CO$_2$C$_{1-6}$alkyl, and —$(CH_2)_n$CO$_2$C$_{2-6}$alkene, and alkyl and alkoxy are unsubstituted or substituted with one to five substituents independently selected from halogen, —OH, —SO$_3$H, —CO$_2$H, and —CO$_2$C$_{1-6}$alkyl, and wherein alkene, aryl and heteroaryl are unsubstituted or substituted with one to five substituents independently selected from halogen, —$C_{1-6}$alkyl, —$C_{1-6}$alkoxy, —$(CH_2)_n$OH, —$(CH_2)_n$CN, —$(CH_2)_n$CF$_3$, —$(CH_2)_n$SO$_3$H, —$(CH_2)_n$CO$_2$H, —$(CH_2)_n$CO$_2$C$_{1-6}$alkyl, and —$(CH_2)_n$CO$_2$C$_{2-6}$alkene, and alkyl and alkoxy are unsubstituted or substituted with one to five substituents independently selected from halogen, —OH, —SO$_3$H, —CO$_2$H, and —CO$_2$C$_{1-6}$alkyl;

each $R^{15}$ is independently selected from the group consisting of:
(1) hydrogen,
(2) —$C_{1-6}$alkyl, unsubstituted or substituted with one to six halogens,
(3) —$C_{3-8}$cycloalkyl, unsubstituted or substituted with one to six halogens,
(4) —SO$_2$R$^{12}$,
(5) —COR$^{12}$, and
(6) —CO$_2$R$^{12}$;

each m is independently 0, 1, 2, 3 or 4;
each n is independently 0, 1, 2, 3, 4, 5, 6, 7 or 8;
each p is independently 0, 1, 2, or 3; and
each q is independently 1, 2, 3 or 4.

In one class of the embodiments, X is N or CR$^6$. In a subclass of this class, X is N. In another subclass of this class, X is CR$^{16}$. In another subclass of this class, X is CH, provided that R$^9$ is not hydrogen.

In another class of the embodiments, Y is N or CR$^{14}$. In a subclass of this class, Y is N. In another subclass of this class, Y is CR$^{14}$. In another subclass of this class, Y is CH.

In another class of the embodiments, R$^1$, R$^2$, R$^3$ and R$^4$ are each independently selected from the group consisting of: hydrogen, halogen, —OH, —$C_{1-6}$alkyl, and —$C_{1-6}$alkoxy, wherein alkyl and alkoxy are unsubstituted or substituted with one to five substituents selected from halogen, OH, $C_{1-6}$alkyl, and $C_{1-6}$alkoxy, or R$^2$ and R$^3$ or R$^3$ and R$^4$ together with the atoms to which they are attached form a 4-8 membered ring containing 0-2 heteroatoms independently selected from oxygen, sulfur, and N—R$^{15}$, and wherein the 4-8 membered ring is unsubstituted or substituted with a substituent selected from OH, halogen, $C_{1-6}$alkyl, and $C_{1-6}$alkoxy.

In another class of the embodiments, R$^1$, R$^2$, R$^3$ and R$^4$ are each independently selected from the group consisting of: hydrogen, halogen, —OH, —$C_{1-6}$alkyl, —$C_{1-6}$alkoxy, and —SC$_{1-6}$-alkyl, —S(O)C$_{1-6}$alkyl, —S(O)$_2$C$_{1-6}$-alkyl, —NHC$_{1-6}$-alkyl, and —N(C$_{1-6}$-alkyl)$_2$, wherein alkyl and alkoxy are unsubstituted or substituted with one to five substituents selected from halogen, OH, $C_{1-6}$alkyl, and $C_{1-6}$alkoxy, and wherein R$^2$ and R$^3$ or R$^3$ and R$^4$ together with the atoms to which they are attached form a 4-8 membered ring containing 0-2 heteroatoms independently selected from oxygen, sulfur, and N—R$^{15}$, and wherein the 4-8 membered ring is unsubstituted or substituted with a substituent selected from OH, halogen, $C_{1-6}$alkyl, and $C_{1-6}$alkoxy.

In a subclass of this class, R$^1$ is selected from the group consisting of: hydrogen, halogen, —OH, —$C_{1-6}$alkyl, —$C_{1-6}$alkoxy, —SC$_{1-6}$alkyl, and —NHC$_{1-6}$-alkyl, wherein alkyl and alkoxy are unsubstituted or substituted with one to five substituents selected from halogen, —OH, $C_{1-6}$alkyl, and $C_{1-6}$alkoxy. In another subclass of this class, R$^1$ is hydrogen. In another subclass of this class, R$^1$ is selected from —OH, —$C_{1-6}$alkyl optionally substituted with fluoride, —OC$_{1-6}$alkyl optionally substituted with fluoride, hydroxy, and halogen. In another subclass of this class, R$^1$ is selected from hydrogen, halogen, and —OCH$_3$. In another subclass of this class, R$^1$ is selected from —OH, —$C_{1-6}$alkyl, and —$C_{1-6}$alkoxy, wherein alkyl and alkoxy are unsubstituted or substituted with one to five substituents selected from halogen, —OH, $C_{1-6}$alkyl, and $C_{1-6}$alkoxy. In another subclass of this class, R$^1$ is selected from hydrogen, —OCH$_3$, and OCH$_2$CH$_3$. In another subclass of this class, R$^1$ is hydrogen.

In a subclass of this class, R$^2$ is selected from the group consisting of: hydrogen, —OH, halogen, —$C_{1-6}$alkyl optionally substituted with fluoride, and —OC$_{1-6}$alkyl optionally substituted with fluoride. In another subclass of this class, R$^2$ is selected from hydrogen, —OCH$_3$, —OCH$_2$CH$_3$, —OH, —O(CH)(CH$_3$)$_2$, CH$_2$CH$_3$, —OCH$_2$CF$_3$, and fluoride. In another subclass of this subclass, R$^2$ is selected from hydrogen, —OCH$_3$, and —OCH$_2$CH$_3$. In another subclass, R$^2$ is —OCH$_2$CH$_3$. In another subclass, R$^2$ is —OCH$_3$. In another subclass, R$^2$ is hydrogen.

In a subclass of this class, R$^3$ is selected from the group consisting of: hydrogen, —OH, halogen, —C$_{1-6}$alkyl optionally substituted with fluoride, and —OC$_{1-6}$alkyl optionally substituted with fluoride. In another subclass of this class, R$^3$ is selected from hydrogen, —OCH$_3$, OCH$_2$CH$_3$, —OH, —O(CH)(CH$_3$)$_2$, CH$_2$CH$_3$, —OCH$_2$CF$_3$, and fluoride. In another subclass of this subclass, R$^3$ is selected from hydrogen, —OCH$_3$, and OCH$_2$CH$_3$. In another subclass of this subclass, R$^3$ is hydrogen.

In a subclass of this class, R$^4$ is selected from the group consisting of: hydrogen, —OH, halogen, —C$_{1-6}$alkyl optionally substituted with fluoride, and —OC$_{1-6}$alkyl optionally substituted with fluoride. In another subclass of this class, R$^4$ is selected from hydrogen, —OCH$_3$, OCH$_2$CH$_3$, —OH, —O(CH)(CH$_3$)$_2$, CH$_2$CH$_3$, —OCH$_2$CF$_3$, and fluoride. In another subclass of this subclass, R$^4$ is selected from hydrogen, —OCH$_3$, and —OCH$_2$CH$_3$. In another subclass, R$^4$ is hydrogen. In another subclass, R$^4$ is —OCH$_3$. In another subclass, R$^4$ is —OCH$_2$CH$_3$.

In another class of the embodiments, R$^2$ and R$^3$ are each independently selected from the group consisting of: OH, C$_{1-6}$alkyl, and C$_{1-6}$alkoxy, wherein alkyl and alkoxy are unsubstituted or substituted with one to five substituents selected from halogen, —OH, C$_{1-6}$alkyl, and —C$_{1-6}$alkoxy, or R$^2$ and R$^3$ together with the atoms to which they are attached form a 4-8 membered ring containing 0-2 heteroatoms independently selected from oxygen, sulfur, and N—R$^{15}$, wherein the 4-8 membered ring is unsubstituted or substituted with a substituent selected from the group consisting of: OH, halogen, C$_{1-6}$alkyl, and C$_{1-6}$alkoxy. In another class of the embodiments, R$^2$ and R$^3$ are each independently selected from the group consisting of: —C$_{1-6}$alkoxy unsubstituted or substituted with one to five substituents selected from halogen, —OH, C$_{1-6}$alkyl, and —C$_{1-6}$alkoxy, or R$^2$ and R$^3$ together with the atoms to which they are attached form a 4-8 membered ring containing 0-2 heteroatoms independently selected from oxygen, sulfur, and N—R$^{15}$, wherein the ring is unsubstituted or substituted with a substituent selected from the group consisting of: OH, halogen, C$_{1-6}$alkyl, and C$_{1-6}$alkoxy.

In another class of the embodiments, R$^3$ and R$^4$ are each independently selected from the group consisting of: OH, C$_{1-6}$alkyl, and C$_{1-6}$alkoxy, wherein alkyl and alkoxy are unsubstituted or substituted with one to five substituents selected from halogen, OH, C$_{1-6}$alkyl, and —C$_{1-6}$alkoxy, or R$^3$ and R$^4$ together with the atoms to which they are attached form a 4-8 membered ring containing 0-2 heteroatoms independently selected from oxygen, sulfur, and N—R$^{15}$, wherein the 4-8 membered ring is unsubstituted or substituted with a substituent selected from the group consisting of: OH, halogen, C$_{1-6}$alkyl, and C$_{1-6}$alkoxy. In another class of the embodiments, R$^3$ and R$^4$ are each independently selected from the group consisting of: —C$_{1-6}$alkoxy unsubstituted or substituted with one to five substituents selected from halogen, —OH, C$_{1-6}$alkyl, and —C$_{1-6}$alkoxy, or R$^3$ and R$^4$ together with the atoms to which they are attached form a 4-8 membered ring containing 0-2 heteroatoms independently selected from oxygen, sulfur, and N—R$^{15}$, wherein the ring is unsubstituted or substituted with a substituent selected from the group consisting of: OH, halogen, C$_{1-6}$alkyl, and C$_{1-6}$alkoxy.

In another class of the embodiments, R$^1$ and R$^2$ are each independently selected from the group consisting of: hydrogen, halogen, —OH, —C$_{1-6}$alkyl, —C$_{1-6}$alkoxy and —SC$_{1-6}$-alkyl, wherein alkyl and alkoxy are unsubstituted or substituted with one to five substituents selected from halogen, —OH, C$_{1-6}$alkyl, and C$_{1-6}$alkoxy, or R$^3$ and R$^4$ are each independently selected from the group consisting of: —OH, —C$_{1-6}$alkyl, and —C$_{1-6}$alkoxy, and alkyl and alkoxy are unsubstituted or substituted with one to five substituents selected from halogen, —OH, C$_{1-6}$alkyl, and C$_{1-6}$alkoxy, and R$^3$ and R$^4$ together with the atoms to which they are attached form a 4-8 membered ring containing 0-2 heteroatoms independently selected from oxygen, sulfur, and N—R$^{15}$, wherein the 4-8 membered ring is unsubstituted or substituted with a substituent selected from —OH, halogen, C$_{1-6}$alkyl, and C$_{1-6}$alkoxy; and pharmaceutically acceptable salts thereof. In a subclass of this class, R$^1$ and R$^2$ are hydrogen. In another subclass of this class, R$^1$ and R$^2$ are hydrogen, and R$^3$ and R$^4$ form a ring selected from dioxane, piperidine, pyrrolidine, tetrahydropyran, dihydropyran, dihydrofuran, tetrahydrofuran, and dioxolane. In another subclass of this class, R$^1$ and R$^2$ are hydrogen, and R$^3$ and R$^4$ form a 1,4-dioxane ring, a 1,3-dioxolane ring, a tetrahydropyran ring, or a pyrrolidine ring. In another subclass of this class, R$^1$ and R$^2$ are hydrogen, and R$^3$ and R$^3$ form a 1,4-dioxane ring.

In another class of the embodiments, R$^1$ and R$^4$ are each independently selected from the group consisting of: hydrogen, halogen, —OH, —C$_{1-6}$alkyl, —C$_{1-6}$alkoxy, and —SC$_{1-6}$-alkyl, wherein alkyl and alkoxy are unsubstituted or substituted with one to five substituents selected from halogen, —OH, C$_{1-6}$alkyl, and C$_{1-6}$alkoxy, or R$^2$ and R$^3$ are each independently selected from the group consisting of: —OH, —C$_{1-6}$alkyl, and —C$_{1-6}$alkoxy, and alkyl and alkoxy are unsubstituted or substituted with one to five substituents selected from halogen, —OH, C$_{1-6}$alkyl, and C$_{1-6}$alkoxy, and R$^2$ and R$^3$ together with the atoms to which they are attached form a 4-8 membered ring containing 0-2 heteroatoms independently selected from oxygen, sulfur, and N—R$^{15}$, wherein the 4-8 membered ring is unsubstituted or substituted with a substituent selected from —OH, halogen, C$_{1-6}$alkyl, and C$_{1-6}$alkoxy; and pharmaceutically acceptable salts thereof. In a subclass of this class, R$^1$ and R$^4$ are hydrogen. In another subclass of this class, R$^1$ and R$^4$ are hydrogen, and R$^2$ and R$^3$ form a ring selected from dioxane, piperidine, pyrrolidine, tetrahydropyran, dihydropyran, dihydrofuran, tetrahydrofuran, and dioxolane. In another subclass of this class, R$^1$ and R$^4$ are hydrogen, and R$^2$ and R$^3$ form a 1,4-dioxane ring, a 1,3-dioxolane ring, a tetrahydropyran ring, or a pyrrolidine ring. In another subclass of this class, R$^1$ and R$^4$ are hydrogen, and R$^2$ and R$^3$ form a 1,4-dioxane ring.

In another class of the embodiments, R$^5$, R$^6$ and R$^7$ are each independently selected from the group consisting of: hydrogen, halogen, —OH, —C$_{1-6}$alkyl, and —C$_{1-6}$alkoxy, wherein alkyl and alkoxy are unsubstituted or substituted with one to five substituents independently selected from halogen, —OH, C$_{1-6}$alkyl, and C$_{1-6}$alkoxy.

In a subclass of this class, R$^5$ is selected from the group consisting of: hydrogen, —OH, halogen, —C$_{1-6}$alkyl optionally substituted with fluoride, and —OC$_{1-6}$alkyl optionally substituted with fluoride. In another subclass of this class, R$^5$ is selected from hydrogen, —OCH$_3$, —CH$_3$, —CH$_2$CH$_3$, —CF$_3$, fluoride and chloride. In another subclass, R$^5$ is selected from —C$_{1-6}$alkyl optionally substituted with fluoride. In another subclass, R$^5$ is selected from —CH$_3$. In another subclass, R$^5$ is hydrogen.

In another subclass of this class, R$^6$ is selected from the group consisting of: hydrogen, —OH, halogen, —C$_{1-6}$alkyl optionally substituted with fluoride, and —OC$_{1-6}$alkyl optionally substituted with fluoride. In another subclass of this class, R$^6$ is selected from hydrogen, —OCH$_3$, OCH$_2$CH$_3$, —OH, —O(CH)(CH$_3$)$_2$, —CH$_2$CH$_3$, —OCH$_2$CF$_3$, and fluoride. In another subclass of this class, R$^6$ is selected from hydrogen, —CH$_3$ and fluoride. In another subclass, R$^6$ is hydrogen, —CH$_3$ and fluoride. In another subclass, R$^6$ is —CH$_3$. In another subclass, R$^6$ is fluoride. In another subclass, R$^6$ is hydrogen.

In a subclass of this class, R$^7$ is selected from the group consisting of: hydrogen, —OH, halogen, —C$_{1-6}$alkyl optionally substituted with fluoride, and —OC$_{1-6}$alkyl optionally substituted with fluoride. In a subclass of this class, R$^7$ is selected from hydrogen, and fluoride. In another subclass of this class, R$^7$ is hydrogen.

In another class of the embodiments, R$^5$ is selected from the group consisting of: hydrogen, halogen, —OH, —C$_{1-6}$alkyl, and —C$_{1-6}$alkoxy, wherein alkyl and alkoxy are unsubstituted or substituted with one to five substituents selected from halogen, —OH, C$_{1-6}$alkyl, and C$_{1-6}$alkoxy, and R$^6$ and R$^7$ are each independently selected from the group consisting of: —OH, —C$_{1-6}$alkyl, and —C$_{1-6}$alkoxy, wherein alkyl and alkoxy are unsubstituted or substituted with one to five substituents selected from halogen, —OH, C$_{1-6}$alkyl, and C$_{1-6}$alkoxy, or R$^6$ and R$^7$ together with the atoms to which they are attached form a 4-8 membered ring containing 0-2 heteroatoms independently selected from oxygen, sulfur, and N—R$^{15}$, wherein the 4-8 membered ring is unsubstituted or substituted with a substituent selected from —OH, halogen, C$_{1-6}$alkyl, and C$_{1-6}$alkoxy; and pharmaceutically acceptable salts thereof. In a subclass of this class, R$^5$ is hydrogen. In another subclass of this class, R$^5$ is hydrogen, and R$^6$ and R$^7$ form a ring selected from dioxane, piperidine, pyrrolidine, tetrahydropyran, dihydropyran, dihydrofuran, tetrahydrofuran, and dioxolane. In another subclass of this class, R$^5$ is hydrogen, and R$^6$ and R$^7$ form a 1,4-dioxane ring, a 1,3-dioxolane ring, a tetrahydropyran ring, or a pyrrolidine ring. In another subclass of this class, R$^5$ is hydrogen, and R$^6$ and R$^7$ form a 1,4-dioxane ring.

In another class of the embodiments, R$^7$ is selected from the group consisting of: hydrogen, halogen, —OH, —C$_{1-6}$alkyl, and —C$_{1-6}$alkoxy, wherein alkyl and alkoxy are unsubstituted or substituted with one to five substituents selected from halogen, —OH, C$_{1-6}$alkyl, and C$_{1-6}$alkoxy, and R$^5$ and R$^6$ are each independently selected from the group consisting of: —OH, —C$_{1-6}$alkyl, and —C$_{1-6}$alkoxy, wherein alkyl and alkoxy are unsubstituted or substituted with one to five substituents selected from halogen, —OH, C$_{1-6}$alkyl, and C$_{1-6}$alkoxy, or R$^5$ and R$^6$ together with the atoms to which they are attached form a 4-8 membered ring containing 0-2 heteroatoms independently selected from oxygen, sulfur, and N—R$^{15}$, wherein the 4-8 membered ring is unsubstituted or substituted with a substituent selected from —OH, halogen, C$_{1-6}$alkyl, and C$_{1-6}$alkoxy; and pharmaceutically acceptable salts thereof. In a subclass of this class, R$^7$ is hydrogen. In another subclass of this class, R$^7$ is hydrogen, and R$^5$ and R$^6$ form a ring selected from dioxane, piperidine, pyrrolidine, tetrahydropyran, dihydropyran, dihydrofuran, tetrahydrofuran, and dioxolane. In another subclass of this class, R$^7$ is hydrogen, and R$^5$ and R$^6$ form a 1,4-dioxane ring, a 1,3-dioxolane ring, a tetrahydropyran ring, or a pyrrolidine ring. In another subclass of this class, R$^7$ is hydrogen, and R$^5$ and R$^6$ form a 1,4-dioxane ring.

In another class of the embodiments, R$^5$ is independently selected from the group consisting of: hydrogen, halogen, —C$_{1-6}$alkyl, —C$_{1-6}$alkoxy, and —C$_{3-6}$cycloalkyl. In a subclass of this class, R$^8$ is hydrogen. In another subclass of this class, R$^8$ is C$_{1-6}$alkyl. In another subclass of this class, R$^8$ is selected from the group consisting of: halogen and —C$_{1-6}$alkyl. In a subclass of this subclass, R$^8$ is halogen. In another subclass of this subclass, R$^8$ is selected from the group consisting of: bromide, chloride, fluoride and iodide. In another subclass of this subclass, R$^8$ is bromide.

In another class of the embodiments, each R$^9$ is independently selected from the group consisting of: hydrogen, —(CH$_2$)$_n$CF$_3$, —(CH$_2$)$_n$OH, —(CH$_2$)$_n$CN, —C$_{1-6}$alkyl, —C$_{1-6}$alkoxy, —(CH$_2$)$_n$C$_{3-8}$cycloalkyl, —(CH$_2$)$_n$NR$^{11}$R$^{12}$, -a 5-10 membered aromatic monocyclic or bicyclic heterocyclic ring, phenyl, —C$_{2-6}$alkene-CO$_2$R$^{12}$, —(CH$_2$)$_n$C(O)R$^{12}$, —(CH$_2$)$_n$CO$_2$R$^{12}$, —(CH$_2$)$_n$OC(O)R$^{12}$, —(CH$_2$)$_n$O(CH$_2$)$_n$CO$_2$R$^{12}$, —(CH$_2$)$_n$O(CH$_2$)$_n$C(O)NR$^{11}$R$^{12}$, —(CH$_2$)$_n$C(O)NR$^{11}$R$^{12}$, —(CH$_2$)$_n$C(O)NR$^{11}$(CH$_2$)$_n$CO$_2$R$^{12}$, —(CH$_2$)$_n$NR$^{11}$C(O)R$^{12}$, —(CH$_2$)$_n$NR$^{11}$C(O)NR$^{11}$R$^{12}$, —(CH$_2$)$_n$NR$^{11}$(CH$_2$)$_n$CO$_2$R$^{12}$, —(CH$_2$)$_n$NR$^{11}$CO$_2$R$^{12}$, and —(CH$_2$)$_n$NR$^{11}$SO$_2$R$^{12}$, wherein alkyl, alkene, alkoxy, cycloalkyl, the heterocyclic ring, phenyl and —(CH$_2$)$_n$ are unsubstituted or substituted with one to eight substituents selected from oxo, halogen, —C$_{1-6}$alkyl, —C$_{1-6}$alkoxy, phenyl, —(CH$_2$)$_n$OH, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene and alkyl and alkoxy are unsubstituted or substituted with one to five substituents selected from halogen, —OH, —SO$_3$H, —CO$_2$H, and —CO$_2$C$_{1-6}$alkyl, provided that at least one of R$^9$ and R$^{16}$ is selected from the group consisting of: —C$_{2-6}$alkene-CO$_2$R$^{12}$, —(CH$_2$)$_n$C(O)R$^{12}$, —(CH$_2$)$_n$CO$_2$R$^{12}$, —(CH$_2$)$_n$OC(O)R$^{12}$, —(CH$_2$)$_n$O(CH$_2$)$_n$CO$_2$R$^{12}$, —(CH$_2$)$_n$O(CH$_2$)$_n$C(O)NR$^{11}$R$^{12}$, —(CH$_2$)$_n$C(O)NR$^{11}$R$^{12}$, —(CH$_2$)$_n$C(O)NR$^{11}$(CH$_2$)$_n$CO$_2$R$^{12}$, —(CH$_2$)$_n$NR$^{11}$C(O)R$^{12}$, —(CH$_2$)$_n$NR$^{11}$C(O)NR$^{11}$R$^{12}$, —(CH$_2$)$_n$NR$^{11}$CO$_2$R$^{12}$, —(CH$_2$)$_n$NR$^{11}$(CH$_2$)$_n$CO$_2$R$^{12}$, —(CH$_2$)$_n$NR$^{11}$CO$_2$R$^{12}$, and —(CH$_2$)$_n$NR$^{11}$SO$_2$R$^{12}$. In a subclass of this class, each R$^9$ is independently selected from the group consisting of: hydrogen, C$_{2-6}$alkene-CO$_2$R$^{12}$, —(CH$_2$)$_n$CO$_2$R$^{12}$, —(CH$_2$)$_n$C(O)R$^{12}$, —(CH$_2$)$_n$OC(O)R$^{12}$, —(CH$_2$)$_n$O(CH$_2$)$_n$CO$_2$R$^{12}$, —(CH$_2$)$_n$O(CH$_2$)$_n$C(O)NR$^{11}$R$^{12}$, —(CH$_2$)$_n$C(O)NR$^{11}$R$^{12}$, —(CH$_2$)$_n$C(O)NR$^{11}$(CH$_2$)$_n$CO$_2$R$^{12}$, —(CH$_2$)$_n$NR$^{11}$C(O)R$^{12}$, —(CH$_2$)$_n$NR$^{11}$C(O)NR$^{11}$R$^{12}$, —(CH$_2$)$_n$NR$^{11}$(CH$_2$)$_n$CO$_2$R$^{12}$, and —(CH$_2$)$_n$NR$^{11}$SO$_2$R$^{12}$, wherein -alkene and (CH$_2$)$_n$ are unsubstituted or substituted with one to eight substituents selected from oxo, halogen, —C$_{1-6}$alkyl, —C$_{1-6}$alkoxy, phenyl, —(CH$_2$)$_n$OH, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene and alkyl and alkoxy are unsubstituted or substituted with one to five substituents selected from halogen, —OH, —SO$_3$H, —CO$_2$H, and —CO$_2$C$_{1-6}$alkyl, provided that at least one of R$^9$ and R$^{16}$ is selected from the group consisting of: —C$_{2-6}$alkene-CO$_2$R$^{12}$, —(CH$_2$)$_n$C(O)R$^{12}$, —(CH$_2$)$_n$CO$_2$R$^{12}$, —(CH$_2$)$_n$OC(O)R$^{12}$, —(CH$_2$)$_n$O(CH$_2$)$_n$CO$_2$R$^{12}$, —(CH$_2$)$_n$O(CH$_2$)$_n$C(O)NR$^{11}$R$^{12}$, —(CH$_2$)$_n$C(O)NR$^{11}$R$^{12}$, —(CH$_2$)$_n$C(O)NR$^{11}$(CH$_2$)$_n$CO$_2$R$^{12}$, —(CH$_2$)$_n$NR$^{11}$C(O)R$^{12}$, —(CH$_2$)$_n$NR$^{11}$C(O)NR$^{11}$R$^{12}$, —(CH$_2$)$_n$NR$^{11}$CO$_2$R$^{12}$, —(CH$_2$)$_n$NR$^{11}$(CH$_2$)$_n$CO$_2$R$^{12}$, and —(CH$_2$)$_n$NR$^{11}$SO$_2$R$^{12}$. In another subclass of this class, each R$^9$ is independently selected from the group consisting of: hydrogen, —C$_{2-6}$alkene-CO$_2$H, —(CH$_2$)$_n$CO$_2$H, —(CH$_2$)$_n$CO$_2$C$_{1-6}$alkyl, —(CH$_2$)$_n$C(O)C$_{2-8}$heterocycloalkyl, —CH$_2$OC(O)C$_{1-6}$alkyl, —(CH$_2$)$_n$O(CH$_2$)$_n$CO$_2$H, —(CH$_2$)$_n$O(CH$_2$)$_n$CO$_2$C$_{1-6}$alkyl, —(CH$_2$)$_n$O(CH$_2$)$_n$C(O)NHC$_{1-6}$alkyl, —(CH$_2$)$_n$C(O)NHC$_{1-8}$alkyl, —(CH$_2$)$_n$C(O)N(C$_{1-8}$alkyl)$_2$, —(CH$_2$)$_n$C(O)NHheteroaryl, —(CH$_2$)$_n$C(O)NHC$_{3-8}$cycloalkyl, —(CH$_2$)$_n$C(O)NR$^{11}$(CH$_2$)$_n$CO$_2$H, —(CH$_2$)$_n$C(O)NH(CH$_2$)$_n$CO$_2$C$_{1-6}$alkyl, —(CH$_2$)$_n$NHC(O)C$_{1-6}$alkyl, —(CH$_2$)$_n$NHC(O)C$_{3-8}$cycloalkyl, —(CH$_2$)$_n$NHC(O)aryl, —CH$_2$NHC(O)

NHC$_{1-6}$alkyl, —(CH$_2$)$_n$NH(CH$_2$)$_n$CO$_2$H, —(CH$_2$)$_n$NHSO$_2$C$_{1-6}$alkyl, —(CH$_2$)$_n$NHSO$_2$aryl, and —(CH$_2$)$_n$NHSO$_2$C$_{3-8}$cycloalkyl, wherein alkyl, alkene, cycloalkyl, heterocycloalkyl, aryl, heteroaryl, and —(CH$_2$)$_n$ are unsubstituted or substituted with one to eight substituents selected from oxo, halogen, —C$_{1-6}$alkyl, —C$_{1-6}$alkoxy, phenyl, —(CH$_2$)$_n$OH, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene and alkyl and alkoxy are unsubstituted or substituted with one to five substituents selected from halogen, —OH, —SO$_3$H, —CO$_2$H, and —CO$_2$C$_{1-6}$alkyl, provided that at least one of R$^9$ and R$^{16}$ is selected from the group consisting of: —C$_{2-6}$alkene-CO$_2$R$^{12}$, —(CH$_2$)$_n$C(O)R$^{12}$, —(CH$_2$)$_n$CO$_2$R$^{12}$, —(CH$_2$)$_n$OC(O)R$^{12}$, —(CH$_2$)$_n$O(CH$_2$)$_n$CO$_2$R$^{12}$, —(CH$_2$)$_n$O(CH$_2$)$_n$C(O)NR$^{11}$R$^{12}$, —(CH$_2$)$_n$C(O)NR$^{11}$R$^{12}$, —(CH$_2$)$_n$C(O)NR$^{11}$(CH$_2$)$_n$CO$_2$R$^{12}$, —(CH$_2$)$_n$NR$^{11}$C(O)R$^{12}$, —(CH$_2$)$_n$NR$^{11}$C(O)NR$^{11}$R$^{12}$, —(CH$_2$)$_n$NR$^{11}$(CH$_2$)$_n$CO$_2$R$^{12}$, —(CH$_2$)$_n$NR$^{11}$CO$_2$R$^{12}$, and —(CH$_2$)$_n$NR$^{11}$SO$_2$R$^{12}$. In a subclass of this subclass, each R$^9$ is independently selected from the group consisting of: hydrogen, —CO$_2$H, —CH$_2$CO$_2$H, —CO$_2$CH$_3$, —C(O)piperidine, —C(O)pyrrolidine, —C(O)morpholine, —CH$_2$OC(O)CH$_3$, —CH$_2$OCH$_2$CO$_2$H, —CH$_2$OCH$_2$C(O)NHCH$_3$, —CH$_2$OCH$_2$C(O)NHCH(CH$_3$)$_2$, —C(O)NHCH$_3$, —C(O)NH(CH$_2$)$_{1-5}$CH$_3$, —C(O)NHCH(CH$_3$)$_2$, —CH$_2$C(O)NHCH(CH$_3$)$_2$, —C(O)N(CH$_3$)$_2$, —C(O)NHC(CH$_3$)$_3$, —C(O)N(CH$_2$CH$_3$)$_2$, —C(O)NH-tetrazole, —C(O)NHCH$_2$CO$_2$H, —CH═CHCO$_2$H, —C(O)NHCH$_2$CO$_2$CH(CH$_3$)$_2$, —CH$_2$NHC(O)CH$_3$, —CH$_2$NHC(O)cyclopropyl, —CH$_2$NHC(O)phenyl, —CH$_2$NHC(O)cyclopentyl, —CH$_2$NHC(O)NHCH$_3$, —CH$_2$NHC(O)NHCH(CH$_3$)$_2$, —CH$_2$NHCH$_2$CO$_2$H, —CH$_2$NHSO$_2$CH$_3$, and —CH$_2$NHSO$_2$cyclopropyl, wherein the alkyl, alkene, cycloalkyl, heterocycloalkyl, phenyl, and heteroaryl substituents, and —(CH$_2$)$_n$ are unsubstituted or substituted with one to eight substituents selected from oxo, halogen, —C$_{1-6}$alkyl, —C$_{1-6}$alkoxy, phenyl, —(CH$_2$)$_n$OH, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene and alkyl and alkoxy are unsubstituted or substituted with one to five substituents selected from halogen, —OH, —SO$_3$H, —CO$_2$H, and —CO$_2$C$_{1-6}$alkyl, provided that at least one of R$^9$ and R$^{16}$ is selected from the group consisting of: —C$_{2-6}$alkene-CO$_2$R$^{12}$, (CH$_2$)$_n$C(O)R$^{12}$, —(CH$_2$)$_n$CO$_2$R$^{12}$, —(CH$_2$)$_n$OC(O)R$^{12}$, —(CH$_2$)$_n$O(CH$_2$)$_n$CO$_2$R$^{12}$, —(CH$_2$)$_n$O(CH$_2$)$_n$C(O)NR$^{11}$R$^{12}$, —(CH$_2$)$_n$C(O)NR$^{11}$R$^{12}$, —(CH$_2$)$_n$C(O)NR$^{11}$(CH$_2$)$_n$CO$_2$R$^{12}$, —(CH$_2$)$_n$NR$^{11}$C(O)R$^{12}$, —(CH$_2$)$_n$NR$^{11}$C(O)NR$^{11}$R$^{12}$, —(CH$_2$)$_n$NR$^{11}$(CH$_2$)$_n$CO$_2$R$^{12}$, —(CH$_2$)$_n$NR$^{11}$CO$_2$R$^{12}$, and —(CH$_2$)$_n$NR$^{11}$SO$_2$R$^{12}$. In another subclass, one R$^9$ is —CO$_2$H.

In another class of the embodiments, q is 1 and R$^9$ is substituted on the carbon alpha to the piperazine or piperidine amide nitrogen.

In another class of the embodiments, each R$^{10}$ is independently selected from the group consisting of: aryl, and heteroaryl, wherein each aryl and heteroaryl ring is unsubstituted or substituted with one to four R$^{14}$ substituents. In a subclass of this class, R$^{10}$ is aryl. In a subclass of this subclass, R$^{10}$ is selected from phenyl and naphthalene. In another subclass of this subclass, R$^{10}$ is naphthalene. In another subclass of this subclass, R$^{10}$ is phenyl. In another subclass of this class, R$^{10}$ is heteroaryl. In a subclass of this subclass, R$^{10}$ is selected from the group consisting of: isoquinoline, benzimidazole, indole, benzothiazole, benzoxazole, quinoline and 1,2,3,4-tetrahydroquinoline. In another subclass of this subclass, R$^{10}$ is quinoline. In another subclass of this subclass, R$^{10}$ is 1,2,3,4-tetrahydroquinoline.

In a class of the embodiments, each R$^{11}$, R$^{12}$ and R$^{13}$ is independently selected from the group consisting of: hydrogen, —C$_{1-8}$alkyl, —(CH$_2$)$_n$C$_{3-8}$cycloalkyl, —(CH$_2$)$_n$C$_{2-8}$heterocycloalkyl, —(CH$_2$)$_n$aryl, and —(CH$_2$)$_n$heteroaryl, wherein alkyl, cycloalkyl, heterocycloalkyl, and —(CH$_2$)$_n$ are unsubstituted or substituted with one to eight substituents selected from oxo, halogen, —C$_{1-6}$alkyl, —C$_{1-6}$alkoxy, —(CH$_2$)$_n$OH, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene, and alkyl and alkoxy are unsubstituted or substituted with one to five substituents selected from halogen, —OH, —SO$_3$H, —CO$_2$H, and —CO$_2$C$_{1-6}$alkyl, and wherein aryl and heteroaryl are unsubstituted or substituted with one to eight substituents independently selected from halogen, —C$_{1-6}$alkyl, —C$_{1-6}$alkoxy, —(CH$_2$)$_n$OH, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene, and alkyl and alkoxy are unsubstituted or substituted with one to five substituents selected from halogen, —OH, —SO$_3$H, —CO$_2$H, and —CO$_2$C$_{1-6}$alkyl, or R$^{11}$ and R$^{12}$ together with the nitrogen to which they are attached form a 4-8 membered heterocyclic ring containing 0-2 additional heteroatoms selected from oxygen, sulfur, and NR$^{15}$, and wherein the 4-8 membered heterocyclic ring is unsubstituted or substituted with one to five substituents independently selected from oxo, halogen, —C$_{1-6}$alkyl, —C$_{1-6}$alkoxy, —(CH$_2$)$_n$OH, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene, and alkyl and alkoxy are unsubstituted or substituted with one to five substituents selected from halogen, —OH, —SO$_3$H, —CO$_2$H, and —CO$_2$C$_{1-6}$alkyl. In a subclass of this class, R$^{11}$ is hydrogen. In a subclass of this subclass, R$^{11}$ is hydrogen and R$^{12}$ is independently selected from the group consisting of: —C$_{1-6}$alkyl, —(CH$_2$)$_n$C$_{3-8}$cycloalkyl, —(CH$_2$)$_n$C$_{2-8}$heterocycloalkyl, —(CH$_2$)$_n$phenyl, and —(CH$_2$)$_n$heteroaryl, wherein alkyl, cycloalkyl, heterocycloalkyl, heteroaryl and —(CH$_2$)$_n$ are unsubstituted or substituted with one to eight substituents selected from the group consisting of halogen, —(CH$_2$)$_n$OH, oxo, —(CH$_2$)$_n$CN, —(CH$_2$)$_n$CF$_3$, —C$_{1-6}$alkyl, —C$_{1-6}$alkoxy, —(CH$_2$)$_n$CO$_2$H, —(CH$_2$)$_n$CO$_2$C$_{1-6}$alkyl, and —(CH$_2$)$_n$SO$_3$H, and alkyl and alkoxy are unsubstituted or substituted with one to five substituents selected from halogen, —CO$_2$H, and —SO$_3$H. In another subclass of this subclass, R$^{11}$ is hydrogen and R$^{12}$ is independently selected from the group consisting of: hydrogen, —C$_{1-6}$alkyl, cyclopropyl, morpholine, piperidine, pyrrolidine, and tetrazole.

In another subclass of this class, R$^{13}$ is hydrogen or —C$_{1-6}$alkyl.

In another class of the embodiments, each R$^{14}$ is independently selected from the group consisting of: hydrogen, —(CH$_2$)$_n$halogen, —(CH$_2$)$_n$CN, —(CH$_2$)$_n$NO$_2$, —(CH$_2$)$_n$OR$^{13}$, —C$_{2-6}$alkene-CO$_2$R$^{12}$, —(CH$_2$)$_n$COR$^{13}$, —(CH$_2$)$_n$CO$_2$R$^{13}$, —(CH$_2$)$_n$C(O)NR$^{11}$R$^{12}$, —(CH$_2$)$_n$CONR$^{11}$COR$^{13}$, —(CH$_2$)$_n$C(O)NR$^{11}$(CH$_2$)$_n$CO$_2$R$^{13}$, —(CH$_2$)$_n$C(O)NR$^{11}$CH(CO$_2$R$^{13}$)$_2$, —(CH$_2$)$_n$NR$^{11}$R$^{12}$, —(CH$_2$)$_n$NR$^{13}$C(O)NR$^{11}$R$^{12}$, —(CH$_2$)$_n$NR$^{13}$C(O)R$^{13}$, —(CH$_2$)$_n$OC(O)NR$^{11}$R$^{12}$, —(CH$_2$)$_n$NR$^{13}$CO$_2$R$^{13}$, (CH$_2$)$_n$NR$^{13}$SO$_2$R$^{13}$, —(CH$_2$)$_n$SO$_2$NR$^{11}$R$^{12}$, —(CH$_2$)$_n$SO$_2$R$^{13}$—(CH$_2$)$_n$SO$_3$H, —(CH$_2$)$_n$PO$_2$R$^{13}$, —(CH$_2$)$_n$PO$_3$H, —C$_{1-6}$alkyl, —(CH$_2$)$_n$aryl, —(CH$_2$)$_n$heteroaryl, —(CH$_2$)$_n$C$_{2-8}$heterocycloalkyl, and —(CH$_2$)$_n$C$_{3-8}$cycloalkyl, wherein alkyl, cycloalkyl, and heterocycloalkyl are unsubstituted or substituted with one to five substituents selected from oxo, halogen, —C$_{1-6}$alkyl, —C$_{1-6}$alkoxy, —(CH$_2$)$_n$OH, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene, and alkyl and alkoxy are unsubstituted or substituted with one to five substituents independently selected from halogen, —OH, —SO$_3$H, —CO$_2$H, and —CO$_2$C$_{1-6}$alkyl, wherein alkene, aryl and heteroaryl are unsubstituted or substituted with one to five substituents independently selected from halogen, —C$_{1-6}$alkyl, —C$_{1-6}$alkoxy, —(CH$_2$)$_n$OH, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene, and alkyl and alkoxy are unsubstituted or substituted with one to five substituents independently selected from halogen, —OH, —SO$_3$H, —CO$_2$H, and —CO$_2$C$_{1-6}$alkyl, and wherein any (CH$_2$)$_n$ carbon atom is unsubstituted or substituted with one to two substituents selected from oxo, halogen, —(CH$_2$)$_n$OH, —C$_{1-6}$alkyl, —C$_{1-6}$alkoxy, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene, and alkyl and alkoxy are unsubstituted or substituted with one to five substituents independently selected from halogen, —OH, —SO$_3$H, —CO$_2$H, and —CO$_2$C$_{1-6}$alkyl. In a subclass of this class, each R$^{14}$ is independently selected from the group consisting of: hydrogen, —(CH$_2$)$_n$halogen, —C$_{2-6}$alkene-CO$_2$R$^{12}$, —(CH$_2$)$_n$COR$^{13}$, —(CH$_2$)$_n$CO$_2$R$^{13}$, —(CH$_2$)$_n$C(O)NR$^{11}$R$^{12}$, —(CH$_2$)$_n$CONHCOR$^{13}$, —(CH$_2$)$_n$C(O)NR$^{11}$(CH$_2$)$_n$CO$_2$R$^{13}$, —(CH$_2$)$_n$C(O)NR$^{11}$CH(CO$_2$R$^{13}$)$_2$, and —(CH$_2$)$_n$heteroaryl, wherein alkene and heteroaryl are unsubstituted or substituted with one to five substituents independently selected from halogen, —C$_{1-6}$alkyl, —C$_{1-6}$alkoxy, —(CH$_2$)$_n$OH, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene, and alkyl and alkoxy are unsubstituted or substituted with one to five substituents independently selected from halogen, —OH, —SO$_3$H, —CO$_2$H, and —CO$_2$C$_{1-6}$alkyl, and wherein any (CH$_2$)$_n$ carbon atom is unsubstituted or substituted with one to two substituents selected from oxo, halogen, —(CH$_2$)$_n$OH, —C$_{1-6}$alkyl, —C$_{1-6}$alkoxy, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene, and alkyl and alkoxy are unsubstituted or substituted with one to five substituents independently selected from halogen, —OH, —SO$_3$H, —CO$_2$H, and —CO$_2$C$_{1-6}$alkyl. In another subclass of this class, each R$^{14}$ is independently selected from the group consisting of: hydrogen, —(CH$_2$)$_n$halogen, —(CH$_2$)$_n$COR$^{13}$, —(CH$_2$)$_n$CO$_2$R$^{13}$, —(CH$_2$)$_n$C(O)NR$^{11}$R$^{12}$, and —(CH$_2$)$_n$C(O)NR$^{11}$(CH$_2$)$_n$CO$_2$R$^{13}$, wherein any (CH$_2$)$_n$ carbon atom is unsubstituted or substituted with one to two substituents selected from oxo, halogen, —(CH$_2$)$_n$OH, —C$_{1-6}$ alkyl, —C$_{1-6}$alkoxy, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene, and alkyl and alkoxy are unsubstituted or substituted with one to five substituents independently selected from halogen, —OH, —SO$_3$H, —CO$_2$H, and —CO$_2$C$_{1-6}$alkyl. In another subclass of this class, each R$^{14}$ is independently selected from the group consisting of: hydrogen, halogen, —C$_{2-6}$alkene-CO$_2$H, —C(O)C$_{2-8}$heterocycloalkyl, —(CH$_2$)$_n$CO$_2$H, —CO$_2$C$_{1-8}$alkyl, —CO$_2$CH$_2$aryl, —CO$_2$C$_{2-8}$heterocycloalkyl, —CONH$_2$, —CONHC$_{1-6}$alkyl, —CON(C$_{1-6}$alkyl)$_2$, —C(O)NHC$_{3-8}$cycloalkyl, —CONHaryl, —C(O)NH(CH$_2$)$_n$OH, —C(O)NHC$_{2-8}$heterocycloalkyl, —C(O)NHCH$_2$CO$_2$H, —C(O)N(C$_{1-6}$alkyl)CH$_2$CO$_2$H, —CONHCOC$_{1-6}$alkyl, —C(O)NHCH(CO$_2$CH$_2$aryl)$_2$, —C(O)NHCH(CO$_2$C$_{1-6}$alkyl)$_2$, and -heteroaryl, wherein alkyl, cycloalkyl, and heterocycloalkyl are unsubstituted or substituted with one to five substituents selected from oxo, halogen, —C$_{1-6}$alkyl, —C$_{1-6}$alkoxy, —(CH$_2$)$_n$OH, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene, wherein alkene, aryl, and heteroaryl are unsubstituted or substituted with one to five substituents independently selected from halogen, —C$_{1-6}$alkyl, —C$_{1-6}$alkoxy, —(CH$_2$)$_n$OH, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene, and wherein any (CH$_2$)$_n$ carbon atom is unsubstituted or substituted with one to two substituents selected from oxo, halogen, —(CH$_2$)$_n$OH, —C$_{1-6}$alkyl, —C$_{1-6}$alkoxy, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene and alkyl and alkoxy are unsubstituted or substituted with one to five substituents independently selected from halogen, —OH, —SO$_3$H, —CO$_2$H, and —CO$_2$C$_{1-6}$alkyl. In another subclass of this class, each R$^{14}$ is independently selected from the group consisting of: hydrogen, halogen, —C(O)C$_{2-8}$heterocycloalkyl, —(CH$_2$)$_n$CO$_2$H, —CONH$_2$, —CONHC$_{1-6}$alkyl, —CON(C$_{1-6}$alkyl)$_2$, —C(O)NHC$_{3-8}$cycloalkyl, —CONHaryl, —C(O)NHCH$_2$CO$_2$H, and —C(O)N(C$_{1-6}$alkyl)CH$_2$CO$_2$H, wherein alkyl, cycloalkyl, and heterocycloalkyl are unsubstituted or substituted with one to five substituents selected from oxo, halogen, —C$_{1-6}$alkyl, —C$_{1-6}$alkoxy, —(CH$_2$)$_n$OH, (CH$_2$)$_n$CN, (CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene, wherein aryl is unsubstituted or substituted with one to five substituents independently selected from halogen, —C$_{1-6}$alkyl, —C$_{1-6}$alkoxy, —(CH$_2$)$_n$OH, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene, and wherein any (CH$_2$)$_n$ carbon atom is unsubstituted or substituted with one to two substituents selected from oxo, halogen, —(CH$_2$)$_n$OH, —C$_{1-6}$alkyl, —C$_{1-6}$alkoxy, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene and alkyl and alkoxy are unsubstituted or substituted with one to five substituents independently selected from halogen, —OH, —SO$_3$H, —CO$_2$H, and —CO$_2$C$_{1-6}$alkyl.

In another subclass of this class, each R$^{14}$ is independently selected from the group consisting of: hydrogen, Cl, —CH═CHCO$_2$H, —C(O)morpholine, —C(O)pyrrolidine, —C(O)piperidine, —CO$_2$H, —CO$_2$CH$_2$phenyl, —CO$_2$CH$_3$, —(CH$_2$)$_2$CO$_2$H, —CO$_2$tetrahydropyran, —CONHCH$_3$, —CONHCH$_2$CH$_3$, —CON(CH$_2$CH$_3$)$_2$, —CON(CH$_3$)$_2$, —CONHCH(CH$_3$)$_2$, —CONHcyclopropyl, —CONHphenyl, —C(O)NHcyclopentyl, —C(O)NH(CH$_2$)$_{1-6}$OH, —C(O)NHtetrahydropyran, —CONHCH$_2$CO$_2$H, —CON(CH$_3$)CH$_2$CO$_2$H, —CONHCOC(CH$_3$)$_3$, —C(O)NHCH(CO$_2$CH$_2$phenyl)$_2$, —C(O)NHCH(CO$_2$CH$_2$CH$_3$)$_2$, and tetrazole, wherein the alkyl, cycloalkyl, and heterocycloalkyl substituents are unsubstituted or substituted with one to five substituents selected from oxo, halogen, —C$_{1-6}$alkyl, —C$_{1-6}$alkoxy, —(CH$_2$)$_n$OH, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene, wherein the alkene, aryl, and heteroaryl substituents are unsubstituted or substituted with one to five substituents independently selected from halogen, —C$_{1-6}$alkyl, —C$_{1-6}$alkoxy, —(CH$_2$)$_n$OH, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene, and wherein any (CH$_2$)$_n$ carbon atom is unsubstituted or substituted with one to two substituents selected from oxo, halogen, —(CH$_2$)$_n$OH, —C$_{1-6}$alkyl, —C$_{1-6}$alkoxy, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene, and alkyl and alkoxy are unsubstituted or substituted with one to five substituents independently selected from halogen, —OH, —SO$_3$H, —CO$_2$H, and —CO$_2$C$_{1-6}$alkyl. In another subclass of this class, each R$^{14}$ is independently selected from the group consisting of: hydrogen, —C(O)morpholine, —C(O)pyrrolidine, —CO$_2$H, —CONHCH$_3$, —CONHCH$_2$CH$_3$, —CON(CH$_2$CH$_3$)$_2$, —CON(CH$_3$)$_2$, —CONHCH(CH$_3$)$_2$, —CONHcyclopropyl, —CONHphenyl, —CONHCH$_2$CO$_2$H, and —CON(CH$_3$)CH$_2$CO$_2$H, wherein the alkyl, cycloalkyl, and heterocycloalkyl substituents are unsubstituted or substituted with one to five substituents selected from oxo, halogen, —C$_{1-6}$alkyl, —C$_{1-6}$alkoxy, —(CH$_2$)$_n$OH, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene, wherein the phenyl substituent is unsubstituted or substituted with one to five substituents independently selected from halogen, —C$_{1-6}$ alkyl, —C$_{1-6}$alkoxy, —(CH$_2$)$_n$OH, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene, and wherein any (CH$_2$)$_n$ carbon atom is unsubstituted or substituted with one to two substituents selected from oxo, halogen, —(CH$_2$)$_n$OH, —C$_{1-6}$alkyl, —C$_{1-6}$alkoxy, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene, and alkyl and alkoxy substituents are unsubstituted or substituted with one to five substituents independently selected from halogen, —OH, —SO$_3$H, —CO$_2$H, and —CO$_2$C$_{1-6}$alkyl. In another subclass, one R$^{14}$ is —CO$_2$H. In another subclass, R$^{14}$ is hydrogen.

In another class of the embodiments, each R$^{15}$ is independently selected from the group consisting of: hydrogen, —C$_{1-6}$ alkyl, —C$_{3-8}$cycloalkyl, —SO$_2$R$^{12}$, —COR$^{13}$, and —CO$_2$R$^{12}$, wherein alkyl and cycloalkyl are unsubstituted or substituted with one to six substituents selected from halogen, —OH, and —(CH$_2$)$_n$CO$_2$H.

In another class of the embodiments, each R$^{16}$ is independently selected from the group consisting of: hydrogen, —(CH$_2$)$_n$CF$_3$, —(CH$_2$)$_n$OH, —(CH$_2$)$_n$CN, —C$_{1-6}$alkyl, —C$_{1-6}$alkoxy, —(CH$_2$)$_n$C$_{3-8}$cycloalkyl, —(CH$_2$)$_n$NR$^{11}$R$^{12}$, -a 5-10 membered aromatic monocyclic or bicyclic heterocyclic ring, phenyl, —C$_{2-6}$alkene-CO$_2$R$^{12}$, —(CH$_2$)$_n$C(O)R$^{12}$, —(CH$_2$)$_n$CO$_2$R$^{12}$, —(CH$_2$)$_n$OC(O)R$^{12}$, —(CH$_2$)$_n$O(CH$_2$)$_n$CO$_2$R$^{12}$, —(CH$_2$)$_n$O(CH$_2$)$_n$C(O)NR$^{11}$R$^{12}$, —(CH$_2$)$_n$C(O)NR$^{11}$R$^{12}$, —(CH$_2$)$_n$C(O)NR$^{11}$(CH$_2$)$_n$CO$_2$R$^{12}$, —(CH$_2$)$_n$NR$^{11}$C(O)R$^{12}$, —(CH$_2$)$_n$NR$^{11}$C(O)NR$^{11}$R$^{12}$, —(CH$_2$)$_n$NR$^{11}$(CH$_2$)$_n$CO$_2$R$^{12}$—(CH$_2$)$_n$NR$^{11}$CO$_2$R$^{12}$, and —(CH$_2$)$_n$NR$^{11}$SO$_2$R$^{12}$, wherein alkyl, alkene, alkoxy, —(CH$_2$)$_n$cycloalkyl, the heterocyclic ring and phenyl are unsubstituted or substituted with one or more substituents selected from C$_{1-6}$alkyl, —OH, C$_{1-6}$alkoxy, —CF$_3$, —CN, phenyl and halogen, provided that at least one of R$^9$ and R$^{16}$ is selected from the group consisting of: —C$_{2-6}$alkene-CO$_2$R$^{12}$, —(CH$_2$)$_n$C(O)R$^{12}$, —(CH$_2$)$_n$CO$_2$R$^{12}$, —(CH$_2$)$_n$OC(O)R$^{12}$, —(CH$_2$)$_n$O(CH$_2$)$_n$CO$_2$R$^{12}$, (CH$_2$)$_n$O(CH$_2$)$_n$C(O)NR$^{11}$R$^{12}$, —(CH$_2$)$_n$C(O)NR$^{11}$R$^{12}$, —(CH$_2$)$_n$C(O)NR$^{11}$(CH$_2$)$_n$CO$_2$R$^{12}$, —(CH$_2$)$_n$NR$^{11}$C(O)R$^{12}$, —(CH$_2$)$_n$NR$^{11}$C(O)NR$^{11}$R$^{12}$, —(CH$_2$)$_n$NR$^{11}$(CH$_2$)$_n$CO$_2$R$^{12}$, —(CH$_2$)$_n$NR$^{11}$CO$_2$R$^{12}$, and —(CH$_2$)$_n$NR$^{11}$SO$_2$R$^{12}$. In a subclass of this class, each R$^{16}$ is independently selected from the group consisting of: hydrogen, —C$_{2-6}$alkene-CO$_2$R$^{12}$, —(CH$_2$)$_n$CO$_2$R$^{12}$, —(CH$_2$)$_n$O(CH$_2$)$_n$CO$_2$R$^{12}$, —(CH$_2$)$_n$C(O)NR$^{11}$R$^{12}$, —(CH$_2$)$_n$C(O)NR$^{11}$(CH$_2$)$_n$CO$_2$R$^{12}$, —(CH$_2$)$_n$NR$^{11}$C(O)R$^{12}$, and —(CH$_2$)$_n$NR$^{11}$C(O)NR$^{11}$R$^{12}$, wherein alkene and —(CH$_2$)$_n$ are unsubstituted or substituted with one or more substituents selected from C$_{1-6}$alkyl, —OH, C$_{1-6}$alkoxy, —CF$_3$, —CN, phenyl and halogen, provided that at least one of R$^9$ and R$^{16}$ is selected from the group consisting of: —C$_{2-6}$alkene-CO$_2$R$^{12}$, —(CH$_2$)$_n$C(O)R$^{12}$, —(CH$_2$)$_n$CO$_2$R$^{12}$, —(CH$_2$)$_n$OC(O)R$^{12}$—(CH$_2$)$_n$O(CH$_2$)$_n$CO$_2$R$^{12}$, —(CH$_2$)$_n$O(CH$_2$)$_n$C(O)NR$^{11}$R$^{12}$, —(CH$_2$)$_n$C(O)NR$^{11}$R$^{12}$, —(CH$_2$)$_n$C(O)NR$^{11}$(CH$_2$)$_n$CO$_2$R$^{12}$, —(CH$_2$)$_n$NR$^{11}$C(O)R$^{12}$, —(CH$_2$)$_n$NR$^{11}$C(O)NR$^{11}$R$^{12}$, —(CH$_2$)$_n$NR$^{11}$(CH$_2$)$_n$CO$_2$R$^{12}$, —(CH$_2$)$_n$NR$^{11}$CO$_2$R$^{12}$, and —(CH$_2$)$_n$NR$^{11}$SO$_2$R$^{12}$. In another subclass of this class, each R$^{16}$ is independently selected from the group consisting of: hydrogen, —CH=CHCO$_2$H, —CO$_2$H, —CH$_2$CO$_2$H, —(CH$_2$)$_2$CO$_2$H, —OCH$_2$CO$_2$H, —OCH$_2$CO$_2$C(CH$_3$)$_3$, —CONHCH$_3$, —CON(CH$_3$)$_2$, —CONH$_2$, —CONHCH$_3$, —CONHCH$_3$, —CONHCH$_3$, —CONHCH$_2$CO$_2$H, —NHCOCH$_3$, and —NHCONHCH$_3$, wherein alkyl and —(CH$_2$)$_n$, are unsubstituted or substituted with one or more substituents selected from C$_{1-6}$alkyl, —OH, C$_{1-6}$alkoxy, —CF$_3$, —CN, phenyl and halogen, provided that at least one of R$^9$ and R$^{16}$ is selected from the group consisting of: —C$_{2-6}$alkene-CO$_2$R$^{12}$, —(CH$_2$)$_n$C(O)R$^{12}$, —(CH$_2$)$_n$CO$_2$R$^{12}$, —(CH$_2$)$_n$OC(O)R$^{12}$, —(CH$_2$)$_n$O(CH$_2$)$_n$CO$_2$R$^{12}$, (CH$_2$)$_n$O(CH$_2$)$_n$C(O)NR$^{11}$R$^{12}$, —(CH$_2$)$_n$C(O)NR$^{11}$R$^{12}$, —(CH$_2$)$_n$C(O)NR$^{11}$(CH$_2$)$_n$CO$_2$R$^{12}$, (CH$_2$)$_n$NR$^{11}$C(O)R$^{11}$, —(CH$_2$)$_n$NR$^{11}$C(O)NR$^{11}$R$^{12}$, —(CH$_2$)$_n$NR$^{11}$(CH$_2$)$_n$CO$_2$R$^{12}$, —(CH$_2$)$_n$NR$^{11}$CO$_2$R$^{12}$, and —(CH$_2$)$_n$NR$^{11}$SO$_2$R$^{12}$. In yet another subclass of this class, each R$^{16}$ is independently selected from the group consisting of: hydrogen, —CO$_2$H, —CH$_2$CO$_2$H, —(CH$_2$)$_2$CO$_2$H, —OCH$_2$CO$_2$H, —CONHCH$_3$, —CON(CH$_3$)$_2$, —CONH$_2$, —CONHCH$_2$CO$_2$H, —NHCOCH$_3$, and —NHCONHCH$_3$, wherein alkyl and —(CH$_2$)$_n$, are unsubstituted or substituted with one or more substituents selected from C$_{1-6}$alkyl, —OH, C$_{1-6}$alkoxy, —CF$_3$, —CN, phenyl and halogen, provided that at least one of R$^9$ and R$^{16}$ is selected from the group consisting of: —C$_{2-6}$alkene-CO$_2$R$^{12}$, —(CH$_2$)$_n$C(O)R$^{12}$, —(CH$_2$)$_n$CO$_2$R$^{12}$, —(CH$_2$)$_n$OC(O)R$^{12}$, —(CH$_2$)$_n$O(CH$_2$)$_n$CO$_2$R$^{12}$, (CH$_2$)$_n$O(CH$_2$)$_n$C(O)NR$^{11}$R$^{12}$, —(CH$_2$)$_n$C(O)NR$^{11}$R$^{12}$, —(CH$_2$)$_n$C(O)NR$^{11}$(CH$_2$)$_n$CO$_2$R$^{12}$, —(CH$_2$)$_n$NR$^{11}$C(O)R$^{12}$, —(CH$_2$)$_n$NR$^{11}$C(O)NR$^{11}$R$^{12}$, —(CH$_2$)$_n$NR$^{11}$(CH$_2$)$_n$CO$_2$R$^{12}$, —(CH$_2$)$_n$NR$^{11}$CO$_2$R$^{12}$, and —(CH$_2$)$_n$NR$^{11}$SO$_2$R$^{12}$.

In another class of the embodiments, each m is independently 0, 1, 2, 3 or 4. In a subclass of this class, m is 0, 1, or 2. In another subclass of this class, m is 0. In another subclass of this class, m is 1. In another subclass of this class, m is 2.

In another class of the embodiments, each n is independently 0, 1, 2, 3, 4, 5, 6, 7 or 8. In a subclass of this class, each n is independently 0, 1, 2, 3, 4, 5 or 6. In a subclass of this class, n is 0, 1, or 2. In another subclass of this class, n is 0. In another subclass of this class, n is 1. In another subclass of this class, n is 2. In another subclass of this class, n is 3. In another subclass of this class, n is 4. In another subclass of this class, n is 5. In another subclass of this class, n is 6.

In another class of the embodiments, each p is independently 0, 1, 2, or 3. In a subclass of this class, p is 1, 2 or 3. In another subclass of this class, p is 1. In another subclass of this class, p is 2. In another subclass of this class, p is 3.

In another class of the embodiments, each q is independently 0, 1, 2, 3 or 4. In a subclass of this class, q is 1, 2 or 3. In another subclass of this class, q is 1. In another subclass of this class, q is 2. In another subclass of this class, q is 3.

In another class of the embodiments, R$^{10}$ is naphthalene, m is 1 and p is 0.

In another class of the embodiments, R$^{10}$ is quinoline, m is 0 and p is 0.

In another embodiment, the compound of formula I is selected from:

(1) 3-{(3S)-4-{[1-(3-ethoxyphenyl)-2-(4-methylphenyl)-1H-imidazol-4-yl]carbonyl}-3-[(isopropylamino)carbonyl]-1-piperazinyl}-1-naphthoic acid, (2) 3-{(3S)-4-{[1-(3-ethoxyphenyl)-2-(2-fluoro-4-methylphenyl)-1H-imidazol-4-yl]carbonyl}-3-[(isopropylamino)carbonyl]-1-piperazinyl}-1-naphthoic acid, (3) 3-((3R)-3-[(acetylamino)methyl]-4-{[1-(3-ethoxyphenyl)-2-(2-fluoro-4-methylphenyl)-1H-imidazol-4-yl]carbonyl}-1-piperazinyl)-1-naphthoic acid, (4) 3-[1-{[1-(2,3-Dihydro-1,4-benzodioxin-6-yl)-2-(4-methylphenyl)-1H-imidazol-4-yl]carbonyl}-4-(2-naphthyl)piperidin-4-yl]propanoic acid,
(5) (2S)-1-{[1-(3-ethoxyphenyl)-2-(4-methylphenyl)-1H-imidazol-4-yl]carbonyl}-4-(3-quinolinyl)-2-piperazinecarboxylic acid, trifluoroacetic acid salt,
(6) (2S)-1-{[1-(3-ethoxyphenyl)-2-(4-methylphenyl)-1H-imidazol-4-yl]carbonyl}-4-(3-quinolinyl)-2-ethyl-4-(3-quinolinyl)-2-piperazinecarboxamide, trifluoroacetic acid salt,
(7) N-{[(2S)-1-{[1-(3-ethoxyphenyl)-2-(4-methylphenyl)-1H-imidazol-4-yl]car bonyl}-4-(3-quinolinyl)-2-piperazinyl]carbonyl}glycine,
(8) {[(2S)-1-{[1-(3-Ethoxyphenyl)-2-(4-methylphenyl)-1H-imidazol-4-yl]carbonyl}-4-(3-quinolinyl)-2-piperazinyl]methoxy}acetic acid,
(9) 3-((3R)-4-{[1-(3-Ethoxyphenyl)-2-(4-methylphenyl)-1H-imidazol-4-yl]carbonyl}-3-{[2-(methylamino)-2-oxoethoxy]methyl}-1-piperazinyl)-1-naphthoic acid,
(10) 3-((3R)-4-([1-(3-Ethoxyphenyl)-2-(4-methylphenyl)-1H-imidazol-4-yl]carbonyl}-3-{[2-(methylamino)-2-oxoethoxy]methyl}-1-piperazinyl)-1-naphthoic acid, and
(11) (2S)-4-(4-Carboxy-2-naphthyl)-1-{[1-(2,3-dihydro-1,4-benzodioxin-6-yl)-2-(4-fluorophenyl)-1H-imidazol-4-yl]carbonyl}-2-piperazinecarboxylic acid;

or a pharmaceutically acceptable salt thereof.

In a class of this embodiment, the compound of formula I is selected from:
(1) 3-{(3S)-4-{[1-(3-ethoxyphenyl)-2-(4-methylphenyl)-1H-imidazol-4-yl]carbonyl}-3-[(isopropylamino)carbonyl]-1-piperazinyl}-1-naphthoic acid,
(2) 3-{(3S)-4-{[1-(3-ethoxyphenyl)-2-(2-fluoro-4-methylphenyl)-1H-imidazol-4-yl]carbonyl}-3-[(isopropylamino)carbonyl]-1-piperazinyl}-1-naphthoic acid,
(3) 3-((3R)-3-[(acetylamino)methyl]-4-{[1-(3-ethoxyphenyl)-2-(2-fluoro-4-methylphenyl)-1H-imidazol-4-yl]carbonyl}-1-piperazinyl)-1-naphthoic acid, and
(4) 3-[1-{[1-(2,3-Dihydro-1,4-benzodioxin-6-yl)-2-(4-methylphenyl)-1H-imidazol-4-yl]carbonyl}-4-(2-naphthyl)piperidin-4-yl]propanoic acid;

or a pharmaceutically acceptable salt thereof.

In a subclass of this class, the compound of formula I is selected from: 3-{(3S)-4-{[1-(3-ethoxyphenyl)-2-(4-methylphenyl)-1H-imidazol-4-yl]carbonyl}-3-[(isopropylamino)carbonyl]-1-piperazinyl}-1-naphthoic acid; or a pharmaceutically acceptable salt thereof. In another subclass of this class, the compound of formula I is selected from 3-{(3S)-4-{[1-(3-ethoxyphenyl)-2-(2-fluoro-4-methylphenyl)-1H-imidazol-4-yl]carbonyl}-3-[(isopropylamino)carbonyl]-1-piperazinyl}-1-naphthoic acid; or a pharmaceutically acceptable salt thereof. In another subclass of this class, the compound of formula I is selected from 3-((3R)-3-[(acetylamino)methyl]-4-{[1-(3-ethoxyphenyl)-2-(2-fluoro-4-methylphenyl)-1H-imidazol-4-yl]carbonyl}-1-piperazinyl)-1-naphthoic acid; or a pharmaceutically acceptable salt thereof. In another subclass of this class, the compound of formula I is selected from 3-[1-{[1-(2,3-Dihydro-1,4-benzodioxin-6-yl)-2-(4-methylphenyl)-1H-imidazol-4-yl]carbonyl}-4-(2-naphthyl)piperidin-4-yl]propanoic acid; or a pharmaceutically acceptable salt thereof.

In another class of the embodiments, the pharmaceutically acceptable salt is a trifluoroacetic acid salt. In another class of the embodiments, the pharmaceutically acceptable salt is a hydrochloric acid salt.

The compounds of formula I, II III and IV are effective as cholecystokinin receptor ligands and are particularly effective as selective ligands of the cholecystokinin-1 receptor. They are therefore useful for the treatment and/or prevention of disorders responsive to the modulation of the cholecystokinin-1 receptor, such as obesity, diabetes, and obesity-related disorders. More particularly, the compounds of formula I, II, III and IV are selective cholecystokinin-1 receptor (CCK-1R) agonists useful for the treatment of disorders responsive to the activation of the cholecystokinin-1 receptor, such as obesity, diabetes, as well as the treatment of gallstones.

One aspect of the present invention provides a method for the treatment or prevention of disorders, diseases or conditions responsive to the modulation of the cholecystokinin-1 receptor in a subject in need thereof which comprises administering to the subject a therapeutically or prophylactically effective amount of a compound of formula I, II, III or IV, or a pharmaceutically acceptable salt thereof.

Another aspect of the present invention provides a method for the treatment or prevention of obesity, diabetes, or an obesity related disorder in a subject in need thereof which comprises administering to said subject a therapeutically or prophylactically effective amount of a cholecystokinin-1 receptor agonist of the present invention. Another aspect of the present invention provides a method for the treatment or prevention of obesity in a subject in need thereof which comprises administering to the subject a therapeutically or prophylactically effective amount of a compound of formula I, II, III or IV, or a pharmaceutically acceptable salt thereof. Another aspect of the present invention provides a method for reducing food intake in a subject in need thereof which comprises administering to the subject a therapeutically or prophylactically effective amount of a compound of formula I, II, III or IV, or a pharmaceutically acceptable salt thereof. Another aspect of the present invention provides a method for increasing satiety in a subject in need thereof which comprises administering to the subject a therapeutically or prophylactically effective amount of a compound of formula I, II, III or IV, or a pharmaceutically acceptable salt thereof. Another aspect of the present invention provides a method for reducing appetite in a subject in need thereof which comprises administering to the subject a therapeutically or prophylactically effective amount of a compound of formula I, II, III or IV, or a pharmaceutically acceptable salt thereof. Another aspect of the present invention provides a method for reducing gastric emptying in a subject in need thereof which comprises administering to the subject a therapeutically or prophylactically effective amount of a compound of formula I, II, III or IV, or a pharmaceutically acceptable salt thereof. Another aspect of the present invention provides a method for the treatment or prevention of bulimia nervosa in a subject in need thereof which comprises administering to the subject a therapeutically or prophylactically effective amount of a compound of formula I, II, III or IV, or a pharmaceutically acceptable salt thereof.

Another aspect of the present invention provides a method for the treatment or prevention of diabetes mellitus in a subject in need thereof comprising administering to the subject a therapeutically or prophylactically effective amount of a compound of formula I, II, III or IV, or a pharmaceutically acceptable salt thereof. Another aspect of the present invention provides a method for the treatment or prevention of dyslipidemia in a subject in need thereof which comprises administering to the subject a therapeutically or prophylactically effective amount of a compound of formula I, II, III or IV, or a pharmaceutically acceptable salt thereof. Another aspect of the present invention provides a method for the treatment or prevention of tardive dyskinesia in a subject in need thereof which comprises administering to said subject a therapeutically or prophylactically effective amount of a cholecystokinin-1 receptor agonist of the present invention.

Another aspect of the present invention provides a method for the treatment or prevention of an obesity-related disorder selected from the group consisting of overeating, binge eating, hypertension, elevated plasma insulin concentrations, insulin resistance, hyperlipidemia, endometrial cancer, breast cancer, prostate cancer, colon cancer, kidney cancer, osteoarthritis, obstructive sleep apnea, heart disease, abnormal heart rhythms and arrythmias, myocardial infarction, congestive heart failure, coronary heart disease, sudden death, stroke, polycystic ovary disease, craniopharyngioma, metabolic syndrome, insulin resistance syndrome, sexual and reproductive dysfunction, infertility, hypogonadism, hirsutism, obesity-related gastro-esophageal reflux, Pickwickian syndrome, inflammation, systemic inflammation of the vasculature, arteriosclerosis, hypercholesterolemia, hyperuricaemia, lower back pain, gallbladder disease, gout, constipation, irritable bowel syndrome, inflammatory bowel syndrome, cardiac hypertrophy, left ventricular hypertrophy, in a subject in need thereof which comprises administering to the subject a therapeutically or prophylactically effective amount of a compound of formula I, II, III or IV, or a pharmaceutically acceptable salt thereof.

Another aspect of the present invention provides a method for the treatment or prevention of cognitive and memory deficiency, including the treatment of Alzheimer's disease, in a subject in need thereof which comprises administering to the subject a therapeutically or prophylactically effective amount of a compound of formula I, II, III or IV, or a pharmaceutically acceptable salt thereof.

Another aspect of the present invention provides a method for the treatment or prevention of pain in a subject in need thereof which comprises administering to the subject a therapeutically or prophylactically effective amount of a compound of formula I, II, III or IV, or a pharmaceutically acceptable salt thereof.

Another aspect of the present invention provides a method for the treatment or prevention of cholelithiasis (gallstones) in a subject in need thereof which comprises administering to the subject a therapeutically or prophylactically effective amount of a compound of formula I, II, III or IV, or a pharmaceutically acceptable salt thereof.

Another aspect of the present invention provides a method for the treatment or prevention of cholecystitis (inflammation of the gallbladder) in a subject in need thereof which comprises administering to the subject a therapeutically or prophylactically effective amount of a compound of formula I, II, III or IV, or a pharmaceutically acceptable salt thereof.

The present invention also relates to methods for treating or preventing obesity by administering a cholecystokinin-1 receptor agonist of the present invention in combination with a therapeutically or prophylactically effective amount of another agent known to be useful to treat or prevent the condition. The present invention also relates to methods for treating or preventing diabetes by administering the cholecystokinin-1 receptor agonist of the present invention in combination with a therapeutically or prophylactically effective amount of another agent known to be useful to treat or prevent the condition. The present invention also relates to methods for treating or preventing obesity related disorders by administering the cholecystokinin-1 receptor agonist of the present invention in combination with a therapeutically or prophylactically effective amount of another agent known to be useful to treat or prevent the condition.

Another aspect of the present invention provides a pharmaceutical composition comprising a compound of formula I, II, III or IV and a pharmaceutically acceptable carrier.

Yet another aspect of the present invention relates to the use of a compound of formula I, II, III, or IV for the manufacture of a medicament useful for the treatment or prevention, or suppression of a disease mediated by the cholecystokinin-1 receptor in a subject in need thereof. Yet another aspect of the present invention relates to the use of a cholecystokinin-1 agonist of the present invention for the manufacture of a medicament useful for the treatment or prevention, or suppression of a disease mediated by the cholecystokinin-1 receptor, wherein the disease is selected from the group consisting of obesity, diabetes and an obesity-related disorder in a subject in need thereof.

Yet another aspect of the present invention relates to the use of a cholecystokinin-1 agonist of the present invention for the manufacture of a medicament useful for the treatment or prevention of gallstones in a subject in need thereof. Yet another aspect of the present invention relates to the use of a cholecystokinin-1 agonist of the present invention for the manufacture of a medicament useful for the treatment or prevention of dyslipidemia in a subject in need thereof. Yet another aspect of the present invention relates to the use of a cholecystokinin-1 agonist of the present invention for the manufacture of a medicament useful for the treatment or prevention of bulimia nervosa in a subject in need thereof. Yet another aspect of the present invention relates to the use of a cholecystokinin-1 agonist of the present invention for the manufacture of a medicament useful for the treatment or prevention of constipation in a subject in need thereof. Yet another aspect of the present invention relates to the use of a cholecystokinin-1 agonist of the present invention for the manufacture of a medicament useful for the treatment or prevention of irritable bowel syndrome in a subject in need thereof.

Yet another aspect of the present invention relates to the use of a therapeutically effective amount of a cholecystokinin-1 receptor agonist of formula I, II, III or IV, or a pharmaceutically acceptable salt thereof, and a therapeutically effective amount of an agent selected from the group consisting of an insulin sensitizer, an insulin mimetic, a sulfonylurea, an α-glucosidase inhibitor, a dipeptidyl peptidase 4 (DPP-4 or DP-IV) inhibitor, a glucagons like peptide 1 (GLP-1) agonist, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanin-concentrating hormone receptor antagonist, a melanocortin 4 receptor agonist, a bombesin receptor subtype 3 agonist, a ghrelin receptor antagonist, PYY, $PYY_{3-36}$, and a NK-1 antagonist, or a pharmaceutically acceptable salt thereof, for the manufacture of a medicament useful for the treatment, control, or prevention of obesity, diabetes or an obesity-related disorder in a subject in need of such treatment. Yet another aspect of the present invention relates to the use of a therapeutically effective amount of a cholecystokinin-1 receptor agonist of formula I, II, III, or IV, and pharmaceutically acceptable salts and esters thereof, and a therapeutically effective amount of an agent selected from the group consisting of an insulin sensitizer, an insulin mimetic, a sulfonylurea, an α-glucosidase inhibitor, a dipeptydyl peptidase 4 inhibitor, a glucagon-like peptide 1 agonist, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanin-concentrating hormone receptor antagonist, a melanocortin 4 receptor agonist, a bombesin receptor subtype 3 agonist, a ghrelin receptor antagonist, PYY, $PYY_{3-36}$, and a NK-1 antagonist, or a pharmaceutically acceptable salt thereof, for the manufacture of a medicament for treatment or prevention of obesity, diabetes or an obesity-related disorder which comprises an effective amount of a cholecystokinin-1 receptor agonist of formula I, II, III, or IV and an effective amount of the agent, together or separately. Yet another aspect of the present invention relates to a product containing a therapeutically effective amount of a cholecystokinin-1 receptor agonist of formula I, II, III, or IV, or a pharmaceutically acceptable salt thereof; and a therapeutically effective amount of an agent selected from the group consisting of an insulin sensitizer, an insulin mimetic, a sulfonylurea, an α-glucosidase inhibitor, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanocortin 4 receptor agonist, a melanin-concentrating hormone receptor antagonist, a bombesin receptor subtype 3 agonist, a ghrelin receptor antagonist, PYY, $PYY_{3-36}$, and a NK-1 antagonist, or a pharmaceutically acceptable salt thereof, as a combined preparation for simultaneous, separate or sequential use in obesity, diabetes, or an obesity-related disorder.

The compounds of formula I, II, III and IV can be provided in kit. Such a kit typically contains an active compound in dosage forms for administration. A dosage form contains a sufficient amount of active compound such that a beneficial effect can be obtained when administered to a patient during regular intervals, such as 1, 2, 3, 4, 5 or 6 times a day, during the course of 1 or more days. Preferably, a kit contains instructions indicating the use of the dosage form for weight reduction (e.g., to treat obesity) and the amount of dosage form to be taken over a specified time period.

Throughout the instant application, the following terms have the indicated meanings:

The term "alkyl", as well as other groups and substituents having the prefix "alk", such as alkoxy, alkanoyl, means carbon chains of the designated length which may be in a straight or branched configuration, or combinations thereof. Examples of alkyl groups and substituents include methyl, ethyl, n-propyl, isopropyl, n-butyl, 1-methylpropyl, 2-methylpropyl, tert-butyl, n-pentyl, 1-methylbutyl, 2-methylbutyl, 3-methylbutyl, 1,2-dimethylpropyl, 1,1-dimethylpropyl, 2,2-dimethylpropyl, n-hexyl, 1-methylpentyl, 2-methylpentyl, 3-methylpentyl, 4-methylpentyl, 1-ethylbutyl, 2-ethylbutyl, 3-ethylbutyl, 1,1-dimethyl butyl, 1,2-dimethylbutyl, 1,3-dimethylbutyl, 2,2-dimethylbutyl, 2,3-dimethylbutyl, 3,3-dimethyl butyl, n-heptyl, 1-methylhexyl, 2-methylhexyl, 3-methylhexyl, 4-methylhexyl, 5-methylhexyl, 1-ethylpentyl, 2-ethylpentyl, 3-ethylpentyl, 4-ethylpentyl, 1-propylbutyl, 2-propylbutyl, 3-propylbutyl, 1,1-dimethylpentyl, 1,2-dimethylpentyl, 1,3-dimethylpentyl, 1,4-dimethylpentyl, 2,2-dimethylpentyl, 2,3-dimethylpentyl. 2,4-dimethylpentyl, 3,3-dimethylpentyl, 3,4-dimethylpentyl, 4,4-dimethylpentyl, 1-methyl-1-ethylbutyl, 1-methyl-2-ethylbutyl, 2-methyl-2-ethylbutyl, 1-ethyl-2-methylbutyl, 1-ethyl-3-methylbutyl, 1,1-diethylpropyl, n-octyl, n-nonyl, and the like.

The term "alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

The term "alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

The term "alkoxy" means alkyl chains of the designated length which contain at least one ether linkage and which may be linear or branched or combinations thereof. Examples of alkoxy include methoxy, ethoxy, 1-propoxy, 2-propoxy, 1-butoxy, 2-butoxy, methylmethoxy, methylethoxy, methyl-1-propoxy, methyl-2-propoxy, ethyl-2-methoxy, ethyl-1-methoxy and the like.

The term "halogen" includes fluorine, chlorine, bromine and iodine.

The term "$C_{1-4}$ alkyliminoyl" means $C_{1-3}C(=NH)—$.

The term "aryl" includes mono- or bicyclic aromatic rings containing only carbon atoms in which at least one ring is aromatic. Examples of aryl include phenyl and naphthalene.

The term "heteroaryl" includes mono- and bicyclic aromatic rings containing from 1 to 4 heteroatoms selected from nitrogen, oxygen and sulfur, in which at least one ring is aromatic. Examples thereof include, but are not limited to, pyridinyl, furyl, thienyl, pyrrolyl, oxazolyl, thiazolyl, triazolyl, triazinyl, tetrazolyl, thiadiazolyl, imidazolyl, isoxazolyl, isothiazolyl, oxadiazolyl, pyrazolyl, pyrimidinyl, pyrazinyl, pyridazinyl, quinolyl, isoquinolyl, benzimidazolyl, benzofuryl, benzothienyl, indolyl, benzthiazolyl, benzoxazolyl, and the like. In one embodiment of the present invention, heteroaryl is selected from the group consisting of pyridinyl, furyl, thienyl, pyrrolyl, oxazolyl, thiazolyl, triazolyl, triazinyl, tetrazolyl, thiadiazolyl, imidazolyl, pyrazolyl, isoxazolyl, isothiazolyl, oxathiazolyl, pyrimidinyl, pyrazinyl, pyridazinyl, quinolyl, isoquinolyl, benzimidazolyl, benzofuryl, benzothienyl, indolyl, benzthiazolyl, and benzoxazolyl. Bicyclic heteroaromatic rings include, but are not limited to, benzothiadiazole, indole, benzothiophene, benzofuran, benzimidazole, benzisoxazole, benzothiazole, quinoline, quinazoline, benzotriazole, benzoxazole, isoquinoline, purine, furopyridine, thienopyridine, benzisodiazole, triazolopyrimidine, 1,2,3,4-tetrahydroquinoline, and 5,6,7,8-tetrahydroquinoline.

The term "cycloalkyl" includes mono- or bicyclic non-aromatic rings containing only carbon atoms. Examples of cycloalkyl include, but are not limited to, cyclopropyl, cyclobutyl, cyclopentyl, cyclohexyl, cycloheptyl.

The term "heterocycloalkyl" is intended to include non-aromatic heterocycles containing one to four heteroatoms selected from nitrogen, oxygen and sulfur. Examples of heterocycloalkyls include, but are not limited to, azetidine, piperidine, morpholine, thiamorpholine, pyrrolidine, imidazolidine, tetrahydrofuran, tetrahydropyran, piperazine, 1-thia-4-aza-cyclohexane.

The term "5-10 membered aromatic monocyclic or bicyclic heterocyclic ring" means a 5- or 6-membered aromatic heterocyclic ring or a fused bicyclic aromatic ring, which may contain one to three of the heteroatoms selected from nitrogen, oxygen and sulfur, and includes, but is not limited to, furyl, thienyl, isoxazolyl, pyridyl, pyrimidinyl, benzofuranyl, and benzothienyl.

Certain of the above defined terms may occur more than once in the above formula and upon such occurrence each term shall be defined independently of the other; thus for example, $NR^4R^4$ may represent $NH_2$, $NHCH_3$, $N(CH_3)CH_2CH_3$, and the like.

The term "subject" means a mammal. One embodiment of the term "mammal" is a "human," said human being either male or female. The instant compounds are also useful for treating or preventing obesity and obesity related disorders in cats and dogs. As such, the term "mammal" includes companion animals such as cats and dogs. The term "mammal in need thereof" refers to a mammal who is in need of treatment or prophylaxis as determined by a researcher, veterinarian, medical doctor or other clinician.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

By a cholecystokinin receptor "agonist" is meant an endogenous or drug substance or compound that can interact with a cholecystokinin receptor and initiate a pharmacological or biochemical response characteristic of cholecystokinin receptor activation. The "agonistic" properties of the compounds of the present invention were measured in the functional assay described below.

By "binding affinity" is meant the ability of a compound/drug to bind to its biological target, in the present instance, the ability of a compound of formula I, II, III, or IV, to bind to a cholecystokinin receptor. Binding affinities for the compounds of the present invention were measured in the binding assay described below and are expressed as $IC_{50}$'s.

"Efficacy" describes the relative intensity of response which different agonists produce even when they occupy the same number of receptors and with the same affinity. Efficacy is the property that describes the magnitude of response. Properties of compounds can be categorized into two groups, those which cause them to associate with the receptors (binding affinity) and those that produce a stimulus (efficacy). The term "efficacy" is used to characterize the level of maximal responses induced by agonists. Not all agonists of a receptor are capable of inducing identical levels of maximal responses. Maximal response depends on the efficiency of receptor coupling, that is, from the cascade of events, which, from the binding of the drug to the receptor, leads to the desired biological effect.

The functional activities expressed as $EC_{50}$'s and the "agonist efficacy" for the compounds of the present invention at a particular concentration were measured in the functional assay described below. The CCK1R active and selective agonists of the present invention have an $IC_{50} \leqq 500$ nM, preferably $IC_{50} < 100$ nM, more preferably $IC_{50} < 10$ nM, and most preferably $IC_{50} < 1$ nM, while having at least 100-fold and preferably greater than 1000-fold selectivity over CCK2R. The CCK1R active and selective agonists of the present invention have an $EC_{50} \leqq 500$ nM, preferably $EC_{50} < 100$ nM, more preferably $EC_{50} < 10$ nM, and most preferably $EC_{50} < 1$ nM, while having at least 100-fold, and preferably greater than 1000-fold selectivity over CCK2R.

Compounds of formula I, II, III, and IV may contain one or more asymmetric or chiral centers and can exist in different stereoisomeric forms, such as racemates and racemic mixtures, single enantiomers, enantiomeric mixtures, individual diastereomers and diastereomeric mixtures. All stereoisomeric forms of the intermediates and compounds of the present invention as well as mixtures thereof, including racemic and diastereomeric mixtures, which possess properties useful in the treatment of the conditions discussed herein or are intermediates useful in the preparation of compounds having such properties, form a part of the present invention.

Generally, one of the enantiomers will be more active biologically than the other enantiomer. Racemic mixtures can subsequently be separated into each enantiomer using standard conditions, such as resolution or chiral chromatography. Diastereomeric mixtures may be separated into their individual diastereoisomers on the basis of their physical chemical differences by methods well known to those skilled in the art, such as by chiral chromatography using an optically active stationary phase and/or fractional crystallization from a suitable solvent. Absolute stereochemistry may be determined by X-ray crystallography of crystalline products or crystalline intermediates which are derivatized, if necessary, with a reagent containing an asymmetric center of known absolute configuration. Enantiomers may be separated by use of a chiral HPLC column and by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Alternatively, any stereoisomer of a compound of the general formula I, II, III, and IV may be obtained by stereospecific synthesis using optically pure starting materials or reagents of known absolute configuration.

The present invention includes all such isomeric forms of the compounds of formula I, II, III, and IV, including the E and Z geometric isomers of double bonds and mixtures thereof. A number of the compounds of the present invention and intermediates therefor exhibit tautomerism and therefore may exist in different tautomeric forms under certain conditions. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is an imidazole moiety where the hydrogen may migrate between the ring nitrogens. Valence tautomers include interconversions by reorganization of some of the bonding electrons. All such tautomeric forms (e.g., all keto-enol and imine-enamine forms) are within the scope of the invention. The depiction of any particular tautomeric form in any of the structural formulas herein is not intended to be limiting with respect to that form, but is meant to be representative of the entire tautomeric set.

The present invention also encompasses isotopically labeled compounds which are identical to the compounds of Formula (I) or intermediates thereof but for the fact that one or more atoms are replaced by an atom having an atomic mass or mass number different from the atomic mass or mass number usually found in nature. Examples of isotopes that can be incorporated into the intermediates or compounds of the invention include isotopes of hydrogen, carbon, nitrogen, oxygen, phosphorus, sulfur, fluorine, iodine, and chlorine, such as 2H, 3H, 11C, 13C, 14C, 13N, 15N, 15O, 17O, 18O, 31P, 32P, 35S, 18F, 123I, 125I and 36Cl, respectively. Compounds of the present invention, prodrugs thereof and pharmaceutically acceptable salts, hydrates and solvates of said compounds and of said prodrugs which contain the aforementioned isotopes and/or other isotopes of other atoms are within the scope of the present invention. Certain isotopically labeled compounds of the present invention (e.g., those labeled with 3H and 14C) are useful in compound and/or substrate tissue distribution assays. Tritiated (i.e., 3H) and carbon-14 (i.e., 14C) isotopes are particularly preferred for their ease of preparation and detectability. Further, substitution with heavier isotopes such as deuterium (i.e., 2H) may afford certain therapeutic advantages resulting from greater metabolic stability (e.g., increased in vivo half-life or reduced dosage requirements) and hence may be preferred in some circumstances. Positron emitting isotopes such as 15O, 13N, 11C, and 18F are useful for positron emission tomography (PET) studies to examine substrate receptor occupancy. Isotopically labeled compounds of the present invention can generally be prepared by following procedures analogous to those disclosed in the Schemes and/or in the Examples herein by substituting an isotopically labeled reagent for a non-isotopically labeled reagent.

The compounds of the present invention and intermediates may exist in unsolvated as well as solvated forms with solvents such as water, ethanol, isopropanol and the like, and both solvated and unsolvated forms are included within the scope of the invention. Solvates for use in the methods aspect of the invention should be with pharmaceutically acceptable solvents. It will be understood that the compounds of the present invention include hydrates, solvates, polymorphs, crystalline, hydrated crystalline and amorphous forms of the compounds of the present invention, and pharmaceutically acceptable salts thereof.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, TEA, trimethylamine, tripropylamine, tromethamine, and the like.

When the compound of formula I, II, III and IV is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Particularly preferred are citric, fumaric, hydrobromic, hydrochloric, maleic, phosphoric, sulfuric, and tartaric acids. It will be understood that, as used herein, references to the compounds of formula I, II, III, and IV are meant to also include the pharmaceutically acceptable salts, such as the hydrochloride salts.

Compounds of formula I, II, III, and IV are cholecystokinin receptor ligands and as such are useful in the treatment, control or prevention of diseases, disorders or conditions responsive to the modulation of one or more of the cholecystokinin receptors. In particular, the compounds of formula I, II, III, and IV act as cholecystokinin-1 receptor agonists useful in the treatment, control or prevention of diseases, disorders or conditions responsive to the activation of the cholecystokinin-1 receptor. Such diseases, disorders or conditions include, but are not limited to, obesity (by reducing food intake, reducing appetite, increasing metabolic rate, increasing satiety, reducing carbohydrate craving, reducing gastric emptying), diabetes mellitus (by enhancing glucose tolerance, decreasing insulin resistance), bulimia nervosa and related eating disorders, dyslipidemia, hypertension, hyperlipidemia, osteoarthritis, cancer, gall stones, cholelithiasis, cholecystitis, gall bladder disease, sleep apnea, depression, anxiety, compulsion, neuroses, irritable bowel syndrome, inflammatory bowel syndrome, constipation, pain, neuroprotective and cognitive and memory enhancement including the treatment of Alzheimer's disease. Such diseases, conditions and disorders also include non-obese overweight conditions and normal weight conditions where weight control or management is desired in order to prevent an obese or overweight condition from developing, or to maintain a healthy weight.

The compounds and compositions of the present invention are useful for the treatment or prevention of disorders associated with excessive food intake, such as obesity and obesity-related disorders. The obesity herein may be due to any cause, whether genetic or environmental.

The obesity-related disorders herein are associated with, caused by, or result from obesity. Examples of obesity-related disorders include overeating, binge eating, bulimia nervosa, hypertension, type 2 diabetes, elevated plasma insulin concentrations, hyperinsulinemia, insulin resistance, glucose intolerance, dyslipidemia, hyperlipidemia, endometrial cancer, breast cancer, prostate cancer, kidney cancer, colon cancer, osteoarthritis, obstructive sleep apnea, cholelithiasis, cholecystitis, gallstones, gout, gallbladder disease, abnormal heart rhythms and arrythmias, myocardial infarction, congestive heart failure, coronary heart disease, angina pectoris, sudden death, stroke, metabolic syndrome, psychological disorders (depression, eating disorders, distorted body-weight, and low self esteem), and other pathological conditions showing reduced metabolic activity or a decrease in resting energy expenditure as a percentage of total fat-free mass, e.g, children with acute lymphoblastic leukemia. Further examples of obesity-related disorders are sexual and reproductive dysfunction, such as polycystic ovary disease, infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. Additionally, the present compounds are useful in the treatment of any condition in which it is desirable to lose weight or to reduce food intake. Additionally, the present compounds are useful in the treatment of any condition in which it is desirable to enhance cognition and memory, such as Alzheimer's Disease. The compositions of the present invention are also useful for reducing the risk of secondary outcomes of obesity, such as reducing the risk of left ventricular hypertrophy. Therefore, the present invention provides methods of treatment or prevention of such diseases, conditions and/or disorders modulated by CCK-1 receptor agonists in an animal which comprises administering to the animal in need of such treatment a compound of formula I, II, III, or IV, in particular a therapeutically or prophylactically effective amount thereof.

Some agonists encompassed by formula I, II, III, and IV show highly selective affinity for the cholecystokinin-1 receptor (CCK-1R) relative to cholecystokinin-2 receptor CCK-2R (also known as the CCK-B receptor), which makes them especially useful in the prevention and treatment of obesity, diabetes, and obesity related disorders. Compounds of the present invention are at least 500 fold more selective for the CCK-1 receptor than for the CCK-2 receptor.

The term "metabolic syndrome", also known as syndrome X, is defined in the Third Report of the National Cholesterol Education Program Expert Panel on Detection, Evaluation and Treatment of High Blood Cholesterol in Adults (ATP-III). E. S. Ford et al., JAMA, vol. 287 (3), Jan. 16, 2002, pp 356-359. Briefly, a person is defined as having metabolic syndrome if the person has three or more of the following symptoms: abdominal obesity, hypertriglyceridemia, low HDL cholesterol, high blood pressure, and high fasting plasma glucose. The criteria for these are defined in ATP-III.

The term "diabetes," as used herein, includes both insulin-dependent diabetes mellitus (i.e., IDDM, also known as type I diabetes) and non-insulin-dependent diabetes mellitus (i.e., NIDDM, also known as Type II diabetes). Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The compositions of the present invention are useful for treating both Type I and Type II diabetes. The compositions are especially effective for treating Type II diabetes. The compounds or combinations of the present invention are also useful for treating and/or preventing gestational diabetes mellitus.

Treatment of diabetes mellitus refers to the administration of a compound or combination of the present invention to treat diabetes. One outcome of treatment may be decreasing the glucose level in a subject with elevated glucose levels. Another outcome of treatment may be improving glycemic control. Another outcome of treatment may be decreasing insulin levels in a subject with elevated insulin levels. Another outcome of treatment may be decreasing plasma triglycerides in a subject with elevated plasma triglycerides. Another outcome of treatment may be lowering LDL cholesterol in a subject with high LDL cholesterol levels. Another outcome of treatment may be increasing HDL cholesterol in a subject with low HDL cholesterol levels. Another outcome may be decreasing the LDL/HDL ratio in a subject in need thereof. Another outcome of treatment may be increasing insulin sensivity. Another outcome of treatment may be enhancing glucose tolerance in a subject with glucose intolerance. Another outcome of treatment may be decreasing insulin resistance in a subject with increased insulin resistance or elevated levels of insulin. Another outcome may be decreading triglycerides in a subject with elevated triglycerides. Yet another outcome may be improving LDL cholestrol, non-HDL cholesterol, triglyceride, HDL cholesterol or other lipid analyte profiles.

Prevention of diabetes mellitus refers to the administration of a compound or combination of the present invention to prevent the onset of diabetes in a subject at risk thereof.

"Obesity" is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 $kg/m^2$. in Asian countries, including Japan, an "obese subject" refers to a subject with at least one obesity-induced or obesity-related co-morbidity that requires weight reduction or that would be improved by weight reduction, with a BMI greater than or equal to 25 $kg/m^2$. In Asia-Pacific, a "subject at risk of obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes, non-insulin dependent diabetes mellitus-type II (2), impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

Treatment of obesity and obesity-related disorders refers to the administration of the compounds or combinations of the present invention to reduce or maintain the body weight of an obese subject. One outcome of treatment may be reducing the body weight of an obese subject relative to that subject's body weight immediately before the administration of the compounds or combinations of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in subjects in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds or combinations of the present invention to reduce or maintain the body weight of a subject at risk of obesity. One outcome of prevention may be reducing the body weight of a subject at risk of obesity relative to that subject's body weight immediately before the administration of the compounds or combinations of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovary disease, cardiovascular diseases, osteoarthritis, hypertension, dyslipidemia, insulin resistance, hypercholesterolemia, hypertriglyceridemia, and cholelithiasis.

The terms "administration of" and or "administering" a compound should be understood to mean providing a compound of the invention or a prodrug of a compound of the invention to a subject in need of treatment. The administration of the compounds of the present invention in order to practice the present methods of therapy is carried out by administering a therapeutically effective amount of the compound to a subject in need of such treatment or prophylaxis. The need for a prophylactic administration according to the methods of the present invention is determined via the use of well known risk factors.

The term "therapeutically effective amount" as used herein means the amount of the active compound that will elicit the biological or medical response in a tissue, system, subject, mammal, or human that is being sought by the researcher, veterinarian, medical doctor or other clinician, which includes alleviation of the symptoms of the disorder being treated. The novel methods of treatment of this invention are for disorders known to those skilled in the art. The term "prophylactically effective amount" as used herein means the amount of the active compound that will elicit the biological or medical response in a tissue, system, subject, mammal, or human that is being sought by the researcher, veterinarian, medical doctor or other clinician, to prevent the onset of the disorder in subjects as risk for obesity or the disorder. The therapeutically or prophylactically effective amount, or dosage, of an individual compound is determined, in the final analysis, by the physician in charge of the case, but depends on factors such as the exact disease to be treated, the severity of the disease and other diseases or conditions from which the patient suffers, the chosen route of administration, other drugs and treatments which the patient may concomitantly require, and other factors in the physician's judgement.

Administration and Dose Ranges

Any suitable route of administration may be employed for providing a subject or mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably the compound of Formula I, II, III, or IV is administered orally or topically.

The effective dosage of active ingredient employed may vary depending on the particular compound employed, the mode of administration, the condition being treated and the severity of the condition being treated. Such dosage may be ascertained readily by a person skilled in the art.

When treating obesity, in conjunction with diabetes and/or hyperglycemia, or alone, generally satisfactory results are obtained when the compound of formula I, II, III, or IV is administered at a daily dosage of from about 0.001 milligram to about 50 milligrams per kilogram of animal body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response.

When treating diabetes mellitus and/or hyperglycemia, as well as other diseases or disorders for which the compound of formula I, II, III, or IV is useful, generally satisfactory results are obtained when the compounds of the present invention are administered at a daily dosage of from about 0.001 milligram to about 50 milligram per kilogram of animal body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response.

When treating dyslipidemia, bulimia nervosa, and gallstones satisfactory results are obtained when the compound of formula I, II, III, or IV is administered at a daily dosage of from about 0.001 milligram to about 50 milligrams per kilogram of animal body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response.

In the case where an oral composition is employed, a suitable dosage range is, e.g. from about 0.01 mg to about 1500 mg of a compound of Formula I, II, III, or IV per day, preferably from about 0.1 mg to about 600 mg per day, more preferably from about 0.1 mg to about 100 mg per day. For oral administration, the compositions are preferably provided in the form of tablets containing from 0.01 to 1,000 mg, preferably 0.01, 0.05, 0.1, 0.5, 1, 2.5, 5, 10, 15, 20, 25, 30, 40, 50, 100, 250, 500, 600, 750, 1000, 1250 or 1500 milligrams of the active ingredient for the symptomatic adjustment of the dosage to the patient to be treated.

For use where a composition for intranasal administration is employed, intranasal formulations for intranasal administration comprising 0.001-10% by weight solutions or suspensions of the compound of formula I, II, III, or IV in an acceptable intranasal formulation may be used.

For use where a composition for intravenous administration is employed, a suitable dosage range is from about 0.001 mg to about 50 mg, preferably from 0.01 mg to about 50 mg, more preferably 0.1 mg to 10 mg, of a compound of formula I, II, III, or IV per kg of body weight per day. This dosage regimen may be adjusted to provide the optimal therapeutic response. It may be necessary to use dosages outside these limits in some cases.

For the treatment of diseases of the eye, ophthalmic preparations for ocular administration comprising 0.001-1% by weight solutions or suspensions of the compound of formula I, II, III, or IV in an acceptable ophthalmic formulation may be used.

The magnitude of prophylactic or therapeutic dosage of the compounds of the present invention will, of course, vary depending on the particular compound employed, the mode of administration, the condition being treated and the severity of the condition being treated. It will also vary according to the age, weight and response of the individual patient. Such dosage may be ascertained readily by a person skilled in the art.

A compound of formula I, II, III, or IV may be used in combination with other drugs that are used in the treatment/prevention/suppression or amelioration of the diseases or conditions for which compounds of formula I, II, III, and IV are useful. Such other drugs may be administered, by a route and in an amount commonly used therefor, contemporaneously or sequentially with a compound of formula I, II, III, or IV. When a compound of formula I, II, III, or IV is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of formula I, II, III, or IV. Examples of other active ingredients that may be combined with a compound of formula I, II, III, and IV for the treatment or prevention of obesity and/or diabetes, either administered separately or in the same pharmaceutical compositions, include, but are not limited to:

(a) insulin sensitizers including (i) PPARγ antagonists such as glitazones (e.g. ciglitazone; darglitazone; englitazone; isaglitazone (MCC-555); pioglitazone; rosiglitazone; troglitazone; tularik; BRIL49653; CLX-0921; 5-BTZD), GW-0207, LG-100641, and LY-300512, and the like), and compounds disclosed in WO 97/10813, WO 97/27857, WO 97/28115, WO 97/28137, and WO 97/27847; (iii) biguanides such as metformin and phenformin;

(b) insulin or insulin mimetics, such as biota, LP-100, novarapid, insulin detemir, insulin lispro, insulin glargine, insulin zinc suspension (lente and ultralente); Lys-Pro insulin, GLP-1 (73-7) (insulintropin); and GLP-1 (7-36)-$NH_2$);

(c) sulfonylureas, such as acetohexamide; chlorpropamide; diabinese; glibenclamide; glipizide; glyburide; glimepiride; gliclazide; glipentide; gliquidone; glisolamide; tolazamide; and tolbutamide;

(d) α-glucosidase inhibitors, such as acarbose, adiposine; camiglibose; emiglitate; miglitol; voglibose; pradimicin-Q; salbostatin; trestatin, tendamistate, CKD-711; MDL-25,637; MDL-73,945; and MOR 14, and the like;

(e) cholesterol lowering agents such as (i) HMG-CoA reductase inhibitors (atorvastatin, itavastatin, fluvastatin, lovastatin, pravastatin, rivastatin, rosuvastatin, simvastatin, and other statins), (ii) bile acid absorbers/sequestrants, such as cholestyramine, colestipol, dialkylaminoalkyl derivatives of a cross-linked dextran; Colestid®; LoCholest®, and the like, (ii) nicotinyl alcohol, nicotinic acid or a salt thereof, (iii) proliferator-activater receptor α agonists such as fenofibric acid derivatives (gemfibrozil, clofibrate, fenofibrate and benzafibrate), (iv) inhibitors of cholesterol absorption such as stanol esters, beta-sitosterol, sterol glycosides such as tiqueside; and azetidinones such as ezetimibe, and the like, and (acyl CoA:cholesterol acyltransferase (ACAT)) inhibitors such as avasimibe, and melinamide, (v) anti-oxidants, such as probucol, (vi) vitamin E, and (vii) thyromimetics;

(f) PPARα agonists such as beclofibrate, benzafibrate, ciprofibrate, clofibrate, etofibrate, fenofibrate, and gemfibrozil; and other fibric acid derivatives, such as Atromid®, Lopid® and Tricor®, and the like, and PPARα agonists as described in WO 97/36579 by Glaxo;

(g) PPARδ agonists, such as those disclosed in WO97/28149;

(h) PPARα/δ agonists, such as muraglitazar, and the compounds disclosed in U.S. Pat. No. 6,414,002;

(i) smoking cessation agents, such as a nicotine agonist or a partial nicotine agonist such as varenicline, or a monoamine oxidase inhibitor (MAOI), or another active ingredient demonstrating efficacy in aiding cessation of tobacco consumption; for example, an antidepressant such as bupropion, doxepine, ornortriptyline; or an anxiolytic such as buspirone or clonidine; and (j) anti-obesity agents, such as (1) growth hormone secretagogues, growth hormone secretagogue receptor agonists/antagonists, such as NN703, hexarelin, ME-0677, SM-130686, CP-424,391, L-692,429, and L-163,255, and such as those disclosed in U.S. Pat. Nos. 5,536,716, and 6,358,951, U.S. Patent Application Nos. 2002/049196 and 2002/022637, and PCT Application Nos. WO 01/56592 and WO 02/32888; (2) protein tyrosine phosphatase-1B (PTP-1B) inhibitors; (3) cannabinoid receptor ligands, such as cannabinoid $CB_1$ receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer), and those disclosed in U.S. Pat. Nos. 5,532,237, 4,973,587, 5,013,837, 5,081,122, 5,112,820, 5,292,736, 5,624,941, 6,028,084, PCT Application Nos. WO 96/33159, WO 98/33765, WO98/43636, WO98/43635, WO 01/09120, WO98/31227, WO98/41519, WO98/37061, WO00/10967, WO00/10968, WO97/29079, WO99/02499, WO 01/58869, WO 01/64632, WO 01/64633, WO 01/64634, WO02/076949, WO 03/007887, WO 04/048317, and WO 05/000809; and EPO Application No. EP-658546, EP-656354, EP-576357; (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A, and such as those disclosed in U.S. Patent Application Nos. 5,705,515, and U.S. Pat. No. 5,451, 677 and PCT Patent Publications WO94/18161, WO95/29159, WO97/46556, WO98/04526 and WO98/32753, WO 01/74782, and WO 02/32897; (6) pancreatic lipase inhibitors, such as orlistat (Xenical®), Triton WR1339, RHC80267, lipstatin, tetrahydrolipstatin, teasaponin, diethylumbelliferyl phosphate, and those disclosed in PCT Application No. WO 01/77094; (7) neuropeptide Y1 antagonists, such as BIBP3226, J-115814, BIBO 3304, LY-357897, CP-671906, GI-264879A, and those disclosed in U.S. Pat. No. 6,001,836, and PCT Patent Publication Nos. WO 96/14307, WO 01/23387, WO 99/51600, WO 01/85690, WO 01/85098, WO 01/85173, and WO 01/89528; (8) neuropeptide Y5 antagonists, such as GW-569180A, GW-594884A, GW-587081X, GW-548118X, FR226928, FR240662, FR252384, 1229U91, GI-264879A, CGP71683A, LY-377897, PD-160170, SR-120562A, SR-120819A and JCF-104, and those disclosed in U.S. Pat. Nos. 6,057,335; 6,043,246; 6,140,354; 6,166,038; 6,180,653; 6,191,160; 6,313,298; 6,335,345; 6,337,332; 6,326,375; 6,329,395; 6,340,683; 6,388,077; 6,462,053; 6,649,624; and 6,723,847, hereby incorporated by reference in their entirety; European Patent Nos. EP-01010691, and EP-01044970; and PCT International Patent Publication Nos. WO 97/19682, WO 97/20820, WO 97/20821, WO 97/20822, WO 97/20823, WO 98/24768; WO 98/25907; WO 98/25908; WO 98/27063, WO 98/47505; WO 98/40356; WO 99/15516; WO 99/27965; WO 00/64880, WO 00/68197, WO 00/69849, WO 01/09120, WO 01/14376; WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, and WO 02/49648; WO 02/094825; WO 03/014083; WO 03/10191; WO 03/092889; WO 04/002986; and WO 04/031175; (9) melanin-concentrating hormone (MCH) receptor antagonists, such as those disclosed in WO 01/21577 and WO 01/21169; (10) melanin-concentrating hormone 1 receptor (MCH1R) antagonists, such as T-226296 (Takeda), and those disclosed in PCT Patent Application Nos. WO 01/82925, WO 01/87834, WO 02/051809, WO 02/06245, WO 02/076929, WO 02/076947, WO 02/04433, WO 02/51809, WO 02/083134, WO 02/094799, WO 03/004027, and Japanese Patent Application Nos. JP 13226269, and JP 2004-139909; (11) melanin-concentrating hormone 2 receptor (MCH2R) agonist/antagonists; (12) orexin-1 receptor antagonists, such as SB-334867-A, and those disclosed in PCT Patent Application Nos. WO 01/96302, WO 01/68609, WO 02/51232, and WO 02/51838; (13) serotonin reuptake inhibitors such as fluoxetine, paroxetine, and sertraline, and those disclosed in U.S. Pat. No. 6,365,633, and PCT Patent Application Nos. WO 01/27060 and WO 01/162341; (14) melanocortin agonists, such as Melanotan II, CHIR86036 (Chiron), ME-10142, and ME-10145 (Melacure), CHIR86036 (Chiron); PT-141, and PT-14 (Palatin); (15) other MC4R (melanocortin 4 receptor) agonists, such as those disclosed in: U.S. Pat. Nos. 6,410,548; 6,294,534; 6,350,760; 6,458,790; 6,472,398; 6,376,509; and 6,818,658; US Patent Publication No. US2002/0137664; US2003/0236262; US2004/009751; US2004/0092501; and PCT Application Nos. WO 99/64002; WO 00/74679; WO 01/70708; WO 01/70337; WO 01/74844; WO 01/91752; WO 01/991752; WO 02/15909; WO 02/059095; WO 02/059107; WO 02/059108; WO 02/059117; WO 02/067869; WO 02/068387; WO 02/068388; WO 02/067869; WO 02/11715; WO 02/12166; WO 02/12178; WO 03/007949; WO 03/009847; WO 04/024720; WO 04/078716; WO 04/078717; WO 04/087159; WO 04/089307; and WO 05/009950; (16) 5HT-2 agonists; (17) 5HT2C (serotonin receptor 2C) agonists, such as BVT933, DPCA37215, WAY161503, R1065, and those disclosed in U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457; (18) galanin antagonists; (19) CCK agonists; (20) other CCK-1 (cholecystokinin-A) agonists, such as AR-R 15849, GI 181771, JMV-180, A-71378, A-71623 and SR146131, and those discribed in U.S. Pat. No. 5,739,106; (21) GLP-1 agonists; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, GT2394 (Gliatech), and those described and disclosed in PCT Application No. WO 02/15905, and O—[3-(1H-imidazol-4-yl)propanol]-carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001)), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)); (25) β-hydroxy steroid dehydrogenase-1 inhibitors (β-HSD-1); 26) PDE (phosphodiesterase) inhibitors, such as theophylline, pentoxifylline, zaprinast, sildenafil, amrinone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists, such as those disclosed in PCT Application Nos. WO 01/87335, and WO 02/08250; (30) leptin, including recombinant human leptin (PEG-OB, Hoffman La Roche) and recombinant methionyl human leptin (Amgen); (31) leptin derivatives, such as those disclosed in U.S. Pat. Nos. 5,552,524, 5,552,523, 5,552,522, 5,521,283, and PCT International Publication Nos. WO 96/23513, WO 96/23514, WO 96/23515, WO 96/23516, WO 96/23517, WO 96/23518, WO 96/23519, and WO 96/23520; (32) BRS3 (bombesin receptor subtype 3) agonists such as [D-Phe6,beta-Ala11,Phe13,Nle14]Bn(6-14) and [D-Phe6,Phe13]Bn(6-13)propylamide, and those compounds disclosed in Pept. Sci. 2002 August; 8(8): 461-75); (33) CNTF (Ciliary neurotrophic factors), such as GI-181771 (Glaxo-SmithKline), SR146131 (Sanofi Synthelabo), butabindide, PD170,292, and PD 149164 (Pfizer); (34) CNTF derivatives, such as axokine (Regeneron), and those disclosed in PCT Application Nos. WO 94/09134, WO 98/22128, and WO 99/43813; (35) monoamine reuptake inhibitors, such as sibutramine, and those disclosed in U.S. Pat. Nos. 4,746,680, 4,806,570, and 5,436,272, U.S. Patent Publication No. 2002/0006964 and PCT Application Nos. WO 01/27068, and WO 01/62341; (36) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), retinoic acid, and those disclosed in PCT Patent Application No. WO 99/00123; (37) thyroid hormone β agonists, such as KB-2611 (KaroBioBMS), and those disclosed in PCT Application No. WO 02/15845, and Japanese Patent Application No. JP 2000256190; (38) FAS (fatty acid synthase) inhibitors, such as Cerulenin and C75; (39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del Mar-Grasa, M. et al., Obesity Research, 9:202-9 (2001); (44) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274-444 and sitagliptin; and the compounds disclosed in U.S. Patent No. 6,699,871, which is incorporated herein by reference; and International Patent Application Nos. WO 03/004498; WO 03/004496; EP 1 258 476; WO 02/083128; WO 02/062764; WO 03/000250; WO 03/002530; WO 03/002531; WO 03/002553; WO 03/002593; WO 03/000180; and WO 03/000181; (46) dicarboxylate transporter inhibitors; (47) glucose transporter inhibitors; (48) phosphate transporter inhibitors; (49) Metformin (Glucophage®); and (50) Topiramate (Topimax®); and (50) peptide YY, PYY 3-36, peptide YY analogs, derivatives, and fragments such as BIM-43073D, BIM-43004C (Olitvak, D. A. et al., Dig. Dis. Sci. 44(3):643-48 (1999)), and those disclosed in U.S. Pat. Nos. 5,026,685, 5,604,203, 5,574,010, 5,696,093, 5,936,092, 6,046,162, 6,046,167, 6,093,692, 6,225,445, 5,604,203, 4,002,531, 4, 179,337, 5,122,614, 5,349,052, 5,552,520, 6,127,355, WO 95/06058, WO 98/32466, WO 03/026591, WO 03/057235, WO 03/027637, and WO 2004/066966, which are incorporated herein by reference; (51) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (52) Neuropeptide Y4 (NPY4) agonists such as pancreatic peptide (PP) as described in Batterham et al., J. Clin. Endocrinol. Metab. 88:3989-3992 (2003), and other Y4 agonists such as 1229U91; (54) cyclooxygenase-2 inhibitors such as etoricoxib, celecoxib, valdecoxib, parecoxib, lumiracoxib, BMS347070, tiracoxib or JTE522, ABT963, CS502 and GW406381, and pharmaceutically acceptable salts thereof; (55) Neuropeptide Y1 (NPY1) antagonists such as BIBP3226, J-115814, BIBO 3304, LY-357897, CP-671906, GI-264879A and those disclosed in U.S. Pat. No. 6,001,836; and PCT Application Nos. WO 96/14307, WO 01/23387, WO 99/51600, WO 01/85690, WO 01/85098, WO 01/85173, and WO 01/89528; (56) Opioid antagonists such as nalmefene (Revex®), 3-methoxynaltrexone, naloxone, naltrexone, and those disclosed in: PCT Application No. WO 00/21509; (57) 11β, HSD-1 (11- beta hydroxy steroid dehydrogenase type 1) inhibitors such as BVT 3498, BVT 2733, and those disclosed in WO 01/90091, WO 01/90090, WO 01/90092, and US Patent No. U.S. Pat. No. 6,730,690 and US Publication No. US 2004-0133011, which are incorporated by reference herein in their entirety; and (58) aminorex; (59) amphechloral; (60) amphetamine; (61) benzphetamine; (62) chlorphentermine; (63) clobenzorex; (64) cloforex; (65) clominorex; (66) clortermine; (67) cyclexedrine; (68) dextroamphetamine; (69) diphemethoxidine, (70) N-ethylamphetamine; (71) fenbutrazate; (72) fenisorex; (73) fenproporex; (74) fludorex; (75) fluminorex; (76) furfurylmethylamphetamine; (77) levamfetamine; (78) levophacetoperane; (79) mefenorex; (80) metamfepramone; (81) methamphetamine; (82) norpseudoephedrine; (83) pentorex; (84) phendimetrazine; (85) phenmetrazine; (86) picilorex; (87) phytopharm 57; (88) zonisamide, (89) neuromedin U and analogs or derivatives thereof, (90) oxyntomodulin and analogs or derivatives thereof; (91) Neurokinin-1 receptor antagonists (NK-1 antagonists) such as the compounds disclosed in: U.S. Pat. Nos. 5,162,339, 5,232,929, 5,242,930, 5,373,003, 5,387,595, 5,459,270, 5,494,926, 5,496,833, and 5,637,699; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165,93/01169, 93/01170,93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997,94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942, 97/21702, and 97/49710; and (92) Qnexa.

Specific compounds of use in combination with a compound of the present invention include: simvastatin, mevastatin, ezetimibe, atorvastatin, sitagliptin, metformin, sibutramine, orlistat, Qnexa, topiramate, naltrexone, bupriopion, phentermine, and losartan, losartan with hydrochlorothiazide. Specific CB1 antagonists/inverse agonists of use in combination with a compound of the present invention include: those described in WO03/077847, including: N-[3-(4-chlorophenyl)-2(S)-phenyl-1(S)-methylpropyl]-2-(4-trifluoromethyl-2-pyrimidyloxy)-2-methylpropanamide, N-[3-(4-chlorophenyl)-2-(3-cyanophenyl)-1-methylpropyl]-2-(5-trifluoromethyl-2-pyridyloxy)-2-methylpropanamide, N-[3-(4-chlorophenyl)-2-(5-chloro-3-pyridyl)-1-methylpropyl]-2-(5-trifluoromethyl-2-pyridyloxy)-2-methylpropanamide, and pharmaceutically acceptable salts thereof; as well as those in WO05/000809, which includes the following: 3-{1-[bis(4-chlorophenyl)methyl]azetidin-3-ylidene}-3-(3,5-difluorophenyl)-2,2-dimethylpropanenitrile, 1-{1-[1-(4-chlorophenyl)pentyl]azetidin-3-yl}-1-(3,5-difluorophenyl)-2-methylpropan-2-ol. 3-((S)-(4-chlorophenyl) {3-[(1S)-1-(3,5-difluorophenyl)-2-hydroxy-2-methylpropyl]azetidin-1-yl}methyl)benzonitrile, 3-((S)-(4-chlorophenyl) {3-[(1S)-1-(3,5-difluorophenyl)-2-fluoro-2-methylpropyl]azetidin-1-yl}methyl)benzonitrile, 3-((4-chlorophenyl) {3-[1-(3,5-difluorophenyl)-2,2-dimethylpropyl]azetidin-1-yl}methyl) benzonitrile, 3-((1S)-1-{1-[(S)-(3-cyanophenyl)(4-cyanophenyl)methyl]azetidin-3-yl}-2-fluoro-2-methylpropyl)-5-fluorobenzonitrile, 3-[(S)-(4-chlorophenyl)(3-{(1S)-2-fluoro-1-[3-fluoro-5-(4H-1,2,4-triazol-4-yl)phenyl]-2-methylpropyl}azetidin-1-yl)methyl]benzonitrile, and 5-((4-chlorophenyl) {3-[(1S)-1-(3,5-difluorophenyl)-2-fluoro-2-methylpropyl]azetidin-1-yl}methyl)thiophene-3-carbonitrile, and pharmaceutically acceptable salts thereof; as well as: 3-[(S)-(4-chlorophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(4-chlorophenyl)(3-{(1S)-2-fluoro-1-[3-fluoro-5-(1,3,4-oxadiazol-2-yl)phenyl]-2-methylpropyl}azetidin-1-yl) methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-chlorophenyl)methyl] benzonitrile, 3-[(S)-(4-cyanophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-cyanophenyl)methyl]benzonitrile, 3-[(S)-(4-cyanophenyl) (3-{(1S)-2-fluoro-1-[3-fluoro-5-(1,3,4-oxadiazol-2-yl) phenyl]-2-methylpropyl}azetidin-1-yl)methyl]benzonitrile, 3-[(S)-(4-chlorophenyl)(3-{(S)-2-fluoro-1-[3-fluoro-5-(1,2,4-oxadiazol-3-yl)phenyl]-2-methylpropyl}azetidin-1-yl) methyl]benzonitrile, 3-[(1S)-1-(1-{(S)-(4-cyanophenyl)[3-(1,2,4-oxadiazol-3-yl)phenyl]-methyl}azetidin-3-yl)-2-fluoro-2-methylpropyl]-5-fluorobenzonitrile, 5-(3-{1-[1-(diphenylmethyl)azetidin-3-yl]-2-fluoro-2-methylpropyl}-5-fluorophenyl)-1H-tetrazole, 5-(3-{1-[1-(diphenylmethyl) azetidin-3-yl]-2-fluoro-2-methylpropyl}-5-fluorophenyl)-1-methyl-1H-tetrazole, 5-(3-{1-[1-(diphenylmethyl)azetidin-3-yl]-2-fluoro-2-methylpropyl}-5-fluorophenyl)-2-methyl-2H-tetrazole, 3-[(4-chlorophenyl)(3-{2-fluoro-1-[3-fluoro-5-(2-methyl-2H-tetrazol-5-yl)phenyl]-2-methylpropyl}azetidin-1-yl)methyl]benzonitrile, 3-[(4-chlorophenyl)(3-{2-fluoro-1-[3-fluoro-5-(1-methyl-1H-tetrazol-5-yl)phenyl]-2-methylpropyl}azetidin-1-yl)methyl] benzonitrile, 3-[(4-cyanophenyl)(3-{2-fluoro-1-[3-fluoro-5-(1-methyl-1H-tetrazol-5-yl)phenyl]-2-methylpropyl}azetidin-1-yl)methyl]benzonitrile, 3-[(4-cyanophenyl)(3-{2-fluoro-1-[3-fluoro-5-(2-methyl-2H-tetrazol-5-yl)phenyl]-2-methylpropyl}azetidin-1-yl)methyl] benzonitrile, 5-{3-[(S)-{3-[(1S)-1-(3-bromo-5-fluorophenyl)-2-fluoro-2-methylpropyl]azetidin-1-yl}(4-chlorophenyl)methyl]phenyl}-1,3,4-oxadiazol-2(3H)-one, 3-[(1S)-1-(1-{(S)-(4-chlorophenyl)[3-(5-oxo-4,5-dihydro-1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-cyanophenyl)[3-(5-oxo-4,5-dihydro-1,3,4-oxadiazol-2-yl) phenyl]methyl}azetidin-3-yl)-2-fluoro-2-methylpropyl]-5-fluorobenzonitrile, 3-[(1S)-1-(1-{(S)-(4-cyanophenyl)[3-(1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-chlorophenyl)[3-(1,3,4-oxadiazol-2-yl)phenyl] methyl}azetidin-3-yl)-2-fluoro-2-methylpropyl]-5-fluorobenzonitrile, 3-((S)-1-{1-[(S)-[3-(5-amino-1,3,4-oxadiazol-2-yl)phenyl](4-chlorophenyl)methyl]azetidin-3-yl}-2-fluoro-2-methylpropyl)-5-fluorobenzonitrile, 3-((1S)-1-{1-[(S)-[3-(5-amino-1,3,4-oxadiazol-2-yl)phenyl](4-cyanophenyl)methyl]azetidin-3-yl}-2-fluoro-2-methylpropyl]-5-fluorobenzonitrile, 3-[(1S)-1-(1-{(S)-(4-cyanophenyl)[3-(1,2,4-oxadiazol-3-yl)phenyl] methyl}azetidin-3-yl)-2-fluoro-2-methylpropyl)-5- fluorobenzonitrile, 3-[(1S)-1-(1-{(S)-(4-chlorophenyl)[3-(1,2,4-oxadiazol-3-yl)phenyl]methyl}azetidin-3-yl)-2-fluoro-2-methylpropyl]-5-fluorobenzonitrile, 5-[3-((S)-(4-chlorophenyl) {3-[(1S)-1-(3,5-difluorophenyl)-2-fluoro-2-methylpropyl]azetidin-1-yl}methyl)phenyl]-1,3,4-oxadiazol-2(3H)-one, 5-[3-((S)-(4-chlorophenyl){3-[(1S)-1-(3,5-difluorophenyl)-2-fluoro-2-methylpropyl]azetidin-1-yl}methyl)phenyl]-1,3,4-oxadiazol-2(3H)-one, 4-{(S)-{3-[(1S)-1-(3,5-difluorophenyl)-2-fluoro-2-methylpropyl]azetidin-1-yl}[3-(5-oxo-4,5-dihydro-1,3,4-oxadiazol-2-yl)phenyl]methyl}-benzonitrile, and pharmaceutically acceptable salts thereof.

Specific NPY5 antagonists of use in combination with a compound of the present invention include: 3-oxo-N-(5-phenyl-2-pyrazinyl)-spiro[isobenzofuran-1(3H), 4'-piperidine]-1'-carboxamide, 3-oxo-N-(7-trifluoromethylpyrido[3,2-b]pyridin-2-yl)spiro-[isobenzofuran-1(3H), 4'-piperidine]-1'-carboxamide, N-[5-(3-fluorophenyl)-2-pyrimidinyl]-3-oxospiro-[isobenzofuran-1(3H), 4'-piperidine]-1'-carboxamide, trans-3'-oxo-N-(5-phenyl-2-pyrimidinyl)spiro[cyclohexane-1,1'(3'H)-isobenzofuran]-4-carboxamide, trans-3'-oxo-N-[1-(3-quinolyl)-4-imidazolyl]spiro[cyclohexane-1,1'(3'H)-isobenzofuran]-4-carboxamide, trans-3-oxo-N-(5-phenyl-2-pyrazinyl)spiro[4-azaiso-benzofuran-1(3H),1'-cyclohexane]-4'-carboxamide, trans-N-[5-(3-fluorophenyl)-2-pyrimidinyl]-3-oxospiro[5-azaisobenzofuran-1(3H),1'-cyclohexane]-4'-carboxamide, trans-N-[5-(2-fluorophenyl)-2-pyrimidinyl]-3-oxospiro[5-azaisobenzofuran-1(3H), 1'-cyclohexane]-4'-carboxamide, trans-N-[1-(3,5-difluorophenyl)-4-imidazolyl]-3-oxospiro[7-azaisobenzofuran-1(3H), 1'-cyclohexane]-4'-carboxamide, trans-3-oxo-N-(1-phenyl-4-pyrazolyl)spiro[4-azaisobenzofuran-1(3H), 1'-cyclohexane]-4'-carboxamide, trans-N-[1-(2-fluorophenyl)-3-pyrazolyl]-3-oxospiro[6-azaisobenzofuran-1(3H), 1'-cyclohexane]-4'-carboxamide, trans-3-oxo-N-(1-phenyl-3-pyrazolyl)spiro[6-azaisobenzofuran-1(3H), 1'-cyclohexane]-4'-carboxamide, trans-3-oxo-N-(2-phenyl-1,2,3-triazol-4-yl)spiro[6-azaisobenzofuran-1(3H), 1'-cyclohexane]-4'-carboxamide, and pharmaceutically acceptable salts and esters thereof.

Specific ACC-1/2 inhibitors of use in combination with a compound of the present invention include: 1'-[(4,8-dimethoxyquinolin-2-yl)carbonyl]-6-(1H-tetrazol-5-yl)spiro[chroman-2,4'-piperidin]-4-one; (5-{1'-[(4,8-dimethoxyquinolin-2-yl)carbonyl]-4-oxospiro[chroman-2,4'-piperidin]-6-yl}-2H-tetrazol-2-yl)methyl pivalate; 5-{1'-[(8-cyclopropyl-4-methoxyquinolin-2-yl)carbonyl]-4-oxospiro[chroman-2,4'-piperidin]-6-yl}nicotinic acid; 1'-(8-methoxy-4-morpholin-4-yl-2-naphthoyl)-6-(1H-tetrazol-5-yl)spiro[chroman-2,4'-piperidin]-4-one; and 1'-[(4-ethoxy-8-ethylquinolin-2-yl)carbonyl]-6-(1H-tetrazol-5-yl)spiro[chroman-2,4'-piperidin]-4-one; and pharmaceutically acceptable salts and esters thereof. Specific MCH1R antagonist compounds of use in combination with a compound of the present invention include: 1-{4-[(1-ethylazetidin-3-yl)oxy]phenyl}-4-[(4-fluorobenzyl)oxy]pyridin-2(1H)-one, 4-[(4-fluorobenzyl)oxy]-1-{4-[(1-isopropylazetidin-3-yl)oxy]phenyl}pyridin-2(1H)-one, 1-[4-(azetidin-3-yloxy)phenyl]-4-[(5-chloropyridin-2-yl)methoxy]pyridin-2(1H)-one, 4-[(5-chloropyridin-2-yl)methoxy]-1-{4-[(1-ethylazetidin-3-yl)oxy]phenyl}pyridin-2(1H)-one, 4-[(5-chloropyridin-2-yl)methoxy]-1-{4-[(1-propylazetidin-3-yl)oxy]phenyl}pyridin-2(1H)-one, and 4-[(5-chloropyridin-2-yl)methoxy]-1-(4-{[(2S)-1-ethylazetidin-2-yl]methoxy}phenyl)pyridin-2(1H)-one, or a pharmaceutically acceptable salt thereof.

Specific DP-IV inhibitors of use in combination with a compound of the present invention are selected from 7-[(3R)-3-amino-4-(2,4,5-trifluorophenyl)butanoyl]-3-(trifluoromethyl)-5,6,7,8-tetrahydro-1,2,4-triazolo[4,3-a]pyrazine. In particular, the compound of formula I is favorably combined with 7-[(3R)-3-amino-4-(2,4,5-trifluorophenyl)butanoyl]-3-(trifluoromethyl)-5,6,7,8-tetrahydro-1,2,4-triazolo[4,3-a]pyrazine, and pharmaceutically acceptable salts thereof.

Specific H3 (histamine H3) antagonists/inverse agonists of use in combination with a compound of the present invention include: those described in WO05/077905, including: 3-{4-[(1-cyclobutyl-4-piperidinyl)oxy]phenyl}-2-ethylpyrido[2,3-d]-pyrimidin-4(3H)-one, 3-{4-[(1-cyclobutyl-4-piperidinyl)oxy]phenyl}-2-methylpyrido[4,3-d]pyrimidin-4(3H)-one, 2-ethyl-3-(4-(3-[(3S)-3-methylpiperidin-1-yl]propoxy}phenyl)pyrido[2,3-d]pyrimidin-4(3H)-one 2-methyl-3-(4-{3-[(3S)-3-methylpiperidin-1-yl]propoxy}phenyl)pyrido[4,3-d]pyrimidin-4(3H)-one, 3-{4-[(1-cyclobutyl-4-piperidinyl)oxy]phenyl}-2,5-dimethyl-4(3H)-quinazolinone, 3-{4-[(1-cyclobutyl-4-piperidinyl)oxy]phenyl}-2-methyl-5-trifluoromethyl-4(3H)-quinazolinone, 3-{4[(1-cyclobutyl-4-piperidinyl)oxy]phenyl}-5-methoxy-2-methyl-4(3H)-quinazolinone, 3-{4-[(1-cyclobutylpiperidin-4-yl)oxy]phenyl}-5-fluoro-2-methyl-4(3H)-quinazolinone, 3-{4-[(1-cyclobutylpiperidin-4-yl)oxy]phenyl}-7-fluoro-2-methyl-4(3H)-quinazolinone, 3-{4-[(1-cyclobutylpiperidin-4-yl)oxy]phenyl}-6-methoxy-2-methyl-4(3H)-quinazolinone, 3-{4-[(1-cyclobutylpiperidin-4-yl)oxy]phenyl}-6-fluoro-2-methyl-4(3H)-quinazolinone, 3-{4-[(1-cyclobutylpiperidin-4-yl)oxy]phenyl}-8-fluoro-2-methyl-4(3H)-quinazolinone, 3-{4-[(1-cyclopentyl-4-piperidinyl)oxy]phenyl}-2-methylpyrido[4,3-d]pyrimidin-4(3H)-one, 3-{4-[(1-cyclobutylpiperidin-4-yl)oxy]phenyl}-6-fluoro-2-methylpyrido[3,4-d]pyrimidin-4(3H)-one, 3-{4-[(1-cyclobutyl-4-piperidinyl)oxy]phenyl}-2-ethylpyrido[4,3-d]pyrimidin-4(3H)-one, 6-methoxy-2-methyl-3-{4-[3-(1-piperidinyl)propoxy]phenyl}pyrido[3,4-d]pyrimidin-4(3H)-one, 6-methoxy-2-methyl-3-{4-[3-(1-pyrrolidinyl)propoxy]phenyl}pyrido[3,4-d]pyrimidin-4(3H)-one, 2,5-dimethyl-3-{4-[3-(1-pyrrolidinyl)propoxy]phenyl}-4(3H)-quinazolinone, 2-methyl-3-{4-[3-(1-pyrrolidinyl)propoxy]phenyl}-5-trifluoromethyl-4(3H)-quinazolinone, 5-fluoro-2-methyl-3-{4-[3-(1-piperidinyl)propoxy]phenyl}-4(3H)-quinazolinone, 6-methoxy-2-methyl-3-{4-[3-(1-piperidinyl)propoxy]phenyl}-4(3H)-quinazolinone, 5-methoxy-2-methyl-3-(4-{3-[(3S)-3-methylpiperidin-1-yl]propoxy}phenyl)-4(3H)-quinazolinone, 7-methoxy-2-methyl-3-(4-{3-[(3S)-3-methylpiperidin-1-yl]propoxy}phenyl)-4(3H)-quinazolinone, 2-methyl-3-(4-{3-[(3S)-3-methylpiperidin-1-yl]propoxy}phenyl)pyrido[2,3-d]pyrimidin-4(3H)-one, 5-fluoro-2-methyl-3-(4-{3-[(2R)-2-methylpyrrolidin-1-yl]propoxy}phenyl)-4(3H)-quinazolinone, 2-methyl-3-(4-{3-[(2R)-2-methylpyrrolidin-1-yl]propoxy}phenyl)pyrido[4,3-d]pyrimidin-4(3H)-one, 6-methoxy-2-methyl-3-(4-{3-[(2R)-2-methylpyrrolidin-1-yl]propoxy}phenyl)-4(3H)-quinazolinone, 6-methoxy-2-methyl-3-(4-{3-[(2S)-2-methylpyrrolidin-1-yl]propoxy}phenyl)-4(3H)-quinazolinone, and pharmaceutically acceptable salts thereof.

Specific CCK1R agonists of use in combination with a compound of the present invention include: 3-(4-{[1-(3-ethoxyphenyl)-2-(4-methylphenyl)-1H-imidazol-4-yl]carbonyl}-1-piperazinyl)-1-naphthoic acid; 3-(4-([1-(3-ethoxyphenyl)-2-(2-fluoro-4-methylphenyl)-1H-imidazol-4-yl]carbonyl}-1-piperazinyl)-1-naphthoic acid; 3-(4-{[1-(3-ethoxyphenyl)-2-(4-fluorophenyl)-1H-imidazol-4-yl]carbonyl}-1-piperazinyl)-1-naphthoic acid; 3-(4-{[1-(3- ethoxyphenyl)-2-(2,4-difluorophenyl)-1H-imidazol-4-yl]carbonyl}-1-piperazinyl)-1-naphthoic acid; and 3-(4-{[1-(2,3-dihydro-1,4-benzodioxin-6-yl)-2-(4-fluorophenyl)-1H-imidazol-4-yl]carbonyl}-1-piperazinyl)-1-naphthoic acid; and pharmaceutically acceptable salts thereof. Specific MC4R agonists of use in combination with a compound of the present invention include: 1) (5S)-1'-{[(3R,4R)-1-tert-butyl-3-(2,3,4-trifluorophenyl)piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 2) (SR)-1'-{[(3R,4R)-1-tert-butyl-3-(2,3,4-trifluorophenyl)-piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 3) 2-(1'-{[(3S,4R)-1-tert-butyl-4-(2,4-difluorophenyl)pyrrolidin-3-yl]carbonyl}-3-chloro-2-methyl-5H-spiro[furo[3,4-b]pyridine-7,4'-piperidin]-5-yl)-2-methylpropanenitrile; 4) 1'-{[(3S,4R)-1-tert-butyl-4-(2,4-difluorophenyl)pyrrolidin-3-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 5) N-[(3R,4R)-3-({3-chloro-2-methyl-5-[1-methyl-1-(1-methyl-1H-1,2,4-triazol-5-yl)ethyl]-1'H,5H-spiro[furo-[3,4-b]pyridine-7,4'-piperidin]-1'-yl)}carbonyl)-4-(2,4-difluorophenyl)-cyclopentyl]-N-methyltetrahydro-2H-pyran-4-amine; 6) 2-[3-chloro-1'-({(1R,2R)-2-(2,4-difluorophenyl)-4-[methyl(tetrahydro-2H-pyran-4-yl)amino]-cyclopentyl}-carbonyl)-2-methyl-5H-spiro[furo[3,4-b]pyridine-7,4'-piperidin]-5-yl]-2-methyl-propane-nitrile; and pharmaceutically acceptable salts thereof. Still further, neurokinin-1 (NK-1) receptor antagonists may be favorably employed in combination with a compound of the present invention. NK-1 receptor antagonists of use in the present invention are fully described in the art. Specific neurokinin-1 receptor antagonists of use in the present invention include: (±)-(2R3R,2S3S)-N-{[2-cyclopropoxy-5-(trifluoromethoxy)-phenyl]methyl}-2-phenylpiperidin-3-amine; 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine; aperpitant; CJ17493; GW597599; GW679769; R673; R067319; R1124; R1204; SSR146977; SSR240600; T-2328; and T2763.; or a pharmaceutically acceptable salts thereof.

Examples of other anti-obesity agents that can be employed in combination with a compound of formula I, II, III, or IV are disclosed in "Patent focus on new anti-obesity agents," *Exp. Opin. Ther. Patents*, 10: 819-831 (2000); "Novel anti-obesity drugs," *Exp. Opin. Invest. Drugs*, 9: 1317-1326 (2000); and "Recent advances in feeding suppressing agents: potential therapeutic strategy for the treatment of obesity, *Exp. Opin. Ther. Patents*, 11: 1677-1692 (2001). The role of neuropeptide Y in obesity is discussed in *Exp. Opin. Invest. Drugs*, 9: 1327-1346 (2000). Cannabinoid receptor ligands are discussed in *Exp. Opin. Invest. Drugs*, 9: 1553-1571 (2000).

The instant invention also includes administration of a single pharmaceutical dosage formulation which contains both the CCK-1R ligand or agonist in combination with a second active ingredient, as well as administration of each active agent in its own separate pharmaceutical dosage formulation. Where separate dosage formulations are used, the individual components of the composition can be administered at essentially the same time, i.e., concurrently, or at separately staggered times, i.e. sequentially prior to or subsequent to the administration of the other component of the composition. The instant invention is therefore to be understood to include all such regimes of simultaneous or alternating treatment, and the terms "administration" and "administering" are to be interpreted accordingly. Administration in these various ways are suitable for the present compositions as long as the beneficial pharmaceutical effect of the combination of the CCK-1R ligand or agonist and the second active ingredient is realized by the patient at substantially the same time. Such beneficial effect is preferably achieved when the target blood level concentrations of each active ingredient are maintained at substantially the same time. It is preferred that the combination of the CCK-1R ligand or agonist and the second active ingredient be co-administered concurrently on a once-a-day dosing schedule; however, varying dosing schedules, such as the CCK-1R ligand or agonist once a day and the second active ingredient once, twice or more times per day or the CCK-1R ligand or agonist three times a day and the second active ingredient once, twice or more times per day, is also encompassed herein. A single oral dosage formulation comprised of both a CCK-1R ligand or agonist and a second active ingredient is preferred. A single dosage formulation will provide convenience for the patient, which is an important consideration especially for patients with diabetes or obese patients who may be in need of multiple medications.

The compounds in the combinations of the present invention may be administered separately, therefore the invention also relates to combining separate pharmaceutical compositions into a kit form. The kit, according to this invention, comprises two separate pharmaceutical compositions: a first unit dosage form comprising a prophylactically or therapeutically effective amount of the cholecystokinin-1 receptor agonist, or a pharmaceutically acceptable salt or ester thereof, and a pharmaceutically acceptable carrier or diluent in a first unit dosage form, and a second unit dosage form comprising a prophylactically or therapeutically effective amount of the second active ingredient or drug, or a pharmaceutically acceptable salt or ester thereof, and a pharmaceutically acceptable carrier or diluent in a second unit dosage form. In one embodiment, the kit further comprises a container. Such kits are especially suited for the delivery of solid oral forms such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days or time in the treatment schedule in which the dosages can be administered.

Another aspect of the present invention provides pharmaceutical compositions which comprise a compound of formula I, II, III, or IV, as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of formula I, II, III, and IV can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the typical oral dosage unit form, in which case solid pharmaceutical carriers are typically employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I, II, III, or IV may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The compounds of formula I, II, III, and IV of the present invention can be prepared according to the procedures of the following Schemes and Examples, using appropriate materials and are further exemplified by the following specific examples. Moreover, by utilizing the procedures described herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogencarbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless otherwise noted. Mass spectra (MS) were measured by electron-spray ion-mass spectroscopy.

The phrase "standard peptide coupling reaction conditions" means coupling a carboxylic acid with an amine using an acid activating agent such as EDC, DCC, and BOP in an inert solvent such as dichloromethane in the presence of a catalyst such as HOBT. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., Protective Groups in Organic Synthesis, John Wiley & Sons, Inc., New York, N.Y., 1991. CBZ and BOC are commonly used protecting groups in organic synthesis, and their removal conditions are known to those skilled in the art. For example, CBZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of CBZ groups can also be achieved by treatment with a solution of hydrogen bromide in acetic acid or by treatment with a mixture of TFA and dimethylsulfide. Removal of BOC protecting groups is carried out with a strong acid, such as trifluoroacetic acid, hydrochloric acid, or hydrogen chloride gas, in a solvent such as methylene chloride, methanol, or ethyl acetate.

Abbreviations Used in the Description of the Preparation of the Compounds of the Present Invention: BOC (Boc) is t-butyloxycarbonyl, BOP is benzotriazol-1-yloxytris(dimethylamino)-phosphonium hexafluorophosphate, Bn is benzyl, Bu is butyl, calc. or calc'd is Calculated, celite is Celite™ diatomaceous earth, CBZ (Cbz) is benzyloxycarbonyl, c-hex is cyclohexyl, c-pen is cyclopentyl, c-pro is cyclopropyl, DCC is dicyclohexylcarbodiimide, DEAD is diethyl azodicarboxylate, DIEA is diisopropyl-ethylamine, DMAP is 4-dimethylaminopyridine, DMF is N,N-dimethylformamide, dppf is 1,1'-bis(diphenylphosphino)ferrocene, EDC is 1-ethyl-3-(3-dimethylaminopropyl) carbodiimide, eq is equivalent(s), ES-MS and ESI-MS are electron spray ionmass spectroscopy, Et is ethyl, EtOAc is ethyl acetate, g is gram(s), h or hr is hour(s), HATU is O-(7-azabenzotriazol-1-yl)-N,N,N',N'-tetramethyluronium hexafluorophosphate, HMPA is hexamethyl phosphoramide, HOAc is acetic acid, HOAT is 1-hydroxy-7-azabenzotriazole, HOBt or HOBT is 1-hydroxybenzotriazole, HPLC is high performance liquid chromatography; h, hr and hrs is hours; i-Pr is —CH(CH$_3$)$_2$, LC/MS or LC-MASS is liquid chromatography mass spectrum, LDA is lithium diisopropylamide, CCK-xR is cholecystokinin receptor (x being a number), L is liter, M is molar, Me is methyl, MeOH is methanol, min is minutes, ME is molecular formula, min is minutes, mg is milligram(s), mL is milliliter, mmol is millimole(s), MPLC is medium pressure liquid chromatography, MS is mass spectrum, Ms is methane sulfonyl, MTBE is tert-butyl methyl ether, N is normal, n-Bu is —(CH$_2$)$_3$CH$_3$, n-Hex is —(CH$_2$)$_5$CH$_3$, n-Pent is —(CH$_2$)$_4$—CH$_3$, n-Pr is —(CH$_2$)$_2$CH$_3$, NaHMDS is sodium hexamethyl disilazide, NaOtBu is sodium tert-butoxide, NMM is N-Methylmorpholine, NMO is N-Methylmorpholine-N-oxide, OTf is trifluoromethanesulfonyl, Pd$_2$(dba)$_3$ is tris(dibenzylideneacetone) dipalladium (0), Ph is phenyl, Phe is phenyl alanine, Pr is propyl, i-Pr is isopropyl, prep. is prepared, PyBOP is benzotriazol-1-yloxytripyrrolidine-phosphonium hexafluorophosphate, PyBrop is bromo-tris-pyrrolidino-phosphonium hexafluoro-phosphate, r.t. or rt is room temperature, SCF CO$_2$ S is super critical fluid carbon dioxide, t-Bu is —C(CH$_3$)$_3$, TEA or Et$_3$N is triethylamine, Tf is triflate or trifluoromethanesulfonate, TFA is trifluoroacetic acid, THF is tetrahydrofuran, and TLC is thin-layer chromatography.

Reaction Schemes 1-10 illustrate the methods employed in the synthesis of the compounds of the present invention of formula I, II, III, and IV. All substituents are as defined above unless indicated otherwise.

The synthesis of the novel compounds of formula I, II, III, and IV, which are the subject of this invention may be accomplished by one or more of several similar routes. The compounds of the present invention can be prepared from one such route using diaryl imidazole carboxamides such as those of formula VI and a substituted piperazine such as VII, or a piperidine such as VIII via standard coupling conditions followed by additional modifications. The preparation of these intermediates is described in the following Schemes, wherein X, Y, and R$^1$ to R$^{16}$ are defined above.

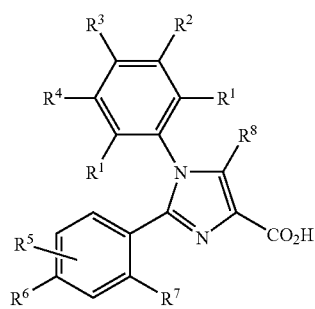

(VI)

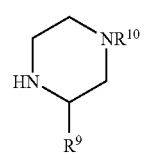

(VII)

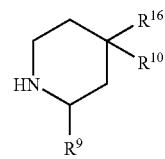

(VIII)

Intermediates of formula VI are known in the literature or may be prepared by a variety of methods familiar to those skilled in the art. One route described in the literature (J. H. M. Lange, et. al. J. Med. Chem. 2005, 48, 1823 and I. K. Khanna, et. al. 3. Med. Chem. 1997, 40, 1634) is illustrated in Scheme 1. Intermediates of formula 1 and 2, which are either commercially available or known in the literature, are treated with a base such as potassium or sodium bis(trimethylsilyl) amide to provide the diaryl amidine 3. Heating amidine 3 with methyl or ethyl bromopyruvate in the presence of a base such as sodium bicarbonate in a solvent, such as 2-propanol, 1,4-dioxane, or tetrahydrofuran, then affords imidazole 4. Subsequent hydrolysis of the ester with, for example, lithium or sodium hydroxide provides acid VI where R$^{1-8}$ are described above.

SCHEME 1

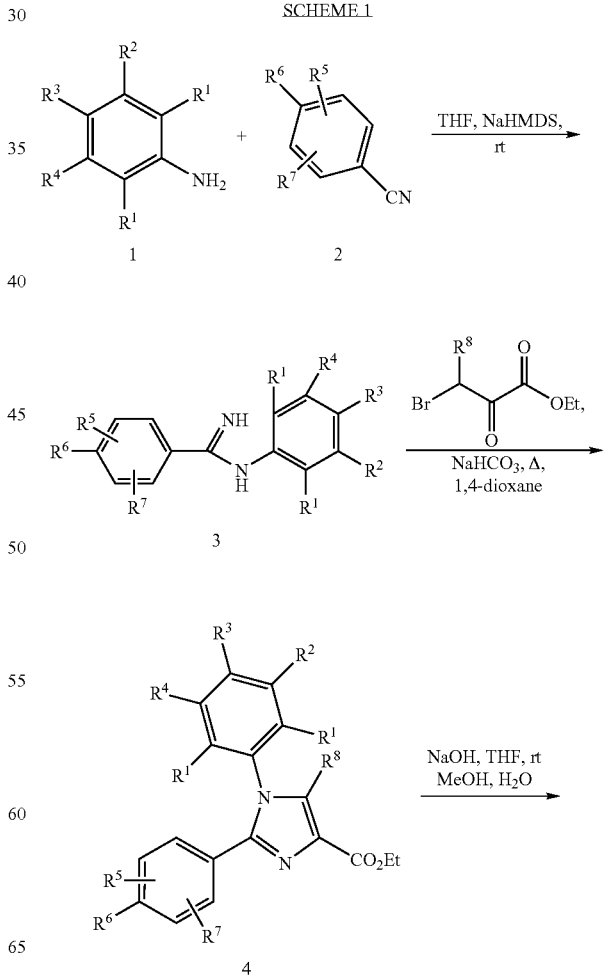

-continued

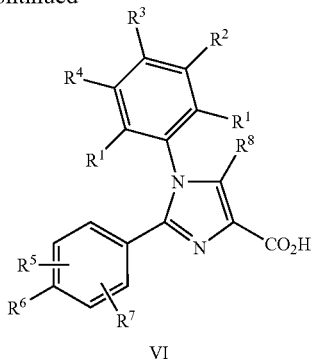

VI

Intermediates VII may be prepared as illustrated in Scheme 2 from intermediates 5 and 6.

Intermediates 5, wherein L is a suitable nitrogen protecting group, such as tert-butoxycarbonyl (Boc), benzyloxycarbonyl (Cbz), and trityl (Tr), are either commercially available or known in the literature. Intermediates 6, wherein X is Cl, Br, I, or triflate and $R^2$ is as defined above, are either commercially available, known in the literature, or prepared by a variety of methods familiar to those skilled in the art. Intermediates 7 may be prepared by heating 5 and 6 together in the presence of a base such as triethylamine or N,N-diisopropylethylamine in solvents such as toluene, N,N-dimethylformamide, or ethylene glycol dimethyl ether according to procedures outlined in L. Toma, et. al. J. Med. Chem. 2002, 45, 4011-4017 and references contained therein. Alternatively, Intermediates 7 may also be prepared by heating 5 and 6 together in the presence of a base such as sodium tert-butoxide, potassium phosphate, or cesium carbonate, in a solvent such as toluene, 1,4-dioxane, or tetrahydrofuran with catalytic amounts of a palladium II source and a trisubstituted phosphine according to procedures outlined in J. P. Wolfe, et. al. J. Org. Chem. 2000, 65, 1144 and J. P. Wolfe, et. al. J. Org. Chem. 2000, 65, 1158. After coupling, racemic Intermediates 7 can be resolved into the pure enantiomers by using chiral chromatography with, for example, a chiralcel AD column or chiralcel OD column using solvent mixtures comprised of ethanol/hexane or 2-propanol/heptane. The L protecting group of 7 is then removed with, for example, trifluoroacetic acid or methanolic hydrogen chloride in the case of Boc to give the desired amine intermediate VII, where $R^9$ and $R^{10}$ are described above.

SCHEME 2

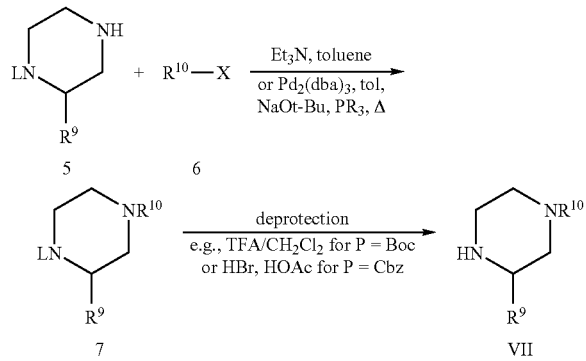

Compound Ia may be prepared as illustrated in Scheme 3 from intermediates VI and VII. Intermediates VI and VII are coupled under standard peptide coupling conditions, for example, using 1-ethyl-3-(3-dimethylaminopropyl)carbodiimide and 1-hydroxybenzotriazole or O-(7-azabenzotriazol-1-yl)-N,N,N',N'-tetramethyluronium hexafluorophosphate and 1-hydroxy-7-azabenzotriazole in the presence of a base such as N,N-diisopropylethylamine or triethylamine in a solvent such as N,N-dimethylformamide or dichloromethane for 3 to 48 hours at ambient temperature to provide compound Ia where $R^1$ to $R^{10}$ are described above. The product is purified from unwanted side products, if necessary, by recrystallization, trituration, preparative thin layer chromatography, flash chromatography on silica gel, such as with a Biotage® apparatus, or HPLC. Compounds that are purified by HPLC may be isolated as the corresponding salt. Purification of intermediates is achieved in the same manner.

Scheme 3

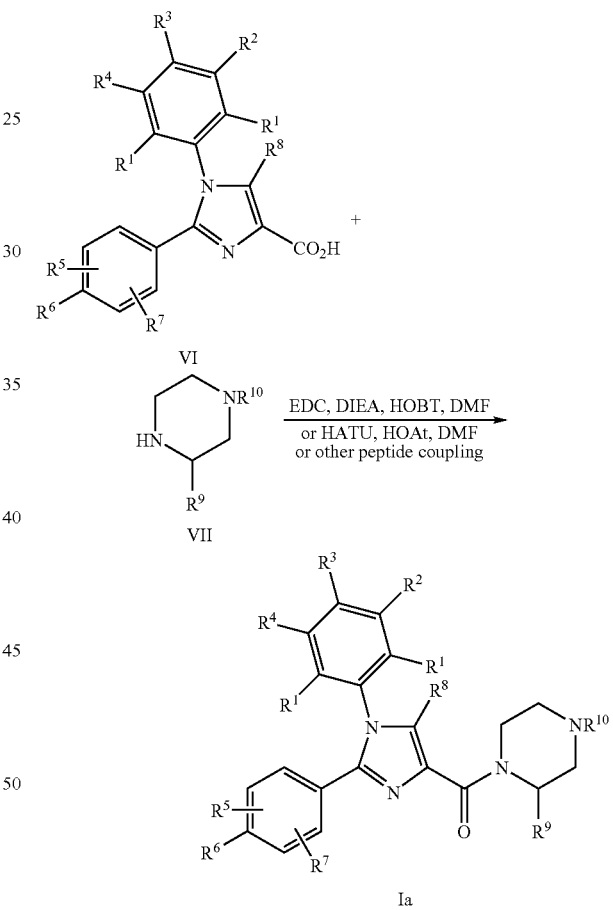

Intermediate VIII may be prepared as illustrated in Scheme 4 from intermediates 8 and 9. Intermediate 8, wherein L is a suitable nitrogen protecting group, such as tert-butoxycarbonyl (Boc), benzyloxycarbonyl (Cbz), and trityl (Tr), is either commercially available, known in the literature, or prepared by a variety of methods familiar to those skilled in the art. Intermediate 9 wherein X is Cl, Br, I, or triflate and $R^{10}$ is as defined above, is either commercially available, known in the literature, or prepared by a variety of methods familiar to those skilled in the art. Intermediate 10 may be prepared by heating 8 and 9 together in the presence of a base such as lithium dicyclohexylamide or lithium diisopropylamide, in a solvent such as toluene with catalytic amounts of a palladium II source and a trisubstituted phosphine such as tri tert-butylphosphine according to procedures outlined in M. Jorgensen, et. al. J. Am. Chem. Soc. 2002, 124, 12557. After coupling, the L protecting group of Intermediate 10 is removed with, for example, trifluoroacetic acid or methanolic hydrogen chloride in the case of Boc to give the desired amine intermediate VIII, where $R^{10}$ is described above.

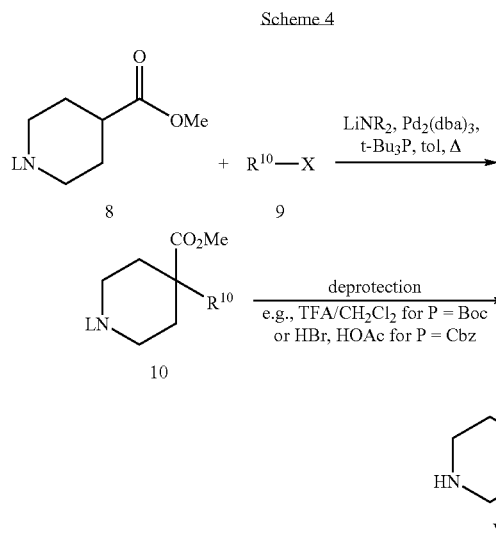

Compounds Ib and Ic may be prepared as illustrated in Scheme 5 from intermediates VI and VIII described above. Intermediates VI and VII are coupled under standard peptide coupling conditions, for example, using methanesulphonyl chloride in the presence of a base such as N-methylimidazole in a solvent such as dichloromethane for 1 to 18 hours at ambient temperature to provide compound Ib. Compound Ib may then be hydrolyzed using, for example, potassium trimethylsilanolate in a solvent such as tetrahydrofuran to afford compound Ic where $R^1$ to $R^{10}$ are described above. The compound Ic is purified from unwanted side products, if necessary, using the methods described above in Scheme 3. Compounds that are purified by HPLC may be isolated as the corresponding salt. Purification of intermediates is achieved in the same manner.

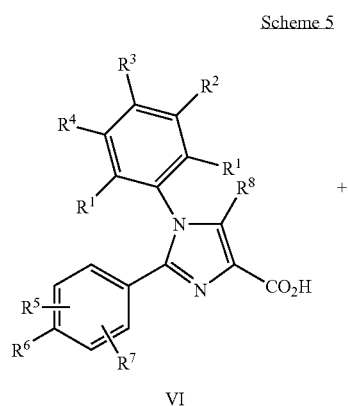

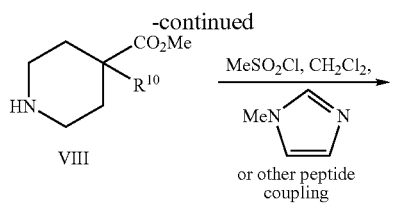

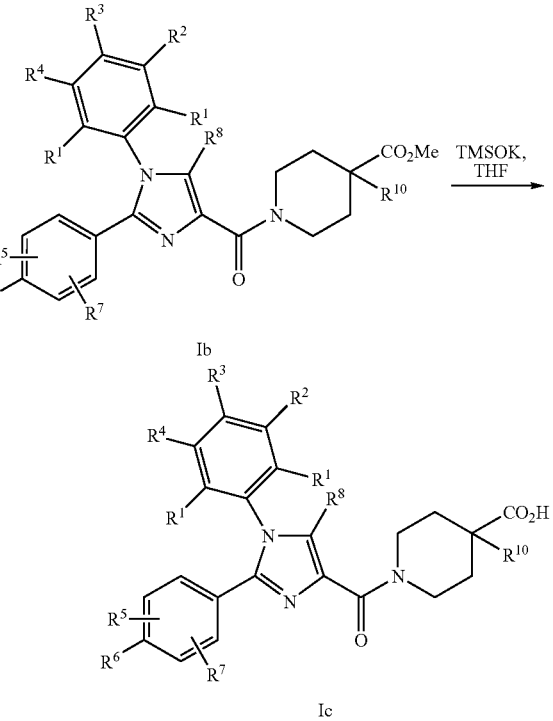

An additional route to product Id is illustrated in Scheme 6. Intermediate 11 wherein L is a suitable nitrogen protecting group such as tert-butoxycarbonyl (Boc), benzyloxycarbonyl (Cbz), and trityl (Tr) are either commercially available or known in the literature. Intermediates VI and 11 are coupled under standard peptide coupling conditions, for example, using methanesulfonyl chloride in the presence of a base such as N-methylimidazole in a solvent such as N,N-dimethylformamide (DMF) or dichloromethane for 1 to 8 hours at ambient temperature to provide compound 12 (Ueki, H.; et. al. J. Org. Chem. 2003, 68, 7104). Next, the methyl ester is reduced using, for example, lithium borohydride in a solvent such as methanol or ethanol to afford alcohol 13. The alcohol 13 can then be protected with, for example, an acetate group by treatment of 13 with acetic anhydride in a solvent such as dichloromethane and a base such as 4-(dimethylamino)-pyridine (DMAP). The nitrogen protecting group of 14 is then removed with, for example, palladium on carbon under a hydrogen atmosphere in methanol in the case of L=Cbz to give the desired amine 15. Compound Id may then be prepared by heating amine 15 and $R^{10}X$ (6) together in the presence of a base such as sodium tert-butoxide, potassium phosphate, or cesium carbonate in a solvent such as toluene, 1,4-dioxane, or tetrahydrofuran with catalytic amounts of a palladium II source and a trisubstituted phosphine according to procedures outlined in J. P. Wolfe, et. al. J. Org. Chem. 2000, 65, 1144 and J. P. Wolfe, et. al. J. Org. Chem. 2000, 65, 1158. The acetate protecting group is then removed with, for example, sodium methoxide in a solvent such as tetrahydrofuran to give the desired alcohol compound Id. The product is purified from unwanted side products, if necessary, using the methods described above in Scheme 3. Compounds that are purified by HPLC may be isolated as the corresponding salt. Purification of intermediates is achieved in the same manner.

Scheme 6

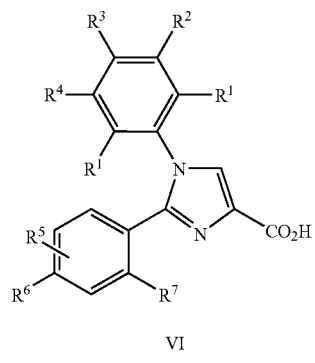

VI

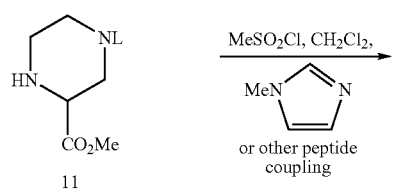

11

MeSO$_2$Cl, CH$_2$Cl$_2$,

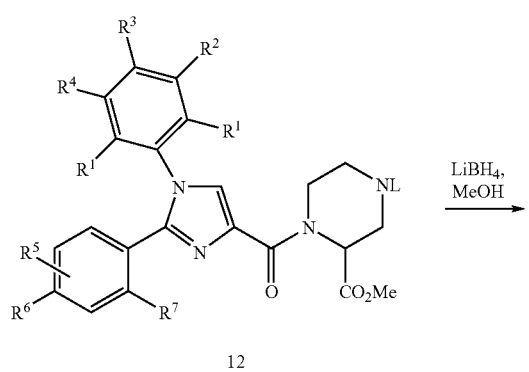

12

LiBH$_4$, MeOH →

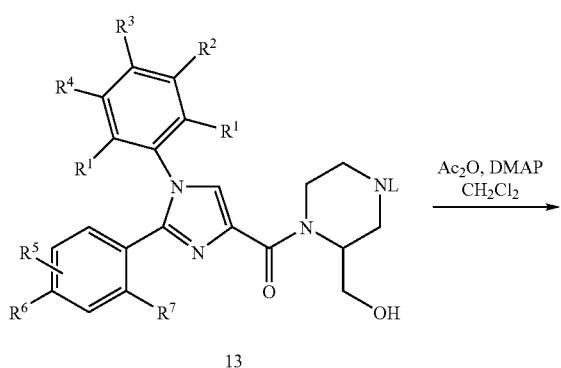

13

Ac$_2$O, DMAP CH$_2$Cl$_2$ →

-continued

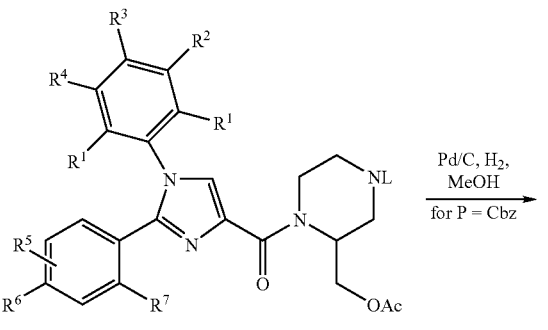

14

Pd/C, H$_2$, MeOH
for P = Cbz →

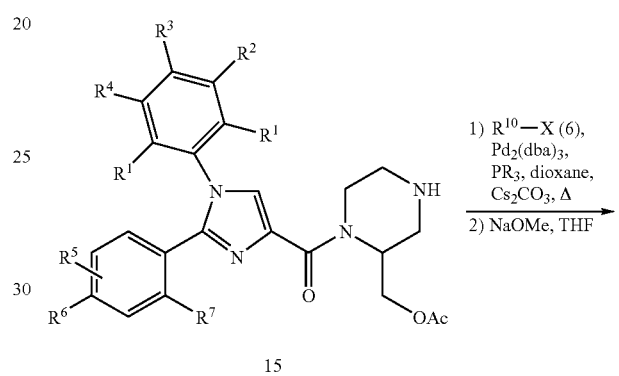

15

1) R$^{10}$—X (6), Pd$_2$(dba)$_3$, PR$_3$, dioxane, Cs$_2$CO$_3$, Δ
2) NaOMe, THF

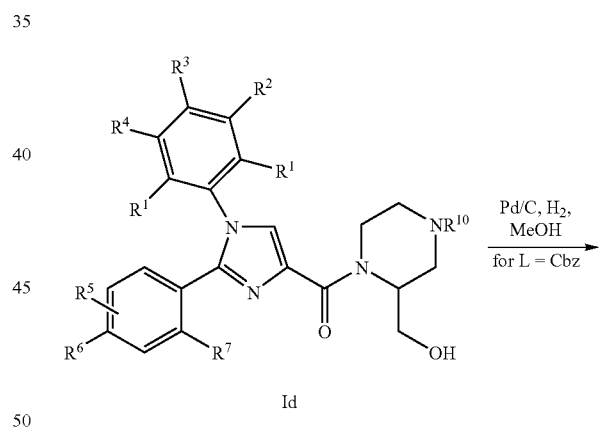

Id

Pd/C, H$_2$, MeOH
for L = Cbz →

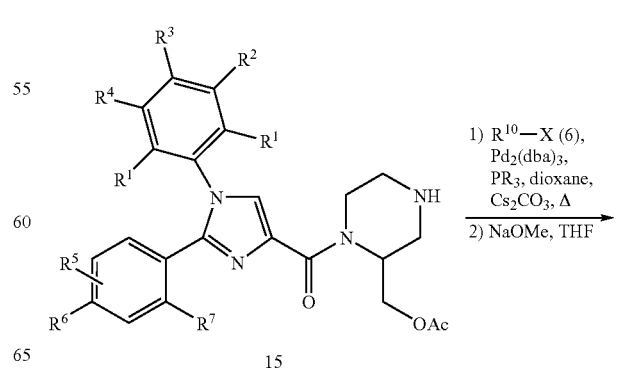

15

1) R$^{10}$—X (6), Pd$_2$(dba)$_3$, PR$_3$, dioxane, Cs$_2$CO$_3$, Δ
2) NaOMe, THF -continued

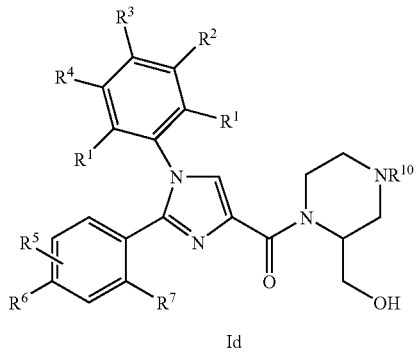

Id

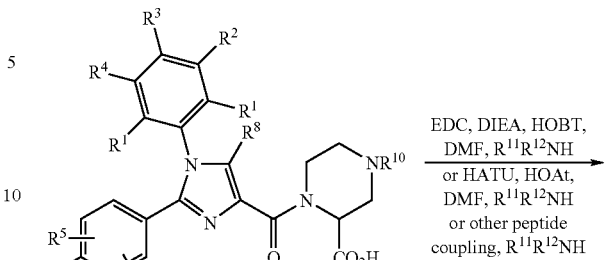

Ie

In some cases the products Ia, Ib, Ic, and Id or the synthetic intermediates illustrated in the above schemes may be further modified, for example, by manipulation of substituents on $R^9$ or $R^{10}$. These manipulations may include, but are not limited to, reduction, oxidation, alkylation, arylation, condensation, acylation, rearrangement, protection, deprotection, substitution, and hydrolysis reactions that are commonly known to those skilled in the art. One such example is illustrated in Scheme 7. Hydrolysis of ester 16 with, for example, lithium or sodium hydroxide provides acid Ie. Further manipulation of Ie was achieved by condensation with amines, under standard peptide coupling conditions, for example, using 1-ethyl-3-(3-dimethylaminopropyl)carbodiimide and 1-hydroxybenzotriazole or O-(7-azabenzotriazol-1-yl)-N,N,N',N'-tetramethyluronium hexafluorophosphate and 1-hydroxy-7-azabenzotriazole in the presence of a base such as N,N-diisopropylethylamine or triethylamine in a solvent such as N,N-dimethylformamide or dichloromethane for 3 to 48 hours at ambient temperature to provide compound If.

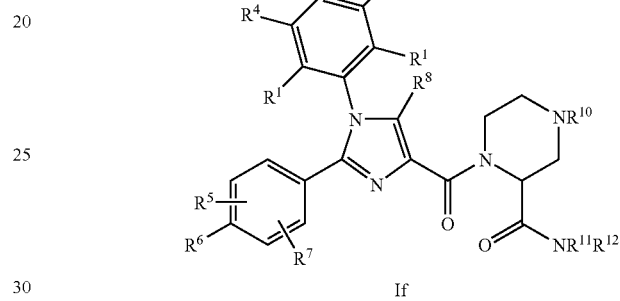

If

Another example of further reactions that may lead to products Ig is illustrated in Scheme 8. Intermediate 17 can be converted to azide 18 by first converting the alcohol to the corresponding mesylate using, for example, methanesulphonyl chloride with N,N-iisopropylethylamine and then treatment of the mesylate with, for example, sodium azide. The azide can then be reduced to the corresponding amine 19 using, for example, hydrogen gas in the presence of a palladium catalyst. Amine 19 can be acylated with, for example, an acid chloride 20 to give amide 21. The methyl ester of 21 can then be hydrolyzed using, for example, lithium or sodium hydroxide in water and tetrahydrofuran to give compound Ig. Amine 19 is a useful intermediate in that it may be acylated with carboxylic acids using, for example, EDC and HOBt or other standard coupling conditions to afford amide 21. Alternatively, amine 19 may be converted to sulphonamides or ureas using standard chemistry via a variety of methods known, to those skilled in the art.

Scheme 7

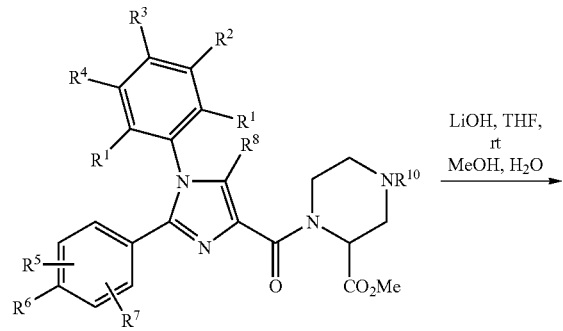

16

Scheme 8

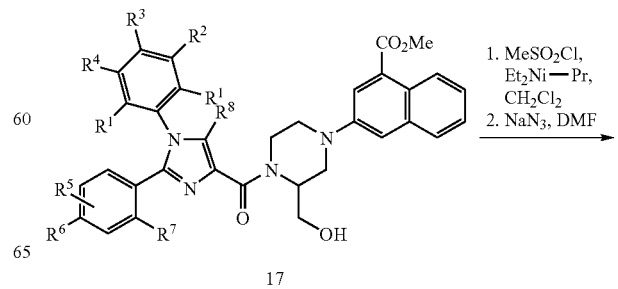

17

-continued

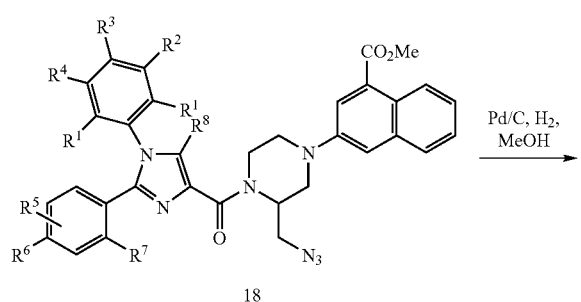

18

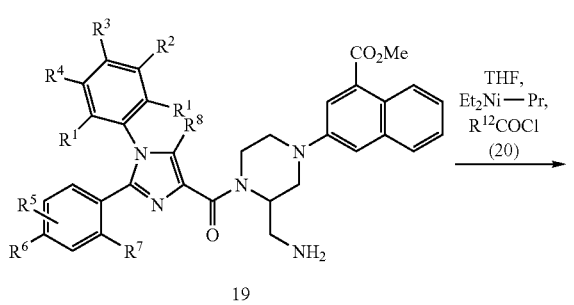

19

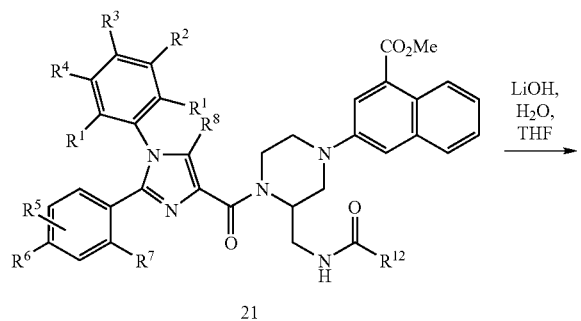

21

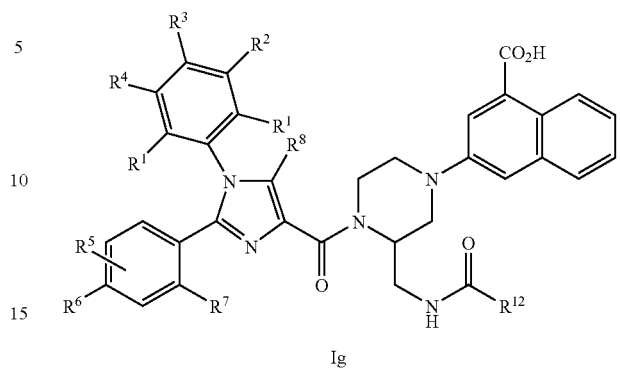

Ig

Another example of further reactions that can lead to products Ih is illustrated in Scheme 9. Piperidine intermediate 22 is synthesized according to methods in Scheme 4 using starting materials that are readily synthesized via a number of methods known to those skilled in the art. Hydrolysis of the methyl ester of 22 to the corresponding acid followed by Curtius rearrangement of the acid and subsequent trapping of the isocyanate intermediate with benzyl alcohol affords the N-carboxybenzyl protected amine 23. The silyl protecting group of 23 may then be removed with, for example, tetrabutylammonium fluoride and the resulting alcohol is oxidized using Dess-Martin's periodinane. This alchohol is further oxidized the corresponding acid using sodium chlorite and the acid is then converted to methyl ester 24. Deprotection of the piperazine nitrogen of 24 is achieved using, for example, trifluoroacetic acid in dichloromethane and the resulting amine is then coupled to acid VI using standard amide bond coupling conditions such as EDC with HOBt to afford compound 25. Deprotection of the N-carboxybenzyl group of 25 to afford the primary amine 26 is then achieved using, for example, hydrogen gas in the presence of a catalyst such as palladium hydroxide or palladium on carbon in a solvent such as methanol. Acylation of amine 26 with acid 27 can then be achieved using standard amide bond forming reaction conditions such as EDC with HOBt in the presence of a base such as N,N-diisopropylethylamine in a solvent such as N,N-dimethylformamide or dichloromethane. The resulting coupled compound is then converted to the desired acid Ih via treatment with, for example, potassium trimethylsilanolate or aqueous lithium hydroxide in solvents such as tetrahydrofuran.

Scheme 9

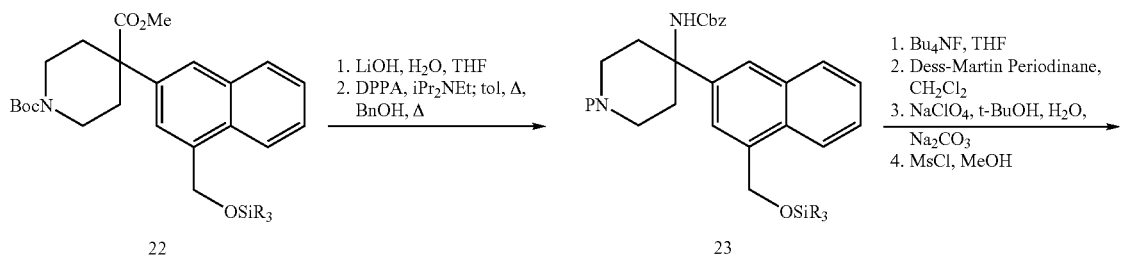

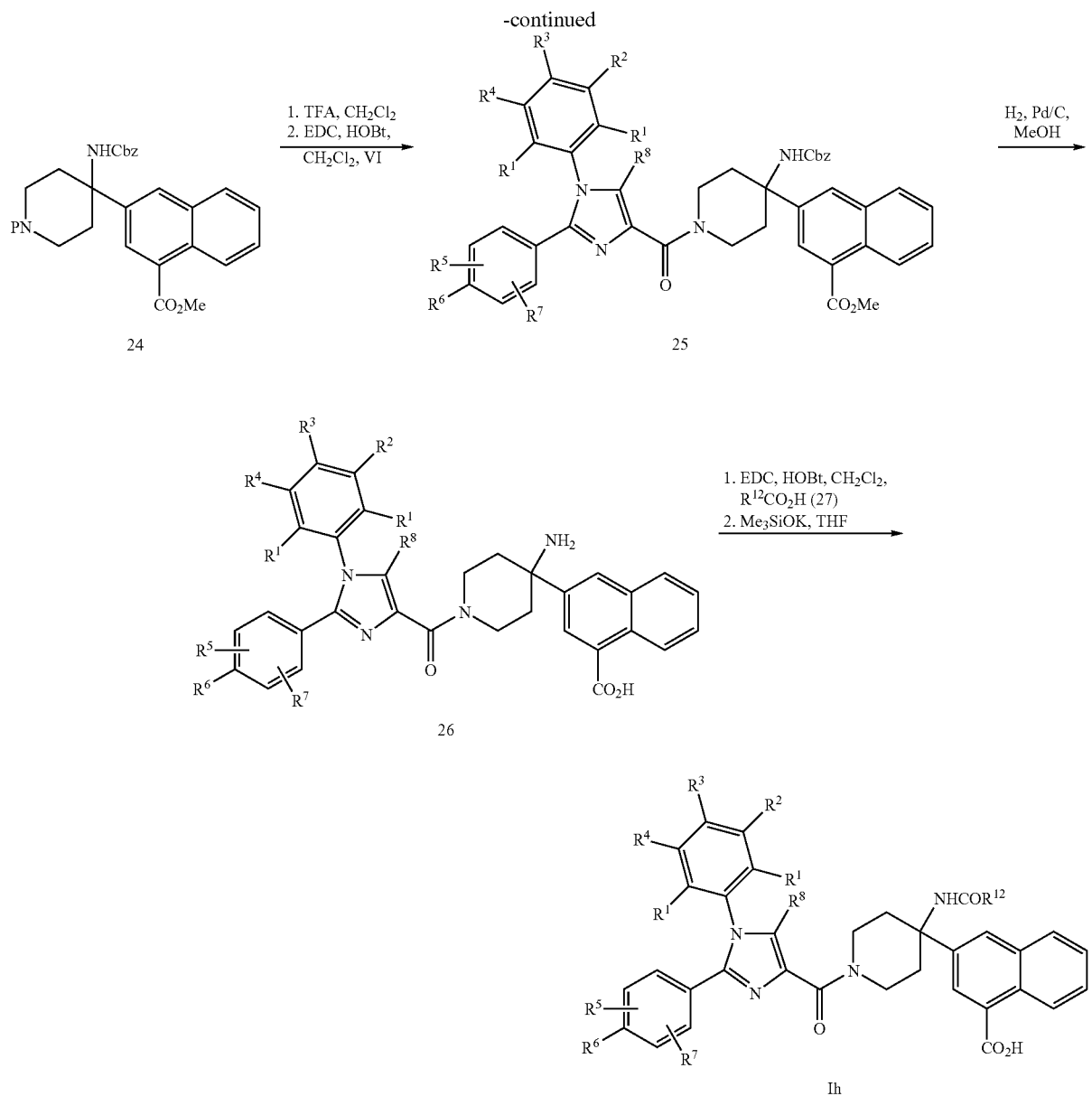

Yet another example of further reactions that may lead to products such as Ii is illustrated in Scheme 10. Piperidine 28 can be synthesized via a number of methods known to those skilled in the art. The ester of piperidine 28 can be converted to aldehyde 29 by removal of the tert-butyl group from the ester followed by treatment of the corresponding acid with borane in tetrahydrofuran. The resulting aldehyde 29 can then be homologated using any of a number of methods known to those skilled in the art. One such method involves treatment of aldehyde 29 with a Horner Emmons phosphonate reagent in the presence of a base such as n-butyl lithium in a solvent such as tetrahydrofuran. Hydrogenation of the resulting olefin also results in deprotection of the piperazine nitrogen to afford intermediate 30. Compound 30 can then be coupled to intermediate VI and the methyl ester hydrolyzed to the corresponding carboxylic acid Ii using standard procedures described in the above schemes.

Scheme 10

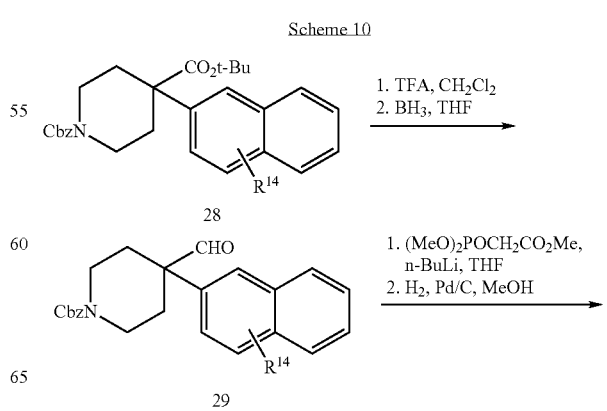

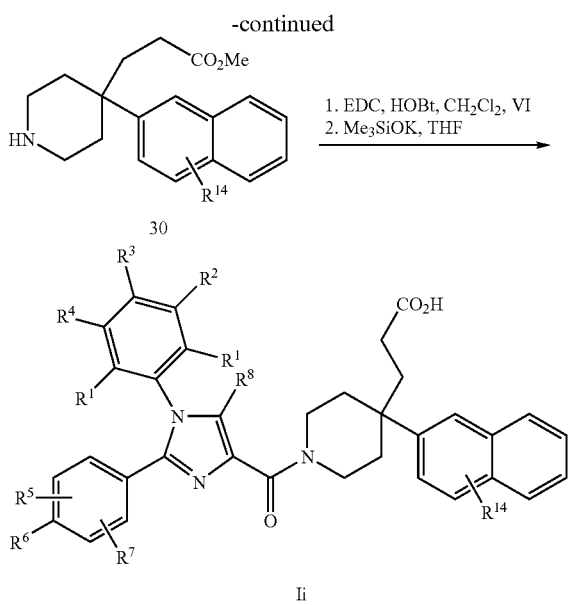

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

INTERMEDIATE 1

1-(3-Ethoxyphenyl)-2-(4-methylphenyl)-1H-imidazole-4-carboxylic acid

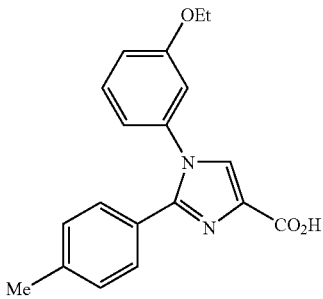

Step A: N-(3-Ethoxyphenyl)-4-methylbenzenecarboxamidine To a solution of 2.2 ml (4.4 mmol) of 2.0 M (in tetrahydrofuran) sodium bis(trimethylsilyl)amide in 5.0 mL of tetrahydrofuran at ambient temperature was added 0.52 mL (4.0 mmol) of 3-ethoxyaniline and the resulting solution was stirred for 20 min. To this reaction mixture was slowly added a solution of 0.47 g (4.0 mmol) of p-tolunitrile in 2.0 mL of tetrahydrofuran. The resulting mixture was stirred at ambient temperature for 5 hrs and then poured into brine (25 mL) and dichloromethane (50 mL). The organic layer was separated, and the aqueous layer was extracted with dichloromethane (25 mL). The combined organic layers were dried over sodium sulfate, filtered and concentrated in vacuo to yield the title compound as yellow solid, which was used without further purification. LC/MS 255.2 (M+1).

Step B: Ethyl 1-(3-ethoxyphenyl)-2-(4-methylphenyl)-1H-imidazole-4-carboxylate To a mixture of 1.1 g (4.0 mmol) of the compound from Step A and 0.80 g (9.5 mmol) of sodium bicarbonate in 10 mL of 1,4-dioxane was added 0.60 mL (4.8 mmol) of ethyl bromopyruvate. The reaction mixture was refluxed overnight. After cooling to room temperature, the solid was filtered off and the filtrate was concentrated in vacuo. Flash chromatography on a Biotage Horizon® system (silica gel, 5 to 40% ethyl acetate in hexanes gradient then 40% ethyl acetate in hexanes) gave the title compound as a yellow oil. LC/MS 351.2 (M+1).

Step C: 1-(3-Ethoxyphenyl)-2-(4-methylphenyl)-1H-imidazole-4-carboxylic acid To a solution of 0.75 g (2.1 mmol) of ethyl 1-(3-ethoxyphenyl)-2-(4-methylphenyl)-1H-imidazole-4-carboxylate from Step B in 10 mL of tetrahydrofuran, 5 mL of water and 5 mL of methanol was added 0.80 mL (4.0 mmol) of 5.0 M NaOH solution. The reaction mixture was stirred at ambient temperature overnight. Then hydrochloric acid (2.0 M) was added to neutralize the reaction mixture. After removal of the organic solvents in vacuo, dichloromethane (20 mL) was added and the organic layer was separated. The aqueous layer was extracted with dichloromethane (10 mL), and the combined organic layers were dried over sodium sulfate, filtered and concentrated in vacuo to yield the title compound as a yellow foam. LC/MS 323.3 (M+1).

INTERMEDIATE 2

1-(3-Ethoxyphenyl)-2-(2-fluoro-4-methylphenyl)-1H-imidazole-4-carboxylic acid

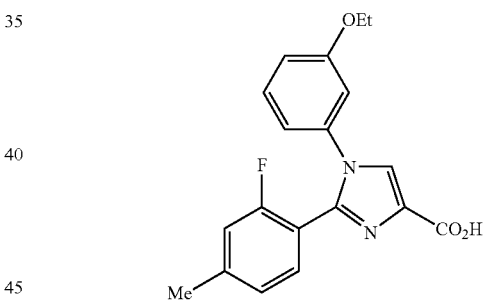

Step A: N-(3-Ethoxyphenyl)-2-fluoro-4-methylbenzenecarboximidamide To a solution of 2.2 ml (4.4 mmol) of 2.0 M (in tetrahydrofuran) sodium bis(trimethylsilyl)amide in 10 mL of tetrahydrofuran at ambient temperature was added 0.52 mL (4.0 mmol) of 3-ethoxyaniline and the resulting solution was stirred for 20 min. To this reaction mixture was added 0.54 g (4.0 mmol) of 4-fluoro-4-methylbenzonitrile. The resulting mixture was stirred at ambient temperature for 3 hrs and then poured into brine (25 mL) and dichloromethane (50 mL). The organic layer was separated and the aqueous layer was extracted with dichloromethane (25 mL). The combined organic layers were dried over sodium sulfate, filtered and concentrated in vacuo to yield the title compound as a pale green solid which was used without further purification. LC/MS 273.2 (M+1).

Step B: Ethyl 1-(3-ethoxyphenyl)-2-(2-fluoro-4-methylphenyl)-1H-imidazole-4-carboxylate To a mixture of the compound from Step A and 0.80 g (9.5 mmol) of sodium bicarbonate in 10 mL of 1,4-dioxane was added 0.60 mL (4.8 mmol) of ethyl bromopyruvate. The reaction mixture was refluxed overnight. After cooling to room temperature, the solid was filtered off and the filtrate was concentrated in vacuo. Flash chromatography on a Biotage Horizon® system (silica gel, 0 to 50% ethyl acetate in hexanes gradient) gave the title compound as a viscous yellow oil.

LC/MS 369.2 (M+1).

Step C: 1-(3-Ethoxyphenyl)-2-(2-fluoro-4-methylphenyl)-1H-imidazole-4-carboxylic acid To a solution of 0.81 g (2.2 mmol) of ethyl 1-(3-ethoxyphenyl)-2-(2-fluoro-4-methylphenyl)-1H-imidazole-4-carboxylate from Step B in 10 mL of tetrahydrofuran, 5 mL of water and 5 mL of methanol was added 1.0 mL (5.0 mmol) of 5.0 M NaOH solution. The reaction mixture was stirred at ambient temperature overnight. Hydrochloric acid (2.0 M) was then added to neutralize the reaction mixture. After removal of the organic solvents in vacuo, dichloromethane (20 mL) was added and the organic layer was separated. The aqueous layer was extracted with dichloromethane (10 mL), and the combined organic layers were dried over sodium sulfate, filtered and concentrated in vacuo to yield the title compound as a yellow foam. LC/MS 341.1 (M+1).

INTERMEDIATE 3

Methyl 4-(3-quinolinyl)-2-piperazinecarboxylate, trifluoroacetic acid salt

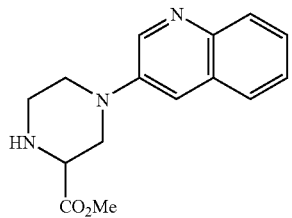

Step A: 1-tert-Butyl 2-methyl 4-quinolin-3-ylpiperazine-1,2-dicarboxylate To a solution of 3.50 g (14.3 mmol) 1-tert-butyl 2-methyl piperazine-1,2-dicarboxylate in 150 mL anhydrous toluene was added 1.62 mL (11.9 mmol) of 3-bromoquinoline. The resulting solution was purged with nitrogen gas for 15 min, and then purged under vacuum for 5 min. Next, 1.59 g (17.6 mmol) of sodium tert-butoxide was added, and the system was again purged for 2 min under vacuum. To this solution were added 444 mg (0.714 mmol) of (±)-2,2'-bis(diphenylphosphino)-1,1'-binaphthalene and 342 mg (0.595 mmol) of bis(dibenzylideneacetone)palladium, and the system was purged one last time for 2 min under vacuum. The mixture was then heated under nitrogen to 95° C. for 3.5 h, taken up in anhydrous diethyl ether, and filtered through a plug of Celite®. The filtrate was concentrated in vacuo to yield a red solid, which was purified using a Biotage Horizon® system (30% ethyl acetate/hexanes mixture) to give the title compound as a racemic mixture. Chiral HPLC separation (Chiralcel AD, 60% 2-propanol/heptane) afforded the R enantiomer (first eluting) and the S enantiomer (second eluting), each in ≧99% ee. For the S enantiomer, $^1$H NMR (CDCl$_3$): δ 8.75 (d, J=2.1 Hz, 1H), 7.99 (d, J=8.2 Hz, 1 H), 7.68 (dd, J=6.9, 1.1 Hz, 1H), 7.53 (ddd, J=8.7, 7.1, 1.6 Hz, 1 H), 7.48 (td, J=8.2, 1.3 Hz, 1 H) 7.36 (d, J=2.5 Hz, 1 H), 4.96 (s, 0.55 H) 4.78 (s, 0.45 H), 4.11 (d, J=7.1, 0.55 H), 4.01 (d, J=13.0 Hz, 0.45 H), 3.80 (d, J=8.0 Hz, 3 H), 3.57 (m, 1 H), 3.44 (t, J=9.4 Hz, 0.55 H), 3.32 (t, J=9.6 Hz, 0.45 H), 3.04 (m, 1 H), 2.89 (q, J=8.6 Hz, 1H) 1.52 (s, 5 H), 1.48 (s, 4 H). LC/MS 372.3 (M+1).

Step B: Methyl 4-(3-quinolinyl)-2-piperazinecarboxylate, trifluoroacetic acid salt To 1.16 g (3.12 mmol) of the S enantiomer from Step A was added 30 mL dichloromethane and 3 mL trifluoroacetic acid. When the reaction was complete by LC-MS (18 h), the solution was concentrated in vacuo and triturated with ethyl ether and filtered to give the title compound as a yellow solid. $^1$H NMR (CD$_3$OD): δ 9.1 (d, J=2.7 Hz, 1 H), 8.37 (d, J=2.5 Hz, 1 H), 8.07 (d, J=8.4 Hz, 2 H), 7.84 (ddd, J=8.3, 7.1, 1.2 Hz, 1 H), 7.77 (t, J=7.5 Hz, 1 H), 4.57 (dd, J=9.1, 3.7 Hz, 1 H), 4.21 (dd, J=9.8, 3.7 Hz, 1 H) 3.92 (t, J=9.5 Hz, 1 H), 3.92 (s, 3 H), 3.66 (m, 2 H), 3.47 (m, 2 H). LC/MS 272.3 (M+1).

INTERMEDIATE 4

((2R)-1-{[1-(3-Ethoxyphenyl)-2-(4-methylphenyl)-1H-imidazol-4-yl]carbonyl}-piperazin-2-yl)methyl acetate

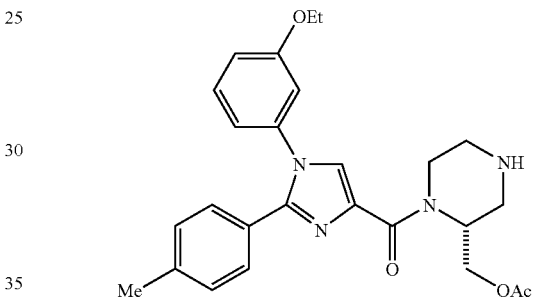

Step A: 1-Benzyl 3-methyl (3R)-4-{[1-(3-ethoxyphenyl)-2-(4-methylphenyl)-1H-imidazol-4-yl]carbonyl}piperazine-1,3-dicarboxylate To a solution of 3.18 g (9.88 mmol) of Intermediate 1 in 75 mL of anhydrous dichloromethane at 0° C. was added 1.5 mL (19 mmol) of 1-methylimidazole followed by 0.80 mL (9.9 mmol) of methanesulfonyl chloride. The resulting mixture was stirred with gradual warming to ambient temperature over 20 min, then re-cooled to 0° C. A solution of 2.39 g (8.59 mmol) of 1-benzyl 3-methyl-(3R)-piperazine-1,3-dicarboxylate in 25 mL of anhydrous dichloromethane was then added and the reaction mixture was allowed to warm to ambient temperature over 1 h. The reaction was then quenched with a saturated aqueous ammonium chloride solution (25 mL) and the layers were separated. The aqueous layer was extracted with dichloromethane (2×100 mL) and the combined organic layers were washed with brine (50 mL), dried over magnesium sulfate, filtered and concentrated in vacuo. The crude residue was purified on a Biotage® purification apparatus (silica gel, 40 to 50% ethyl acetate in hexanes gradient) to yield the title compound as a colorless solid. LC/MS 583.5 (M+1).

Step B: Benzyl (3R)-4-{[1-(3-ethoxyphenyl)-2-(4-methylphenyl)-1H-imidazol-4-yl]carbonyl}-3-(hydroxymethyl)piperazine-1-carboxylate To a solution of 4.10 g (7.04 mmol) of 1-benzyl 3-methyl (3R)-4-{[1-(3-ethoxyphenyl)-2-(4-methylphenyl)-1H-imidazol-4-yl]carbonyl}piperazine-1,3-dicarboxylate from Step A in 75 mL of anhydrous methanol at 0° C. under a nitrogen atmosphere was added 460 mg (21.1 mmol) of lithium borohydride. An additional 460 mg (21.1 mmol) of lithium borohydride was added to the reaction mixture every hour for 3 hours and stirred for one hour after the final addition. The reaction was quenched with a saturated aqueous ammonium chloride solution (50 mL) followed by concentration in vacuo to remove the methanol. The residue was diluted with water (15 mL) and extracted with dichloromethane (2×75 mL). The combined organic layers were washed with brine (50 mL), dried over magnesium sulfate, filtered and concentrated in vacuo. The crude residue was purified on a Biotage® purification apparatus (silica gel, 65% ethyl acetate in hexanes) to yield the title compound as a colorless solid. LC/MS 555.2 (M+1).

Step, C: Benzyl (3R)-3-[(acetyloxy)methyl]-4-{[1-(3-ethoxyphenyl)-2-(4-methylphenyl)-1H-imidazol-4-yl]carbonyl}piperazine-1-carboxylate To a stirred solution of 3.40 g (6.13 mmol) of benzyl (3R)-4-{[1-(3-ethoxyphenyl)-2-(4-methylphenyl)-1H-imidazol-4-yl]carbonyl}-3-(hydroxymethyl)-piperazine-1-carboxylate from Step B in 60 mL of anhydrous dichloromethane was added 2.30 mL (13.4 mmol) of N,N-diisopropylethylamine, 1.20 ml (12.2 mmol) of acetic anhydride and 4.0 mg (0.30 mmol) of 4-(dimethylamino)-pyridine. The resulting solution was stirred at ambient temperature overnight, quenched with a saturated aqueous ammonium chloride solution (20 mL). The aqueous layer was separated and extracted with dichloromethane (2×75 mL), and the combined organic layers were washed with brine (50 mL), dried over magnesium sulfate, filtered and concentrated in vacuo. The resulting crude residue was purified on a Biotage® purification apparatus (silica gel, 50 to 75% ethyl acetate in hexanes gradient) to yield the title compound as a colorless foam. LC/MS 597.2 (M+1).

Step D: ((2R)-1-{[1-(3-Ethoxyphenyl)-2-(4-methylphenyl)-1H-imidazol-4-yl]carbonyl}piperazin-2-yl)methyl acetate To 350 mg (0.330 mmol) of 10% palladium on carbon was added a solution of 3.55 g (5.95 mmol) of benzyl (3R)-3-[(acetyloxy)methyl]-4-{[1-(3-ethoxyphenyl)-2-(4-methylphenyl)-1H-imidazol-4-yl]carbonyl}piperazine-1-carboxylate from Step C in 50 mL of anhydrous methanol. The resulting suspension was agitated under an atmosphere of hydrogen at 40 psi for 2 hours then filtered through a plug of Celite®. The plug was washed with methanol (75 mL), and the combined filtrates were concentrated in vacuo to yield the title compound as a colorless foam, which was used without further purification. $^1$H NMR (DMSO-$d_6$): δ 7.85 (s, 1 H), 7.33 (t, J=8.2 Hz, 1 H), 7.21 (d, J=8.5 Hz, 2 H), 7.13 (d, J=8.5 Hz, 2 H), 6.98-7.00 (m, 1 H), 6.92 (s, 1 H), 6.77-6.79 (m, 1 H), 4.68-5.81 (m, 2 H), 4.18-4.59 (m, 3 H), 4.00 (q, J=6.8 Hz, 2 H), 2.72-3.02 (m, 4 H), 2.57-2.62 (m, 1 H), 2.27 (s, 3 H), 1.78-2.00 (m, 3 H), 1.27 (t, J=6.8 Hz, 3 H). LC/MS 463.5 (M+1).

INTERMEDIATE 5

Methyl 3-bromo-1-naphthoate

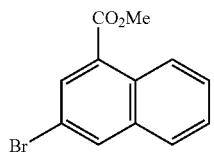

Step A: Methyl 3-nitro-1-naphthoate To a suspension of 22.0 g (0.101 mol) of 3-nitro-1-napthalene-carboxylic acid prepared according to procedures in Duffy, K. J., et al., in J. Med. Chem. 2001, 44, 3730-3745) in 1 L of anhydrous dichloromethane at 0° C. under an atmosphere of nitrogen was added 9.8 mL (0.11 mol) of oxalyl chloride followed by 0.80 mL (10 mmol) of anhydrous N,N-dimethylformamide. The reaction mixture was allowed to gradually warm to ambient temperature for 3 h until gas evolution ceased, and the resulting homogeneous solution was concentrated in vacuo to remove all volatiles. The residue was then dissolved in 1 L of anhydrous dichloromethane and 20 mL (0.51 mol) of anhydrous methanol was added. After stirring for 1 h, the reaction was carefully quenched with a saturated aqueous sodium bicarbonate solution (500 mL). The organic layer was separated and the aqueous layer was extracted with dichloromethane (2×250 mL). The combined organic layers were washed with brine (300 mL), dried over magnesium sulfate, filtered and concentrated in vacuo to yield the title compound as a pale yellow solid which was used without further purification. LC/MS 232.2 (M+1).

Step B: Methyl 3-amino-1-naphthoate To 1.15 g (1.08 mmol) of 10% palladium on carbon was added a suspension of 11.6 g (50.0 mmol) of methyl 3-nitro-1-naphthoate from Step A in 150 mL of anhydrous ethanol and 40 ml of anhydrous dichloromethane. The resulting suspension was agitated under an atmosphere of hydrogen at 40 psi for 3 h during which time all solids dissolved. The reaction mixture was filtered through a plug of Celite®, which was subsequently washed with dichloromethane (300 mL). The combined filtrates were concentrated in vacuo to yield the title compound as a pale green gum, which was used without further purification.

LC/MS 202.1 (M+1).

Step C: Methyl 3-bromo-1-naphthoate A solution of 4.34 g (62.9 mmol) of sodium nitrite in 40 mL of water was added dropwise to a 0° C. solution of 11.5 g (57.2 mmol) of methyl 3-amino-1-naphthoate from Step B in 300 mL of ethanol and 60 mL of 48% aqueous hydrobromic acid while maintaining an internal reaction temperature below 10° C. The resulting dark red reaction mixture was stirred at 0° C. for an additional 30 min. The cooled (0° C.) reaction mixture was then added over 20 min to a suspension of 8.21 g (57.2 mmol) of cuprous bromide in 60 mL of ethanol and 60 mL of 48% aqueous hydrobromic acid heated to 95° C. After stirring for 30 min the reaction mixture was cooled to 0° C. and carefully partitioned between ethyl ether (250 mL) and water (600 mL). The organic layer was separated and the aqueous layer was extracted with ethyl ether (2×300 mL). The combined organic layers were washed with brine (100 mL), dried over magnesium sulfate, filtered and concentrated in vacuo. The residue was passed through a plug of silica gel eluting with 30% dichloromethane in hexanes and the filtrate concentrated in vacuo. Flash chromatography on a Biotage® purification apparatus (silica gel, 7% dichloromethane/hexanes) yielded the title compound as a colorless solid. $^1$H NMR (DMSO-$d_6$): δ 8.67 (d, J=8.4 Hz, 1 H), 8.50 (s, 1 H), 8.15 (s, 1 H), 8.02 (d, J=8.0 Hz, 1 H), 7.68-7.71 (m, 1 H), 7.63-7.66 (t, J=7.6 Hz, 1 H), 3.94 (s, 3 H). LC/MS 265.0 (M+1) and 267.0 (M+3).

INTERMEDIATE 6

Methyl 3-{(3S)-3-[(isoprolylamino)carbonyl]-1-piperazinyl}-1-naphthoate

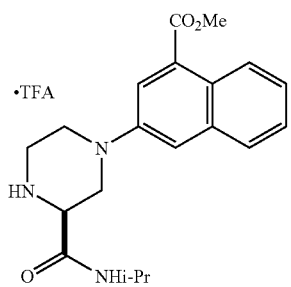

Step A: 4-Benzyl 1-tert-butyl 2-[(isopropylamino)carbonyl]piperazine-1,4-dicarboxylate To 200 mg (0.549 mmol) of 4-[(benzoyloxy)carbonyl]-1-(tert-butoxycarbonyl)piperazine-2-carboxylic acid in 5 mL of anhydrous dichloromethane at 0° C. was added 0.042 mL (0.55 mmol) of methanesulfonyl chloride and 0.110 mL (1.37 mmol) 1-methylimidazole. The reaction was allowed to stir under nitrogen for 30 min prior to the addition of 0.042 mL (0.49 mmol) of isopropylamine, and the reaction mixture was next allowed to warm to room temperature. The mixture was then poured into saturated sodium bicarbonate (10 mL) and extracted with dichloromethane (2×5 mL). The combined organic layers were washed with brine (10 mL) and dried with magnesium sulfate. The mixture was concentrated in vacuo to give a yellow oil, and carried forward without purification. LC/MS 406.2 (M+1).

Step B: tert-Butyl 2-[(isopropylamino)carbonyl]piperazine-1-carboxylate To 220 mg (0.54 mmol) of the product from Step A was added 15 mL methanol and nitrogen was bubbled through the solution for 15 min. Next, 40 mg of palladium (10% on carbon) was added, and the system was again purged with nitrogen. Next, the flask was carefully purged with hydrogen and the reaction mixture was allowed to stir for 45 min at room temperature under 1 atm of hydrogen gas until the reaction was complete by LC-MS. After purging the system with nitrogen, the solution was carefully filtered through a Celite® plug to remove the palladium and then rinsed with methanol (100 mL), and the filtrate was concentrated in vacuo to yield a pale yellow solid. $^1$H NMR (DMSO-$d_6$): δ 4.35 (br s, 1 H), 4.00 (q, J=6.4 Hz, 1 H), 3.77 (d, J=3.0 Hz, 1 H), 3.72 (s, 1 H), 3.23 (dt, J=9.3 Hz, 3.0 Hz, 1 H), 2.92 (br, 1 H), 2.86 (d, J=10 Hz, 1 H), 2.63 (t, J=11.2 Hz, 1 H), 1.45 (s, 9 H), 1.17 (m, 6 H). LC/MS 272.1 (M+1).

Step C: tert-Butyl (2S)-2-[(isopropylamino)carbonyl]-4-[4-methoxycarbonyl)-2-naphthyl]piperazine-1-carboxylate To 162 mg (0.597 mmol) of the compound from step B and 191 mg (0.597 mmol) of Intermediate 5 was added 6 mL anhydrous 1,4-dioxane. The system was purged for 5 min and then flushed with nitrogen. Next, 291 mg (0.895 mmol) of cesium carbonate was added to the flask, and the system was again purged for 5 min with nitrogen, and then flushed with nitrogen. Next, 28 mg (0.070 mmol) of 2-dicyclohexylphosphino-2'(N,N-dimethylamino)biphenyl, and 7 mg (0.01 mmol) of bis(dibenzylideneacetone)palladium were added, and the system was again purged with nitrogen. Finally the reaction mixture was heated at 85° C. under nitrogen for 24 h. After cooling to room temperature, the solution was filtered through Celite® and concentrated in vacuo to yield an orange oil, which was purified using a Biotage Horizon® system (15%-40% ethyl acetate in hexanes gradient) to give the title compound as a racemic mixture. Chiral HPLC separation (Chiralcel AD, 20% 2-propanol/heptane) afforded the R enantiomer (first eluting) and the S enantiomer (second eluting), each in ≧99% ee. For the S enantiomer: $^1$H NMR (CD$_3$OD): δ 8.63 (d, J=8.7 Hz, 1 H), 7.91 (s, 1 H), 7.88 (d, J=8.0 Hz, 1 H), 7.76 (d, J=8.0 Hz, 1 H), 7.42 (t, J=5.5 Hz, 1 H), 7.37 (t, J=7.4 Hz, 2 H), 4.56 (s, br, 2 H), 4.20 (br, 1 H), 3.99 (m, 2 H), 3.96 (s, 3 H), 3.67 (br, 1 H), 3.60 (t, J=2.9 Hz, 1 H), 3.19 (br, 2 H), 2.94 (s, 1 H), 1.48 (s, 9 H), 1.16 (d, J=6.6 Hz, 6 H).

LC/MS 456.1 (M+1).

Step D: Methyl 3-{(3S)-3-[(isopropylamino)carbonyl]-1-piperazinyl}-1-naphthoate To 96 mg (0.21 mmol) of the S enantiomer from Step C was added 5 mL dichloromethane and 0.5 mL trifluoroacetic acid. When the reaction was complete by LC-MS (1 h), the solution was concentrated in vacuo. The reddish oil was next triturated with ethyl ether (3 mL), and filtered to give the title compound as a beige solid. LC/MS 356.1 (M+1).

INTERMEDIATE 7

[(3-Bromo-1-naphthyl)methoxy](triisopropyl)silane

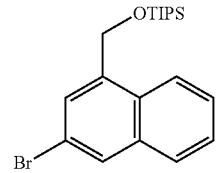

Step A: (3-Bromo-1-naphthyl)methanol To a solution of 5.10 g (19.2 mmol) of Intermediate 5 in 20 mL of anhydrous tetrahydrofuran at −78° C. under an atmosphere of nitrogen was added 48 mL (48 mmol) of a 1.0 M solution of diisobutylaluminum hydride in toluene. The resulting solution was allowed to gradually warm to 0° C. over 90 min and quenched with a saturated aqueous solution of potassium sodium tartrate (25 mL). The resulting suspension was vigorously stirred with gradual warming to ambient temperature over 2 h and the layers separated. The aqueous layer was extracted with ethyl acetate (3×20 mL) and the combined organic layers were washed with brine (30 mL), dried over magnesium sulfate, filtered and concentrated in vacuo to afford the title compound as a white solid which was used without further purification LC/MS 237.0 (M+1) and 239.0 (M+3).

Step B: [(3-Bromo-1-naphthyl)methoxy](triisopropyl)silane To a solution of 4.56 g (19.2 mmol) of (3-bromo-1-naphthyl)methanol from Step A in 10 mL of anhydrous N,N-dimethylformamide was added 2.88 g (42.3 mmol) of imidazole, 117 mg (0.962 mmol) of 4-(dimethylamino)pyridine and 4.5 mL (21 mmol) of triisopropylsilyl chloride. The resulting solution was stirred at ambient temperature for 15 h, diluted with a saturated aqueous ammonium chloride solution (100 mL) and extracted with ether (3×40 mL). The combined organic layers were washed with water (2×30 mL) then brine (25 mL), dried over magnesium sulfate, filtered and concentrated in vacuo. The crude residue was purified on a Biotage® purification apparatus (silica gel, 3% methylene chloride in hexanes) to yield Intermediate 7 as a colorless oil. $^1$H NMR (CDCl$_3$): δ 7.92-7.91 (m, 1H), 7.89-7.86 (m, 1H), 7.78-7.75

(m, 2H), 7.52-7.48 (m, 2H), 5.27 (s, 2H), 1.28-1.21 (m, 3H), 1.13 (d, J=7.4 Hz, 18H). LC/MS 393.0 (M+1) and 395.0 (M+3).

INTERMEDIATE 8

1-(2,3-Dihydro-1,4-benzodioxin-6-yl)-2-(4-fluorophenyl)-1H-imidazole-4-carboxylic acid

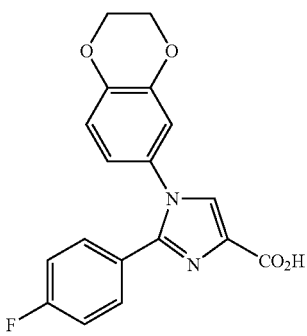

Step A: N-(2,3-Dihydro-1,4-benzodioxin-6-yl)-4-fluorobenzenecarboxamidine To a solution of 2.39 g (15.8 mmol) of 1,4-benzodioxan-6-amine in 30 mL of tetrahydrofuran at ambient temperature was added 8.7 ml (17.4 mmol) of 2.0 M (in tetrahydrofuran) sodium bis(trimethylsilyl)amide and the resulting solution was stirred for 20 min. To this reaction mixture was added 1.91 g (15.8 mmol) of 4-fluorobenzonitrile all at once. The resulting mixture was stirred at ambient temperature overnight and then poured into brine (50 mL) and dichloromethane (150 mL). The organic layer was separated and the aqueous layer was extracted with dichloromethane (50 mL). The combined organic layers were dried over sodium sulfate, filtered and concentrated in vacuo to yield the title compound as yellow solid, which was used without further purification. LC/MS 273.2 (M+1).

Step B: Ethyl 1-(2,3-dihydro-1,4-benzodioxin-6-yl)-2-(4-fluorophenyl)-1H-imidazole-4-carboxylate To a mixture of the product from Step A and 4.0 g (48 mmol) of sodium bicarbonate in 50 mL of 1,4-dioxane was added 3.0 mL (24 mmol) of ethyl bromopyruvate. The reaction mixture was refluxed overnight. After cooling to room temperature, the solid was filtered off and the filtrate was concentrated in vacuo. Flash chromatography on a Biotage Horizon® system (silica gel, 0 to 50% ethyl acetate in hexanes gradient) gave the title compound as a yellow solid. LC/MS 369.1 (M+1).

Step C: 1-(2,3-Dihydro-1,4-benzodioxin-6-yl)-2-(4-fluorophenyl)-1H-imidazole-4-carboxylic acid To a solution of 2.1 g (5.7 mmol) of ethyl 1-(2,3-dihydro-1,4-benzodioxin-6-yl)-2-(4-fluorophenyl)-1H-imidazole-4-carboxylate in 20 mL of tetrahydrofuran, 10 mL of water and 10 mL of methanol was added 2.0 mL (10 mmol) of 5.0 M NaOH solution. The reaction mixture was stirred at ambient temperature overnight. Hydrochloric acid (2.0 M) was then added to neutralize the reaction mixture. After removal of the organic solvents in vacuo, dichloromethane (20 mL) was added and the organic layer was separated. The aqueous layer was extracted with dichloromethane (10 mL), and the combined organic layers were dried over sodium sulfate, filtered and concentrated in vacuo to yield the title compound as a pale yellow foam. LC/MS 341.0 (M+1).

INTERMEDIATE 9

1-Benzyl 4-tert-butyl 4-(2-naphthyl)piperidine-1,4-dicarboxylate

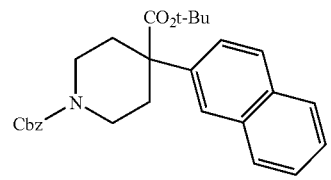

Step A: tert-Butyl 2-naphthylacetate To a solution of 5.0 g (26.9 mmol) of 2-napthylacetic acid in 75 mL of dichloromethane was added 2.60 mL (29.5 mmol) of oxalyl chloride followed by 0.20 mL (2.7 mmol) of N,N-dimethylformamide. The resulting solution was stirred at ambient temperature for 1 h and then all volatiles were removed in vacuo. The resulting residue was dissolved in 15 mL of dichloromethane and 15 mL of 2-methyl-2-propanol, and the resulting solution was stirred for 2.5 h. All volatiles were removed in vacuo and the crude residue was purified on a Biotage® purification apparatus (silica gel, 7% ethyl acetate in hexanes) to afford the title compound as a colorless oil. LC/MS 243.1 (M+1).

Step B: 1-Benzyl 4-tert-butyl 4-(2-naphthyl)piperidine-1,4-dicarboxylate To a suspension of 695 mg (17.4 mmol) of a 60% dispersion of sodium hydride in mineral oil in 4 mL of anhydrous N,N-dimethylformamide at 0° C. under an atmosphere of nitrogen was added a solution of 2.0 g (7.2 mmol) of benzyl bis(2-chloroethyl)carbamate in 5 mL of anhydrous N,N-dimethylformamide, followed by a solution of 1.9 g (8.0 mmol) of tert-butyl 2-naphthylacetate from Step A in 5 mL of anhydrous N,N-dimethylformamide. The resulting mixture was stirred with gradual warming to ambient temperature over 1 h. A solution of 134 mg (0.362 mmol) of tetrabutylammonium iodide in 1 mL of anhydrous N,N-dimethylformamide was added to the mixture, and the resulting orange suspension was heated at 70° C. for 1.5 h. After cooling to ambient temperature the reaction was quenched with water (100 mL) and extracted with ethyl acetate (3×25 mL). The combined organic layers were washed with water (2×20 mL), brine (20 mL), dried over magnesium sulfate, filtered and concentrated in vacuo. The crude residue was purified on a Biotage® purification apparatus (silica gel, 10% acetone in hexanes) to afford the title compound as a yellow oil. $^1$H NMR (CDCl$_3$): δ 7.85-7.76 (m, 5H), 7.52-7.45 (m, 3H), 7.38-7.26 (m, 4H), 5.14 (s, 2H), 4.15-4.10 (m, 2H), 3.17 (br s, 2H), 2.59 (br s, 2H), 1.92-1.93 (m, 2H), 1.38 (s, 9H). LC/MS 446.5 (M+1).

INTERMEDIATE 10

Benzyl 4-formyl-4-(2-naphthyl)piperidine-1-carboxylate

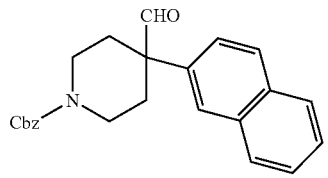

Step A: 1-[(Benzyloxy)carbonyl]-4-(2-naphthyl)piperidine-4-carboxylic acid To a solution of 1.60 g (3.59 mmol) of Intermediate 9 in 10 mL of anhydrous dichloromethane was added 10 mL of trifluoroacetic acid. The resulting mixture was stirred at ambient temperature for 2 h and then all volatiles were removed in vacuo. The resulting residue was dissolved in 15 mL of anhydrous toluene and all volatiles were again removed in vacuo to afford the title compound as a white solid. LC/MS 390.2 (M+1).

Step B: Benzyl 4-formyl-4-(2-naphthyl)piperidine-1-carboxylate To a solution of 1.45 g (3.72 mmol) of the above 1-[(benzyloxy)carbonyl]-4-(2-naphthyl)piperidine-4-carboxylic acid from Step A in 25 mL of anhydrous tetrahydrofuran at 0° C. was added 3.7 mL (3.7 mmol) of a 1.0 M solution of borane-tetrahydrofuran complex in tetrahydrofuran. The resulting mixture was stirred with gradual warming to ambient temperature over 12 h, re-cooled to 0° C., and quenched with 0.75 mL (18 mmol) of methanol. The mixture was diluted with water (25 mL) and extracted with ethyl acetate (3×10 mL). The combined organic layers were washed with water (10 mL), brine (10 mL), dried over magnesium sulfate, filtered and evaporated in vacuo. The crude residue was purified on a Biotage® purification apparatus (silica gel, 10-60% ethyl acetate in hexanes gradient) to afford the title compound as a white solid. $^1$H NMR (CDCl$_3$): δ 9.48 (s, 1H), 7.86 (d, J=8.7 Hz, 1H), 7.84-7.82 (m, 2H), 7.74 (s, 1H), 7.52-7.50 (m, 2H), 7.38-7.26 (m, 6H), 5.14 (s, 2H), 4.00 (br s, 2H), 3.26 (br s, 2H), 2.51-2.49 (m, 2H), 2.17-2.10 (m, 2H). LC/MS 396.1 (M+Na).

EXAMPLE 1

(2S)-{[1-(3-ethoxyphenyl)-2-(4-methylphenyl)-1H-imidazol-4-yl]carbonyl}-4-(3-quinolinyl)-2-piperazinecarboxylic acid, trifluoroacetic acid salt

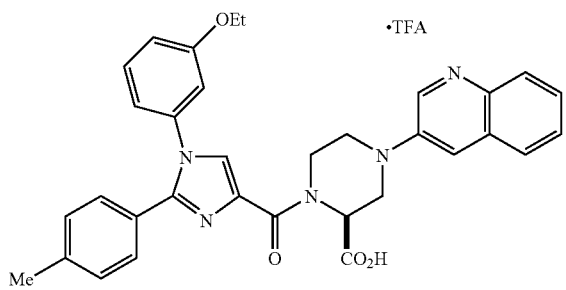

Step A: Methyl (2S)-1-{[1-(3-Ethoxyphenyl)-2-(4-methylphenyl)-1H-imidazol-4-yl]carbonyl}-4-quinolin-3-ylpiperazine-2-carboxylate, trifluoroacetic acid salt To a solution of 334 mg (1.03 mmol) of Intermediate 1 and 440 mg (1.14 mmol) of Intermediate 3 (S enantiomer) in 10 mL N,N-dimethylformamide was added 200 mg (1.14 mmol) of N-(3-dimethylaminopropyl)-N'-ethylcarboiimide hydrochloride, 153 mg (1.14 mmol) 1-hydroxybenzotriazole, and 0.716 mL (4.12 mmol) N,N-diisopropylethylamine. The solution was allowed to stir at room temperature overnight. The reaction was quenched with 0.01% trifluoroacetic acid in water (2.0 mL), and the reaction mixture was purified directly by reverse phase HPLC (TMC Pro-Pac C18; 30-100% 0.01% trifluoroacetic acid in acetonitrile/0.01% trifluoroacetic acid in water gradient). The pure fractions were lyophilized overnight to yield a yellow solid. LC-MS 576.2 (M+1).

Step B: (2S)-1-{[1-(3-Ethoxyphenyl)-2-(4-methylphenyl)-1H-imidazol-4-yl]carbonyl}-4-quinolin-3-ylpiperazine-2-carboxylic acid, trifluoroacetic acid salt To a solution of 52 mg (0.075 mmol) of the S enantiomer from Step A in 10 mL of tetrahydrofuran was added 2 mL methanol and 2 mL 1M lithium hydroxide solution. When the reaction was complete by LC-MS (2 h), the solution was partitioned between 1N hydrochloric acid (10 mL) and ethyl acetate (100 mL). The organic layer was separated, dried over magnesium sulfate, filtered and concentrated in vacuo to afford a yellow oil. The oil was taken up in acetonitrile (2 mL), filtered, and purified by reverse phase HPLC (TMC Pro-Pac C18; 30-100% 0.01% trifluoroacetic acid in acetonitrile/0.01% trifluoroacetic acid in water gradient). The pure fractions were lyophilized overnight to give the title compound as a yellow solid. $^1$H NMR (CDCl$_3$): δ 9.26 (s, 1H), 8.26 (d, J=7.1 Hz, 1H), 7.87 (s, 1H), 7.83 (m, 2H), 7.67 (m, 2H), 7.32 (m, 1H), 7.24 (s, 1H), 7.11 (m, 2H), 6.98 (d, J=7.7 Hz, 1H), 6.80 (m, 2H), 5.75 (b, 1H), 4.71 (m, 2H), 4.44 (m, 2H) 3.97 (q, J=6.8 Hz, 2H), 3.86 (m, 1H), 3.49-3.35 (m, 4H), 2.32 (s, 3H), 1.38 (t, J=6.8 Hz, 3H). LC-MS 562.2 (M+1).

EXAMPLE 2

(2S)-1-{[1-(3-ethoxyphenyl)-2-(4-methylphenyl)-1H-imidazol-4-yl]carbonyl}-4-(3-quinolinyl)-2-ethyl-4-(3-quinolinyl)-2-piperazinecarboxamide, trifluoroacetic acid salt

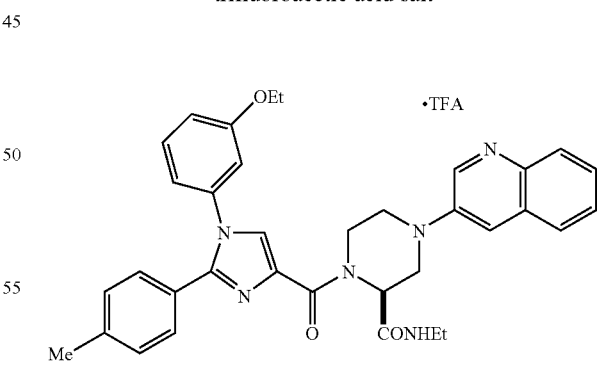

Step A: To a solution of 35 mg (0.062 mmol) of the product of Example 1 (S enantiomer) in N,N-dimethylformamide was added 0.187 mL (0.374 mmol) of 2.0 M ethylamine in tetrahydrofuran, 13 mg (0.068 mmol) N-(3-dimethylaminopropyl)-N'-ethylcarboiimide hydrochloride, 9.0 mg (0.068 mmol) 1-hydroxybenzotriazole, and the resulting solution was heated to 35° C. overnight. The solution was quenched with 0.01% trifluoroacetic acid in water (0.5 mL), and purified directly by reverse phase HPLC (TMC Pro-Pac C18; 30-100% 0.01% trifluoroacetic acid in acetonitrile/0.01% trifluoroacetic acid in water gradient). The resulting pure fractions were lyophilized overnight to give the titled compound as a yellow solid. ¹H NMR (CD₃OD): δ 9.04 (d, J=2.7 Hz, 1H), 8.35 (d, J=2.1 Hz, 1H), 8.06 (m, 3H), 7.80 (m, 2H), 7.32 (m, 3H), 7.19 (b, 2H), 7.04 (d, J=7.5 Hz, 1H), 6.88 (br, 2H), 6.09 (br, s, 0.5H), 5.28 (br, s, 0.5H), 4.59 (m, 1H), 3.97 (m, 4H), 3.54 (br, 1H), 3.39 (br, 1H), 3.24 (q, J=7.2 Hz, 2H), 2.33 (s, 3H), 1.32 (t, J=6.8 Hz, 3H), 1.04 (br, 3H). LC/MS 589.2 (M+1).

EXAMPLE 3

N-{[(2S)-1-{[1-(3-ethoxyphenyl)-2-(4-methylphenyl)-1H-imidazol-4-yl]carbonyl}-4-(3-quinolinyl)-2-piperazinyl]carbonyl}glycine, trifluoroacetic acid salt

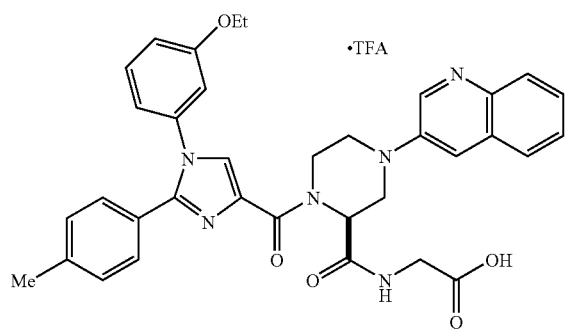

Step A: To a mixture of 31 mg (0.049 mmol) of the product Example 1 (S enantiomer), 6.5 mg (0.049 mmol) of glycine, tert-butyl ester, 19 mg (0.10 mmol) of N-(3-dimethylaminopropyl)-N'-ethylcarboiimide hydrochloride, and 14 mg (0.10 mmol) of 1-hydroxybenzotriazole in 0.5 ml of N,N-dimethylformamide was added 0.05 ml (0.3 mmol) of N,N-diisopropylethylamine. After being stirred at ambient temperature overnight, the reaction was quenched with 1.5 ml of water. After filtration, the unpurified solid product was dissolved in 0.5 ml of dichloromethane and 0.2 ml of trifluoroacetic acid. The reaction mixture was stirred at ambient temperature for 3 hours. The volatiles were removed under vacuum and the resulting residue was purified by reverse phase HPLC (TMC Pro-Pac C18; 30-90% 0.01% trifluoroacetic acid in acetonitrile/0.01% trifluoroacetic acid in water gradient). The resulting pure fractions were lyophilized overnight to give the titled compound as a yellow solid. ¹H NMR (DMSO-d₆): δ 8.96 (d, J=2.8 Hz, 1 H), 8.62 (m, 0.5H), 8.41 (m, 0.5H), 8.01-7.86 (m, 4H), 7.61-7.57 (m, 2H), 7.35 (t, J=8.1 Hz, 1H), 7.26 (m, 2H), 7.17-7.12 (m, 2H), 7.02 (dd, J=8.2, 2.3 Hz, 1H), 6.96 (s, 1H), 6.82 (d, J=7.3 Hz, 1H), 6.46 (s, 0.5H), 5.60 (d, J=12.1 Hz, 0.5H), 5.26 (s, 0.5H), 4.54-4.46 (m, 1.5H), 4.50 (q, J=6.9 Hz, 2H), 3.89-3.76 (m, 3.5H), 3.43 (m, 0.5H), 3.25 (m, 1H), 3.13 (m, 0.5H), 3.00 (m, 0.5H), 2.28 (s, 3H), 1.27 (t, J=7.0 Hz, 3H). LC/MS 619.2 (M+1).

EXAMPLE 4

{[(2S)-1-{[1-(3-Ethoxyphenyl)-2-(4-methylphenyl)-1H-imidazol-4-yl]carbonyl}-4-(3-quinolinyl)-2-piperazinyl]methoxy}acetic acid, trifluoroacetic acid salt

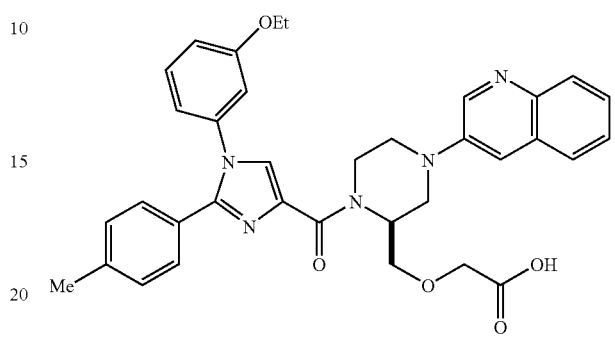

Step A: ((2S)-1-{[1-(3-Ethoxyphenyl)-2-(4-methylphenyl)-1H-imidazol-4-yl]carbonyl}-4-quinolin-3-ylpiperazin-2-yl)methyl acetate To 108 mg (0.118 mmol) of tris(dibenzylideneacetone)dipalladium(0), 279 mg (0.708 mmol) of 2-dicyclohexylphosphino-2'-(N,N-dimethylamino)biphenyl, 1.92 g (5.90 mmol) of cesium carbonate, and 1.82 g (3.93 mmol) of ((2S)-1-{[1-(3-Ethoxyphenyl)-2-(4-methylphenyl)-1H-imidazol-4-yl]carbonyl}piperazin-2-yl)methyl acetate (synthesized from Intermediate 1 and 1-benzyl 3-methyl-(3S)-piperazine-1,3-dicarboxylate according to the procedures outlined for the preparation of Intermediate 4) was added 982 mg (4.72 mmol) of 3-bromoquinoline. The flask was flushed with nitrogen and 20 mL of anhydrous 1,4-dioxane was added. The resulting reaction mixture was heated to 85° C. for 15 h, cooled to room temperature and diluted with water (25 mL). After extraction with ethyl acetate (3×10 mL), the combined organic layers were washed with brine (10 mL), dried over magnesium sulfate, filtered and concentrated in vacuo. The crude residue was purified on a Biotage® purification apparatus (silica gel, 75% ethyl acetate in hexanes then 100% ethyl acetate) to yield the title compound as a yellow foam. LC/MS 590.2 (M+1).

Step B: ((2S)-1-{[1-(3-ethoxyphenyl)-2-(4-methylphenyl)-1H-imidazol-4-yl]carbonyl}-4-quinolin-3-ylpiperazin-2-yl)methanol To a solution of 1.65 g (2.80 mmol) of ((2S)-1-{[1-(3-ethoxyphenyl)-2-(4-methylphenyl)-1H-imidazol-4-yl]carbonyl}-4-quinolin-3-ylpiperazin-2-yl)methyl acetate from Step A in 40 mL of tetrahydrofuran and 9 mL of methanol at 0° C. was added 1.1 mL (0.56 mmol) of a 0.5 M solution of sodium methoxide in methanol and the resulting mixture was stirred for 2 hours. The reaction was quenched with a saturated aqueous ammonium chloride solution (10 mL) and the layers were separated. The aqueous layer was extracted with ethyl acetate (3×10 mL) and the combined organic layers were washed with brine (10 mL), dried over magnesium sulfate, filtered and concentrated in vacuo. The crude residue was purified on a Biotage® purification apparatus (silica gel, 30% acetone in hexanes) to yield the title compound as a yellow foam. LC/MS 548.1 (M+1).

Step C: tert-butyl[((2S)-1-{[1-(3-ethoxyphenyl)-2-(4-methylphenyl)-1H-imidazol-4-yl]carbonyl}-4-quinolin-3-ylpiperazin-2-yl)methoxy]acetate To a suspension of 4 mg (0.1 mmol) of a 60% dispersion of sodium hydride in mineral oil in 3 mL tetrahydrofuran at 0° C. under a nitrogen atmosphere was added 50 mg (0.09 mmol) of ((2S)-1-{[1-(3-ethoxyphenyl)-2-(4-methylphenyl)-1H-imidazol-4-yl]carbonyl}-4-quinolin-3-ylpiperazin-2-yl)methanol from Step B. The resulting solution was allowed to warm to ambient temperature and 0.018 mL (0.12 mmol) of tert-butyl bromoacetate was added. After stirring for 2 hours the reaction was quenched with water (5 mL) and extracted with a 3:1 chloroform/isopropyl alcohol mixture (3×5 mL). The organic layers were combined, dried over magnesium sulfate, filtered, and evaporated in vacuo to yield a crude oil which was carried forward without purification. LC/MS 662.3 (M+1).

Step D: {[(2S)-1-{[1-(3-Ethoxyphenyl)-2-(4-methylphenyl)-1H-imidazol-4-yl]carbonyl}-4-(3-quinolinyl)-2-piperazinyl]methoxy}acetic acid, trifluoroacetic acid salt To a stirred solution of 40 mg (0.060 mmol) of tert-butyl[((2S)-1-{[1-(3-ethoxyphenyl)-2-(4-methylphenyl)-1H-imidazol-4-yl]carbonyl}-4-quinolin-3-ylpiperazin-2-yl)methoxy]acetate from Step C in 1 mL dichloromethane was added 1.5 mL of trifluoroacetic acid. The resulting solution was stirred at ambient temperature for 2 hours and concentrated in vacuo to yield a viscous crude oil, which was purified by reverse phase HPLC(YMC Pro C-18 column, gradient elution, 10 to 90% acetonitrile/water with 0.1% trifluoroacetic acid). The resulting pure fractions were lyophilized overnight to give the title compound as a yellow solid. $^1$H NMR (CD$_3$OD): δ 9.11 (s, 1 H), 8.38 (s, 1 H), 8.03-8.19 (m, 3 H), 7.78-7.82 (m, 2 H), 7.33-7.40 (m, 3 H), 7.21-7.22 (m, 2 H), 7.04-7.06 (m, 1 H), 6.93 (br s, 2H), 4.65-5.39 (m, 2H), 3.70-4.40 (m, 8H), 3.16-3.60 (m, 3H), 2.36 (s, 3H), 1.31-1.35 (m, 3H). LC/MS 606.5 (M+1).

Following essentially the procedures outlined for Examples 1-4, the Examples listed in Tables 1 and 2 were prepared.

TABLE 1

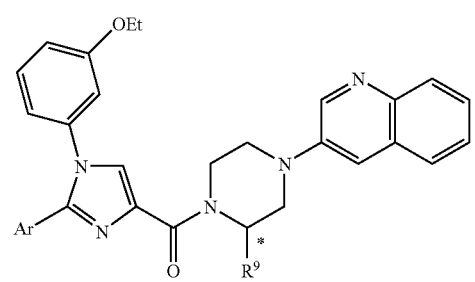

| Example | *Enantiomer | R$^4$ | R$^6$ | Y | MS (M + 1) |
|---|---|---|---|---|---|
| 5 | R | OCH$_3$ | CH$_3$ | CH | 547.3 |
| 6 | S | OCH$_3$ | CH$_3$ | CH | 547.3 |
| 7 | R | OCH$_3$ | CH$_3$ | N | 548.3 |
| 8 | S | OCH$_3$ | CH$_3$ | N | 548.3 |
| 9 | S | OCH$_2$CH$_3$ | CH$_3$ | N | 562.3 |
| 10 | R | OCH$_2$CH$_3$ | F | N | 566.3 |
| 11 | S | OCH$_2$CH$_3$ | F | N | 566.3 |

TABLE 2

| Example | *Enantiomer | R$^9$ | Ar | MS (M + 1) |
|---|---|---|---|---|
| 12 | R | CONHCH$_3$ | 4-CH$_3$Phenyl | 575.2 |
| 13 | S | CONHCH$_3$ | 4-CH$_3$Phenyl | 575.3 |
| 14 | R | CONHCH$_2$CH$_3$ | 4-CH$_3$Phenyl | 589.2 |
| 15 | R | CON(CH$_2$CH$_3$)$_2$ | 4-CH$_3$Phenyl | 617.3 |
| 16 | S | CON(CH$_2$CH$_3$)$_2$ | 4-CH$_3$Phenyl | 617.3 |
| 17 | R | CONHCH(CH$_3$)$_2$ | 4-CH$_3$Phenyl | 603.5 |
| 18 | S | CONHCH(CH$_3$)$_2$ | 4-CH$_3$Phenyl | 603.5 |
| 19 | R | CONHC(CH)$_3$ | 4-CH$_3$Phenyl | 617.3 |
| 20 | S | CONHC(CH)$_3$ | 4-CH$_3$Phenyl | 617.3 |
| 21 | R | CONH(CH$_2$)$_2$CH$_3$ | 4-CH$_3$Phenyl | 603.3 |
| 22 | S | CONH(CH$_2$)$_2$CH$_3$ | 4-CH$_3$Phenyl | 603.3 |
| 23 | R | CONH(CH$_2$)$_3$CH$_3$ | 4-CH$_3$Phenyl | 617.4 |
| 24 | S | CONH(CH$_2$)$_3$CH$_3$ | 4-CH$_3$Phenyl | 617.4 |
| 25 | S | 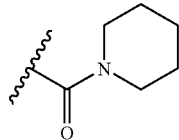 | 4-CH$_3$Phenyl | 629.2 |

TABLE 2-continued

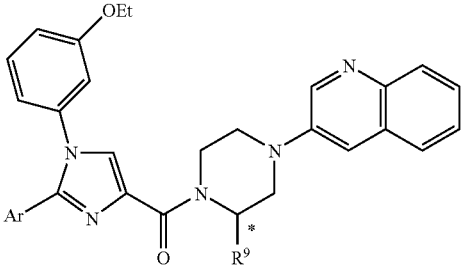

| Example | *Enantiomer | R⁹ | Ar | MS (M + 1) |
|---|---|---|---|---|
| 26 | S | 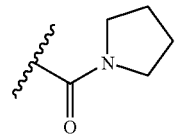 | 4-CH₃Phenyl | 615.3 |
| 27 | S | 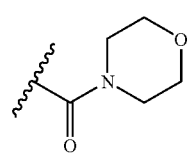 | 4-CH₃Phenyl | 631.3 |
| 28 | S | CON(CH₃)₂ | 4-CH₃Phenyl | 589.3 |
| 29 | S | CONH(CH₂)₄CH₃ | 4-CH₃Phenyl | 631.3 |
| 30 | S | CONH(CH₂)₅CH₃ | 4-CH₃Phenyl | 645.2 |
| 31 | S | 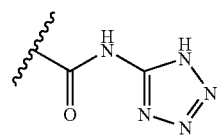 | 4-CH₃Phenyl | 630.3 |
| 32 | S | 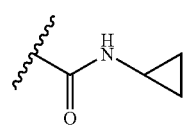 | 4-CH₃Phenyl | 601.2 |
| 33 | R | CH₂CO₂H | 4-CH₃Phenyl | 576.2 |
| 34 | S | CH₂CO₂H | 4-CH₃Phenyl | 576.2 |
| 35 | R | CH₂OC(O)CH₃ | 4-CH₃Phenyl | 590.2 |
| 36 | S | CH₂OC(O)CH₃ | 4-CH₃Phenyl | 590.2 |
| 37 | R | CH₂OCH₂CO₂H | 4-CH₃Phenyl | 606.2 |
| 38 | S | CH₂NHCOCH₃ | 4-CH₃Phenyl | 589.6 |
| 39 | R | CH₂NHCOCH₃ | 4-CH₃Phenyl | 589.2 |
| 40 | S | CH₂NHCOCH(CH₃)₂ | 4-CH₃Phenyl | 616.9 |
| 41 | S | 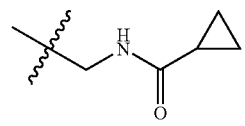 | 4-CH₃Phenyl | 615.4 |
| 42 | S | 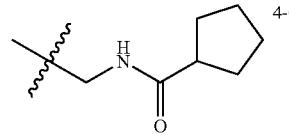 | 4-CH₃Phenyl | 643.3 |
| 43 | S | CH₂NHCOPhenyl | 4-CH₃Phenyl | 651.6 |
| 44 | R | CH₂NHCONHCH(CH₃)₂ | 4-CH₃Phenyl | 632.0 |
| 45 | S | CH₂NHCONHCH(CH₃)₂ | 4-CH₃Phenyl | 632.0 |
| 46 | S | CH₂NHCONHCH₃ | 4-CH₃Phenyl | 604.2 |
| 47 | R | CH₂NHSO₂CH₃ | 4-CH₃Phenyl | 625.1 |
| 48 | S | CH₂NHSO₂CH₃ | 4-CH₃Phenyl | 625.2 |

TABLE 2-continued

| Example | *Enantiomer | R⁹ | Ar | MS (M + 1) |
|---|---|---|---|---|
| 49 | R | (CH₂)NHSO₂-cyclopropyl group | 4-CH₃Phenyl | 651.5 |
| 50 | S | CH₂NHCH₂CO₂H | 4-CH₃Phenyl | 605.2 |
| 51 | R | CH₂NHCH₂CO₂H | 4-CH₂Phenyl | 605.2 |
| 52 | S | CO₂H | 2,4-difluorophenyl | 584.1 |

EXAMPLE 53

3-{(3S)-4-{[1-(3-Ethoxyphenyl)-2-(4-methylphenyl)-1H-imidazol-4-yl]carbonyl}-3-[(isopropylamino)carbonyl]-1-piperazinyl}-1-naphthoic acid, trifluoroacetic acid salt

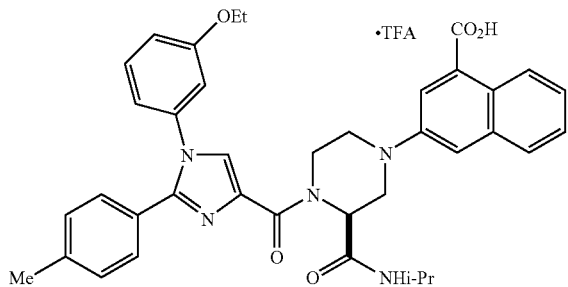

Step A: Methyl 3-{(3S)-4-{[1-(3-ethoxyphenyl)-2-(4-methylphenyl)-1H-imidazol-4-yl]carbonyl}-3-[(isopropylamino)carbonyl]-1-piperazinyl}-1-naphthoate, trifluoroacetic acid salt To a solution of 72 mg (0.22 mmol) of Intermediate 1 and 105 mg (0.223 mmol) of Intermediate 6 in 3 mL N,N-dimethylformamide was added 48 mg (0.25 mmol) of N-(3-dimethylaminopropyl)-N'-ethylcarboiimide hydrochloride, 33 mg (0.25 mmol) of 1-hydroxybenzotriazole, and 0.097 mL (0.56 mmol) N,N-diisopropylethylamine. The solution was allowed to stir at room temperature overnight. The reaction was quenched with 2 mL 0.01% trifluoroacetic acid in water, and the reaction mixture was purified directly by reverse phase HPLC (TMC Pro-Pac C18; 30-100% 0.01% trifluoroacetic acid in acetonitrile/0.01% trifluoroacetic acid in water gradient). The pure fractions were concentrated in vacuo to yield a yellow oil. LC/MS 660.1 (M+1).

Step B: 3-{(3S)-4-{[1-(3-ethoxyphenyl)-2-(4-methylphenyl)-1H-imidazol-4-yl]carbonyl}-3[(isopropylamino)carbonyl]-1-piperazinyl}-1-naphthoic acid, trifluoroacetic acid salt To a solution of 150 mg (0.19 mmol) of the product of Step A in 6 mL of tetrahydrofuran was added 1.0 mL methanol and 1.0 mL (1.0 mmol) of 1N lithium hydroxide solution. When the reaction was complete by LC-MS (2 h) the solution was partitioned between 1N hydrochloric acid (5 mL) and ethyl acetate (100 mL). The organic layer was separated, dried over magnesium sulfate, filtered and concentrated in vacuo to afford a yellow oil. The oil was taken up in N,N-dimethylformamide (2 mL), diluted with 0.01% trifluoroacetic acid in water (0.5 mL), and purified by reverse phase HPLC (TMC Pro-Pac C18; 30-100% 0.01% trifluoroacetic acid in acetonitrile/0.01% trifluoroacetic acid in water gradient). The pure fractions were lyophilized overnight to give the title compound as a pale yellow solid. ¹H NMR (DMSO-d₆): δ 8.63 (d, J=8.4 Hz, 1H), 8.08-7.93 (m, 3H), 7.79 (d, J=8.2 Hz, 1H), 7.45 (t, J=7.2 Hz, 1H), 7.38-7.34 (m, 3H), 7.27 (br, 2H), 7.17-7.11 (m, 2H), 7.02 (d, J=8.3 Hz, 1H), 6.96 (br, 1H), 6.82 (br, 1H), 6.15 (s, 0.5H), 5.48 (br, 0.5H), 5.05 (s, 0.5H), 4.49 (m, 0.5H), 4.39 (m, 1H), 4.01 (q, J=6.6 Hz, 2H), 3.94-3.84 (br, 1.5H), 3.75 (br, 1H), 3.46 (m, 0.5H), 3.13 (m, 1H), 3.03 (m, 0.5H), 2.90 (m, 0.5H), 2.29 (s, 3H), 1.28 (t, J=6.8 Hz, 3H), 1.11-1.01 (br, 6H). LC/MS 646.1 (M+1).

EXAMPLE 54

3-((3R)-4-{[1-(3-Ethoxyphenyl)-2-(4-methylphenyl)-1H-imidazol-4-yl]-carbonyl}-3-{[2-(methylamino)-2-oxoethoxy]methyl}-1-piperazinyl)-1-naphthoic acid, trifluoroacetic acid salt

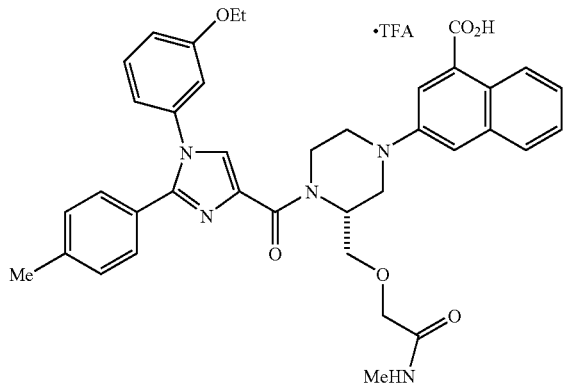

Step A: Methyl 3-[(3R)-4-{[1-(3-ethoxyphenyl)-2-(4-methylphenyl)-1H-imidazol-4-yl]carbonyl}-3-(hydroxymethyl)piperazin-1-yl]-1-naphthoate To 62 mg (0.070 mmol) of tris(dibenzylideneacetone)-dipalladium(0), 161 mg (0.410 mmol) of 2-dicyclohexylphosphino-2'-(N,N-dimethylamino)biphenyl, 824 mg (2.53 mmol) of cesium carbonate and 780 mg (1.70 mmol) of Inter-mediate 4 was added 493 mg (1.86 mmol) of Intermediate 5. The flask was flushed with nitrogen and 10 mL of anhydrous 1,4-dioxane was added. The resulting reaction mixture was heated to 85° C. for 15 h, cooled to room temperature and diluted with a saturated aqueous ammonium chloride solution (10 mL). After extraction with ethyl acetate (2×10 mL), the combined organic layers were washed with brine (5 mL), dried over magnesium sulfate, filtered and concentrated in vacuo. The resulting crude residue was purified on a Biotage® purification apparatus (silica gel, 60% ethyl acetate in hexanes) to yield the title compound as a colorless solid. LC/MS 605.5 (M+1).

Step B: Methyl 3-((3R)-3-[(2-tert-butoxy-2-oxoethoxy)methyl]-4-{[1-(3-ethoxyphenyl)-2-(4-methylphenyl)-1H-imidazol-4-yl]carbonyl}piperazin-1-yl)-1-naphthoate To a suspension of 4.0 mg (0.10 mmol) of a 60% dispersion of sodium hydride in mineral oil in 2 ml anhydrous tetrahydrofuran at ambient temperature under a nitrogen atmosphere was added 50 mg (0.08 mmol) of methyl 3-[(3R)-4-{[1-(3-ethoxyphenyl)-2-(4-methylphenyl)-1H-imidazol-4-yl]carbonyl}-3-(hydroxymethyl)-piperazin-1-yl]-1-naphthoate from Step A. After 15 min of stirring, 0.020 mL (0.010 mmol) of tert-butyl bromoacetate was added, and the reaction mixture was stirred an additional 3 h. Next, the reaction was quenched with a saturated aqueous ammonium chloride solution (5 mL) and diluted with ethyl acetate (15 mL). The layers were separated and the organic layer was washed with brine (15 mL), dried over magnesium sulfate, filtered and concentrated in vacuo to yield the title compound as a colorless gum, which was used without further purification. LC/MS 719.3 (M+1).

Step C: ({(2R)-1-{[1-(3-ethoxyphenyl)-2-(4-methylphenyl)-1H-imidazol-4-yl]carbonyl}-4-[4-(methoxycarbonyl)-2-naphthyl]piperazin-2-yl}methoxy)acetic acid To a stirred solution of 16 mg (0.020 mmol) of methyl 3-((3R)-3-[(2-tert-butoxy-2-oxoethoxy)methyl]-4-{[1-(3-ethoxyphenyl)-2-(4-methylphenyl)-1H-imidazol-4-yl]carbonyl}piperazin-1-yl)-1-naphthoate from Step B in 1 mL of dichloromethane at ambient temperature was added 1.5 mL of trifluoroacetic acid. The resulting solution was stirred at ambient temperature for 2 h and concentrated in vacuo. The residue was diluted with a saturated aqueous sodium bicarbonate solution (5 mL) and extracted with dichloromethane (10 mL). The organic layer was washed with brine (2 mL), dried over magnesium sulfate, filtered and concentrated in vacuo to yield the title compound as a colorless gum, which was used without further purification. LC/MS 663.2 (M+1).

Step D: Methyl 3-((3R)-4-{[1-(3-ethoxyphenyl)-2-(4-methylphenyl)-1H-imidazol-4-yl]carbonyl}-3-{[2-(methylamino)-2-oxoethoxy]methyl}piperazin-1-yl)-1-naphthoate To a solution of 15 mg (0.023 mmol) of ({(2R)-1-{[1-(3-ethoxyphenyl)-2-(4-methylphenyl)-1H-imidazol-4-yl]carbonyl}-4-[4-(methoxy-carbonyl)-2-naphthyl]piperazin-2-yl}methoxy)acetic acid from Step C in 1 mL of anhydrous dichloro-methane at 0° C. was added 0.0040 mL (0.050 mmol) of 1-methylimidazole followed by 0.002 mL (0.025 mmol) of methanesulfonyl chloride. The resulting mixture was stirred with gradual warming to ambient temperature over 10 min. After re-cooling the reaction mixture to 0° C., 0.012 mL (0.025 mmol) of a 2M solution of methylamine in methanol was added and the reaction mixture was allowed to warm to ambient temperature over 1 h. The reaction was quenched with a saturated aqueous ammonium chloride solution (2 mL) and the layers were separated. The aqueous layer was extracted with dichloromethane (4 mL) and the combined organic layers were washed with brine (2 mL), dried over magnesium sulfate, filtered and concentrated in vacuo to yield the title compound as a colorless solid, which was used without further purification. LC/MS 676.1 (M+1).

Step E: 3-((3R)-4-{[1-(3-Ethoxyphenyl)-2-(4-methylphenyl)-1H-imidazol-4-yl]carbonyl}-3-{[2-(methylamino)-2-oxoethoxy]methyl}-1-piperazinyl)-1-naphthoic acid, trifluoroacetic acid salt To 10 mg (0.015 mmol) of methyl 3-((3R)-4-{[1-(3-ethoxyphenyl)-2-(4-methylphenyl)-1H-imidazol-4-yl]carbonyl}-3-{[2-(methylamino)-2-oxoethoxy]methyl}piperazin-1-yl)-1-naphthoate from Step D in 2 mL of tetrahydrofuran, 0.7 mL of methanol, and 0.7 mL of water was added 3.0 mg (0.075 mmol) of lithium hydroxide monohydrate. The resulting solution was stirred at ambient temperature for 2 h, quenched with 0.10 mL (0.10 mmol) of a 1M aqueous hydrochloric acid solution, concentrated in vacuo and purified directly by reverse phase HPLC (TMC Pro-Pac C18; 10-100% 0.01% trifluoroacetic acid in acetonitrile/0.01% trifluoroacetic acid in water gradient). The resulting pure fractions were lyophilized overnight to give the title compound as a white solid. LC/MS 662.2 (M+1).

EXAMPLE 55

3-((3R)-3-[(Carboxymethoxy)methyl]-4-{[1-(3-ethoxyphenyl)-2-(4-methylphenyl)-1H-imidazol-4-yl]carbonyl}-1-piperazinyl)-1-naphthoic acid, trifluoroacetic acid salt

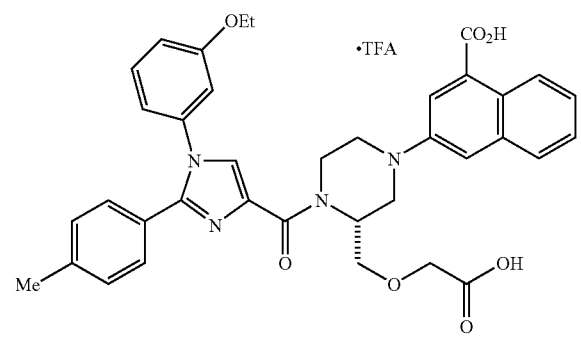

Step A: To 15 mg (0.023 mmol) of ({(2R)-1-{[1-(3-ethoxyphenyl)-2-(4-methylphenyl)-1H-imidazol-4-yl]carbonyl}-4-[4-(methoxycarbonyl)-2-naphthyl]piperazin-2-yl}methoxy)acetic acid in 1 mL of tetrahydrofuran and 0.3 mL of methanol was added 0.3 mL of a 1M lithium hydroxide solution. The resulting solution was stirred at ambient temperature for 2 h then quenched with 1 mL of a 1M aqueous hydrochloric acid solution. The aqueous layer was extracted with a 3:1 chloroform/isopropyl alcohol mixture (3×5 mL) and the combined organic layers were dried over magnesium sulfate, filtered, and evaporated in vacuo to yield a viscous crude oil, which was purified by reverse phase HPLC(YMC Pro C-18 column, gradient elution, 10 to 90% acetonitrile/water with 0.1% trifluoroacetic acid). The resulting pure fractions were lyophilized overnight to give the title compound as a white solid. $^1$H NMR (CD$_3$OD): δ 8.70-8.72 (m, 1 H), 8.30-8.50 (m, 1 H), 8.03 (s, 1 H), 7.79-7.80 (m, 1 H), 7.37-7.46 (m, 5 H), 7.27-7.28 (m, 2 H), 6.97-7.09 (m, 4 H), 4.66-

5.03 (m, 2H), 3.91-4.18 (m, 8H), 2.96-3.60 (m, 3H), 2.38 (s, 3H), 1.29-1.35 (m, 3H). LC/MS 648.9 (M+1).

EXAMPLE 56

3-((3R)-3-[(Acetylamino)methyl]-4-{[1-(3-ethoxyphenyl)-2-(4-methylphenyl)-1H-imidazol-4-yl]carbonyl}-1-piperazinyl)-1-naphthoic acid trifluoroacetic acid salt

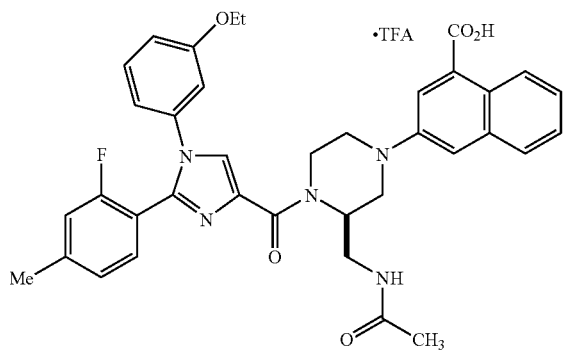

Step A: [(2S)-1-{[1-(3-Ethoxyphenyl)-2-(2-fluoro-4-methylphenyl)-1H-imidazol-4-yl]carbonyl}-4-(4-{[(triisopropylsilyl)oxy]methyl}-2-naphthyl)piperazin-2-yl]methyl acetate To 37 mg (0.041 mmol) of tris(dibenzylideneacetone)dipalladium(0), 97 mg (0.25 mmol) of 2-dicyclohexylphosphino-2'-(N,N-dimethylamino)biphenyl, 666 mg (2.05 mmol) of cesium carbonate and 655 mg (1.36 mmol) of ((2S)-1-{[1-(3-ethoxyphenyl)-2-(2-fluoro-4-methylphenyl)-1H-imidazol-4-yl]carbonyl}piperazin-2-yl)methyl acetate (synthesized from Intermediate 2 and 1-benzyl 3-methyl-(3S)-piperazine-1,3-dicarboxylate according to the procedures outlined for the preparation of Intermediate 4) was added 644 mg (1.64 mmol) of Intermediate 7. The flask was flushed with nitrogen and 10 mL of anhydrous 1,4-dioxane was added. The resulting reaction mixture was heated to 85° C. for 15 h, cooled to room temperature and diluted with water (5 mL). After extraction with ethyl acetate (3×15 mL), the combined organic layers were dried over magnesium sulfate, filtered and concentrated in vacuo. The crude residue was purified on a Biotage® purification apparatus (silica gel, 20 to 35% ethyl acetate in hexanes gradient) to yield the title compound as a yellow solid. LC/MS 793.1 (M+1).

Step B: {(2S)-1-{[1-(3-Ethoxyphenyl)-2-(2-fluoro-4-methylphenyl)-1H-imidazol-4-yl]carbonyl}-4-[4-(hydroxymethyl)-2-naphthyl]piperazin-2-yl}methyl acetate To a solution of 950 mg (1.20 mmol) of [(2S)-1-{[1-(3-ethoxyphenyl)-2-(2-fluoro-4-methylphenyl)-1H-imidazol-4-yl]carbonyl}-4-(4-{[(triisopropylsilyl)oxy]methyl}-2-naphthyl)piperazin-2-yl]methyl acetate from Step A in 10 mL of tetrahydrofuran was added 1.3 mL (1.3 mmol) of a 1M solution of tetrabutylammonium fluoride in tetrahydrofuran. After stirring for 1 h the reaction was diluted with a saturated aqueous sodium bicarbonate solution (15 mL), the layers separated, and the aqueous phase extracted with ethyl acetate (2×15 mL). The combined organic layers were washed with brine (5 mL), dried over magnesium sulfate, filtered and concentrated in vacuo. The crude residue was purified on a Biotage® purification apparatus (silica gel, 90% ethyl acetate in hexanes) to yield the title compound as a white foam. LC/MS 636.9 (M+1).

Step C: [(2S)-1-{[1-(3-Ethoxyphenyl)-2-(2-fluoro-4-methylphenyl)-1H-imidazol-4-yl]carbonyl}-4-(4-formyl-2-naphthyl)piperazin-2-yl]methyl acetate To a solution of 763 mg (1.20 mmol) of {(2S)-1-{[1-(3-ethoxyphenyl)-2-(2-fluoro-4-methylphenyl)-1H-imidazol-4-yl]carbonyl}-4-[4-(hydroxymethyl)-2-naphthyl]piperazin-2-yl}methyl acetate from Step B in 15 mL of anhydrous dichloromethane under an atmosphere of nitrogen was added 0.15 mL (1.8 mmol) of pyridine, then 534 mg (1.26 mmol) of Dess-Martin periodinane. The resulting solution was stirred at ambient temperature for 3 h, then quenched with a saturated aqueous sodium bicarbonate solution (5 mL). The layers were separated and the aqueous phase extracted with dichloromethane (2×10 mL). The combined organic layers were washed with brine (25 mL), dried over magnesium sulfate, filtered and evaporated in vacuo. The crude residue was purified on a Biotage® purification apparatus (silica gel, 40% ethyl acetate in hexanes) to yield the title compound as a yellow gum. LC/MS 634.9 (M+1).

Step D: Methyl 3-((3S)-3-[(acetyloxy)methyl]-4-{[1-(3-ethoxyphenyl)-2-(2-fluoro-4-methylphenyl)-1H-imidazol-4-yl]carbonyl}piperazin-1-yl)-1-naphthoate To a solution of 650 mg (1.02 mmol) of [(2S)-1-{[1-(3-ethoxyphenyl)-2-(2-fluoro-4-methylphenyl)-1H-imidazol-4-yl]carbonyl}-4-(4-formyl-2-naphthyl)piperazin-2-yl]methyl acetate from Step C in 6 mL of 2-methyl-2-propanol was added 0.55 mL (5.1 mmol) of 2-methyl-2-butene followed by dropwise addition of a solution of 184 mg (1.54 mmol) of sodium dihydrogen phosphate and 174 mg (1.54 mmol) of sodium chlorite in 6 mL of water. The resulting mixture was stirred at ambient temperature for 18 h then evaporated in vacuo to remove all volatiles. The residue was diluted with water (5 mL) and an aqueous 1 N hydrochloric acid solution was then added dropwise to the stirred mixture until a pH of 5 was achieved. The aqueous phase was then extracted with ethyl acetate (3×10 mL) and the combined organic layers were washed with brine (5 mL), dried over magnesium sulfate, filtered and evaporated in vacuo. The residue was then dissolved in 3 mL of diethyl ether and 3 mL of methanol, and the resulting solution cooled to 0° C. To this was added 0.68 mL (1.4 mmol) of a 2M trimethylsilyl (diazomethane) solution in hexanes, and the mixture was stirred for 30 min. The reaction was quenched with 0.25 mL (4.4 mmol) of glacial acetic acid and then evaporated in vacuo. The crude residue was purified by preparative thin layer chromatography (silica gel, 50% ethyl acetate in hexanes) to yield the title compound as a yellow solid. LC/MS 665.3 (M+1).

Step E: Methyl 3-[(3S)-4-{[1-(3-ethoxyphenyl)-2-(2-fluoro-4-methylphenyl)-1H-imidazol-4-yl]carbonyl}-3-(hydroxymethyl)piperazin-1-yl]-1-naphthoate To a solution of 292 mg (0.439 mmol) of methyl 3-((3S)-3-[(acetyloxy)methyl]-4-{[1-(3-ethoxyphenyl)-2-(2-fluoro-4-methylphenyl)-1H-imidazol-4-yl]carbonyl}piperazin-1-yl)-1-naphthoate from Step D in 8 mL of tetrahydrofuran and 2 mL of methanol at 0° C. was added 0.18 mL (0.088 mmol) of a 0.5 M solution of sodium methoxide in methanol and the resulting mixture was stirred for 2 h. The reaction was quenched with a saturated aqueous ammonium chloride solution (5 mL) and the layers were separated. The aqueous layer was extracted with ethyl acetate (3×5 mL) and the combined organic layers were washed with brine (5 mL), dried over magnesium sulfate, filtered and concentrated in vacuo to afford the title compound as a white solid, which was used without further purification. LC/MS 623.0 (M+1).

Step F: Methyl 3-((3S)-3-(azidomethyl)-4-{[1-(3-ethoxyphenyl)-2-(2-fluoro-4-methylphenyl)-1H-imidazol-4-yl]carbonyl}piperazin-1-yl)-1-naphthoate To 200 mg (0.321 mmol) of methyl 3-[(3S)-4-{[1-(3-ethoxyphenyl)-2-(2-fluoro-4-methylphenyl)-1H-imidazol-4-yl]carbonyl}-3-(hydroxymethyl)piperazin-1-yl]-1-naphthoate from Step E in 5 mL of anhydrous dichloromethane at 0° C. was added 0.066 mL (0.38 mmol) of N,N-diisopropylethylamine and 0.027 mL (0.35 mmol) of methanesulfonyl chloride. The reaction was allowed to warm to ambient temperature over 1 h, then concentrated in vacuo to dryness. The residue was dissolved in 2 mL of anhydrous N,N-dimethylformamide and 104 mg (1.60 mmol) of sodium azide was added to the solution. The resulting reaction mixture was stirred for 2 h, quenched with water (10 mL) and extracted with ethyl acetate (2×10 mL). The organic layer was washed with brine (5 mL), dried over magnesium sulfate, filtered and concentrated in vacuo to afford the title compound as a yellow oil, which was used without further purification. LC/MS 648.1 (M+1).

Step G: Methyl 3-((3R)-3-(aminomethyl)-4-{[1-(3-ethoxyphenyl)-2-(2-fluoro-4-methylphenyl)-1H-imidazol-4-yl]carbonyl}piperazin-1-yl)-1-naphthoate To 16 mg (0.011 mmol) of 20% palladium hydroxide on carbon was added a solution of 165 mg (0.255 mmol) of methyl 3-((3S)-3-(azidomethyl)-4-{[1-(3-ethoxyphenyl)-2-(2-fluoro-4-methylphenyl)-1H-imidazol-4yl]carbonyl}piperazin-1-yl)-1-naphthoate from Step F in 5 mL of anhydrous methanol. The resulting suspension was agitated under an atmosphere of hydrogen at 30 psi for 2 h then filtered through a plug of Celite®. The plug was washed with methanol (15 mL), and the combined filtrates were concentrated in vacuo to afford the title compound as a colorless foam, which was used without further purification. LC/MS 622.1 (M+1).

Step H: Methyl 3-((3R)-3-[(acetylamino)methyl]-4-{[1-(3-ethoxyphenyl)-2-(2-fluoro-4-methylphenyl)-1H-imidazol-4-yl]carbonyl}piperazin-1-yl)-1-naphthoate To a stirred solution of 39 mg (0.065 mmol) of methyl 3-((3R)-3-(aminomethyl)-4-{[1-(3-ethoxyphenyl)-2-(2-fluoro-4-methylphenyl)-1H-imidazol-4-yl]carbonyl}piperazin-1-yl)-1-naphthoate from Step G in 3 mL of anhydrous dichloromethane at 0° C. was added 0.017 mL (0.10 mmol) of N,N-diisopropylethylamine followed by 0.007 mL (0.1 mmol) of acetyl chloride. The resulting solution was allowed to warm to ambient temperature over 1 h and concentrated in vacuo to afford the title compound as a yellow gum, which was used without further purification. LC/MS 664.1 (M+1).

Step I: 3-((3R)-3-[(Acetylamino)methyl]-4-{[1-(3-ethoxyphenyl)-2-(2-fluoro-4-methylphenyl)-1H-imidazol-4-yl]carbonyl}piperazin-1-yl)-1-naphthoic acid, trifluoroacetic acid salt To a stirred solution of 43 mg (0.065 mmol) of methyl 3-((3R)-3-[(acetylamino)methyl]-4-{[1-(3-ethoxyphenyl)-2-(2-fluoro-4-methylphenyl)-1H-imidazol-4-yl]carbonyl}piperazin-1-yl)-1-naphthoate from Step H in 2 mL tetrahydrofuran was added 43 mg (0.33 mmol) of potassium trimethylsilanolate. The resulting solution was stirred at ambient temperature for 15 h, then quenched with 0.5 mL (0.5 mmol) of a 1M aqueous hydrochloric acid solution, concentrated in vacuo and purified directly by reverse phase HPLC (TMC Pro-Pac C18; 10-100% 0.01% trifluoroacetic acid in acetonitrile/0.01% trifluoroacetic acid in water gradient). The resulting pure fractions were lyophilized overnight to give the titled compound as a white solid. $^1$H NMR (CD$_3$OD): δ 8.71 (d, J=8.5 Hz, 1H), 8.19 (br s, 1H), 8.05 (s, 1H), 7.80 (d, J=8.1 Hz, 1H), 7.46-7.37 (m, 4H), 7.33-7.30 (m, 2H), 7.12 (d, J=7.8 Hz, 1H), 6.98 (d, J=10.1 Hz, 2H), 6.89-6.85 (m, 2H), 5.29-4.62 (m, 2H), 3.98-3.65 (m, 5H), 3.65-2.89 (m, 4H), 2.38 (s, 3H), 1.93-1.84 (m, 3H), 1.34-1.31 (m, 3H). LC/MS 650.2 (M+1).

EXAMPLE 57

3-{(3S)-4-{[1-(3-Ethoxyphenyl)-2-(2-fluoro-4-methylphenyl)-1H-imidazol-4-yl]carbonyl}-3-[(isopropylamino)carbonyl]-1-piperazinyl}-1-naphthoic acid, trifluoroacetic acid salt

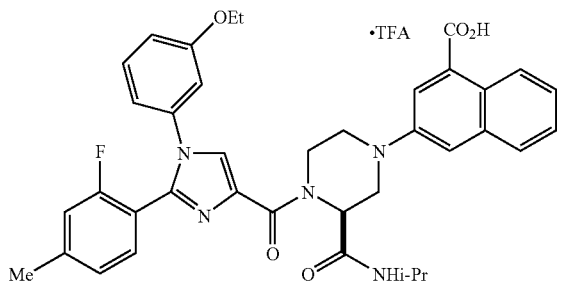

Step A: Methyl 3-{(3S)-4-{[1-(3-ethoxyphenyl)-2-(2-fluoro-4-methylphenyl)-1H-imidazol-4-yl]carbonyl}-3-[(isopropylamino)carbonyl]-1-piperazinyl}-1-naphthoate, trifluoroacetic acid salt To a solution of 15 mg (0.044 mmol) of Intermediate 2 and 20 mg (0.043 mmol) of Intermediate 6 in 1 mL N,N-dimethylformamide was added 9 mg (0.05 mmol) of N-(3-dimethylaminopropyl)-N'-ethylcarboiimide hydrochloride, 6 mg (0.05 mmol) of 1-hydroxybenzotriazole, and 0.026 mL (0.15 mmol) N,N-diisopropylethylamine. The solution was allowed to stir at room temperature overnight. The reaction was quenched with 1 mL of 0.01% trifluoroacetic acid in water, and the reaction mixture was purified directly by reverse phase HPLC (TMC Pro-Pac C18; 30-100% 0.01% trifluoroacetic acid in acetonitrile/0.01% trifluoroacetic acid in water gradient). The pure fractions were concentrated in vacuo to yield a yellow oil. LC/MS 678.3 (M+1).

Step B: 3-{(3S)-4-{[1-(3-Ethoxyphenyl)-2-(2-fluoro-4-methylphenyl)-1H-imidazol-4-yl]carbonyl}-3-[(isopropylamino)carbonyl]-1-piperazinyl}-1-naphthoic acid, trifluoroacetic acid salt To a solution of 15 mg (0.020 mmol) of the product of Step A in 3 mL of tetrahydrofuran was added 1.0 mL methanol and 1.0 mL (1.0 mmol) of 1N lithium hydroxide solution. When the reaction was complete by LC-MS (2 h) the solution was partitioned between 1N hydrochloric acid (5 mL) and ethyl acetate (50 mL). The organic layer was separated, dried over magnesium sulfate, filtered and concentrated in vacuo to afford a yellow oil. This material was taken up in N,N-dimethylformamide (2 mL), diluted with 0.01% trifluoroacetic acid in water (0.5 mL), and purified by reverse phase HPLC (TMC Pro-Pac C18; 30-100% 0.01% trifluoroacetic acid in acetonitrile/0.01% trifluoroacetic acid in water gradient). The pure fractions were lyophilized overnight to give the title compound as a pale yellow solid. $^1$H NMR (DMSO-d$_6$): δ 8.62 (d, J=8.7 Hz, 1H), 8.11 (s, 0.5H), 8.07 (s, 0.5H), 8.01 (d, J=7.1 Hz, 0.5H), 7.95 (d, J=7.4 Hz, 0.5H), 7.92 (s, 1H), 7.78 (d, J=8.0 Hz, 1H), 7.48-7.42 (m, 2H), 7.39-7.34 (m, 2H), 7.28 (t, J=7.8 Hz, 1H), 7.10 (br, 1H), 7.06-6.98 (m, 1H), 6.93 (d, J=8.2 Hz, 1H), 6.86 (d, J=12.5 Hz, 1H), 6.74 (m, 1H), 6.09 (s, 0.5H), 5.44 (d, J=12.6 Hz, 0.5H), 5.05 (s, 0.5H), 4.47 (d, J=12.4 Hz, 0.5H), 4.37 (d, J=12.6 Hz, 1H), 3.96 (q, J=6.6 Hz, 2H), 3.92-3.82 (br, 1.5H) 3.75 (br, 1H), 3.44 (br, 0.5H), 3.13

(br, 1H), 3.01 (br, 0.5H), 2.99 (br, 0.5H), 2.33 (s, 3H), 1.25 (t, J=6.7 Hz, 3H), 1.12-0.98 (br, 6H). LC/MS 664.2 (M+1).

Following essentially the procedures outlined in the Examples above, the Examples listed in Table 3 were prepared.

TABLE 3

| Example | $R^5$ | *Enantiomer | $R^9$ | acid position | MS (M + 1) |
|---|---|---|---|---|---|
| 58 | H | racemate | $CO_2H$ | 3-acid | 605.2 |
| 59 | H | R | $CO_2H$ | 4-acid | 605.3 |
| 60 | H | S | $CO_2H$ | 4-acid | 605.3 |
| 61 | H | R | $CONHCH(CH_3)_2$ | 4-acid | 646.4 |
| 62 | H | R | $CH_2CONHCH(CH_3)_2$ | 4-acid | 660.3 |
| 63 | H | S | $CH_2CONHCH(CH_3)_2$ | 4-acid | 660.3 |
| 64 | H | S | $CH_2OCH_2CONHCH(CH_3)_2$ | 4-acid | 690.3 |
| 65 | H | R | $CH_2NHSO_2CH_3$ | 4-acid | 668.2 |
| 66 | H | S | $CH_2NHCONHCH_3$ | 4-acid | 647.3 |
| 67 | H | S | $CH_2NHCOCH_3$ | 4-acid | 632.2 |
| 68 | F | S | $CH_2OCH_2CO_2H$ | 4-acid | 666.8 |
| 69 | F | S | $CH_2NHSO_2CH_3$ | 4-acid | 686.1 |
| 70 | F | S | $CH_2NHCONHCH_3$ | 4-acid | 665.0 |

EXAMPLE 71

(2S)-4-(4-Carboxy-2-naphthyl)-1-{[1-(2,3-dihydro-1,4-benzodioxin-6-yl)-2-(4-fluorophenyl)-1H-imidazol-4-yl]carbonyl}-2-piperazinecarboxylic acid, trifluoroacetic acid salt

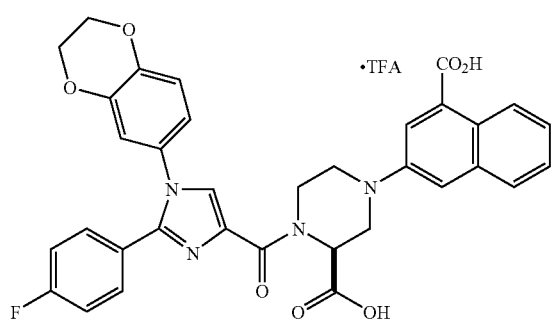

Step A: 1-tert-butyl 2-methyl (2S)-4-[4-(methoxycarbonyl)-2-naphthyl]piperazine-1,2-dicarboxylate To 150 mg (0.614 mmol) of 1-tert-butyl 2-methyl piperazine-1,2-dicarboxylate and 195 mg (0.737 mmol) of Intermediate 5 was added 6 mL anhydrous 1,4-dioxane. The system was purged for 5 min and then flushed with nitrogen. Next, 299 mg (0.921 mmol) of cesium carbonate was added to the flask, and the system was again purged for 5 min, and then flushed with nitrogen. Next, 29 mg (0.074 mmol) of 2-dicyclohexylphosphino-2'(N,N-dimethylamino)biphenyl, and 7 mg (0.01 mmol) of bis(dibenzylideneacetone)palladium were added, and the system was again purged with nitrogen. Finally the reaction mixture was heated at 85° C. under nitrogen for 24 h. After cooling to room temperature, the solution was filtered through Celite® and concentrated in vacuo to yield an orange oil, which was purified using a Biotage Horizon® system (10%-20% ethyl acetate in hexanes gradient) to give the title compound as a racemic mixture. Chiral HPLC separation (Chiralcel AD, 30% 2-propanol/heptane) afforded the R enantiomer (first eluting) and the S enantiomer (second eluting), each in ≧99% ee. LC/MS 429.2 (M+1).

Step B: Methyl (2S)-4-[4-(methoxycarbonyl)-2-naphthyl]piperazine-1,2-dicarboxylate To 75 mg (0.18 mmol) of the S enantiomer from Step A was added 5 mL dichloromethane and 0.5 mL trifluoroacetic acid. When the reaction was complete by LC-MS (1 h), the solution was concentrated in vacuo. The reddish oil was next triturated with ethyl ether (3 mL), and filtered to give the title compound as a beige solid. LC/MS 329.2 (M+1).

Step C: Methyl (2S)-4-(4-carboxy-2-naphthyl)-1-{[1-(2,3-dihydro-1,4-benzodioxin-6-yl)-2-(4-fluorophenyl)-1H-imidazol-4-yl]carbonyl}-2-piperazinecarboxylate, trifluoroacetic acid salt To a solution of 49 mg (0.143 mmol) of intermediate 8 and 63 mg (0.143 mmol) of the compound from Step B in 1.5 mL N,N-dimethylformamide was added 31 mg (0.157 mmol) of N-(3-dimethylaminopropyl)-N'-ethylcarboiimide hydrochloride, 21 mg (0.157 mmol) of 1-hydroxybenzotriazole, and 0.062 mL (0.36 mmol) N,N-diisopropylethylamine. The solution was allowed to stir at room temperature overnight. The reaction was quenched with 2 mL 0.01% trifluoroacetic acid in water, and the reaction mixture was purified directly by reverse phase HPLC (TMC Pro-Pac C18; 30-100% 0.01% trifluoroacetic acid in acetonitrile/ 0.01% trifluoroacetic acid in water gradient). The pure fractions were concentrated in vacuo to yield a yellow oil. LC/MS 660.2 (M+1).

Step D: (2S)-4-(4-Carboxy-2-naphthyl)-1-{[1-(2,3-dihydro-1,4-benzodioxin-6-yl)-2-(4-fluorophenyl)-1H-imidazol-4-yl]carbonyl}-2-piperazinecarboxylic acid, trifluoroacetic acid salt To a solution of 95 mg (0.123 mmol) of the product of Step A in 6 mL of tetrahydrofuran was added 3.0 mL methanol and 3.0 mL (1.0 mmol) of 1N lithium hydroxide solution. When the reaction was complete by LC-MS (2 h), the solution was partitioned between 1N hydrochloric acid (5 mL) and ethyl acetate (100 mL). The organic layer was separated, dried over magnesium sulfate, filtered and concentrated in vacuo to afford a yellow oil. This material was taken up in N,N-dimethylformamide (2 mL), diluted with 0.01% trifluoroacetic acid in water (0.5 mL), and purified by reverse phase HPLC (TMC Pro-Pac C18; 30-100% 0.01% trifluoroacetic acid in acetonitrile/0.01% trifluoroacetic acid in water gradient). The pure fractions were lyophilized overnight to give the title compound as a pale yellow solid. $^1$H NMR (DMSO-$d_6$): δ 8.65 (d, J=8.7 Hz, 1H), 7.98-7.92 (m, 2H), 7.84 (d, J=8.3 Hz, 1H), 7.51-7.37 (m, 5H), 7.25-7.18 (m, 2H), 7.00 (dd, J=5.9 Hz, 2.5 Hz, 1H), 6.94 (d, J=8.7 Hz, 1H), 6.80 (m, 1H), 6.67 (s, 0.5H), 5.55 (d, J=12.4, 0.5H), 5.29 (s, 0.5H), 4.47 (d, J=13.3 Hz, 0.5H), 4.34 (d, J=12.2 Hz, 1H), 4.28 (m, 4H), 3.86 (d, J=11.2 Hz, 0.5H), 3.80 (d, J=11.2 Hz, 0.5H), 3.69 (dt, J=13.5 Hz, 2.9 Hz, 0.5H), 3.28 (dt, J=13.3 Hz, 3.5 Hz, 0.5H) 3.15 (dd, J=12.6 Hz, 3.9 Hz, 0.5H), 3.08 (dd, J=12.6 Hz, 3.9 Hz, 0.5H), 2.96 (m, 0.5H), 2.86 (m, 0.5H). LC/MS 623.2 (M+1).

Following essentially the procedures outlined in the Examples above, the Examples listed in Table 4 were prepared.

EXAMPLE 78

3-[1-{[1-(2,3-Dihydro-1,4-benzodioxin-6-yl)-2-(4-methylphenyl)-1H-imidazol-4-yl]carbonyl}-4-(2-naphthyl)piperidin-4-yl]propanoic acid, trifluoracetic acid salt

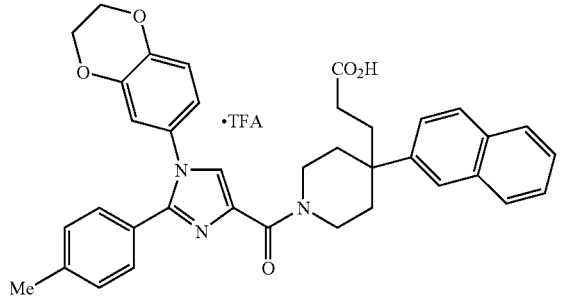

Step A: Benzyl 4-[(1E)-3-methoxy-3-oxoprop-1-en-1-yl]-4-(2-naphthyl)piperidine-1-carboxylate To a solution of 0.30 mL (2.0 mmol) of trimethyl phosphonoacetate in 5 mL of anhydrous tetrahydrofuran at 0° C. was added 0.540 mL (1.34 mmol) of a 2.5 M solution of n-butyl lithium in hexanes. The resulting mixture was stirred for 1 h, then a solution of 250 mg (0.670 mmol) of Intermediate 10 in anhydrous tetrahydrofuran was added. The resulting mixture was stirred with gradual warming to ambient temperature over 3 h, and then quenched with a saturated aqueous ammonium chloride solution (15 mL). The aqueous layer was extracted with diethyl ether

TABLE 4

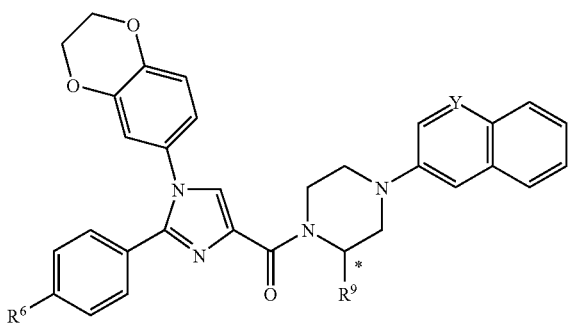

| Example | *Enantiomer | $R^9$ | $R^6$ | Y | $R^{14}$ | MS (M + 1) |
|---------|-------------|-------|-------|---|----------|------------|
| 72 | R | $CO_2H$ | $CH_3$ | N | — | 576.6 |
| 73 | S | $CO_2H$ | $CH_3$ | N | — | 576.6 |
| 74 | S | $CONHCH_2CH_3$ | $CH_3$ | N | — | 603.3 |
| 75 | R | $CO_2H$ | F | N | — | 580.2 |
| 76 | S | $CO_2H$ | F | N | — | 580.2 |
| 77 | S | $CONHCH(CH_3)_2$ | $CH_3$ | $CR^{14}$ | $CO_2H$ | 660.2 |

(3×10 mL), and the combined organic layers were washed with water (2×5 mL), brine (5 mL), dried over magnesium sulfate, filtered and concentrated in vacuo. The crude residue was purified by preparative thin layer chromatography (silica gel, 35% ethyl acetate in hexanes) to afford the title compound as a clear oil. LC/MS 452.1 (M+Na).

Step B: Methyl 3-[4-(2-naphthyl)piperidin-4-yl]propanoate To 20 mg (0.028 mmol) of 20% palladium hydroxide on carbon was added a solution of 180 mg (0.419 mmol) of benzyl 4-[(1E)-3-methoxy-3-oxoprop-1-en-1-yl]-4-(2-naphthyl)piperidine-1-carboxylate from Step A in 15 mL of anhydrous methanol. The resulting suspension was agitated under an atmosphere of hydrogen at 30 psi for 2 h then filtered through a plug of Celite®. The plug was washed with methanol (15 mL), and the combined filtrates were concentrated in vacuo to afford the title compound as a tan solid, which was used without further purification. LC/MS 298.2 (M+1).

Step C: Methyl 3-[1-{[1-(2,3-dihydro-1,4-benzodioxin-6-yl)-2-(4-methylphenyl)-1H-imidazol-4yl]carbonyl}-4-(2-naphthyl)piperidin-4-yl]propanoate To a solution of 25 mg (0.074 mmol) of 1-(2,3-dihydro-1,4-benzodioxin-6-yl)-2-(4-methylphenyl)-1H-imidazole-4-carboxylic acid (prepared according to the procedures outlined for Intermediate 8) and 44 mg (0.015 mmol) of methyl 3-[4-(2-naphthyl)piperidin-4-yl]propanoate from Step B in 2 mL of anhydrous dichloromethane was added 0.052 mL (0.30 mmol) N,N-diisopropylethylamine, 21 mg (0.11 mmol) of N-(3-dimethylaminopropyl)-N'-ethylcarboiimide hydrochloride, and 15 mg (0.11 mmol) of 1-hydroxy-7-azabenzotriazole. The solution was allowed to stir at ambient temperature overnight. The reaction was quenched with a saturated aqueous ammonium chloride solution (5 mL) and the aqueous layer was extracted with dichloromethane (3×5 mL). The combined organic layers were dried over magnesium sulfate, filtered and concentrated in vacuo. The resulting crude residue was purified by preparative thin layer chromatography (silica gel, 85% ethyl acetate in hexanes) to afford the title compound as a white solid. LC/MS 616.2 (M+1).

Step D: 3-[1-{[1-(2,3-Dihydro-1,4-benzodioxin-6-yl)-2-(4-methylphenyl)-1H-imidazol-4-yl]carbonyl}-4-(2-naphthyl)piperidin-4-yl]propanoic acid, trifluoracetic acid salt To a stirred solution of 45 mg (0.073 mmol) of methyl 3-[1-{[1-(2,3-dihydro-1,4-benzodioxin-6-yl)-2-(4-methylphenyl)-1H-imidazol-4-yl]carbonyl}-4-(2-naphthyl)piperidin-4-yl] propanoate from Step C in 1 mL of tetrahydrofuran was added 28 mg (0.22 mmol) of potassium trimethylsilanolate. The resulting solution was stirred at ambient temperature for 18 h, quenched with 0.5 mL (0.5 mmol) of a 1M aqueous hydrochloric acid solution and concentrated in vacuo. The crude residue was purified directly by reverse phase HPLC (TMC Pro-Pac C18; 10-100% 0.01% trifluoroacetic acid in acetonitrile/0.01% trifluoroacetic acid in water gradient). The resulting pure fractions were lyophilized overnight to give the titled compound as a white solid. $^1$H NMR (DMSO-$d_6$): δ 7.92-7.88 (m, 5H), 7.60 (d, J=8.7 Hz, 1H), 7.51-7.46 (m, 2H), 7.27 (d, J=8.0 Hz, 2H), 7.18 (d, J=8.0 Hz, 2H), 6.99 (d, J=2.5 Hz, 1H), 6.92 (d, J=8.7 Hz, 1H), 6.78 (dd, J=8.5, 2.3 Hz, 1H), 4.50 (br s, 1H), 4.27-4.26 (m, 4H), 4.02 (br s, 1H), 3.68 (br s, 1H), 3.22 (br s, 1H), 2.35-2.33 (m, 2H), 2.30 (s, 3H), 1.96-1.93 (m, 2H), 1.85-1.82 (m, 4H). LC/MS 602.4 (M+1).

EXAMPLE 79

4-(4-Carboxy-2-naphthyl)-1-{[1-(3-ethoxyphenyl)-2-(4-methylphenyl)-1H-imidazol-4-yl]carbonyl}-4-piperidinecarboxylic acid, trifluoracetic acid salt

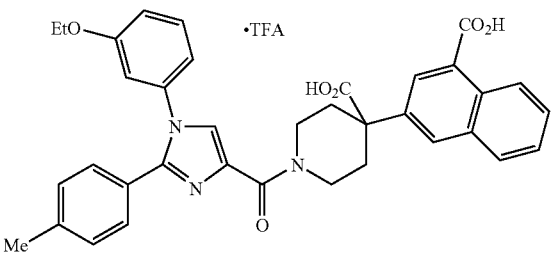

Step A: 1-tert-Butyl 4-methyl 4-(4-{[(triisopropylsilyl)oxy]methyl}-2-naphthyl)piperidine-1,4-dicarboxylate To a solution of 1.5 mL (7.6 mmol) of dicyclohexylamine in 15 mL of anhydrous toluene at −78° C. under an atmosphere of nitrogen was added 3.0 mL (7.6 mmol) of a 2.5 M solution of n-butyl lithium in hexanes. The resulting mixture was stirred with gradual warming to ambient temperature over 30 min then recooled to −78° C. A solution of 1.86 g (7.63 mmol) of 1-tert-butyl 4-methyl piperidine-1,4-dicarboxylate in 5 mL of anhydrous toluene was added and the resulting mixture was stirred with gradual warming to ambient temperature over 30 min. Next, 145 mg (0.159 mmol) of tris(dibenzylideneacetone)-dipalladium(0), 0.970 mL (0.318 mmol) of a 10% solution of tri-tert-butylphosphine in hexanes and a solution of 2.50 g (6.35 mmol) of Intermediate 7 in 10 mL of anhydrous toluene were added in sequence and the resulting dark brown suspension was stirred overnight at ambient temperature under an atmosphere of nitrogen. All volatiles were then removed in vacuo and the residue diluted with 100 mL of water and 50 mL of ethyl acetate. The layers were separated and the aqueous layer was extracted with ethyl acetate (2×50 mL). The combined organic layers were washed with brine (5 mL), dried over magnesium sulfate, filtered and concentrated in vacuo. The crude residue was purified on a Biotage® purification apparatus (silica gel, 10% ethyl acetate in hexanes) to yield the title compound as a yellow gum. LC/MS 578.2 (M+Na$^+$).

Step B: 1-tert-Butyl 4-methyl 4-[4-(hydroxymethyl)-2-naphthyl]piperidine-1,4-dicarboxylate To a solution of 1.90 g (3.42 mmol) of the above 1-tert-butyl 4-methyl 4-(4-{[(triisopropylsilyl)oxy]methyl}-2-naphthyl)piperidine-1,4-dicarboxylate in 30 mL of tetrahydrofuran was added 5.1 mL (5.1 mmol) of a 1.0 M solution of tetrabutylammonium fluoride in tetrahydrofuran. After stirring for 30 min the reaction mixture was concentrated in vacuo and the crude residue was purified on a Biotage® purification apparatus (silica gel, 40% ethyl acetate in hexanes) to yield the title compound as a white solid. LC/MS 422.1 (M+Na$^+$).

Step C: 1-tert-Butyl 4-methyl 4-(4-formyl-2-naphthyl)piperidine-1,4-dicarboxylate To a solution of 1.40 g (3.50 mmol) of the above 1-tert-butyl 4-methyl 4-[4-(hydroxymethyl)-2-naphthyl]piperidine-1,4-dicarboxylate in 25 mL of anhydrous dichloromethane under an atmosphere of nitrogen was added 1.4 mL (17 mmol) of pyridine followed by 1.78 g (4.21 mmol) of Dess-Martin periodinane. The resulting solution was stirred at ambient temperature for 30 min then quenched with a saturated aqueous sodium bicarbonate solution (10 mL). The layers were separated and the aqueous phase extracted with dichloromethane (2×50 mL). The combined organic layers were washed with brine (25 mL), dried over magnesium sulfate, filtered and evaporated in vacuo. The crude residue was purified on a Biotage® purification apparatus (silica gel, 7% ethyl acetate in hexanes) to yield the title compound as a white solid. LC/MS 420.2 (M+Na$^+$).

Step D: 3-[1-(tert-Butoxycarbonyl)-4-(methoxycarbonyl) piperidin-4-yl]-1-naphthoic acid To a solution of 1.23 g (3.09 mmol) of the above 1-tert-butyl 4-methyl 4-(4-formyl-2-naphthyl)piperidine-1,4-dicarboxylate in 23 mL of 2-methyl-2-propanol was added 0.990 mL (9.28 mmol) of 2-methyl-2-butene followed by dropwise addition of a solution of 743 mg (6.19 mmol) of sodium dihydrogen phosphate and 644 mg (7.12 mmol) of sodium chlorite in 23 mL of water. The resulting mixture was stirred at ambient temperature for 3 h then evaporated in vacuo to remove all volatiles. The residue was diluted with a saturated aqueous sodium carbonate solution (25 mL) and water (25 mL) and then extracted with diethyl ether (2×10 mL). An aqueous 2 N hydrochloric acid solution was then added dropwise to the aqueous phase until a pH of 6 was achieved. The aqueous phase was then extracted with diethyl ether (3×25 mL) and the combined organic layers were washed with brine (15 mL), dried over magnesium sulfate, filtered and evaporated in vacuo to yield the title compound as a white solid. LC/MS 436.1 (M+Na$^+$).

Step E: 1-tert-Butyl 4-methyl 4-{4-[(benzyloxy)carbonyl]-2-naphthyl}piperidine-1,4-dicarboxylate To a solution of 1.20 g (2.90 mmol) of the above 3-[1-(tert-butoxycarbonyl)-4-(methoxycarbonyl)piperidin-4-yl]-1-naphthoic acid in 30 mL of anhydrous dichloromethane at 0° C. was added 0.580 mL (7.26 mmol) of 1-methylimidazole followed by 0.250 mL (3.19 mmol) of methanesulfonyl chloride and the resulting mixture was stirred with gradual warming to ambient temperature over 30 min. After re-cooling the reaction mixture to 0° C., 0.900 mL (8.71 mmol) of benzyl alcohol and 18 mg (0.15 mmol) of 4-(dimethylamino)pyridine were added and the reaction mixture was allowed to warm to ambient temperature over 1 h. The reaction was quenched with a saturated aqueous ammonium chloride solution (20 mL) and the layers were separated. The aqueous layer was extracted with dichloromethane (2×25 mL) and the combined organic layers were washed with brine (15 mL), dried over magnesium sulfate, filtered and concentrated in vacuo. The crude residue was purified on a Biotage® purification apparatus (silica gel, 5 to 10% gradient of ethyl acetate in hexanes) to yield the title compound as a colorless gum. LC/MS 526.1 (M+Na$^+$).

Step F: Methyl 4-{4-[(benzyloxy)carbonyl]-2-naphthyl}piperidine-4-carboxylate To a stirred solution of 1.24 g (2.46 mmol) of 1-tert-butyl 4-methyl 4-{4-[(benzyloxy)carbonyl]-2-naphthyl}piperidine-1,4-dicarboxylate in 10 mL of dichloromethane at ambient temperature was added 10 mL of trifluoroacetic acid. The resulting solution was stirred at ambient temperature for 2 h and concentrated in vacuo. The residue was diluted with a saturated aqueous sodium bicarbonate solution (25 mL) and extracted with dichloromethane (3×20 mL). The organic layer was washed with brine (10 mL), dried over magnesium sulfate, filtered and concentrated in vacuo to yield the title compound as a colorless gum, which was used without further purification. LC/MS 404.4 (M+1).

Step G: Methyl 4-{4-[(benzyloxy)carbonyl]-2-naphthyl}-1-{[1-(3-ethoxyphenyl)-2-(4-methylphenyl)-1H-imidazol-4-yl]carbonyl}piperidine-4-carboxylate To a solution of 352 mg (1.09 mmol) of Intermediate 1 in 10 mL of anhydrous dichloromethane at 0° C. was added 0.200 mL (2.48 mmol) of 1-methylimidazole followed by 0.085 mL (1.09 mmol) of methanesulfonyl chloride. The resulting mixture was stirred with gradual warming to ambient temperature over 30 min then re-cooled to 0° C. A solution of 400 mg (0.991 mmol) of the above methyl 4-{4-[(benzyloxy)carbonyl]-2-naphthyl}piperidine-4-carboxylate in 7 ml of anhydrous dichloromethane and 6.0 mg (0.050 mmol) of 4-(dimethylamino)-pyridine were then added and the reaction mixture was allowed to warm to ambient temperature over 2 h. The reaction was quenched with a saturated aqueous ammonium chloride solution (10 mL) and the layers were separated. The aqueous layer was extracted with dichloromethane (3×10 mL) and the combined organic layers were dried over magnesium sulfate, filtered and concentrated in vacuo. The crude residue was purified on a Biotage® purification apparatus (silica gel, 40% ethyl acetate in hexanes) to yield the title compound as a colorless gum. LC/MS 708.2 (M+1).

Step H: 4-(4-Carboxy-2-naphthyl)-1-{[1-(3-ethoxyphenyl)-2-(4-methylphenyl)-1H-imidazol-4-yl]carbonyl}-4-piperidinecarboxylic acid, trifluoracetic acid salt To a stirred solution of 25 mg (0.035 mmol) of the above methyl 4-{4-[(benzyloxy)carbonyl]-2-naphthyl}-1-{[1-(3-ethoxyphenyl)-2-(4-methylphenyl)-1H-imidazol-4-yl]carbonyl}piperidine-4-carboxylate in 2 mL of tetrahydrofuran was added 14 mg (0.10 mmol) of potassium trimethylsilanolate. The resulting solution was stirred at ambient temperature for 15 h, quenched with 0.200 mL of trifluoroacetic acid, concentrated in vacuo and purified directly by reverse phase HPLC (TMC Pro-Pac C18; 10-100% 0.01% trifluoroacetic acid in acetonitrile/0.01% trifluoroacetic acid in water gradient). The resulting pure fractions were lyophilized overnight to give the titled compound as a white solid. $^1$H NMR (DMSO-d$_6$): δ 13.05 (br s, 1H), 8.80 (d, J=8.0 Hz, 1H), 8.21 (s, 2H), 8.05 (d, J=8.5 Hz, 1H), 7.96 (s, 1H), 7.64-7.67 (m, 2H), 7.34 (t, J=8.0 Hz, 1H), 7.26 (d, J=8.0 Hz, 2H), 7.16 (d, J=8.0 Hz, 2H), 7.02-6.98 (m, 2H), 6.83 (d, J=8.0 Hz, 1H), 4.96 (br s, 1H), 4.36 (br s, 1H), 4.00 (q, J=7.0 Hz, 2H), 3.61 (br s, 1H), 3.17 (br s, 1H), 2.62 (d, J=12.5 Hz, 2H), 2.28 (s, 3H), 2.00 (br s, 2H), 1.26 (t, J=7.0 Hz, 3H). LC/MS 604.3 (M+1).

Following essentially the procedures outlined in the Examples above, the Examples listed in Tables 5 and 6 were prepared.

TABLE 5

[Structure: core scaffold with substituents R5, R16, Y, R14 as tabulated]

| Example | R⁵ | R¹⁶ | Y | R¹⁴ | MS (M + 1) |
|---|---|---|---|---|---|
| 80 | H | CO₂H | CR¹⁴ | H | 560.1 |
| 81 | H | OCH₂CO₂H | N | — | 591.1 |
| 82 | H | CO₂H | N | — | 561.0 |
| 83 | H | CO₂H | CR¹⁴ | CONHCH₃ | 617.3 |
| 84 | H | CO₂H | CR¹⁴ | CON(CH₃)₂ | 631.4 |
| 85 | H | CO₂H | CR¹⁴ | CONHCH(CH₃)₂ | 645.4 |
| 86 | H | CONHCH₃ | CR¹⁴ | CO₂H | 617.2 |
| 87 | H | CON(CH₃)₂ | CR¹⁴ | CO₂H | 631.3 |
| 88 | H | CO₂H | CR¹⁴ | -C(O)NH-cyclopropyl | 643.5 |
| 89 | H | CO₂H | CR¹⁴ | CONHCH₂CH₃ | 631.3 |
| 90 | H | CO₂H | CR¹⁴ | CONHPhenyl | 679.4 |
| 91 | H | CO₂H | CR¹⁴ | CON(CH₂CH₃)₂ | 659.5 |
| 92 | H | CO₂H | CR¹⁴ | CONHCH₂CO₂H | 661.3 |
| 93 | H | CO₂H | CR¹⁴ | CON(CH₃)CH₂CO₂H | 675.3 |
| 94 | H | CO₂H | CR¹⁴ | -C(O)-pyrrolidinyl | 657.0 |
| 95 | H | CO₂H | CR¹⁴ | -C(O)-morpholinyl | 673.5 |
| 96 | F | CO₂H | CR¹⁴ | CO₂H | 622.0 |
| 97 | F | CO₂H | CR¹⁴ | CONHCH₂CO₂H | 679.0 |
| 98 | F | CONHCH₂CO₂H | CR¹⁴ | CO₂H | 679.0 |
| 99 | F | CO₂H | CR¹⁴ | CONH₂ | 621.0 |
| 100 | F | CONH₂ | CR¹⁴ | CO₂H | 621.0 |

TABLE 6

| Example | R⁵ | R¹⁶ | Y | R¹⁴ | MS (M + 1) |
|---|---|---|---|---|---|
| 101 | H | NHCOMe | $CR^{14}$ | $CO_2H$ | 631.2 |
| 102 | H | NHCONHMe | $CR^{14}$ | $CO_2H$ | 646.0 |
| 103 | H | $CH_2CO_2H$ | $CR^{14}$ | H | 588.3 |
| 104 | H | trans-$CHCHCO_2H$ | $CR^{14}$ | H | 600.3 |

BIOLOGICAL ASSAYS

A. Cholecystokinin-1 Receptor (CCK1R) and Cholecystokinin-2 Receptor (CCK2R) Binding Assays Cells were cultured to confluence and harvested by aspirating culture medium and rinsed twice with 1×PBS without $Mg^{++}$ and $Ca^{++}$. 3 ml of Cell Dissociate Solution was added to each T-175 flask until all cells dissociated and then an additional 15 ml 1×PBS without $Mg^{++}$ and $Ca^{++}$ was added to each flask. Dissociated cells were collected in a centrifuge tube by centrifuging at 1000 rpm for 10 min. The cell pellet was homogenized at 4° C. using a Polytron (setting 40, 20 stokes) in about 10 ml/T175 flask membrane preparation buffer (10 mM Tris pH 7.4, 0.01 mM Pefabloc, 10 μM phosphoramidon and 40 μg/ml Bacitracin). After centrifugation at 2200 rpm (1000×g) for 10 min at 4° C., the supernatant was transferred to a clean centrifuge tube and spun at 18,000 rpm (38,742×g) for 15 min. at 4° C. Membranes were resuspended with the above membrane preparation buffer (1000 μl per T-175 flask), homogenized, aliquoted, quickly frozen in liquid nitrogen and stored at −80° C. The specific binding of $^{125}$I-Bolton Hunter-CCK-8S to CCK1R or CCK2R was measured by filtration binding assay in 96 well plate format. 0.5 μg membrane/well in binding buffer (50 mM Tris pH 7.4, 5 mM $MgCl_2$, 200 μg/ml Bacitracin and protease inhibitor cocktail) was mixed with agonists in 1% DMSO (final concentration) and 0.1 nM $^{125}$I-Bolton Hunter-CCK-8S was added. After incubation for 1-2 hrs at room temperature, membrane-bound $^{125}$I-Bolton Hunter-CCK8S was separated from the free $^{125}$I-Bolton Hunter-CCK8S by filtering through GF/C filters presoaked in 0.2% BSA solution. The filters were washed with ice-cold washing buffer (50 mM Tris pH 7.4, 10 mM $MgCl_2$, 2 mM EDTA and 0.04% Tween 20). The radioactivity was determined by adding 30 μl of microscintillant/well after each plate was dried at room temperature overnight or placed at 55° C. for 30 mins. A Packard Top Count was then used to read each filter plate. The data in cpms was plotted vs. the log molar concentration of receptor ligand (compound). The $IC_{50}$ was reported as the inflection point of the resulting sigmoidal curve. The maximum inhibition observed at the highest compound concentration was reported for compounds which do not generate a curve.

B. Cell Culture of Cholecystokinin-1 Receptor (CCK1R) and Cholecystokinin-2 Receptor (CCK2R) Cell Lines Stable CHO cell lines expressing the human CCK1R and CCK2R cDNA and stable HEK293 cell lines expressing the human CCK2R cDNA were generated using standard cell biology techniques. One CCK1R clone identified as CHO_WT23 was used for both FLIPR and IP3 functional and binding assays. One CCK2R clone called CHO_B101 was used for FLIPR functional assays and another CCK2R clone, CHO_hCCK2R, was used for IP3 functional assays. Both WT23 and B101 cells were routinely cultured in T175 flasks in Iscoves Modified Dulbecco's Medium (Invitrogen #12440-046) supplemented with 10% FBS (cat# SH30070.03, Hyclone, Logan, Utah), 1×HT Supplement (0.1 mM Sodium Hypoxanthine and 16 μM Thymidine), 100 units/ml Pennicillin-G and 100 μg/ml Streptomycin, 2 mM L-Glutamine and 1 mg/ml Geneticin. hCCK2R/CHO/Flip-in cells were routinely cultured in T175 flasks in F-12 Nutrient Mixture (Ham) supplemented with 10% FBS (cat# SH30070.03, Hyclone, Logan, Utah), 100 units/ml Pennicillin-G and 100 μg/ml Streptomycin, 2 mM L-Glutamine and 150 μg/ml Hygromycin. One Hek293 hCCK2R clone identified as Hek293_hCCK2R#37 was used for binding assays. Hek293_hCCK2R#37 cells were routinely cultured in T175 flasks in Dulbecco's Modified Eagle Medium, with high glucose (Invitrogen Cat # 11965-084) supplemented with 10% FBS (cat# SH30070.03, Hyclone, Logan, Utah), 25 mM of HEPES Buffer Solution (Invitrogen cat#15630-080), 500 μg/ml Geneticin (Invitrogen cat# 10131-027) and 200 μg/ml Hygromycin. Cells were grown as attached monolayers in tissue culture flasks under appropriate media in an incubator at 37° C. with 5% $CO_2$. Cells were passed 1:5 for CHO_WT23, B101 and CHO_hCCK2R cells and 1:3 for HEK 293_hCCK2R#37 twice a week. Cell culture media, antibiotics, Fetal Bovine Serum were all from Invitrogen Technologies Inc. unless otherwise specified.

C. Cholecystokinin-1 Receptor (CCK1R) and Cholecystokinin-2 Receptor (CCK2R) Functional Assays 1) FLIPR (Flurometric Imaging Plate Reader, Molecular Devices, Sunnyvale, Calif.)

CHO_WT23 and B101 cells cultured as described above were detached with Trypsin-EDTA and 20 μl volume of cells were seeded in 384 well plate at 62,500 cells/ml. The cells grew overnight at 37° C. with 5% $CO_2$ in a humidified atmosphere. On the day of the assay, the cells were loaded with 20 μl/well of No-wash assay buffer (HBSS, 0.1% BSA, 20 mM HEPES, 2.5mM Probenecid and 1.6 mM TR40 Quenching Solution) containing 8 μM Fluo-4 AM in the dark at room temperature for 1.5 hrs. Agonists were dissolved in DMSO and diluted into assay buffer. 13.3 μl/well of 4× concentration of agonist solution was added to cells while measuring fluorescence. The $EC_{50}$ for activation of the CCK1R or CCK2R receptor was reported as the inflection point of the resulting sigmoidal curve.

2) Inositol Phosphate SPA Assay (IP3) to Measure IP3 Accumulation

This functional assay was performed in a 96-well format. On the first day, 75 μl of CHO cells at 62,500/ml were plated on poly-D-lysine plates. On the afternoon of the next day, the plates were aspirated, and the cells were washed with PBS w/o Mg++, Ca++. Next 150 µl of ³H-inositol labeling media, Inositol-free DMEM media ICN #1642954 supplemented with 10% FBS, 1× pen/strep/glutamine to which ³H-myo-inositol (NEN #NET114A) was added, 1 mCi/ml, 25 Ci/mmol diluted 1:150 in loading medium (final specific radioactivity of 1 µCi/150 µl). After 18 hours of labeling, 5 µl 300 mM LiCl was added to the wells, mixed, and incubated for 20 minutes at 37° C., then 1.5 µl DMSO of 200× compounds were added to wells and incubated for an additional 90 minutes at 37° C. Plates were aspirated, and then the reaction was terminated and cells were lysed with the addition of 60 µl 10 mM formic acid for 60 minutes at room temperature. 20 µl of lysate was transferred to clear-bottom Opti-plates which contained RNA binding YSi SPA-beads (Amershamn RPNQ0013) that were suspended in 10% glycerol at 1 mg beads/70 µl of solution and dispensed at 70 µl per well. After mixing, the plates sit at room temperature for 2 hrs and were then counted using a Wallac Microbeta reader. The $EC_{50}$ for activation of the CCK1F or CCK2R receptor was calculated from the titration curve of the compounds.

D. In Vivo Overnight Food Intake and Body Weight in C57 Lean Male Mice

Methods: Male C57 mice, approximately 8 weeks old (weighing approximately 25 g) were individually housed and acclimated for several days prior to testing. Mice were orally dosed (PO; n=8) with either vehicle controls (10% Tween-water) or CCK1R agonists (various doses). A known CB1 inverse agonist, AM251 (3 mg/kg) was used as the positive control for inter- and intra-experimental control. CCK1R agonists were dosed (PO) approximately 60-120 minutes prior to the onset of the dark cycle. Overnight food intake (g) and body weight (g) (±SEM) were collected and analyzed. All data were presented as mean±SEM (n=8). Statistical significance was calculated using Student's t-test to determine whether compared the groups were statistically distinct. Differences were considered significant when p<0.05.

Compounds useful in the present invention decrease overnight food intake by at least 10% and/or decrease body weight overnight by at least 1% relative to placebo.

E. Mouse Gallbladder Emptying Assay for CCK-1R Binding Specificity

Methods: Male CD-1 mice, approximately 7-8 weeks old (weighing 25 g) were housed (8 mice per cage), and fasted for 18 hours with ad lib access to water. Mice were orally dosed (PO; n=8) with either vehicle controls (10% Tween-water) or CCK1R agonists (various doses) for 4 h. After 4 h, mice were deeply anesthetized with $CO_2$ inhalant; blood samples were drawn via cardiac puncture and stored at −20° C. (for future assays). Gall bladders were isolated, removed and weighed. Gallbladder weights were normalized to body weight (g/kg) and compared to vehicle control group. The entire assay typically required approximately 30-40 minutes for tissue collection. All data were presented as mean±SEM (n=8) and Statistical significance was calculated using Student's t-test to determine whether compared the groups were statistically distinct. Differences were considered significant when p<0.05.

Representative compounds of the present invention were tested and found to bind to the cholecystokinin-1 receptor. Representative compounds of the present invention were found to have $IC_{50}$ values less than or equal to 500 nM. Representative compounds of the present invention were also tested in the functional assay and found to activate the cholecystokinin-1 receptor with $EC_{50}$ values less than or equal to 500 nM.

Examples of Pharmaceutical Compositions

As a specific embodiment of an oral composition of a composition of the present invention, 5 mg of Example 1 is formulated with sufficient finely divided lactose to provide a total amount of 580 to 590 mg to fill a size O hard gelatin capsule.

As another specific embodiment of an oral composition of a compound of the present invention, 2.5 mg of Example 1 is formulated with sufficient finely divided lactose to provide a total amount of 580 to 590 mg to fill a size O hard gelatin capsule.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the subject or mammal being treated obesity, diabetes, obesity-related disorders, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and embodiments of the present invention. It is intended, therefore, that the invention be limited only by the scope of the claims which follow and that such claims be interpreted as broadly as is reasonable.

What is claimed is:
1. A compound of formula I:

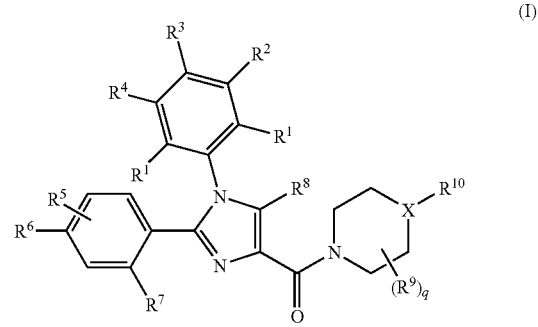

or a pharmaceutically acceptable salt thereof; wherein
X is N or $CR^{16}$;
$R^1$ is selected from the group consisting of:
(1) hydrogen,
(2) halogen,
(3) —OH,
(4) —$C_{1-6}$alkyl,
(5) —$C_{1-6}$alkoxy,
(6) —$SC_{1-6}$-alkyl, and
(7) —$NHC_{1-6}$-alkyl,
wherein alkyl and alkoxy are unsubstituted or substituted with one to five substituents selected from halogen, —OH, $C_{1-6}$alkyl, and $C_{1-6}$alkoxy;

$R^2$ is selected from the group consisting of:
(1) hydrogen,
(2) —OH,
(3) halogen,
(4) —$C_{1-6}$alkyl optionally substituted with fluoride, and
(5) —$OC_{1-6}$alkyl optionally substituted with fluoride;

$R^3$ and $R^4$ are each independently selected from the group consisting of:
(1) —OH,
(2) —$C_{1-6}$alkyl, and
(3) —$C_{1-6}$alkoxy, wherein alkyl and alkoxy are unsubstituted or substituted with one to five substituents selected from halogen, OH, $C_{1-6}$alkyl, and —$C_{1-6}$alkoxy, or $R^3$ and $R^4$ together with the atoms to which they are attached form a 5-6 membered ring containing 1-2 heteroatoms independently selected from oxygen, sulfur, and N—$R^{15}$;

$R^5$, $R^6$ and $R^7$ are each independently selected from the group consisting of:
(1) hydrogen,
(2) halogen,
(3) —OH,
(4) —$C_{1-6}$alkyl, and
(5) —$C_{1-6}$alkoxy, wherein alkyl and alkoxy are unsubstituted or substituted with one to five substituents independently selected from halogen, —OH, $C_{1-6}$alkyl, and $C_{1-6}$alkoxy, or $R^5$ and $R^6$ or $R^6$ and $R^7$ together with the atoms to which they are attached form a 4-8 membered ring containing 0-2 heteroatoms independently selected from oxygen, sulfur, and N—$R^{15}$, and wherein the 4-8 membered ring is unsubstituted or substituted with a substituent selected from OH, halogen, $C_{1-6}$alkyl, and $C_{1-6}$alkoxy;

$R^8$ is independently selected from the group consisting of:
(1) hydrogen,
(2) halogen,
(3) —$C_{1-6}$alkyl,
(4) —$C_{1-6}$alkoxy, and
(5) —$C_{3-6}$cycloalkyl;

$R^9$ and $R^{16}$ are each independently selected from the group consisting of:
(1) hydrogen,
(2) —$(CH_2)_nCF_3$,
(3) —$(CH_2)_nOH$,
(4) —$(CH_2)_nCN$,
(5) —$C_{1-6}$alkyl,
(6) —$C_{1-6}$alkoxy,
(7) —$(CH_2)_nC_{3-8}$cycloalkyl,
(8) —$(CH_2)_nNR^{11}R^{12}$,
(9) phenyl,
(10) —$C_{2-6}$alkene-$CO_2R^{12}$,
(11) —$(CH_2)_nC(O)R^{12}$,
(12) —$(CH_2)_nCO_2R^{12}$,
(13) —$(CH_2)_nOC(O)R^{12}$,
(14) —$(CH_2)_nO(CH_2)_nCO_2R^{12}$,
(15) —$(CH_2)_nO(CH_2)_nC(O)NR^{11}R^{12}$,
(16) —$(CH_2)_nC(O)NR^{11}R^{12}$,
(17) —$(CH_2)_nC(O)NR^{11}(CH_2)_2R^{12}$,
(18) —$(CH_2)_nNR^{11}C(O)R^{12}$,
(19) —$(CH_2)_nNR^{11}C(O)NR^{11}R^{12}$,
(20) —$(CH_2)_nNR^{11}(CH_2)_nCO_2R^{12}$,
(21) —$(CH_2)_nNR^{11}CO_2R^{12}$, and
(22) —$(CH_2)_nNR^{11}SO_2R^{12}$, wherein alkyl, alkene, alkoxy, cycloalkyl, phenyl and —$(CH_2)_n$ are unsubstituted or substituted with one to eight substituents selected from oxo, halogen, —$C_{1-6}$alkyl, —$C_{1-6}$alkoxy, phenyl, —$(CH_2)_nOH$, —$(CH_2)_nCN$, —$(CH_2)_nCF_3$, —$(CH_2)_nSO_3H$, —$(CH_2)_nCO_2H$, —$(CH_2)_nCO_2C_{1-6}$alkyl, and —$(CH_2)_nCO_2C_{2-6}$alkene, and alkyl and alkoxy are unsubstituted or substituted with one to five substituents selected from halogen, —OH, —$SO_3H$, —$CO_2H$, and —$CO_2C_{1-6}$alkyl, provided that at least one of $R^9$ and $R^{16}$ is selected from the group consisting of: —$C_{2-6}$alkene-$CO_2R^{12}$, —$(CH_2)_nC(O)R^{12}$, —$(CH_2)_nCO_2R^{12}$ —$(CH_2)_nOC(O)R^{12}$, —$(CH_2)_nO(CH_2)_nCO_2R^{12}$, —$(CH_2)_nO(CH_2)_nC(O)NR^{11}R^{12}$, —$(CH_2)_nC(O)NR^{11}R^{12}$, —$(CH_2)_nC(O)NR^{11}(CH_2)_nCO_2R^{12}$, —$(CH_2)_nNR^{11}C(O)R^{12}$, —$(CH_2)_nNR^{11}C(O)NR^{11}R^{12}$, —$(CH_2)_nNR^{11}(CH_2)_nCO_2R^{12}$, —$(CH_2)_nNR^{11}CO_2R^{12}$, and —$(CH_2)_nNR^{11}SO_2R^{12}$;

$R^{10}$ is naphthalene, or quinoline, wherein each naphthalene and quinoline is unsubstituted or substituted with one to four $R^{14}$ substituents;

each $R^{11}$, $R^{12}$ and $R^{13}$ is independently selected from the group consisting of:
(1) hydrogen,
(2) —$C_{1-8}$alkyl,
(3) —$(CH_2)_nOH$,
(4) —$(CH_2)_nC_{3-8}$cycloalkyl,
(5) —$(CH_2)_nC_{2-8}$heterocycloalkyl,
(6) —$(CH_2)_n$aryl, and
(7) —$(CH_2)_n$5-membered heteroaryl, wherein alkyl, cycloalkyl, heterocycloalkyl, and —$(CH_2)_n$ are unsubstituted or substituted with one to eight substituents selected from oxo, halogen, —$C_{1-6}$alkyl, —$C_{1-6}$alkoxy, —$(CH_2)_nOH$, —$(CH_2)_nCN$, —$(CH_2)_nCF_3$, —$(CH_2)_nSO_3H$, —$(CH_2)_nCO_2C_{1-6}$alkyl, and —$(CH_2)_nCO_2C_{2-6}$alkene, and alkyl and alkoxy are unsubstituted or substituted with one to five substituents selected from halogen, —OH, —$SO_3H$, —$CO_2H$, and —$CO_2C_{1-6}$alkyl, and wherein aryl and 5 membered heteroaryl are unsubstituted or substituted with one to four substituents independently selected from halogen, —$C_{1-6}$ alkyl, —$C_{1-6}$alkoxy, —$(CH_2)_nOH$, —$(CH_2)_nCN$, —$(CH_2)_nCF_3$, —$(CH_2)_nSO_3H$, —$(CH_2)_nCO_2H$, —$(CH_2)_nCO_2C_{1-6}$alkyl, and —$(CH_2)_nCO_2C_{2-6}$alkene, and alkyl and alkoxy are unsubstituted or substituted with one to five substituents selected from halogen, —OH, —$SO_3H$, —$CO_2H$, and —$CO_2C_{1-6}$alkyl, or $R^{11}$ and $R^{12}$ together with the nitrogen to which they are attached form a 4-8 membered heterocyclic ring containing 0-2 additional heteroatoms selected from oxygen, sulfur, and $NR^{15}$, and wherein the 4-8 membered heterocyclic ring is unsubstituted or substituted with one to five substituents independently selected from oxo, halogen, —$C_{1-6}$alkyl, —$C_{1-6}$alkoxy, —$(CH_2)_nOH$, —$(CH_2)_nCN$, —$(CH_2)_nCF_3$, —$(CH_2)_nSO_3H$, —$(CH_2)_nCO_2H$, —$(CH_2)_nCO_2C_{1-6}$alkyl, and —$(CH_2)_nCO_2C_{2-6}$alkene and alkyl and alkoxy are unsubstituted or substituted with one to five substituents selected from halogen, —OH, —$SO_3H$, —$CO_2H$, and —$CO_2C_{1-6}$alkyl;

each $R^{14}$ is independently selected from the group consisting of:
(1) hydrogen,
(2) halogen,
(3) —$C(O)C_{2-8}$heterocycloalkyl,
(4) —$(CH_2)_nCO_2H$,
(5) —$CONH_2$,
(6) —$CONHC_{1-6}$alkyl,
(7) —$CON(C_{1-6}$alkyl$)_2$,
(8) —$C(O)NHC_{3-8}$cycloalkyl,
(9) —CONHaryl,
(10) —$C(O)NHCH_2CO_2H$, and
(11) —$C(O)N(C_{1-6}$alkyl$)CH_2CO_2H$, wherein alkyl, cycloalkyl, and heterocycloalkyl are unsubstituted or substituted with one to five substituents selected from oxo, halogen, —$C_{1-6}$alkyl, —$C_{1-6}$alkoxy, —$(CH_2)_nOH$, —(CH$_2$)$_n$CN, —(CH$_2$)$_n$CF$_3$, —(CH$_2$)$_n$SO$_3$H, —(CH$_2$)$_n$ CO$_2$H, —(CH$_2$)$_n$CO$_2$C$_{1-6}$alkyl, and —(CH$_2$)$_n$CO$_2$C$_{2-6}$alkene, wherein aryl is unsubstituted or substituted with one to five substituents independently selected from halogen, —C$_{1-6}$ alkyl, —C$_{1-6}$alkoxy, —(CH$_2$)$_n$OH, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$ CO$_2$C$_{1-6}$alkyl, and —(CH$_2$)$_n$CO$_2$C$_{2-6}$alkene, and wherein any (CH$_2$)$_n$ carbon atom is unsubstituted or substituted with one to two substituents selected from oxo, halogen, —(CH$_2$)$_n$ OH, —C$_{1-6}$alkyl, —C$_{1-6}$alkoxy, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene and alkyl and alkoxy are unsubstituted or substituted with one to five substituents independently selected from halogen, —OH, —SO$_3$H, —CO$_2$H, and —CO$_2$C$_{1-6}$alkyl;

each R$^{15}$ is independently selected from the group consisting of:
(1) hydrogen,
(2) —C$_{1-6}$alkyl,
(3) —C$_{3-8}$cycloalkyl,
(4) —SO$_2$R$^{12}$,
(5) —COR$^{13}$, and
(6) —CO$_2$R$^{12}$, wherein alkyl and cycloalkyl are unsubstituted or substituted with one to six substituents selected from halogen, —OH, and —(CH$_2$)$_n$CO$_2$H;

each n is independently 0, 1, 2, 3, 4, 5, 6, 7 or 8; and
each q is independently 1, 2, 3 or 4.

2. The compound of claim 1 wherein R$^8$ is hydrogen; or a pharmaceutically acceptable salt thereof.

3. The compound of claim 1 wherein X is N; or a pharmaceutically acceptable salt thereof.

4. The compound of claim 1 wherein X is CR$^{16}$; or a pharmaceutically acceptable salt thereof.

5. The compound of claim 4 wherein R$^9$ is hydrogen; or a pharmaceutically acceptable salt thereof.

6. The compound of claim 1 wherein R$^9$ is independently selected from the group consisting of: hydrogen, —C$_{2-6}$alkene-CO$_2$R$^{12}$, —(CH$_2$)$_n$C(O)R$^{12}$, —(CH$_2$)$_n$CO$_2$R$^{12}$, —(CH$_2$)$_n$ OC(O)R$^{12}$, —(CH$_2$)$_n$O(CH$_2$)$_n$CO$_2$R$^{12}$, —(CH$_2$)$_n$ O(CH$_2$)$_n$C(O)NR$^{11}$R$^{12}$, —(CH$_2$)$_n$C(O)NR$^{11}$R$^{12}$, —(CH$_2$)$_n$ NR$^{11}$CO$_2$R$^{12}$, —(CH$_2$)$_n$C(O)NR$^{11}$(CH$_2$)$_n$CO$_2$R$^{12}$, —(CH$_2$)$_n$ NR$^{11}$C(O)R$^{12}$, —(CH$_2$)$_n$NR$^{11}$C(O)NR$^{11}$R$_{12}$, —(CH$_2$)$_n$NR$^{11}$SO$_2$R$^{12}$, and —(CH$_2$)$_n$NR$^{11}$(CH$_2$)$_n$CO$_2$R$^{12}$, wherein alkene, and —(CH$_2$)$_n$ are unsubstituted or substituted with one to eight substituents selected from oxo, halogen, —C$_{1-6}$ alkyl, —C$_{1-6}$alkoxy, phenyl, —(CH$_2$)$_n$OH, —(CH$_2$)$_n$CN, —(CH$_2$)$_n$CF$_3$, —(CH$_2$)$_n$SO$_3$H, —(CH$_2$)$_n$ CO$_2$H, —(CH$_2$)$_n$CO$_2$C$_{1-6}$alkyl, and —(CH$_2$)$_n$CO$_2$C$_{2-6}$alkene, and alkyl and alkoxy are unsubstituted or substituted with one to five substituents selected from halogen, —OH, —SO$_3$H, —CO$_2$H, and —CO$_2$C$_{1-6}$alkyl, provided that at least one of R$^9$ and R$^{16}$ is selected from the group consisting of: —C$_{2-6}$alkene-CO$_2$R$^{12}$, —(CH$_2$)$_n$C(O)R$^{12}$, —(CH$_2$)$_n$ CO$_2$R$^{12}$, —(CH$_2$)$_n$OC(O)R$^{12}$, —(CH$_2$)$_n$O(CH$_2$)$_n$CO$_2$R$^{12}$, —(CH$_2$)$_n$O(CH$_2$)$_n$C(O)NR$^{11}$R$^{12}$, —(CH$_2$)$_n$C(O)NR$^{11}$R$^{12}$, —(CH$_2$)$_n$C(O)NR$^{11}$(CH$_2$)$_n$CO$_2$R$^{12}$, —(CH$_2$)$_n$NR$^{11}$CO$_2$R$^{12}$, —(CH$_2$)$_n$NR$^{11}$C(O)R$^{12}$, —(CH$_2$)$_n$NR$^{11}$C(O)NR$^{11}$R$^{12}$, —(CH$_2$)$_n$NR$^{11}$(CH$_2$)$_n$CO$_2$R$^{12}$, and —(CH$_2$)$_n$NR$^{11}$SO$_2$R$^{12}$; or a pharmaceutically acceptable salt thereof.

7. The compound of claim 1 of formula III:

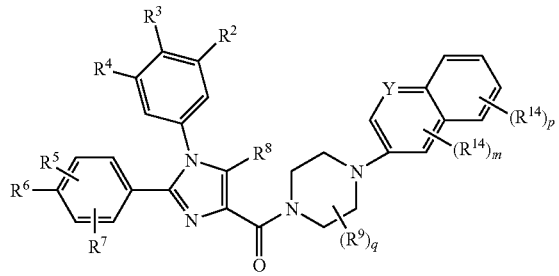

(III)

or a pharmaceutically acceptable salt thereof; wherein
Y is N or CR$^{14}$;
R$^2$ is selected from the group consisting of:
(1) hydrogen,
(2) —OH,
(3) halogen,
(4) —C$_{1-6}$alkyl optionally substituted with fluoride, and
(5) —OC$_{1-6}$alkyl optionally substituted with fluoride;
R$^3$ and R$^4$ are each independently selected from the group consisting of:
(1) —OH,
(2) —C$_{1-6}$alkyl, and
(3) —C$_{1-6}$alkoxy,
wherein alkyl and alkoxy are unsubstituted or substituted with one to five substituents selected from halogen, OH, C$_{1-6}$alkyl, and —C$_{1-6}$alkoxy, or R$^3$ and R$^4$ together with the atoms to which they are attached form a 5-6 membered ring containing 1-2 heteroatoms independently selected from oxygen, sulfur, and N—R$^{15}$;
R$^5$, R$^6$ and R$^7$ are each independently selected from the group consisting of:
(1) hydrogen,
(2) halogen,
(3) —OH,
(4) —C$_{1-6}$alkyl, and
(5) —C$_{1-6}$alkoxy,
wherein alkyl and alkoxy are unsubstituted or substituted with one to five substituents independently selected from halogen, —OH, C$_{1-6}$alkyl, and C$_{1-6}$alkoxy;
R$^8$ is independently selected from the group consisting of:
(1) hydrogen,
(2) halogen,
(3) —C$_{1-6}$alkyl,
(4) —C$_{1-6}$alkoxy, and
(5) —C$_{3-6}$cycloalkyl;
R$^9$ is independently selected from the group consisting of:
(1) —C$_{2-6}$alkene-CO$_2$R$^{12}$,
(2) —(CH$_2$)$_n$C(O)R$^{12}$,
(3) —(CH$_2$)$_n$CO$_2$R$^{12}$,
(4) —(CH$_2$)$_n$OC(O)R$^{12}$,
(5) —(CH$_2$)$_n$O(CH$_2$)$_n$CO$_2$R$^{12}$,
(6) —(CH$_2$)$_n$O(CH$_2$)$_n$C(O)NR$^{11}$R$^{12}$,
(7) —(CH$_2$)$_n$C(O)NR$^{11}$R$^{12}$,
(8) —(CH$_2$)$_n$C(O)NR$^{11}$(CH$_2$)$_n$CO$_2$R$^{12}$,
(9) —(CH$_2$)$_n$NR$^{11}$C(O)R$^{12}$,
(10) —(CH$_2$)$_n$NR$^{11}$C(O)NR$^{11}$R$^{12}$,
(11) —(CH$_2$)$_n$NR$^{11}$(CH$_2$)$_n$CO$_2$R$^{12}$,
(12) —(CH$_2$)$_n$NR$^{11}$CO$_2$R$^{12}$, and
(13) —(CH$_2$)$_n$NR$^{11}$SO$_2$R$^{12}$, wherein alkene, and —(CH$_2$)$_n$are unsubstituted or substituted with one to eight substituents selected from oxo, halogen, —C$_{1-6}$alkyl, —C$_{1-6}$alkoxy, phenyl, —(CH$_2$)$_n$OH, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene, and alkyl and alkoxy are unsubstituted or substituted with one to five substituents selected from halogen, —OH, —SO$_3$H, —CO$_2$H, and —CO$_2$C$_{1-6}$alkyl;

each R$^{11}$, R$^{12}$ and R$^{13}$ is independently selected from the group consisting of:
(1) hydrogen,
(2) —C$_{1-8}$alkyl,
(3) —(CH$_2$)$_n$OH,
(4) —(CH$_2$)$_n$C$_{3-8}$cycloalkyl,
(5) —(CH$_2$)$_n$C$_{2-8}$heterocycloalkyl,
(6) —(CH$_2$)$_n$aryl, and
(7) —(CH$_2$)$_n$5 membered heteroaryl, wherein alkyl, cycloalkyl, heterocycloalkyl, —(CH$_2$)$_n$ are unsubstituted or substituted with one to eight substituents selected from oxo, halogen, —C$_{1-6}$alkyl, —C$_{1-6}$alkoxy, —(CH$_2$)$_n$OH, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene and alkyl and alkoxy are unsubstituted or substituted with one to five substituents selected from halogen, —OH, —SO$_3$H, —CO$_2$H, and —CO$_2$C$_{1-6}$alkyl, wherein aryl, and heteroaryl are unsubstituted or substituted with one to eight substituents independently selected from halogen, —C$_{1-6}$alkyl, —C$_{1-6}$alkoxy, —(CH$_2$)$_n$OH, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene, and alkyl and alkoxy are unsubstituted or substituted with one to five substituents selected from halogen, —OH, —SO$_3$H, —CO$_2$H, and —CO$_2$C$_{1-6}$alkyl, or R$^{11}$ and R$^{12}$ together with the nitrogen to which they are attached form a 4-8 membered heterocyclic ring containing 0-2 additional heteroatoms selected from oxygen, sulfur, and NR$^{15}$, and wherein the 4-8 membered heterocyclic ring is unsubstituted or substituted with one to five substituents independently selected from oxo, halogen, —C$_{1-6}$alkyl, —C$_{1-6}$alkoxy, —(CH$_2$)$_n$OH, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene and alkyl and alkoxy are unsubstituted or substituted with one to five substituents selected from halogen, —OH, —SO$_3$H, —CO$_2$H, and —CO$_2$C$_{1-6}$alkyl;

each R$^{14}$ is independently selected from the group consisting of:
(1) hydrogen,
(2) halogen,
(3) —C(O)C$_{2-8}$heterocycloalkyl,
(4) —(CH$_2$)$_n$CO$_2$H,
(5) —CONH$_2$,
(6) —CONHC$_{1-6}$alkyl,
(7) —CON(C$_{1-6}$alkyl)$_2$,
(8) —C(O)NHC$_{3-8}$cycloalkyl,
(9) —CONHaryl,
(10) —C(O)NHCH$_2$CO$_2$H, and
(11) —C(O)N(C$_{1-6}$alkyl)CH$_2$CO$_2$H, wherein alkyl, cycloalkyl, and heterocycloalkyl are unsubstituted or substituted with one to five substituents selected from oxo, halogen, —C$_{1-6}$alkyl, —C$_{1-6}$alkoxy, —(CH$_2$)$_n$OH, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene, wherein aryl is unsubstituted or substituted with one to five substituents independently selected from halogen, —C$_{1-6}$ alkyl, —C$_{1-6}$alkoxy, —(CH$_2$)$_n$OH, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene, and wherein any (CH$_2$)$_n$ carbon atom is unsubstituted or substituted with one to two substituents selected from oxo, halogen, —(CH$_2$)$_n$OH, —C$_{1-6}$alkyl, —C$_{1-6}$alkoxy, —(CH$_2$)$_n$CN, —(CH$_2$)$_n$CF$_3$, —(CH$_2$)$_n$SO$_3$H, —(CH$_2$)$_n$CO$_2$H, —(CH$_2$)$_n$CO$_2$C$_{1-6}$alkyl, and —(CH$_2$)$_n$CO$_2$C$_{2-6}$alkene and alkyl and alkoxy are unsubstituted or substituted with one to five substituents independently selected from halogen, —OH, —SO$_3$H, —CO$_2$H, and —CO$_2$C$_{1-6}$alkyl;

each R$^{15}$ is independently selected from the group consisting of:
(1) hydrogen,
(2) —C$_{1-6}$alkyl, unsubstituted or substituted with one to six halogens,
(3) —C$_{3-8}$cycloalkyl, unsubstituted or substituted with one to six halogens,
(4) —SO$_2$R$^{12}$,
(5) —COR$^{12}$, and
(6) —CO$_2$R$^{12}$;

each m is independently 0, 1, 2, 3 or 4;
each n is independently 0, 1, 2, 3, 4, 5, 6, 7 or 8;
each p is independently 0, 1, 2, or 3; and
each q is independently 1, 2, 3 or 4.

8. The compound of claim 7 wherein p is 0; or a pharmaceutically acceptable salt thereof.

9. The compound of claim 1 of formula IV:

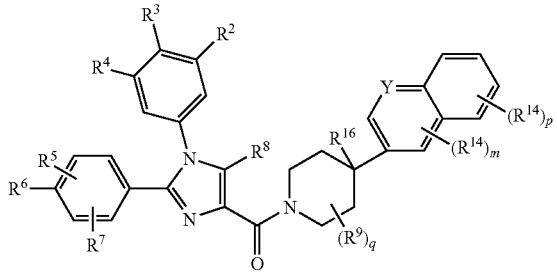

(IV)

or a pharmaceutically acceptable salt thereof; wherein
Y is N or CR$^{14}$;
R$^2$ is selected from the group consisting of:
(1) hydrogen,
(2) —OH,
(3) halogen,
(4) —C$_{1-6}$alkyl optionally substituted with fluoride, and
(5) —OC$_{1-6}$alkyl optionally substituted with fluoride;

R$^3$ and R$^4$ are each independently selected from the group consisting of:
(1) —OH
(2) —C$_{1-6}$alkyl, and
(3) —C$_{1-6}$alkoxy, wherein alkyl and alkoxy are unsubstituted or substituted with one to five substituents selected from halogen, OH, C$_{1-6}$alkyl, and —C$_{1-6}$alkoxy, or R$^3$ and R$^4$ together with the atoms to which they are attached form a 5-6 membered ring containing 1-2 heteroatoms independently selected from oxygen, sulfur, and N—R$^{15}$, wherein the 5-6 membered ring is unsubstituted or substituted with a substituent selected from the group consisting of: OH, halogen, C$_{1-6}$alkyl, and C$_{1-6}$alkoxy;

R$^5$, R$^6$ and R$^7$ are each independently selected from the group consisting of:
(1) hydrogen,
(2) halogen, (3) —OH,
(4) —$C_{1-6}$alkyl, and
(5) —$C_{1-6}$alkoxy,
wherein alkyl and alkoxy are unsubstituted or substituted with one to five substituents independently selected from halogen, —OH, $C_{1-6}$alkyl, and $C_{1-6}$alkoxy;

$R^8$ is independently selected from the group consisting of:
(1) hydrogen,
(2) halogen,
(3) —$C_{1-6}$alkyl,
(4) —$C_{1-6}$alkoxy, and
(5) —$C_{3-6}$cycloalkyl;

$R^9$ and $R^{16}$ are each independently selected from the group consisting of:
(1) hydrogen,
(2) —$(CH_2)_nCF_3$,
(3) —$(CH_2)_nOH$,
(4) —$(CH_2)_nCN$,
(5) —$C_{1-6}$alkyl,
(6) —$C_{1-6}$alkoxy,
(7) —$(CH_2)_nC_{3-8}$cycloalkyl,
(8) —$(CH_2)_nNR^{11}R^{12}$,
(9) phenyl,
(10) —$C_{2-6}$alkene-$CO_2R^{12}$,
(11) —$(CH_2)_nC(O)R^{12}$,
(12) —$(CH_2)_nCO_2R^{12}$,
(13) —$(CH_2)_nOC(O)R^{12}$,
(14) —$(CH_2)_nO(CH_2)_nCO_2R^{12}$,
(15) —$(CH_2)_nO(CH_2)_nC(O)NR^{11}R^{12}$,
(16) —$(CH_2)_nC(O)NR^{11}R^{12}$,
(17) —$(CH_2)_nC(O)NR^{11}(CH_2)_nCO_2R^{12}$,
(18) —$(CH_2)_nNR^{11}C(O)R^{12}$,
(19) —$(CH_2)_nNR^{11}C(O)NR^{11}R^{12}$,
(20) —$(CH_2)_nNR^{11}(CH_2)_nCO_2R^{12}$,
(21) —$(CH_2)_nNR^{11}CO_2R^{12}$ and
(22) —$(CH_2)_nNR^{11}SO_2R^{12}$, wherein alkyl, alkene, alkoxy, cycloalkyl, phenyl and —$(CH_2)_n$ are unsubstituted or substituted with one to eight substituents selected from oxo, halogen, —$C_{1-6}$alkyl, —$C_{1-6}$alkoxy, phenyl, —$(CH_2)_nOH$, —$(CH_2)_nCN$, —$(CH_2)_nCF_3$, —$(CH_2)_nSO_3H$, —$(CH_2)_nCO_2H$, —$(CH_2)_nCO_2C_{1-6}$alkyl, and —$(CH_2)_nCO_2C_{2-6}$ alkene, and alkyl and alkoxy are unsubstituted or substituted with one to five substituents selected from halogen, —OH, —$SO_3H$, —$CO_2H$, and —$CO_2C_{1-6}$alkyl, provided that at least one of $R^9$ and $R^{16}$ is selected from the group consisting of: —$C_{2-6}$alkene-$CO_2R^{12}$, —$(CH_2)_nC(O)R^{12}$, —$(CH_2)_nCO_2R^{12}$, —$(CH_2)_nOC(O)R^{12}$, —$(CH_2)_nO(CH_2)_nCO_2R^{12}$, —$(CH_2)_nO(CH_2)_nC(O)NR^{11}R^{12}$, —$(CH_2)_nC(O)NR^{11}R^{12}$, —$(CH_2)C(O)NR^{11}(CH_2)_nCO_2R^{12}$, —$(CH_2)_nNR^{11}C(O)R^{12}$, —$(CH_2)_nNR^{11}C(O)NR^{11}R^{12}$, —$(CH_2)_nNR^{11}(CH_2)_nCO_2R^{12}$, —$(CH_2)_nNR^{11}CO_2R^{12}$, and —$(CH_2)_nNR^{11}SO_2R^{12}$;

each $R^{11}$, $R^{12}$ and $R^{13}$ is independently selected from the group consisting of:
(1) hydrogen,
(2) —$C_{1-8}$alkyl,
(3) —$(CH_2)_nOH$,
(4) —$(CH_2)_nC_{3-8}$cycloalkyl,
(5) —$(CH_2)_nC_{2-8}$ heterocycloalkyl,
(6) —$(CH_2)_n$aryl, and
(7) —$(CH_2)_n$5 membered heteroaryl, wherein alkyl, cycloalkyl, heterocycloalkyl, and —$(CH_2)_n$ are unsubstituted or substituted with one to eight substituents selected from oxo, halogen, —$C_{1-6}$alkyl, —$C_{1-6}$alkoxy, —$(CH_2)_nOH$, —$(CH_2)_nCN$, —$(CH_2)_nCF_3$,—$(CH_2)_nSO_3H$, —$(CH_2)_nCO_2H$, —$(CH_2)_nCO_2C_{1-6}$alkyl, and —$(CH_2)_nCO_2C_{2-6}$alkene, and alkyl and alkoxy are unsubstituted or substituted with one to five substituents selected from halogen, —OH, —$SO_3H$, —$CO_2H$, and —$CO_2C_{1-6}$alkyl, and wherein aryl and 5-6 membered heteroaryl are unsubstituted or substituted with one to eight substituents independently selected from halogen, —$C_{1-6}$alkyl, —$C_{1-6}$alkoxy, —$(CH_2)_nOH$, —$(CH_2)_nCN$, —$(CH_2)_nCF_3$, —$(CH_2)_nSO_3H$, —$(CH_2)_nCO_2H$, —$(CH_2)_nCO_2C_{1-6}$ alkyl, and —$(CH_2)_nCO_2C_{2-6}$alkene, and alkyl and alkoxy are unsubstituted or substituted with one to five substituents selected from halogen, —OH, —$SO_3H$, —$CO_2H$, and —$CO_2C_{1-6}$alkyl, or $R^{11}$ and $R^{12}$ together with the nitrogen to which they are attached form a 4-8 membered heterocyclic ring containing 0-2 additional heteroatoms selected from oxygen, sulfur, and $NR^{15}$, and wherein the 4-8 membered heterocyclic ring is unsubstituted or substituted with one to five substituents independently selected from oxo, halogen, —$C_{1-6}$alkyl, —$C_{1-6}$alkoxy, —$(CH_2)_nOH$, —$(CH_2)_nCN$, —$(CH_2)_nCF_3$, —$(CH_2)_nSO_3H$, —$(CH_2)_nCO_2H$, —$(CH_2)_nCO_2C_{1-6}$alkyl, and —$(CH_2)_nCO_2C_{2-6}$alkene, and alkyl and alkoxy are unsubstituted or substituted with one to five substituents selected from halogen, —OH, —$SO_3H$, —$CO_2H$, and —$CO_2C_{1-6}$alkyl;

each $R^{14}$ is independently selected from the group consisting of:
(1) hydrogen,
(2) halogen,
(3) —$C(O)C_{2-8}$heterocycloalkyl,
(4) —$(CH_2)_nCO_2H$,
(5) —$CONH_2$,
(6) —$CONHC_{1-6}$alkyl,
(7) —$CON(C_{1-6}$alkyl$)_2$,
(8) —$C(O)NHC_{3-8}$cycloalkyl,
(9) —CONHaryl,
(10) —$C(O)NHCH_2CO_2H$, and
(11) —$C(O)N(C_{1-6}$alkyl$)CH_2CO_2H$, wherein alkyl, cycloalkyl, and heterocycloalkyl are unsubstituted or substituted with one to five substituents selected from oxo, halogen, —$C_{1-6}$alkyl, —$C_{1-6}$alkoxy, —$(CH_2)_nOH$, —$(CH_2)_nCN$, —$(CH_2)_nCF_3$, —$(CH_2)_nSO_3H$, —$(CH_2)_nCO_2H$, —$(CH_2)_nCO_2C_{1-6}$alkyl, and —$(CH_2)_nCO_2C_{2-6}$alkene, wherein aryl is unsubstituted or substituted with one to five substituents independently selected from halogen, —$C_{1-6}$ alkyl, —$C_{1-6}$alkoxy, —$(CH_2)_nOH$, —$(CH_2)_nCN$, —$(CH_2)_nCF_3$, —$(CH_2)_nSO_3H$, —$(CH_2)_nCO_2H$, —$(CH_2)_nCO_2C_{1-6}$ alkyl, and —$(CH_2)_nCO_2C_{2-6}$alkene, and wherein any $(CH_2)_n$ carbon atom is unsubstituted or substituted with one to two substituents selected from oxo, halogen, —$(CH_2)_nOH$, —$C_{1-6}$alkyl, —$C_{1-6}$alkoxy, —$(CH_2)_nCN$, —$(CH_2)_nCF_3$, —$(CH_2)_nSO_3H$, —$(CH_2)_nCO_2H$, —$(CH_2)_nCO_2C_{1-6}$alkyl, and —$(CH_2)_nCO_2C_{2-6}$alkene and alkyl and alkoxy are unsubstituted or substituted with one to five substituents independently selected from halogen, —OH, —$SO_3H$, —$CO_2H$, and —$CO_2C_{1-6}$alkyl;

each $R^{15}$ is independently selected from the group consisting of:
(1) hydrogen,
(2) —$C_{1-6}$alkyl, unsubstituted or substituted with one to six halogens,
(3) —$C_{3-8}$cycloalkyl, unsubstituted or substituted with one to six halogens,
(4) —$SO_2R^{12}$,
(5) —$COR^{12}$, and
(6) —$CO_2R^{12}$;

each m is independently 0, 1, 2, 3 or 4;
each n is independently 0, 1, 2, 3, 4, 5, 6, 7 or 8;
each p is independently 0, 1, 2, or 3; and
each q is independently 1, 2, 3 or 4.

10. The compound of claim 9 wherein p is 0; or a pharmaceutically acceptable salt thereof.

11. The compound of claim 1 selected from the group consisting of:
- (1) 3-{(3S)-4-{[1-(3-ethoxyphenyl)-2-(4-methylphenyl)-1H-imidazol-4-yl]carbonyl}-3-[(isopropylamino)carbonyl]-1-piperazinyl}-1-naphthoic acid,
- (2) 3-{(3S)-4-{[1-(3-ethoxyphenyl)-2-(2-fluoro-4-methylphenyl)-1H-imidazol-4-yl]carbonyl}-3-[(isopropylamino)carbonyl]-1-piperazinyl}-1-naphthoic acid,
- (3) 3-((3R)-3-[(acetylamino)methyl]-4-{[1-(3-ethoxyphenyl)-2-(2-fluoro-4-methylphenyl)-1H -imidazol-4-yl]carbonyl}-1-piperazinyl)-1-naphthoic acid,
- (4) 3-[1-{[1-(2,3-Dihydro-1,4-benzodioxin-6-yl)-2-(4-methylphenyl)-1H-imidazol-4-yl]carbonyl}-4-(2-naphthyl)piperidin-4-yl]propanoic acid,
- (5) (2S)-1-{[1-(3-ethoxyphenyl)-2-(4-methylphenyl)-1H-imidazol-4-yl]carbonyl}-4-(3-quinolinyl)-2-piperazinecarboxylic acid, trifluoroacetic acid salt,
- (6) (2S)-1-{[1-(3-ethoxyphenyl)-2-(4-methylphenyl)-1H-imidazol-4-yl]carbonyl}-4-(3 -quinolinyl)-2-ethyl-4-(3-quinolinyl)-2-piperazinecarboxamide, trifluoroacetic acid salt,
- (7) N-{[(2S)-1-{[1-(3-ethoxyphenyl)-2-(4-methylphenyl)-1H-imidazol-4-yl]carbonyl}-4-(3 -quinolinyl)-2-piperazinyl]carbonyl}glycine,
- (8) {[(2S)-1-{[1-(3-Ethoxyphenyl)-2-(4-methylphenyl)-1H-imidazol-4-yl]carbonyl}-4-(3-quinolinyl)-2-piperazinyl]methoxy}acetic acid,
- (9) 3-((3R)-4-{[1-(3-Ethoxyphenyl)-2-(4-methylphenyl)-1H-imidazol-4-yl]carbonyl}-3-{[2-(methylamino)-2-oxoethoxy]methyl}-1-piperazinyl)-1-naphthoic acid,
- (10) 3-((3R)-4-{[1-(3-Ethoxyphenyl)-2-(4-methylphenyl)-1H-imidazol-4-yl]carbonyl}-3-{[2-(methylamino)-2-oxoethoxy]methyl}-1-piperazinyl)-1-naphthoic acid, and
- (11) (2S)-4-(4-Carboxy-2-naphthyl)-1-{[1-(2,3-dihydro-1,4-benzodioxin-6-yl)-2-(4-fluorophenyl)-1H-imidazol-4-yl]carbonyl}-2-piperazinecarboxylic acid;

or a pharmaceutically acceptable salt thereof.

12. The compound of claim 11 selected from the group consisting of: 3-{(3S)-4-{[1-(3-ethoxyphenyl)-2-(4-methylphenyl)-1H-imidazol-4-yl]carbonyl}-3-[(isopropylamino)carbonyl]-1-piperazinyl}-1-naphthoic acid, or a pharmaceutically acceptable salt thereof.

13. The compound of claim 11 selected from the group consisting of: 3-{(3S)-4-{[1-(3-ethoxyphenyl)-2-(2-fluoro-4-methylphenyl)-1H-imidazol-4-yl]carbonyl}-3-[(isopropylamino)carbonyl]-1-piperazinyl}-1-naphthoic acid, or a pharmaceutically acceptable salt thereof.

14. The compound of claim 11 selected from the group consisting of: 3-((3R)-3-[(acetylamino)methyl]-4-{[1-(3-ethoxyphenyl)-2-(2-fluoro-4-methylphenyl)-1H-imidazol-4-yl]carbonyl}-1-piperazinyl)-1-naphthoic acid, or a pharmaceutically acceptable salt thereof.

15. The compound of claim 11 selected from the group consisting of: 3-[1-{[1-(2,3-Dihydro-1,4-benzodioxin-6-yl)-2-(4-methylphenyl)-1H-imidazol-4-yl]carbonyl}-4-(2-naphthyl)piperidin-4-yl]propanoic acid; or a pharmaceutically acceptable salt thereof.

16. The compound of claim 11 wherein the pharmaceutically acceptable salt thereof is a trifluoroacetic acid salt.

17. A pharmaceutical composition which comprises a compound of claim 1, or a pharmaceutically acceptable salt thereof, and a pharmaceutically acceptable carrier.

* * * * *